(12) United States Patent
Looper et al.

(10) Patent No.: US 10,440,955 B2
(45) Date of Patent: *Oct. 15, 2019

(54) METHODS COMPRISING A BIOCIDAL POLYAMINE

(71) Applicants: Curza Global, LLC, Provo, UT (US); University of Utah Research Foundation, Salt Lake City, UT (US)

(72) Inventors: Ryan Looper, Salt Lake City, UT (US); Dustin Williams, Bountiful, UT (US); Sujeevini Jeyapalina, Salt Lake City, UT (US); Travis Haussener, Midvale, UT (US); Paul R. Sebahar, Sandy, UT (US); Hariprasada R. Kanna Reddy, Salt Lake City, UT (US)

(73) Assignees: CURZA GLOBAL, LLC, Provo, UT (US); UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/806,701

(22) Filed: Nov. 8, 2017

(65) Prior Publication Data

US 2018/0125070 A1 May 10, 2018

Related U.S. Application Data

(63) Continuation of application No. 15/222,576, filed on Jul. 28, 2016, now Pat. No. 9,839,219, which is a
(Continued)

(51) Int. Cl.
| | | |
|---|---|---|
| *A01N 47/28* | (2006.01) | |
| *A01N 43/84* | (2006.01) | |
| *A01N 33/04* | (2006.01) | |
| *C07C 233/78* | (2006.01) | |
| *C07D 317/58* | (2006.01) | |
| *A01N 43/30* | (2006.01) | |
| *C07D 295/135* | (2006.01) | |
| *A01N 43/10* | (2006.01) | |
| *A01N 43/40* | (2006.01) | |
| *A61K 31/135* | (2006.01) | |
| *C07C 211/27* | (2006.01) | |
| *C07C 271/20* | (2006.01) | |
| *C07C 275/14* | (2006.01) | |
| *C07C 211/29* | (2006.01) | |
| *C07C 217/58* | (2006.01) | |
| *A01N 33/10* | (2006.01) | |

(Continued)

(52) U.S. Cl.
CPC ............ *A01N 47/28* (2013.01); *A01N 33/04* (2013.01); *A01N 33/08* (2013.01); *A01N 33/10* (2013.01); *A01N 37/30* (2013.01); *A01N 37/40* (2013.01); *A01N 43/10* (2013.01); *A01N 43/30* (2013.01); *A01N 43/40* (2013.01); *A01N 43/54* (2013.01); *A01N 43/56* (2013.01); *A01N 43/84* (2013.01); *A01N 47/12* (2013.01); *A61K 8/41* (2013.01); *A61K 8/42* (2013.01); *A61K 8/49* (2013.01); *A61K 8/494* (2013.01); *A61K 8/4926* (2013.01); *A61K 8/4953* (2013.01); *A61K 8/4973* (2013.01); *A61K 8/4986* (2013.01); *A61K 31/135* (2013.01); *A61K 31/166* (2013.01); *A61L 2/232* (2013.01); *A61L 29/14* (2013.01); *A61L 31/14* (2013.01); *A61Q 5/02* (2013.01); *A61Q 15/00* (2013.01); *A61Q 19/007* (2013.01); *A61Q 19/10* (2013.01); *C07C 211/27* (2013.01); *C07C 211/29* (2013.01); *C07C 217/58* (2013.01); *C07C 233/78* (2013.01); *C07C 271/20* (2013.01); *C07C 275/14* (2013.01); *C07D 295/135* (2013.01); *C07D 317/58* (2013.01); *C09D 5/14* (2013.01); *A61L 2/18* (2013.01); *A61L 2/22* (2013.01); *A61L 2/235* (2013.01); *A61L 12/14* (2013.01); *A61L 2202/21* (2013.01); *A61L 2202/24* (2013.01); *C07C 2601/14* (2017.05); *C08K 5/17* (2013.01)

(58) Field of Classification Search
None
See application file for complete search history.

(56) References Cited

U.S. PATENT DOCUMENTS

| | | |
|---|---|---|
| 4,038,312 A | 7/1977 | Atkins |
| 4,340,756 A | 7/1982 | Dybas et al. |

(Continued)

FOREIGN PATENT DOCUMENTS

| | | |
|---|---|---|
| FR | 2 860 129 A1 | 1/2005 |
| WO | 93/12097 A1 | 6/1993 |

(Continued)

OTHER PUBLICATIONS

Bachrach et al., "Antibacterial Action of Oxidized Spermine," J. gen. Microbiol., 1964, vol. 37, pp. 195-204.
Barry et al., "Methods for Determining Bactericidal Activity of Antimicrobial Agents: Approved Guidelines," NCCLS, Sep. 1999, vol. 19(18), pp. 1-28.
Baxter et al., "Reductive Aminations of Carbonyl Compounds with Borohydride and Borane Reducing Agents," Org Reac, 2004, 1, 59.
Boncher et al., "Polyamine-based analogues as biochemical probes and potential therapeutics," Biochemical Society Transactions, 2007, 35(part 2); 356-363.

(Continued)

*Primary Examiner* — Brian J Davis
(74) *Attorney, Agent, or Firm* — Kilpatrick Townsend & Stockton LLP

(57) ABSTRACT

Compounds, compositions, and methods comprising a polyamine compound are described, which may be used to kill, disperse, treat, or reduce biofilms, or to inhibit or substantially prevent biofilm formation. In certain aspects, the present invention relates to compounds, compositions, and methods comprising polyamine compounds that have antimicrobial or dispersing activity against a variety of bacterial strains capable of forming biofilms.

17 Claims, 43 Drawing Sheets

Related U.S. Application Data continuation of application No. 14/507,701, filed on Oct. 6, 2014, now Pat. No. 9,439,433, which is a continuation-in-part of application No. 14/076,143, filed on Nov. 8, 2013, now Pat. No. 8,853,278.

(60) Provisional application No. 62/001,604, filed on May 21, 2014, provisional application No. 61/938,111, filed on Feb. 10, 2014, provisional application No. 61/902,135, filed on Nov. 8, 2013, provisional application No. 61/887,267, filed on Oct. 4, 2013, provisional application No. 61/836,555, filed on Jun. 18, 2013, provisional application No. 61/834,149, filed on Jun. 12, 2013, provisional application No. 61/826,761, filed on May 23, 2013, provisional application No. 61/826,453, filed on May 22, 2013.

(51) Int. Cl.

| | | |
|---|---|---|
| *A01N 37/30* | (2006.01) | |
| *A01N 37/40* | (2006.01) | |
| *A01N 43/54* | (2006.01) | |
| *A01N 43/56* | (2006.01) | |
| *A01N 47/12* | (2006.01) | |
| *A61K 31/166* | (2006.01) | |
| *A01N 33/08* | (2006.01) | |
| *A61K 8/41* | (2006.01) | |
| *A61K 8/42* | (2006.01) | |
| *A61K 8/49* | (2006.01) | |
| *A61L 2/232* | (2006.01) | |
| *A61L 29/14* | (2006.01) | |
| *A61L 31/14* | (2006.01) | |
| *A61Q 5/02* | (2006.01) | |
| *A61Q 15/00* | (2006.01) | |
| *A61Q 19/00* | (2006.01) | |
| *A61Q 19/10* | (2006.01) | |
| *C09D 5/14* | (2006.01) | |
| *A61L 2/18* | (2006.01) | |
| *A61L 2/22* | (2006.01) | |
| *A61L 2/235* | (2006.01) | |
| *A61L 12/14* | (2006.01) | |
| *C08K 5/17* | (2006.01) | |

(56) References Cited

U.S. PATENT DOCUMENTS

| | | | |
|---|---|---|---|
| 4,505,861 | A | 3/1985 | Bergeron, Jr. |
| 4,522,811 | A | 6/1985 | Eppstein et al. |
| 5,583,239 | A | 12/1996 | Regen |
| 6,077,954 | A | 6/2000 | Cook et al. |
| 6,149,822 | A | 11/2000 | Fabri et al. |
| 6,329,523 | B1 | 12/2001 | Cook et al. |
| 6,395,189 | B1 | 5/2002 | Fabri et al. |
| 6,555,228 | B2 | 4/2003 | Guritza |
| 6,613,435 | B1 | 9/2003 | Guritza |
| 6,982,351 | B2 | 1/2006 | Frydman et al. |
| 7,425,579 | B2 | 9/2008 | Poulin et al. |
| 8,853,278 | B1 | 10/2014 | Looper et al. |
| 9,034,927 | B2 | 5/2015 | Williams et al. |
| 9,220,267 | B2 | 12/2015 | Williams et al. |
| 9,439,433 | B2 | 9/2016 | Looper et al. |
| 9,839,219 | B2 | 12/2017 | Looper et al. |
| 2004/0209926 | A1 | 10/2004 | Burns et al. |
| 2007/0208082 | A1 | 9/2007 | Woster et al. |
| 2008/0199509 | A1 | 8/2008 | Nick et al. |
| 2008/0274929 | A1 | 11/2008 | Whitekettle et al. |
| 2009/0124591 | A1 | 5/2009 | Diamond et al. |
| 2010/0093973 | A1 | 4/2010 | Nakagawa et al. |
| 2012/0015865 | A1 | 1/2012 | Zelphati et al. |
| 2014/0350017 | A1 | 11/2014 | Williams et al. |
| 2015/0038512 | A1 | 2/2015 | Looper et al. |
| 2015/0038705 | A1 | 2/2015 | Williams et al. |
| 2015/0274639 | A1 | 10/2015 | Williams et al. |

FOREIGN PATENT DOCUMENTS

| | | |
|---|---|---|
| WO | 94/19311 A1 | 9/1994 |
| WO | 97/01360 A2 | 1/1997 |
| WO | 2005/105729 A1 | 11/2005 |
| WO | 2007/071396 A2 | 6/2007 |
| WO | 2008/137195 A1 | 11/2008 |
| WO | 2010/010345 A2 | 1/2010 |
| WO | 2010/148390 A2 | 12/2010 |
| WO | 2012/151554 A1 | 11/2012 |
| WO | 2012/151555 A1 | 11/2012 |
| WO | 2013/072491 A1 | 5/2013 |
| WO | 2013/148230 A1 | 10/2013 |
| WO | 2014/078801 A1 | 5/2014 |
| WO | 2014/190096 A1 | 11/2014 |
| WO | 2014/190097 A1 | 11/2014 |

OTHER PUBLICATIONS

Bottcher et al., "Synthesis and Activity of Biomimetic Biofilm Disruptors," J. of the American Chem. Society, 2013, vol. 135, pp. 2927-2930.

Company et al., "$O_2$ Chemistry of Dicopper Complexes with Alkyltriamine Ligands. Comparing Synergistic Effects on $O_2$ Binding," Inorganic Chemistry, 2006, 45(14), 5239-41.

Company et al., "$O_2$ Chemistry of Dicopper Complexes with Alkyltriamine Ligands. Comparing Synergistic Effects on $O_2$ Binding," Inorganic Chemistry, 2006, Supporting Information, 14 pages.

Database CAPLUS in STN, Acc. No. 1996:198207, Rehse et al., Archiv der Pharmazie (1996), 329(3), pp. 155-160 (abstract).

Database CAPLUS on STN, Acc. No. 2003:265709, Ambrosi et al., Polyhedron (2003), 22(8), pp. 1135-1146 (abstract).

Database CAPLUS on STN, Acc. No. 2006:525185, Company et al., Inorganic Chemistry (2006), 45(14), pp. 5239-5241 (abstract).

Database CAPLUS on STN, Acc. No. 2010:1600778, Phanstiel et al., WO2010/148390 A2, Dec. 23, 2010 (abstract).

De Almeida et al., "Synthesis and antitubercular activity of lipophilic moxifloxacin and gatifloxacin derivatives," Bioorganic and Medicinal Chemistry Letters, 2007, vol. 17, pp. 5661-5664.

Dietrich et al., "123. Synthesis and Protonation Features of 24-, 27- and 32-membered Macrocyclic Polyamines," Helvetica Chimica Acta, 1983, vol. 66, Fasc. 4,—Nr. 123.

Dou, D. et al., "Design and synthesis of inhibitors of noroviruses by scaffold hopping," Bioorganic & Medicinal Chemistry, Pergamon, GB, vol. 19, No. 19, Aug. 15, 2011, pp. 5749-5755.

Jayaraman et al., "Inhibiting sulfate-reducing bacteria in biofilms by expressing the antimicrobial peptides indolicidin and bactenecin," Journal of Industrial Microbiology & Biotechnology, 1999, vol. 22, pp. 167-175.

Joshi et al., "Synthesis, antibacterial activity and mode of action of novel linoleic acid—dipeptide—spermidine conjugates," Org. Biomol. Chem, 2012, vol. 10, pp. 8326-8335.

Karatan et al., "NspS, a Predicted Polyamine Sensor, Mediates Activation Of *Vibrio cholera* Biofilm Formation by Norspermidine," Journal of Bacteriology, Nov. 2005, vol. 187(21), pp. 7434-7443, doi: 10.1128/jb.187.21.7434-7443.2005.

Kaur et al., "A Comparison of Chloroambucil- and Xylene-Containing Polyamines Leads to Improved Ligands for Accessing the Polyamine Transport System," J. Med. Chem., 2008, vol. 51, pp. 1393-1401.

Kikuchi et al., "Antimicrobial activities of squalamine mimics," Antimicrob. Agents Chemother., 1997, vol. 41(7):1433-1438.

Kim et al., "Synthesis and Antimicrobial Activity of Squalamine Analogue," Bioorganic & Medicinal Chemistry, 2000, vol. 8, pp. 2059-2065.

Kolodkin-Gal et al., "D-Amino Acids Trigger Biofilm Disassembly," Science, Apr. 2010, vol. 328, pp. 627-629.

Kolodkin-Gal et al., "A Self-Produced Trigger for Biofilm Disassembly that Targets Exopolysaccharide," Cell, Apr. 2012, vol. 149, pp. 684-692.

(56) References Cited

OTHER PUBLICATIONS

Kuca et al., "Preparation of Benzalkonium Salts Differing in the Length of a Side Alkyl Chain," Molecules, 2007, vol. 12, pp. 2341-2347.
Kwon et al., "Polyamine Effects on Antibiotic Susceptibility in Bacteria," Antimicrobial Agents and Chemotherapy, Jun. 2007, vol. 51(6), pp. 2070-2077.
LaDow et al., "Bicephalic amphiphile architecture affects antibacterial activity," European Journal of Medicinal Chemistry, 2011, vol. 46, pp. 4219-4226.
Liao et al., "Polyamine Transport as a Target for Treatment of *Pneumocystis* Pneumonia," Antimicrobial Agents and Chemotherapy, Dec. 2009, vol. 53(12), pp. 5259-5264.
Loncle et al., "Synthesis of new 7-aminosterol squalamine analogues with high antimicrobial activities through a stereoselective titanium reductive amination reaction," Tetrahedron, 2007, vol. 63, pp. 12968-12974.
Martin, B. et al., "N-Benzylpolyamines as vectors of boron and fluorine for cancer therapy and imaging: Synthesis and biological evaluation," Journal of Medicinal Chemistry, American Chemical Society, US, vol. 44, No. 22, Oct. 25, 2001, pp. 3653-3664.
Muth et al., "Polyamine transport inhibitors: design, synthesis, and combination therapies with Difluoromethylornithine," Journal of Medicinal Chemistry, 2014, vol. 57, pp. 348-363.
Patel et al., "Polyamines are essential for the formation of plague biofilm," Journal of Bacteriology, 2006, 188(7); 2355-2363.
Pernak et al., "Antimicrobial activities of new analogues of benzalkonium chloride," Eur. J. Med. Chem., 1999, vol. 34, pp. 765-771.
PubChem CID 24807066, http://pubchem.ncbi.nlm.nih.gov/summary/summary.cgi?q=all&cid=24807066, retrieve date Feb. 12, 2014, 3 pages.
PubChem CID 24807068, http://pubchem.ncbi.nlm.nih.gov/summary/summary.cgi?q=all&cid=24807068, retrieve date Feb. 12, 2014, 3 pages.
PubChem CID 24807458, http://pubchem.ncbi.nlm.nih.gov/summary/summary.cgi?q=all&cid=24807458, retrieve date Feb. 12, 2014, 2 pages.
Randazzo et al., "A series of cationic sterol lipids with gene transfer and bactericidal activity," Bioorganic & Medicinal Chemistry, 2009, vol. 17, pp. 3257-3265.
Rehse et al., "Antimicrobial Effects of Oligoamines," Arch. Pharm. Pharm. Med. Chem., 1996, vol. 329, pp. 155-160.
Rozansky et al., "Studies on the Antibacterial Action of Spermine," J. gen. Microbiol., 1954, vol. 10, pp. 11-16.
Sadownik et al., "Rapid Construction of a Squalamine Mimic," J. Am. Chem. Soc., 1995, vol. 117, pp. 6138-6139.
Salunke et al., "Bile acid-polyamine conjugates as synthetic ionophores," Arkivoc, 2003 (ix) 115-125.
Shu et al., "The synthesis of spermine analogs of the shark aminosterol squalamine," Steroids, 2002, vol. 67, pp. 291-304.
Tan et al., Pharm. Res. 24:2297-2308 (2007).
Thorsteinsson et al., "Soft Antimicrobial Agents: Synthesis and Activity of Labile Environmentally Friendly Long Chain Quarternary Ammonium Compounds," J. Med. Chem., 2003, vol. 46, pp. 4173-4181.
Wang et al., "Defining the Molecular Requirements for the Selective Delivery of Polyamine Conjugates into Cells Containing Active Polyamines Transporters," J. Med. Chem., 2003, vol. 46, pp. 5129-5138.
Williams et al., Experimental model of biofilm implant-related osteomyelitis to test combination biomaterial using biofilms as initial inocula, J. Biomed Mat Res A 100, 1888-1900 (2012).
Williams et al., "In Vivo Efficacy of a Silicone-Catonic Steriod Antimicrobial Coating to Prevent Implant-Related Infection," Biomaterials 33, 8641-8656 (2012).
Williams et al., "A modified CDC biofilm reactor to produce mature biofilms on the surface of Peek membranes for an in vivo animal model application," Curr Microbiol 62, 1657-1663 (2011).
Williams et al., "Observing the Biofilm Matrix of *Staphylococcus epidermidis* ATCC 35984 Grown Using the CDC Biofilm Reactor," Microsc. Microanal. 16,, 143-152, 2010, doi: 10.1017/s143192760999136x.
Williams, Preventing Biofilm Implant-Related Osteomyelitis Using a Novel Synthetic Analog of Antimicrobial Peptides, 2012, Doctoral Dissertation, 296 pages.
Williams et al., "Use of delrin plastic in a modified CDC biofilm reactor," Res J. Microbiol 6, 425-429 (2011).
Williams et al., "Using biofilms as initial inocula in animal models of biofilm-related infections," J Biomed Mater Res Part B Appl. Biomater. 2012, 100, 1163-69; 10.1002/jbm.b.31979.
U.S. Appl. No. 14/076,143, filed Nov. 8, 2013.
U.S. Appl. No. 14/076,149, filed Nov. 8, 2013.
U.S. Appl. No. 61/887,267, filed Oct. 4, 2013.
U.S. Appl. No. 61/902,135, filed Nov. 8, 2013.
U.S. Appl. No. 61/870,730, filed Aug. 27, 2013.
U.S. Appl. No. 14/076,143, Non-Final Office Action, dated Feb. 6, 2014, 20 pages.
U.S. Appl. No. 14/076,143, Final Office Action, dated Apr. 3, 2014.
U.S. Appl. No. 14/507,701, filed Oct. 6, 2014.
U.S. Appl. No. 14/683,075, filed Apr. 9, 2015.
U.S. Appl. No. 14/507,701, Non-Final Office Action, dated Sep. 17, 2015, 17 pages.
PCT/US2014/039039, International Search Report and Written Opinion, dated Aug. 11, 2014, 11 pages.
PCT/US2014/039040, International Search Report and Written Opinion, dated Aug. 11, 2014, 10 pages.
PCT/US2014/039039, International Preliminary Report on Patentability, dated Dec. 3, 2015, 10 pages.
PCT/US2014/039040, International Preliminary Report on Patentability, dated Dec. 3, 2015, 8 pages.
U.S. Appl. No. 14/507,701, Final Office Action, dated Apr. 13, 2016, 10 pages.
U.S. Appl. No. 14/683,075, Non-final Office Action, dated Sep. 23, 2016, 14 pages.
European Application No. 14735722.2, Office Action dated Oct. 31, 2016, 5 pages.
Chinese Application No. 201480041542.1, First Office Action dated Nov. 7, 2016, 7 pages.
U.S. Appl. No. 14/683,075, Final Office Action dated Apr. 7, 2017, 23 pages.
European Application No. 14735722.2, Communication pursuant to Article 94(3) EPC, dated Nov. 9, 2017, 4 pages.
European Application No. 14735722.2, Communication pursuant to Article 94(3) EPC, dated Feb. 28, 2019, 4 pages.

— Prior Art Compounds—

— Prior Art Compounds —

— Prior Art Compounds— norspermine $n^1 = n^2 = n^3 = 1$
MIC = 800 norspermidine $n^1 = n^2 = 1$
MIC = 900

All MIC are in µg/mL n = 1; MIC = 1,300
n = 10; MIC = 100 n = 1; MIC = 1,175
n = 2; MIC = 1,200
n = 4; MIC = >1,400
n = 10; MIC = 950 n = 1; MIC = 300
n = 10; MIC = 50

$R^1$ = H; n = 1; MIC = >1,000
$R^1$ = $CH_2NH(CH_2)_3NH(CH_2)_3NH_2$ n = 1;
MIC = 50 n = 1; MIC = 75
n = 2; MIC = 50

| Compound | EBEC (μg/mL) | EBEC (μM) |
|---|---|---|
| 1 | | |
| 2 | | |
| 3 | | |
| 4 | | |
| 5 | 1,000 | |
| 6 | 800 | |
| 7 | | |
| 8 | ~750 | |
| 9 | ~750 | |
| 10 | ~750 | |
| 11 | | |
| 12 | | |
| Norspermidine | >1,000 | |
| Spermine | <1,600 | |
| Spermidine | <1,600 | |
| Vancomycin | >3,000 | |

*FIG. 12B*

– Prior Art –

— Prior Art —

— Prior Art —

— Prior Art —

METHODS COMPRISING A BIOCIDAL POLYAMINE

CROSS-REFERENCES TO RELATED APPLICATIONS

This application is a continuation of U.S. application Ser. No. 15/222,576 (filed Jul. 28, 2016), which is a continuation of U.S. application Ser. No. 14/507,701 (filed Oct. 6, 2014, and issued as U.S. Pat. No. 9,439,433), which is a continuation-in-part of U.S. application Ser. No. 14/076,143 (filed Nov. 8, 2013, and issued as U.S. Pat. No. 8,853,278), which claims the benefit of U.S. Provisional Application Nos. 61/826,453 (filed May 22, 2013), 61/826,761 (filed May 23, 2013), 61/834,149 (filed Jun. 12, 2013); and 61/836,555 (filed Jun. 18, 2013). This application also claims the benefit of U.S. Provisional Application Nos. 61/887,267 (filed Oct. 4, 2013), 61/902,135 (filed Nov. 8, 2013), 61/938,111 (filed Feb. 10, 2014), and 62/001,604 (filed May 21, 2014). These applications are incorporated by reference in their entirety for all purposes.

FIELD OF THE INVENTION

The present invention is directed to polyamine compounds, compositions, and methods, which preferably have antimicrobial or dispersing activity against a variety of bacterial strains capable of forming biofilms. Various aspects and embodiments relate generally to polyamine compounds and to methods of preparing or using such compounds.

BACKGROUND OF THE INVENTION

Antimicrobial compounds, such as traditional antibiotics, have the ability to kill or to retard the growth of bacteria, fungi, and other microorganisms. Some antimicrobial compounds also are effective against viruses. Antimicrobial compounds are used in a wide variety of clinical settings, industrial applications, food production facilities and environmental applications all across the globe in an effort to reduce the risk of, for example, bacterial colonization and development of disease in people.

Traditional antibiotics are primarily derivatives or synthetic mimics of natural compounds secreted by bacteria, plants, or fungi. These compounds typically have very specific methods of action against a cell wall/membrane component of bacteria, or an enzyme/protein in a metabolic pathway. Examples of traditional antibiotics on the market include penicillin, oxacillin, vancomycin, gentamicin, rifampicin and amoxicillin, among others.

Because bacteria have the ability to develop resistance genes to these antibiotics as a result of genetic mutations or acquired defense mechanisms that target the specific activity of the antibiotics, bacteria typically have the ability to develop resistance to traditional antibiotics. Increasingly more prevalent bacterial resistance has made traditional antibiotics to become less and less effective in a variety of applications.

Bacterial resistance to antibiotics represents one of the most underappreciated threats to modern society. See Zhang et al., *Antibiotic resistance as a global threat: Evidence from China, Kuwait and the United States*, Global Health 2, 6 (2006). Currently, more than 90% of clinical isolates of *Staphylococcus aureus* display resistance to penicillin. See Balaban et al., *Control of Biofilm Infections by Signal Manipulation*, Ch. 1, 1-11 (Springer, 2008). Recent reports have even indicated that bacteria in natural ecosystems metabolize antibiotics as an energy source. See Leslie, *Germs Take a Bite Out of Antibiotics*, Science 320, 33 (2008). The trend of bacterial resistance continues to increase as indicated by almost daily scientific publications and world news reports of antibiotic resistant superbugs such as carbapenem-resistant Enterobacteriacea, vancomycin-resistant Enterococci, multidrug-resistant *Pseudomonas aeruginosa* and methicillin-resistant *Staphylococcus aureus* (MRSA). See, e.g., FoxNews.com. Europe in the Grip of Drug-Resistant Superbugs (2011); Melnick, M., TIME (2010); Arias et al., The rise of the *Enterococcus*: beyond vancomycin resistance, Nat Rev Microbiol 10, 266-278 (2012); Jain, R. et al., *Veterans affairs initiative to prevent methicillin-resistant Staphylococcus aureus infections*, N Engl J Med 364, 1419-1430 (2011); Nordmann et al., *The real threat of Klebsiella pneumoniae carbapenemase-producing bacteria*, Lancet Infect Dis 9, 228-236 (2009); Aloush et al., *Multidrug-resistant Pseudomonas aeruginosa: risk factors and clinical impact*, Antimicrob Agents Chem 50, 43-48 (2006). In addition to adversely affecting civilian patients, antibiotic-resistant bacteria affect injured military personnel. Multiple reports from Operation Iraqi Freedom/Operation Enduring Freedom have indicated that multidrug-resistant bacteria and antibiotic resistance constitute one of the most disconcerting aspects of military theater treatment. See, e.g., Calhoun et al., *Multidrug-resistant Organisms in Military Wounds from Iraq and Afghanistan*, Clinical Orthopaedics and Related Research 466, 1356-1362 (2008); Murray et al., *Bacteriology of War Wounds at the Time of Injury*, Military Medicine 171, 826-829 (2006); Hujer et al., *Analysis of Antibiotic Resistance Genes in Multidrug-Resistant Acinetobacter sp. Isolates from Military and Civilian Patients Treated at the Walter Reed Army Medical Center*, Antimicrobial Agents and Chemotherapy 50, 4114-4123 (2006).

Multiple factors contribute to bacterial cells' ability to resist the effects of antibiotics. See, e.g., Morita et al., *Antibiotic Inducibility of the MexXY Multidrug Efflux System of Pseudomonas aeruginosa: Involvement of the Antibiotic-Inducible PA5471 Gene Product*, Journal of Bacteriology 188, 1847-1855 (2006); Tran et al., *Heat-Shock Protein ClpL/HSP100 Increases Penicillin Tolerance in Streptococcus pneumoniae*, Advances in Oto-rhino-laryngology 72, 126-128 (2011); Livorsi et al., *Virulence Factors of Gram-Negative Bacteria in Sepsis With a Focus on Neisseria meningitidis*, Contributions to Microbiology 17, 31-47 (2011); Nostro, et al., *Specific Ion Effects on the Growth Rates of Staphylococcus aureus and Pseudomonas aeruginosa*, Physical Biology 2, 1-7 (2005). Amongst these factors is the ability of bacteria to develop a biofilm. See, e.g., Costerton et al., *How bacteria stick*, Sci Am 238, 86-95 (1978); Lawrence et al., *Optical sectioning of microbial biofilms*, J Bacteriol 173, 6558-6567 (1991); ZoBell, *The Effect of Solid Surfaces upon Bacterial Activity*, Journal of Bacteriology 46, 39-56 (1943). Biofilms have unique characteristics that allow them to withstand, or defend themselves against a variety of perturbations including exposure to antibiotics.

Biofilms are surface-attached communities of bacteria, often polymicrobial, that produce a slimy, extracellular polysaccharide substance (EPS) that encapsulates them. The EPS provides protection, Leid et al., *The Exopolysacharide Alginate Protects Pseudomonas aeruginosa Biofilm Bacteria from IFN-γ-Mediated Macrophage Killing*, The Journal of Immunology 175, 7512-7518 (2005), as well as a reserve of nutrients, water and trace elements to sustain life. Costerton et al., *The Bacterial Glycocalyx in Nature and Disease*, Annual Review of Microbiology 35, 299-324 (1981). Biofilms are the predominant phenotype of bacteria in natural ecosystems. Gram-negative bacteria, Gram-positive bacteria, and mycobacteria, in addition to other unicellular organisms, can produce biofilms.

Within the biofilm community, bacteria may have several methods of defending themselves against the biocidal effects of antibiotics. First, they have strength in numbers. Biofilms may contain millions or trillions of cells in a very small volume. Second, bacteria in a biofilm have the ability to rapidly transfer genetic material, such as plasmids, that specifically code for the production of molecules that protect them against antibiotics. Lujan et al., *Disrupting Antibiotic Resistance Propagation by Inhibiting the Conjugative DNA Relaxase*, PNAS 104, 12282-12287 (2007); Lederberg et al., *Gene Recombination in Escherichia coli*. Nature 158, 529-564 (1946). Rates of plasmid transfer in biofilms have been shown to be much higher than amongst planktonic bacteria, which are free-floating in an environment. Hausner et al., *High Rates of Conjugation in Bacterial Biofilms as Determined by Quantitative In Situ Analysis*, Applied and Environmental Microbiology 65, 3710-3713 (1999). Third, as a biofilm community matures, it creates an oxygen gradient such that an oxygen-rich environment exists on the outer edges of a biofilm, whereas an oxygen-deprived, or anaerobic, area exists in the deepest portions of a biofilm. Walters et al., *Contributions of Antibiotic Penetration, Oxygen Limitation, and Low Metabolic Activity to Tolerance of Pseudomonas aeruginosa biofilms to Ciprofloxacin and Tobramycin*, Antimicrobial Agents and Chemotherapy 47, 317-323 (2003); Borriello et al., *Oxygen Limitation Contributes to Antibiotic Tolerance of Pseudomonas aeruginosa in Biofilms*, Antimicrobial Agents and Chemotherapy 48, 2659-2664 (2004). This may result in reduced metabolic activity in those cells that dwell in the interior of the biofilm. Importantly, traditional antibiotics are typically effective against bacterial cells that are rapidly dividing, i.e., in a logarithmic phase of growth. Mandell, *Interaction of Intraleukocytic Bacteria and Antibiotics*, The Journal of Clinical Investigation 52, 1673-1673 (1973); Gilbert et al., *Influence of Growth Rate on Susceptibility to Antimicrobial Agents: Biofilms, Cell Cycle, Dormancy, and Stringent Response*, Antimicrobial Agents and Chemotherapy 34, 1865-1868 (1990). Fourth, in a mature biofilm, water channels form throughout the community. Stoodley et al., *Liquid flow in biofilm systems*, App Env Microbiol 60, 2711-2716 (1994). These water channels have the ability to diffuse, remove or prevent toxic byproducts as well as antibiotics from interacting with cells in the biofilm. For novel antimicrobial agents to be effective over the long term, addressing each of these four characteristics may increase the potential for success in a variety of applications including healthcare, industrial, environmental, agricultural and sanitation industries. Furthermore, biofilms tend to secrete proteoglycan materials that create an extracellular matrix, which has the ability to potentially bind and hinder the activity of antibiotics.

Alternative approaches to killing bacteria include the use of antimicrobial agents that have fast-acting and nonspecific mode of activity against the cell membrane of bacteria. These alternate compounds include detergents, squalamine, quaternary ammonium compounds, and naturally occurring antimicrobial peptides, among others. By attacking and depolarizing the cell membrane in a nonspecific fashion at a faster rate, agents that attack the cell membrane globally can kill bacteria before they have time to upregulate their defense mechanisms. In addition, modes of action of these alternate antimicrobials are not limited to a specific protein or enzyme within a metabolic pathway.

However, as important as it is to kill bacteria and prevent their ability to cause infections in humans or animals, or contaminate unwanted processes in industrial, agricultural or environmental applications, when bacteria are attached to a surface, it sometimes may be more beneficial to not only kill bacteria, but also to cause them to "fall off" of a surface as well, e.g. disperse or dislodge bacteria in a biofilm community. In certain aspects, the present invention provides compounds, compositions, and methods that have shown the ability to disperse or dislodge bacterial cells in a biofilm, such that the cells are no longer able to reattach and form new biofilm communities, and, notably, the same compounds, compositions, and methods kill substantially all bacteria cells in a biofilm.

By dispersing a biofilm and killing the cells within it, at least two benefits are provided. This may be particularly important when considering the fact that although bacteria in a biofilm, which may be attached to a surface, can be killed by an antimicrobial agent, the dead cells and extracellular matrix residues may provide an attachment point for viable bacteria to re-adhere and form a biofilm once again with greater affinity. If biofilms are dispersed and killed, viable bacteria that are introduced to a surface will have reduced ability to preferentially adhere to that area. This can be particularly important in industrial applications wherein the formation of biofilms on a surface can be problematic, as well as medical applications wherein bacteria may adhere to the surface of a medical device. It has been surprisingly discovered that compositions of the present invention have significant potential to eradicate bacteria within a biofilm as well as cause the biofilm to disperse or dislodge, resulting in a variety of potential applications across multiple settings.

Thus, there is a need for novel compounds, compositions, and methods that have potent antimicrobial and anti-biofilm activity against a variety of bacterial strains, especially at high bacterial concentrations and against antibiotic-resistant bacteria.

BRIEF SUMMARY OF THE INVENTION

It is an object of the present invention to provide novel compounds, compositions, and methods having antimicrobial activity and dispersing activity against a wide variety of bacterial strains capable of forming biofilms. In some preferred aspects, the invention provides compounds, compositions, and methods that are effective against antibiotic-resistant bacterial biofilms.

It has been discovered that compounds, compositions, and methods of the present invention rapidly disperse biofilms and kill microorganisms such as bacteria, so that the microorganisms do not have an opportunity to upregulate their defense mechanisms. Thus, there may be a reduced risk of bacteria developing resistance to the compounds, compositions, and methods of the present invention. Furthermore, such compounds, compositions, and methods may not be limited to eradicating bacteria that are in log-phase growth. The ability of compounds, compositions, and methods of the present invention to disperse biofilms while demonstrating antimicrobial activity may address many of the characteristics that make biofilm communities difficult to treat using traditional antibiotics. More specifically, by dispersing and killing bacteria in a biofilm, water channels and the bacterial community as a whole may be broken apart, allowing for broader distribution of antimicrobial agent(s) to a greater number, or even substantially all, of the cells within a biofilm.

Aspects of this disclosure feature methods of killing, dispersing, dislodging, treating, and reducing biofilms as well as preventing or inhibiting biofilm formation. In some embodiments, the method comprises exposing a biofilm to an effective amount of a composition of the present invention to thereby kill, disperse, dislodge, treat, reduce, prevent, or inhibit bacterial biofilms.

In one embodiment, the present invention provides a polyamine compound.

In a second embodiment, the present invention provides a composition for treatment of biofilms, the composition comprising, consisting of, or consisting essentially of a polyamine compound as set forth in any of the embodiments, aspects, or combination of aspects herein.

In a third embodiment, the present invention provides a method of treating a biofilm comprising, consisting of, or consisting essentially of the step of administering a polyamine compound, or a composition comprising the polyamine compound, as set forth in any of the embodiments, aspects, or combination of aspects herein.

In a fourth embodiment, the present invention provides a method of making a polyamine compound, or a composition comprising, consisting essentially of, or consisting of the polyamine compound, as set forth in any of the embodiments, aspects, or combination of aspects herein.

These and other objects, aspects, and embodiments will become more apparent when read with the following detailed description and drawings.

BRIEF DESCRIPTION OF THE DRAWINGS

Various embodiments and aspects of the present invention are shown and described in reference to the numbered drawings.

FIG. 12B is a table showing the effect biofilm eradication concentration ("EBEC") of certain polyamine compounds represented in FIG. 8A and EBECs of certain polyamines.

FIG. 30B shows a control without added polyamine compounds.

Figure 1:
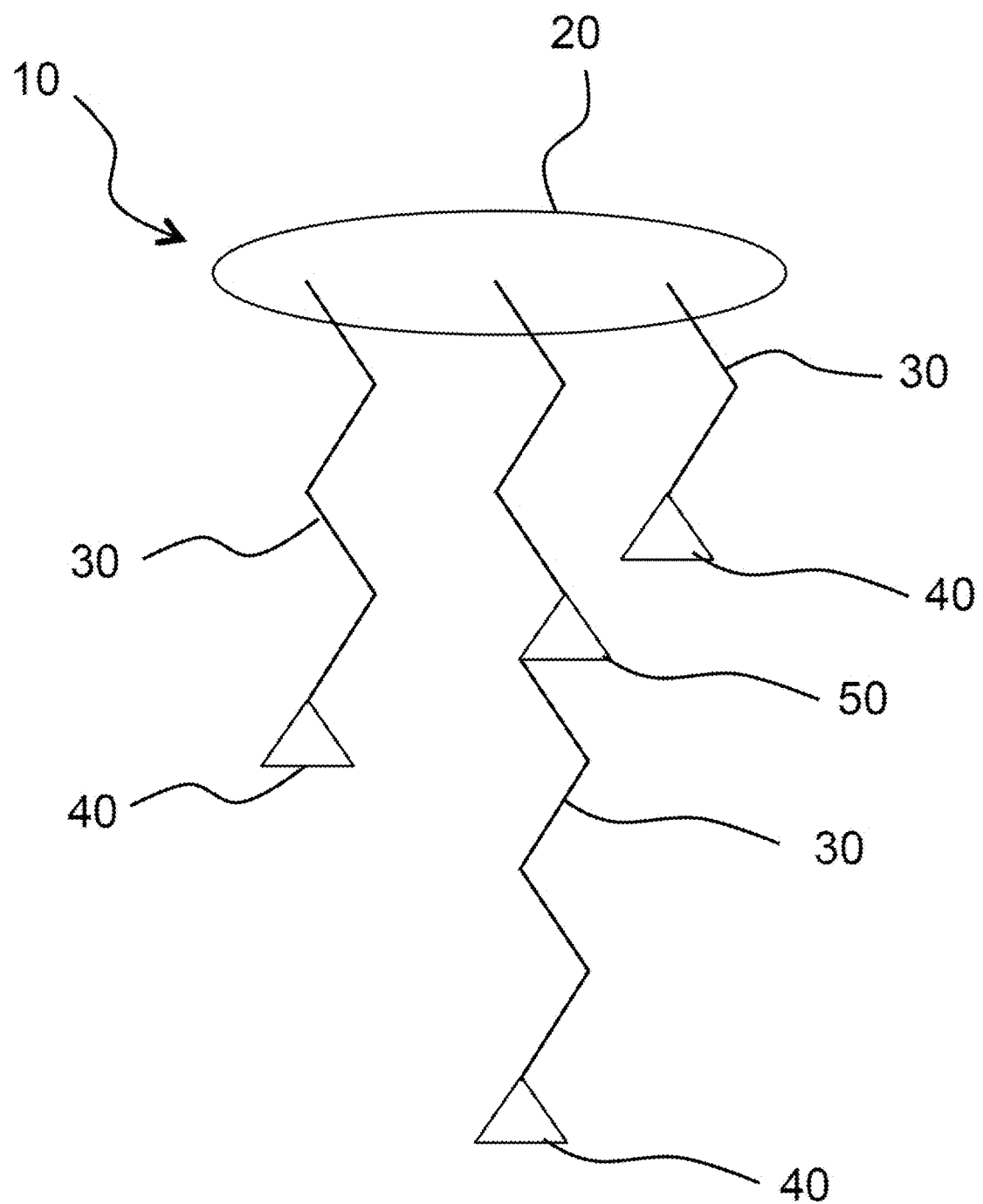
FIG. 1 shows a simplified schematic representation of one embodiment of a class of polyamine compounds.
Figure 2A:
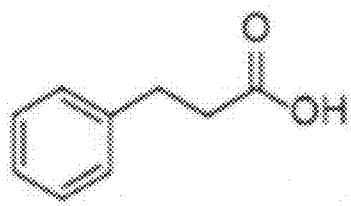
FIG. 2A through FIG. 2H show exemplary starting materials or reactants that may be used to prepare certain specific embodiments of polyamine compounds as set forth herein.
Figure 2B:
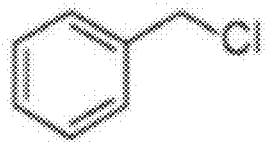
Figure 2C:
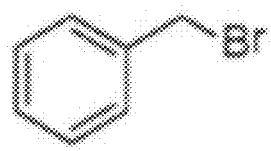
Figure 2D:
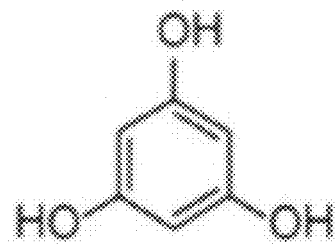
Figure 2E:
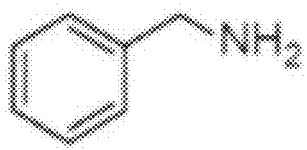
Figure 2F:
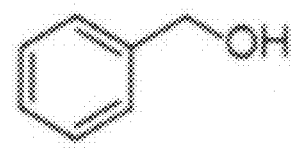
Figure 2G:
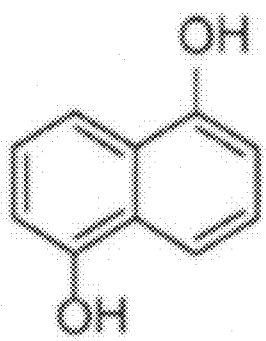
Figure 2H:
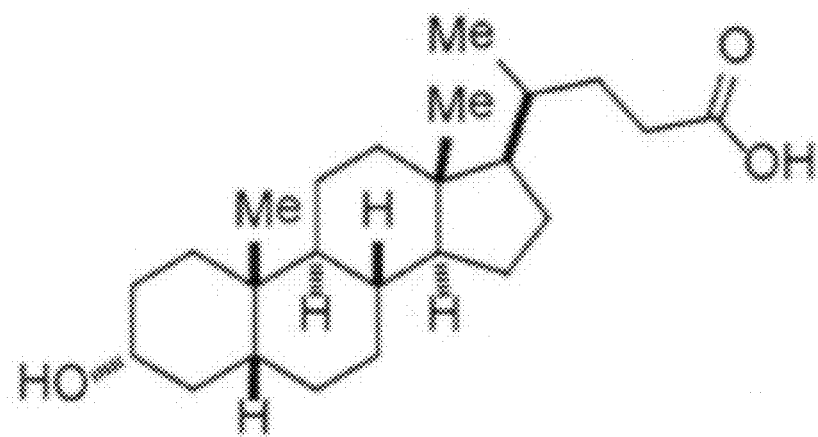

It will be appreciated that the drawings are illustrative and not limiting of the scope of the invention, which is defined by the appended claims. The embodiments shown accomplish various aspects and objects of the invention; however, it will be understood that other aspects, features or modifications may be within the scope of the appended claims. It is appreciated that it is not possible to clearly show each element and aspect of the invention in a single figure, and as such, multiple figures are presented to separately illustrate various details of the invention in greater clarity. Similarly, not every embodiment need accomplish all advantages of the present invention.

DETAILED DESCRIPTION OF THE INVENTION

The invention and accompanying drawings will now be discussed in reference to the numerals provided therein so as to enable one skilled in the art to practice the present invention. The skilled artisan will understand, however, that the inventions described below can be practiced without employing these specific details, or that they can be used for purposes other than those described herein. Indeed, they can be modified and can be used in conjunction with products and techniques known to those of skill in the art in light of the present disclosure. The drawings and descriptions are intended to be exemplary of various aspects of the invention and are not intended to narrow the scope of the appended claims. Furthermore, it will be appreciated that the drawings may show aspects of the invention in isolation and the elements in one figure may be used in conjunction with elements shown in other figures.

It will be appreciated that reference throughout this specification to aspects, features, advantages, or similar language does not imply that all of the aspects and advantages that may be realized with the present invention should be or are in any single embodiment of the invention. Rather, language referring to the aspects and advantages is understood to mean that a specific aspect, feature, advantage, or characteristic described in connection with an embodiment is included in at least one embodiment of the present invention. Thus, discussion of the aspects and advantages, and similar language, throughout this specification may, but does not necessarily, refer to the same embodiment.

The described aspects, features, advantages, and characteristics of the invention may be combined in any suitable manner in one or more further embodiments. Furthermore, one skilled in the relevant art will recognize that the invention may be practiced without one or more of the specific aspects or advantages of a particular embodiment. In other instances, additional aspects, features, and advantages may be recognized and claimed in certain embodiments that may not be present in all embodiments of the invention.

Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety, including U.S. Appl. Nos. 61/482,522; 61/482,523; 61/591,601; 61/616,944; 61/826,453; 61/826,761; 61/836,555; 61/834,149; Ser. Nos. 13/379,191; 14/076,143; and 14/076,149 as well as Int'l Pat. Publ. Nos. WO 2010/148390, 2012/151555, and 2013/148230 and PCT Appl. No. PCT/US14/39039. In case of conflict, the present specification, including these definitions, will control.

The terms "a," "an," and "the" as used herein not only includes aspects with one member, but also includes aspects with more than one member. For example, an embodiment including "a polyamine compound and an excipient" should be understood to present certain aspects with at least a second polyamine compound, at least a second excipient, or both.

The term "about" as used herein to modify a numerical value indicates a defined range around that value. If "X" were the value, "about X" would generally indicate a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X." When the quantity "X" only includes whole-integer values (e.g., "X carbons"), "about X" indicates from (X−1) to (X+1). In this case, "about X" as used herein specifically indicates at least the values X, X−1, and X+1.

When "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11%" is equivalent to "about 7%, about 9%, or about 11%."

The term "acyl" as used herein includes an alkanoyl, aroyl, heterocyclyl, or heteroaroyl group as defined herein. Examples of acyl groups include, but are not limited to, acetyl, benzoyl, and nicotinoyl.

The term "alkanoyl" as used herein includes an alkyl-C (O)— group wherein the alkyl group is as defined herein. Examples of alkanoyl groups include, but are not limited to, acetyl and propanoyl.

The term "agent" as used herein includes a compound or mixture of compounds that, when added to a composition, tend to produce a particular effect on the composition's properties. For example, a composition comprising a thickening agent is likely to be more viscous than an otherwise identical comparative composition that lacks the thickening agent.

The term "alkenyl" as used herein includes a straight or branched chain hydrocarbon containing at least one carbon-carbon double bond. The chain may contain an indicated number of carbon atoms. For example, "$C_1$-$C_{12}$ alkenyl" indicates that the group may have from 1 to 12 (inclusive) carbon atoms and at least one carbon-carbon double bond. When the indicated number of carbon atoms is 1, then the $C_i$ alkenyl is double bonded to a carbon (i.e., a carbon equivalent to an oxo group). In certain aspects, the chain includes 1 to 12, about 2 to 15, about 2 to 12, about 2 to 8, or about 2 to 6 carbon atoms. Examples of an alkenyl group may include, but are not limited to, ethenyl (i.e., vinyl), allyl, propenyl, butenyl, crotyl, pentenyl, hexenyl, heptenyl, octenyl, nonenyl, decenyl, dodecenyl, cyclopentenyl, cyclohexenyl, 2-isopentenyl, allenyl, butadienyl, pentadienyl, 3-(1,4-pentadienyl), and hexadienyl.

An alkenyl group can be unsubstituted or optionally substituted. When optionally substituted, one or more hydrogen atoms of the alkenyl group (e.g., from 1 to 4, from 1 to 2, or 1) may be replaced with a moiety independently selected from fluoro, hydroxy, alkoxy, amino, alkylamino, acylamino, thio, and alkylthio, with the proviso that no hydrogen atom substituent on the carbon-carbon double bond is replaced by a hydroxy, amino, or thio group. In some aspects, the alkenyl group is unsubstituted or not optionally substituted.

The term "alkyl" as used herein includes an aliphatic hydrocarbon chain that may be straight chain or branched. The chain may contain an indicated number of carbon atoms: For example, $C_1$-$C_{12}$ indicates that the group may have from 1 to 12 (inclusive) carbon atoms in it. If not otherwise indicated, an alkyl group contains from 1 to about 20 carbon atoms. In some aspects, alkyl groups have 1 to about 12 carbon atoms in the chain. In some aspects, alkyl groups ("lower alkyl") have 1 to about 6 carbon atoms in the chain. Examples may include, but are not limited to, methyl, ethyl, propyl, isopropyl (iPr), 1-butyl, 2-butyl, isobutyl (iBu), tert-butyl, pentyl, 2-methylbutyl, 1,1-dimethylpropyl, hexyl, heptyl, octyl, nonyl, decyl, or dodecyl.

An alkyl group can be unsubstituted or optionally substituted. When optionally substituted, one or more hydrogen atoms of the alkyl group (e.g., from 1 to 4, from 1 to 2, or 1) may be replaced with a moiety independently selected from fluoro, hydroxy, alkoxy, amino, alkylamino, acylamino, thio, and alkylthio. In some aspects, the alkyl group is unsubstituted or not optionally substituted.

The term "alkoxy" as used herein includes a straight or branched chain saturated or unsaturated hydrocarbon containing at least one oxygen atom in an ether group (e.g., EtO—). The chain may contain an indicated number of carbon atoms. For example, "$C_1$-$C_{12}$ alkoxy" indicates that the group may have from 1 to 12 (inclusive) carbon atoms and at least one oxygen atom. Examples of a $C_1$-$C_{12}$ alkoxy group include, but are not limited to, methoxy, ethoxy, isopropoxy, butoxy, n-pentoxy, isopentoxy, neopentoxy, and hexoxy.

An alkoxy group can be unsubstituted or optionally substituted. When optionally substituted, one or more hydrogen atoms of the alkoxy group (e.g., from 1 to 4, from 1 to 2, or 1) may be replaced with a moiety independently selected from fluoro, hydroxy, alkoxy, amino, alkylamino, acylamino, thio, and alkylthio, with the proviso that no hydrogen atom alpha to the ether oxygen is replaced by a hydroxy, amino, or thio group. In some aspects, the alkoxy group is unsubstituted or not optionally substituted.

The term "alkynyl" as used herein includes a straight, branched, or cyclic hydrocarbon containing at least one carbon-carbon triple bond. Examples may include, but are not limited to, ethynyl, propargyl, propynyl, butynyl, pentynyl, hexynyl, heptynyl, octynyl, nonynyl, decynyl, or decynyl.

An alkynyl group can be unsubstituted or optionally substituted. When optionally substituted, one or more hydrogen atoms of the alkynyl group (e.g., from 1 to 4, from 1 to 2, or 1) may be replaced with a moiety independently selected from fluoro, hydroxy, alkoxy, amino, alkylamino, acylamino, thio, and alkylthio, with the proviso that no sp-hybridized hydrogen atom substituent is replaced by a hydroxy, amino, or thio group. In some aspects, the alkynyl group is unsubstituted or not optionally substituted.

The term "aroyl" as used herein includes an aryl-CO—group wherein aryl is as defined herein. Examples include, but are not limited to, benzoyl, naphth-1-oyl and naphth-2-oyl.

The term "aryl" as used herein includes cyclic aromatic carbon ring systems containing from 6 to 18 carbons. Examples of an aryl group include, but are not limited to, phenyl, naphthyl, anthracenyl, tetracenyl, biphenyl and phenanthrenyl.

An aryl group can be unsubstituted or optionally substituted. When optionally substituted, one or more hydrogen atoms of the aryl group (e.g., from 1 to 5, from 1 to 2, or 1) may be replaced with a moiety independently selected from alkyl, cyano, acyl, halo, hydroxy, alkoxy, amino, alkylamino, acylamino, thio, and alkylthio. In some aspects, the alkoxy group is unsubstituted or not optionally substituted.

The term "arylalkyl" or "aralkyl" as used herein includes an alkyl group as defined herein where at least one hydrogen substituent has been replaced with an aryl group as defined herein. Examples include, but are not limited to, benzyl, 1-phenylethyl, 4-methylbenzyl, and 1,1,-dimethyl-1-phenyl-methyl.

A arylalkyl or aralkyl group can be unsubstituted or optionally substituted as per its component groups. For example, but without limitation, the aryl group of an arylalkyl group can be substituted, such as in 4-methylbenzyl, 2,4,6-trimethylbenzyl, 4-tert-butylbenzyl, 4-isopropylbenzyl, and the like. In some aspects, the group is unsubstituted or not optionally substituted, especially if including a defined substituent, such as a hydroxyalkyl or alkylaminoalkoxy group.

The term "comprising" or "comprises" as used herein is used non-exclusionarily. For example, a composition comprising A must include A, but could also include other components (e.g., A and B; A, B, and C; A, B, D, and E; and the like). A composition or method comprising certain claim elements presents an aspect that consists of those claim elements and an aspect that consists essentially of those claim elements. For example, the description of a method comprising the step A is intended to present (and provide support for) a method consisting of the step A and a method consisting essentially of the step A.

The term "cycloalkyl" as used herein includes a cyclic hydrocarbon group that may contain an indicated number of carbon atoms: For example, $C_3$-$C_{12}$ indicates that the group may have from 3 to 12 (inclusive) carbon atoms in it. If not otherwise indicated, a cycloalkyl group includes about 3 to about 20 carbon atoms. In some aspects, cyclo alkyl groups have 3 to about 12 carbon atoms in the group. In some aspects, cycloalkyl groups have 3 to about 7 carbon atoms in the group. Examples may include, but are not limited to, cyclopropyl, cyclobutyl, cyclopentyl, cyclohexyl, 4,4-dimethylcyclohexyl, and cycloheptyl.

A cycloalkyl group can be unsubstituted or optionally substituted. When optionally substituted, one or more hydrogen atoms of the cycloalkyl group (e.g., from 1 to 4, from 1 to 2, or 1) may be replaced with a moiety independently selected from fluoro, hydroxy, alkoxy, amino, alkylamino, acylamino, thio, and alkylthio. In some aspects, a substituted cycloalkyl group can incorporate an exo- or endocyclic alkene (e.g., cyclohex-2-en-1-yl). In some aspects, a cycloalkyl group is unsubstituted or not optionally substituted.

As used herein, "cycloalkylalkyl" includes an alkyl group wherein the alkyl group includes one or more cycloalkyl substituents (typically one). Examples include, but are not limited to, cyclohexylmethyl, cyclopentylmethyl, and cyclopropylmethyl.

The terms "disorder," "disease," and "condition" are used herein interchangeably for a condition in a subject. A disorder is a disturbance or derangement that affects the normal function of the body of a subject. A disease is a pathological condition of an organ, a body part, or a system resulting from various causes, such as infection, genetic defect, or environmental stress that is characterized by an identifiable group of symptoms. A disorder or disease can refer to a biofilm-related disorder or disorder caused by a planktonic bacterial phenotype that is characterized by a disease-related growth of bacteria.

The term "effective amount" or "effective dose" as used herein includes an amount sufficient to achieve the desired result and accordingly will depend on the ingredient and its desired result. Nonetheless, once the desired effect is identified, determining the effective amount is within the skill of a person skilled in the art.

As used herein, "fluoroalkyl" includes an alkyl group wherein the alkyl group includes one or more fluoro-substituents. Examples include, but are not limited to, trifluoromethyl.

As used herein, "geminal" substitution includes two or more substituents that are directly attached to the same atom. An example is 3,3-dimethyl substitution on a cyclohexyl or spirocyclohexyl ring.

As used herein, "halo" or "halogen" includes fluoro, chloro, bromo, or iodo.

The term "heteroaryl" includes mono and bicyclic aromatic groups of about 4 to about 14 ring atoms (e.g., 4 to 10 or 5 to 10 atoms) containing at least one heteroatom. Heteroatom as used in the term heteroaryl refers to oxygen, sulfur and nitrogen. A nitrogen atom of a heteroaryl is optionally oxidized to the corresponding N-oxide. Examples include, but are not limited to, pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl.

A heteroaryl group can be unsubstituted or optionally substituted. When optionally substituted, one or more hydrogen atoms of the heteroaryl group (e.g., from 1 to 5, from 1 to 2, or 1) may be replaced with a moiety independently selected from alkyl, cyano, acyl, halo, hydroxy, alkoxy, amino, alkylamino, acylamino, thio, and alkylthio. In some aspects, the heteroaryl group is unsubstituted or not optionally substituted.

In one embodiment, a heteroaryl group includes mono and bicyclic aromatic groups of about 4 to about 14 ring atoms (e.g., 4 to 10 or 5 to 10 atoms) containing at least one heteroatom, but no such groups with a six-membered ring bonded to the site to which the heteroaryl group is a substituent (i.e., a "non-six-membered heteroaryl" or "n6m heteroaryl"). For example, for a group A with a non-six-membered heteroaryl substituent, A could be bonded to an indolyl moiety at the indole nitrogen, the 2-position, or the 3-position, but not at the positions on the indolyl's phenyl ring (i.e., the six-membered ring).

The term "heteroaroyl" as used herein includes a heteroaryl-C(O)— group wherein heteroaryl is as defined herein. Heteroaroyl groups include, but are not limited to, thiophenoyl, nicotinoyl, pyrrol-2-ylcarbonyl, and pyridinoyl.

The term "heterocycloyl" as used herein includes a heterocyclyl-C(O)— group wherein heterocyclyl is as defined herein. Examples include, but are not limited to, N-methyl prolinoyl and tetrahydrofuranoyl.

As used herein, "heterocyclyl" includes a non-aromatic saturated monocyclic or multicyclic ring system of about 3 to about 10 ring atoms (e.g., 5 to about 10 ring atoms, or 3 to about 6 ring atoms), in which one or more of the atoms in the ring system is an element or elements other than carbon, e.g., nitrogen, oxygen or sulfur. A heterocyclyl group optionally comprises at least one $sp^2$-hybridized atom (e.g., a ring incorporating an carbonyl, endocyclic olefin, or exocyclic olefin). In some embodiments, a nitrogen or sulfur atom of the heterocyclyl is optionally oxidized to the corresponding N-oxide, S-oxide or S,S-dioxide. Examples of monocyclic heterocyclyl rings include, but are not limited to, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, and tetrahydrothiopyranyl.

A heterocycyl group can be unsubstituted or optionally substituted. When optionally substituted, one or more hydrogen atoms of the group (e.g., from 1 to 4, from 1 to 2, or 1) may be replaced with a moiety independently selected from fluoro, hydroxy, alkoxy, amino, alkylamino, acylamino, thio, and alkylthio. In some aspects, a substituted heterocycyl group can incorporate an exo- or endocyclic alkene (e.g., cyclohex-2-en-1-yl). In some aspects, the heterocycyl group is unsubstituted or not optionally substituted.

The term "hydrophobic moiety" or "hydrophobic group" as used herein includes a moiety or a functional group that repels water. Examples may include, but are not limited to, a non-polar alkyl moiety, such as an unsubstituted alkyl group having more than five carbons; a phenyl group; and an anthracenyl group.

As used herein, the terms "hydrophilic moiety" or "hydrophilic group" includes a moiety or a functional group that has a strong affinity to water. Examples may include, but are not limited to, a charged moiety, such as a cationic moiety or an anionic moiety, or a polar uncharged moiety, such as an alkoxy group or an amine group.

As used herein, the term "hydroxyalkyl" includes an alkyl group where at least one hydrogen substituent has been replaced with an alcohol (—OH) group. In certain aspects, the hydroxyalkyl group has one alcohol group. In certain aspects, the hydroxyalkyl group has one or two alcohol groups, each on a different carbon atom. In certain aspects, the hydroxyalkyl group has 1, 2, 3, 4, 5, or 6 alcohol groups. Examples may include, but are not limited to, hydroxymethyl, 2-hydroxyethyl, and 1-hydroxyethyl.

When any two substituent groups or any two instances of the same substituent group are "independently selected" from a list of alternatives, the groups may be the same or different. For example, if $R^a$ and $R^b$ are independently selected from alkyl, fluoro, amino, and hydroxyalkyl, then a molecule with two $R^a$ groups and two $R^b$ groups could have all groups be an alkyl group (e.g., four different alkyl groups). Alternatively, the first $R^a$ could be alkyl, the second $R^a$ could be fluoro, the first $R^b$ could be hydroxyalkyl, and the second $R^b$ could be amino (or any other substituents taken from the group). Alternatively, both $R^a$ and the first $R^b$ could be fluoro, while the second $R^b$ could be alkyl (i.e., some pairs of substituent groups may be the same, while other pairs may be different).

As used herein, "polyamine" includes a compound that has at least two amine groups, which may be the same or different. The amine group may be a primary amine, a secondary amine, a tertiary amine, or quaternary ammonium salt. Examples may include, but are not limited to, 1,3-diaminopropane, 1,4-diaminobutane, hexamethylenediamine, dodecan-1,12-diamine, spermine, spermidine, norspermine, and norspermidine.

As used herein, "or" should in general be construed non-exclusively. For example, an embodiment of "a composition comprising A or B" would typically present an aspect with a composition comprising both A and B, and an embodiment of "a method to disperse or kill biofilms" could disperse, kill, or a combination of both. "Or" should, however, be construed to exclude those aspects presented that cannot be combined without contradiction (e.g., a composition pH that is between 9 and 10 or between 7 and 8).

As used herein, "spirocycloalkyl" includes a cycloalkyl in which geminal substituents on a carbon atom are replaced to join in forming a 1,1-substituted ring. For example, but without limitation, for a —C($R^1$)($R^2$)— group that was part of a longer carbon chain, if $R^1$ and $R^2$ joined to form a cyclopropyl ring incorporating the carbon to which $R^1$ and $R^2$ were bonded, this would be a spirocycloalkyl group (i.e., spirocyclopropyl).

As used herein, the term "salt" refers to acid or base salts of a compound, although for a polyamine compound, the salt is generally an acid salt of the polyamine. Illustrative examples of pharmaceutically acceptable acid salts are mineral acids (e.g., hydrochloric acid, hydrobromic acid, phosphoric acid, and the like) salts, organic carboxylic acid (e.g., acetic acid, propionic acid, glutamic acid, citric acid, and the like) salts, and organic sulfonic acid (methanesulfonic acid) salts. In some aspects, a salt may be a quaternary ammonium salts produced by reaction with an alkylating agent (e.g., methyl iodide, ethyl iodide, and the like). Additional information on suitable pharmaceutically acceptable salts can be found in Remington's, Pharmaceutical Sciences (current edition), Mack Publishing Co., Easton, Pa., which is incorporated herein by reference.

As used herein, a reference to a composition of formula A, B, C, or a salt thereof may indicate A, a salt of A, B, a salt of B, C, or a salt of C.

As used herein, "spiroheterocyclyl" includes a heterocloalkyl in which geminal substituents on a carbon atom are replaced to join in forming a 1,1-substituted ring. For example, but without limitation, for a —C($R^1$)($R^2$)— group that was part of a longer carbon chain, if $R^1$ and $R^2$ joined to form a pyrrolidine ring incorporating the carbon to which $R^1$ and $R^2$ were bonded, this would be a spiroheterocyclyl group.

As used herein, the term "treat," "treating," or "treatment" includes administering or applying a composition (e.g., a composition described herein) in an amount, manner (e.g., schedule of administration), and mode (e.g., route of administration) that is effective to improve a disorder or a symptom thereof, or to prevent, to retard, or to slow the progression of a disorder or a symptom thereof. Such improvements can include, but are not limited to, alleviation or amelioration of one or more symptoms or conditions, diminishment of the extent of a disease, stabilizing (i.e., not worsening) the state of disease, prevention of a disease's transmission or spread, delaying or slowing of disease progression, amelioration or palliation of the disease state, diminishment of the reoccurrence of disease, and remission, whether partial or total and whether detectable or undetectable.

This can be evidenced by, e.g., an improvement in a parameter associated with a biofilm or with a biofilm-related disorder or an indication or symptom thereof, a biofilm-related industrial, agricultural, environmental, etc. condition, e.g., to a statistically significant degree or to a degree detectable to one skilled in the art. For example, "treating" a planktonic bacteria with the polyamine composition may provide a decrease in the rate or extent of biofilm formation from the planktonic bacteria as compared to a similar system without the polyamine composition. An effective amount, manner, or mode can vary depending on the surface, application, or subject and may be tailored to the surface, application, or subject. By eradicating a biofilm or preventing or slowing progression of a biofilm or of a biofilm-related disorder or an indication or symptom thereof, or a biofilm-related industrial, agricultural, environmental, etc. condition, a treatment can prevent or slow deterioration or corrosion resulting from a biofilm or from a biofilm-related disorder or an indication or symptom thereof on an affected surface or in an affected or diagnosed subject.

"Treating" and "treatment" as used herein also include prophylactic treatment. In certain embodiments, treatment methods comprise administering to a subject a therapeutically effective amount of a composition of the invention. The administering step may consist of a single administration or may comprise a series of administrations. The length of the treatment period depends on a variety of factors, such as the severity of the condition, the age of the patient, the concentration of active agent in the composition, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some aspects, chronic administration may be required. For example, the compositions are administered to the subject in an amount, and for a duration, sufficient to treat the patient.

In the Summary of the Invention above, Detailed Description, and the claims below, reference is made to particular features and aspects of the invention, including method steps. The disclosure of the invention in this specification includes all possible combinations of such particular features within the embodiments of the invention disclosed, at least to the extent that such combinations are non-contradictory. For example, if the Detailed Description presents aspects A, B, and C of an embodiment, it is understood that this also discloses particular embodiments including both aspects A and B, both aspects B and C, and both aspects A and C, as well as an embodiment with aspects A, B, and C.

Polyamine Compounds

Aliphatic polyamines, for example, spermine, spermidine, norspermine, norspermidine, hexamethylenediamine, 1,12-diaminododecane, 1,3-diaminopropane, etc., have been shown to have some activity against a variety of bacterial strains when used alone. In particular, it has been shown that norspermine and norspermidine may be effective in dispersing various biofilm strains. However, it does not appear that these polyamines have sufficient bactericidal activity.

It has been surprisingly discovered that by attaching one or more polyamine chains to a lipophilic or hydrophobic moiety, examples of which may include cyclic or aromatic backbone molecules, results in novel compounds that are capable of dispersing biofilms and that also have substantial antimicrobial activity against a variety of strains of bacteria (e.g., by killing the bacteria).

Referring now to FIG. 1, there is shown a simplified schematic of an exemplary polyamine compound of the present invention, generally indicated at 10. The polyamine compound 10 may be generally characterized as including a lipophilic or hydrophobic moiety 20, and one or more cationic residues 30. In some embodiments, the polyamine compound 10 may include one or more cationic residues 30 comprising primary amines 40 and one or more secondary amines 50. In some embodiments, the polyamine compound 10 may include one or more cationic residues 30 having a tertiary or quaternary amine (not shown).

As depicted in FIG. 1, exemplary polyamine compounds 10 of the present invention may be amphipathic, e.g. the cationic residues 30 may be generally disposed along one face of the molecule, while the lipophilic or hydrophobic moiety 20 is generally disposed along the opposite face of the molecule.

In certain embodiments, the present invention provides polyamine compounds and compositions and methods comprising such compounds. In certain embodiments, the polyamine compounds comprise one or more polyamine side chains (e.g., 1, 2, 3, 4, 5, 6, 7, 8, . . . n polyamine moieties/side chains) that may be the same or different. In certain embodiments, the amino groups of the one or more polyamine side chains may be ionizable. In certain embodiments, the amino groups may be positively charged. In some embodiments, the polyamine side chains are branched. In some embodiments, the polyamine chains are linear.

FIGS. 2A-2H show exemplary backbone molecules, which may be used to prepare certain novel polyamine compounds. It will be appreciated by those skilled in the art that alternative backbone molecules may be used to produce polyamine compounds according to certain aspects of the present invention. Without being bound by theory, it is believed that the lipophilicity or hydrophobicity of a backbone molecule of novel polyamine compounds may contribute to the antimicrobial activity or biofilm dispersing activity of these novel compounds.

Figure 3:
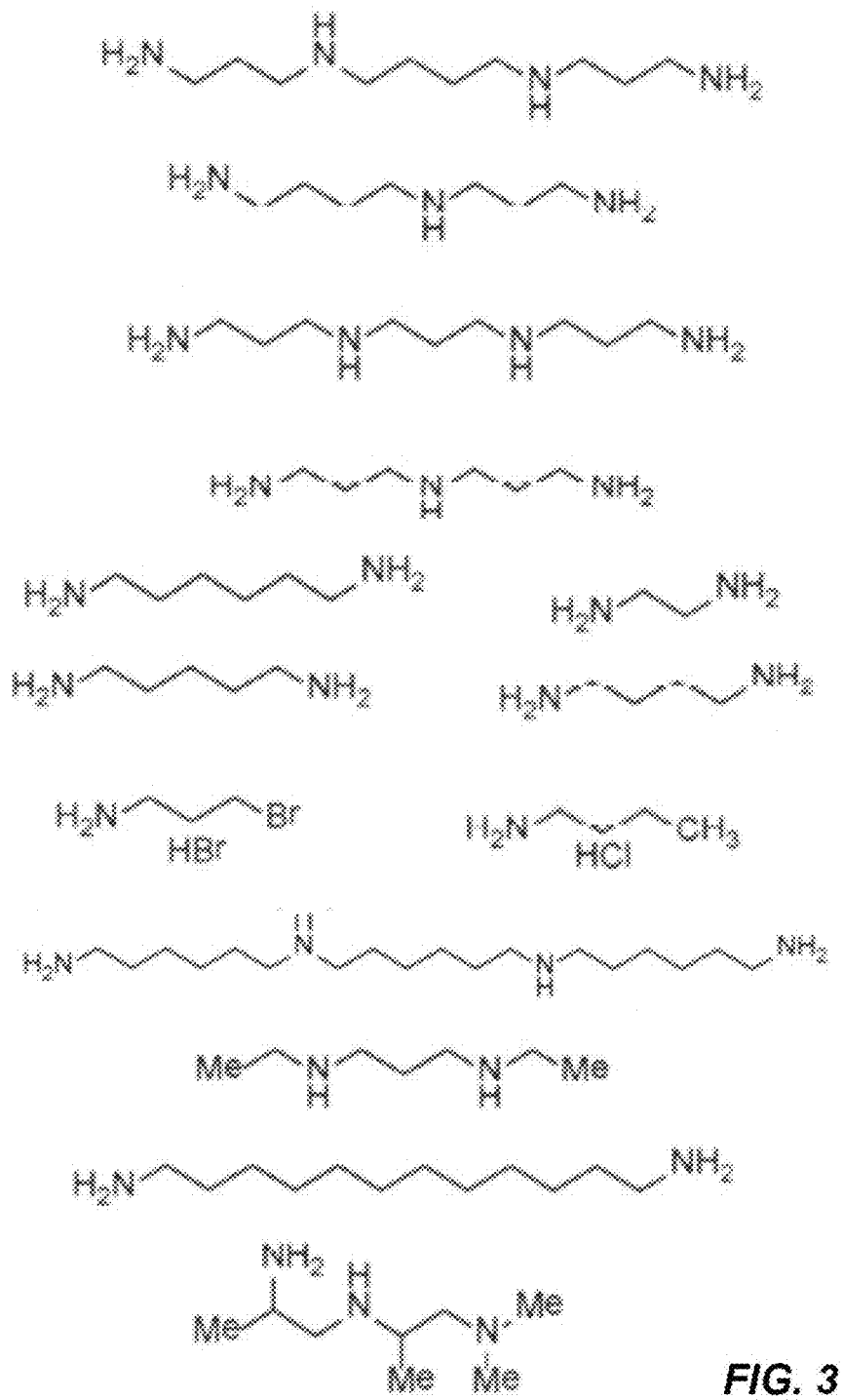
FIG. 3 shows exemplary polyamine chains that may be used to prepare certain specific embodiments of polyamine compounds as set forth herein.

FIG. 3 shows exemplary polyamine chains, which may be used to prepare certain novel polyamine compounds according to certain aspects of the present invention. It will be appreciated by those skilled in the art that polyamine chains are intended to only be representative. Without being bound by theory, it is believed that increasing the number of primary or secondary amines of polyamine compounds of the present invention may increase the antimicrobial activity or biofilm dispersing activity of these novel compounds.

Figure 4A:
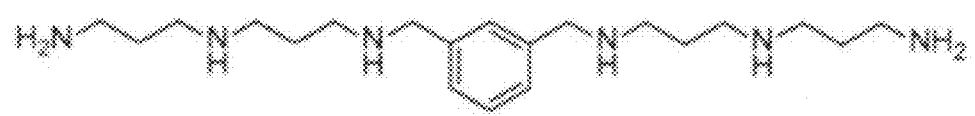
FIG. 4A through FIG. 4P show exemplary polyamine compounds according to aspects of the present invention.
Figure 4B:
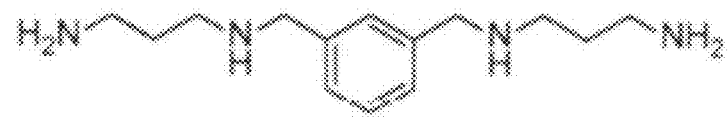
Figure 4C:
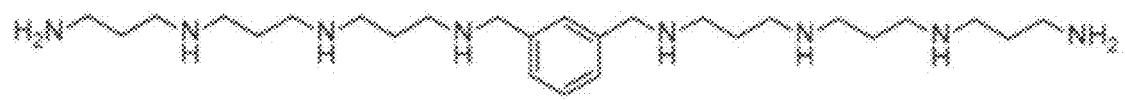
Figure 4D:
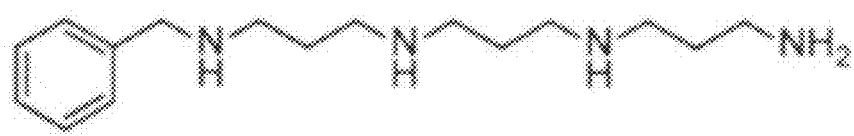
Figure 4E:
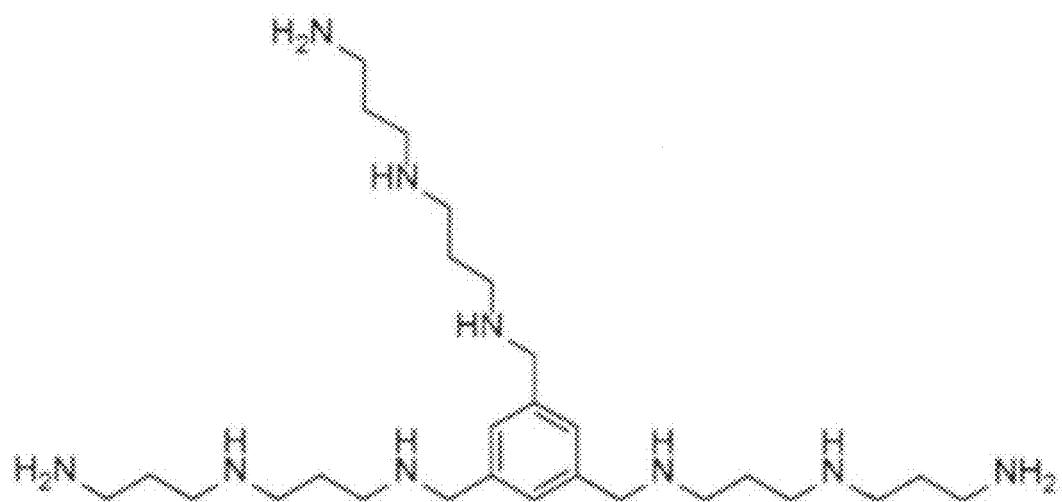
Figure 4F:
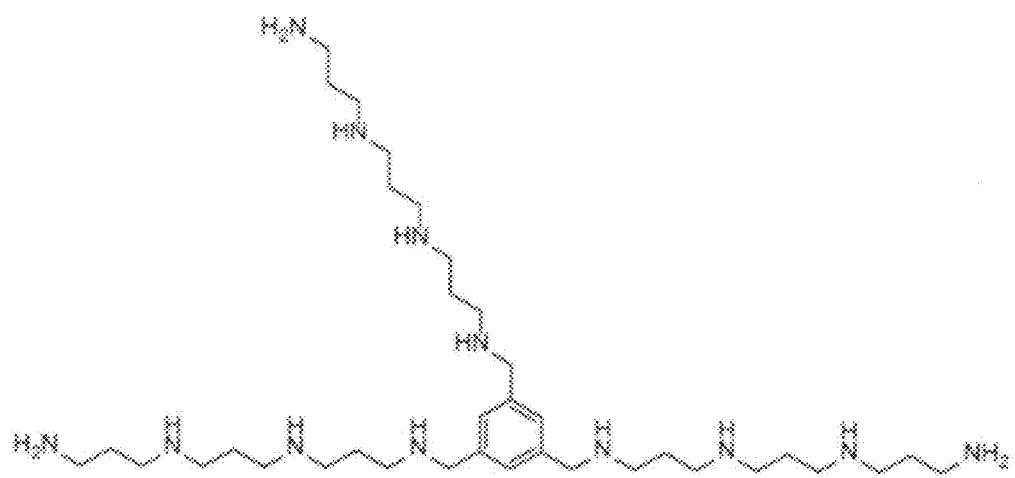
Figure 4G:
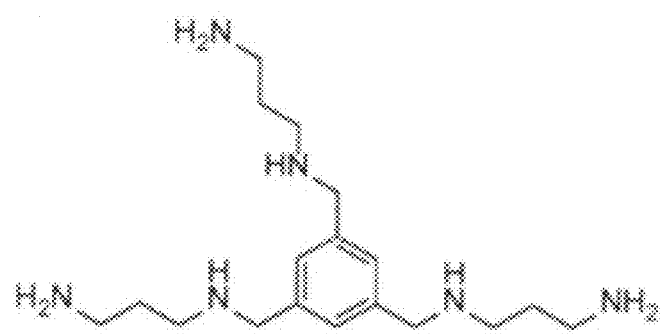
Figure 4H:
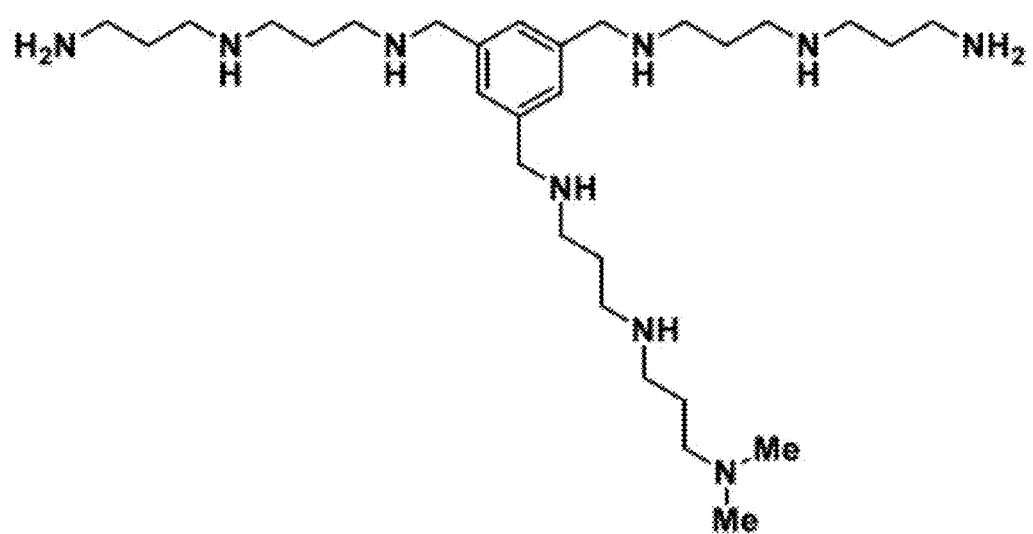
Figure 4I:
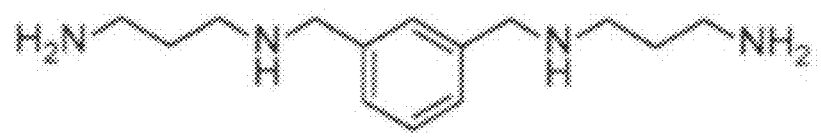
Figure 4J:
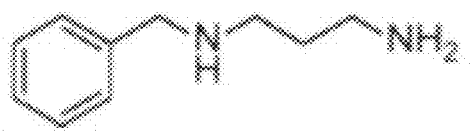
Figure 4K:
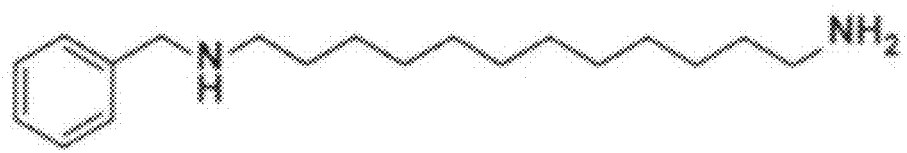
Figure 4L:
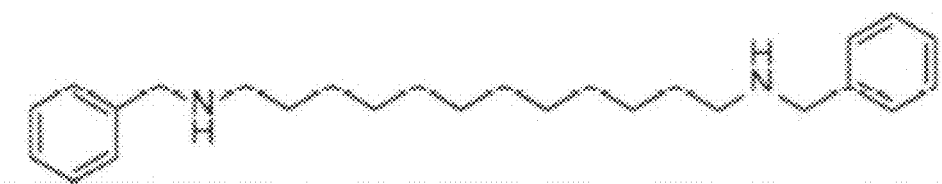
Figure 4M:
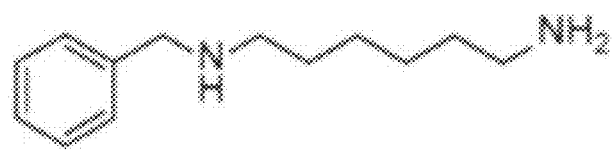
Figure 4N:
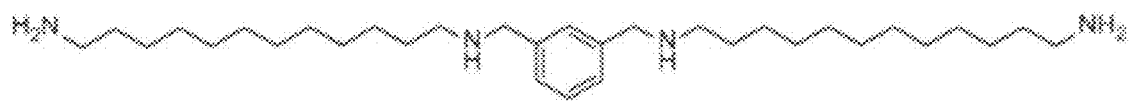
Figure 4O:
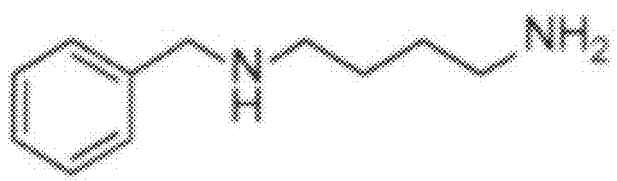
Figure 4P:
Figure 5A:
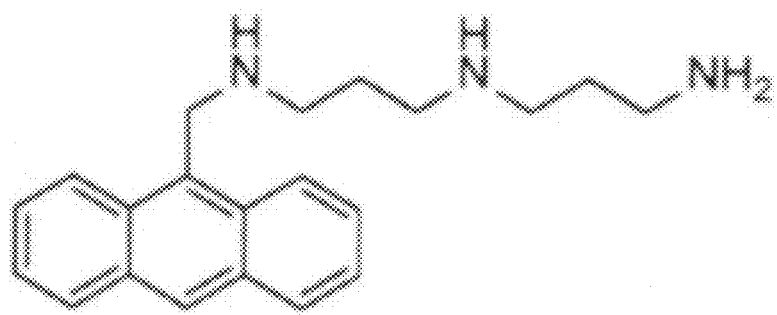
FIG. 5A through FIG. 5B show exemplary polyamine compounds according to aspects of the present invention.
Figure 5B:
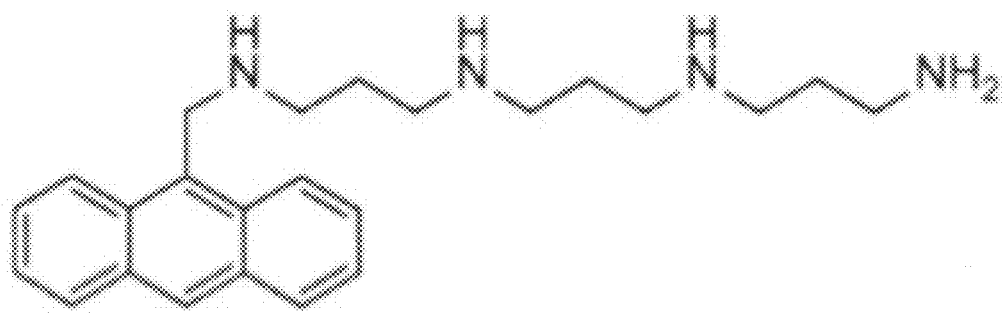
Figure 6A:
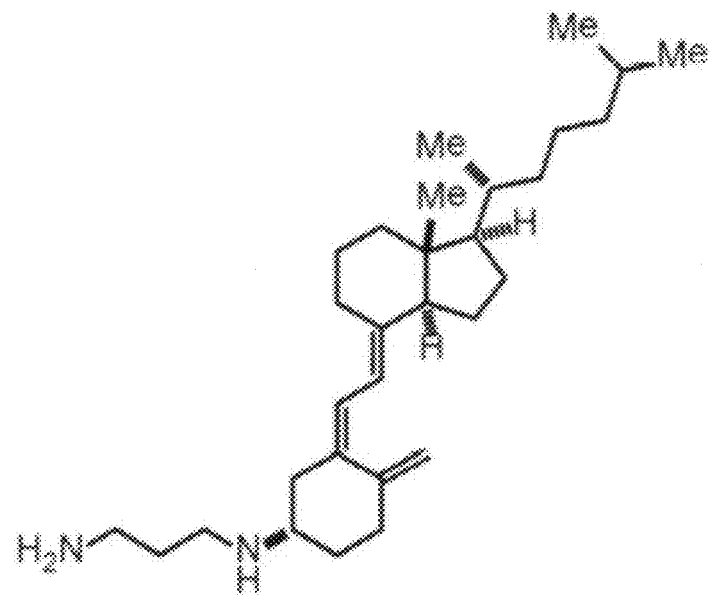
FIG. 6A through FIG. 6E show exemplary polyamine compounds according to aspects of the present invention.
Figure 6B:
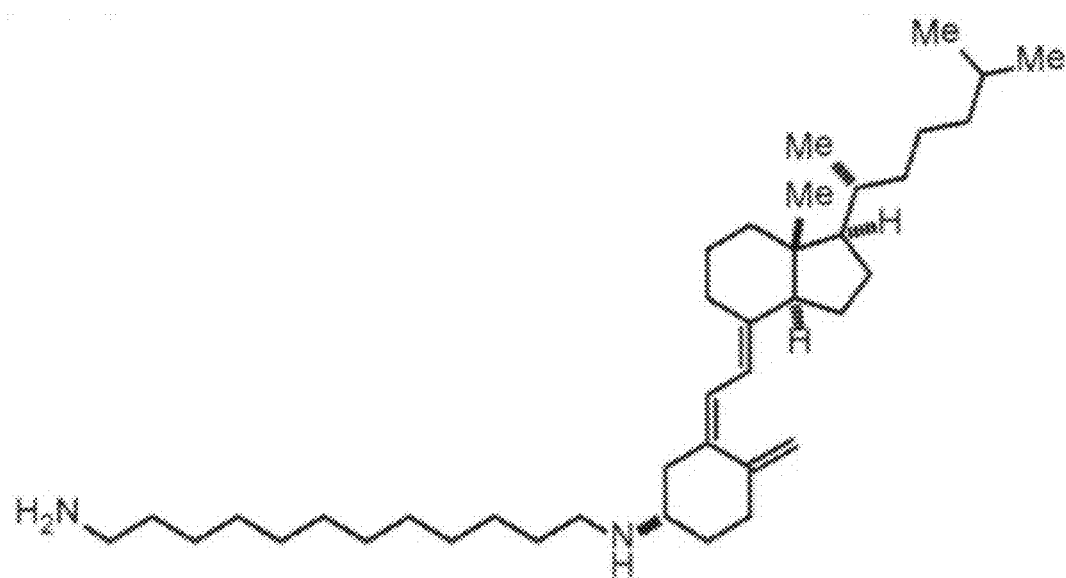
Figure 6C:
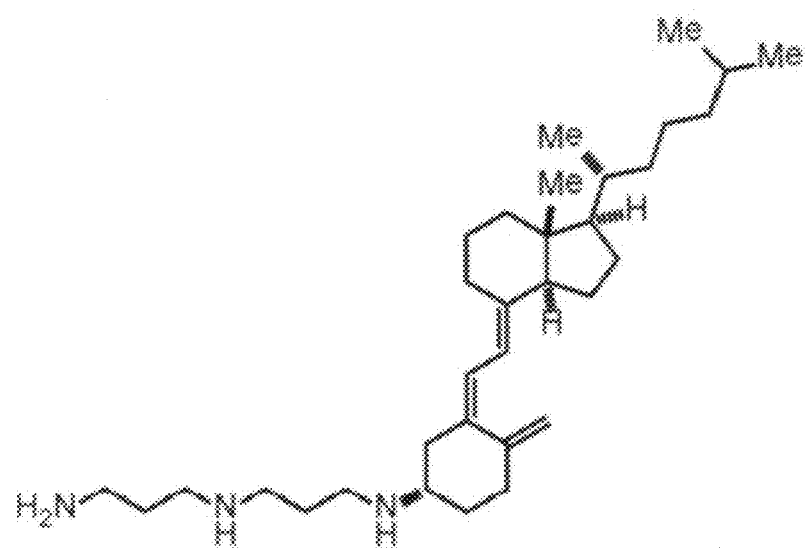
Figure 6D:
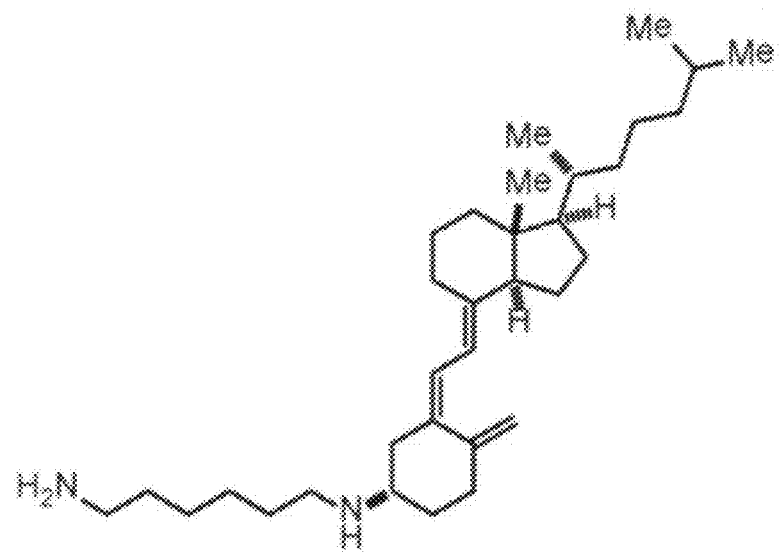
Figure 6E:
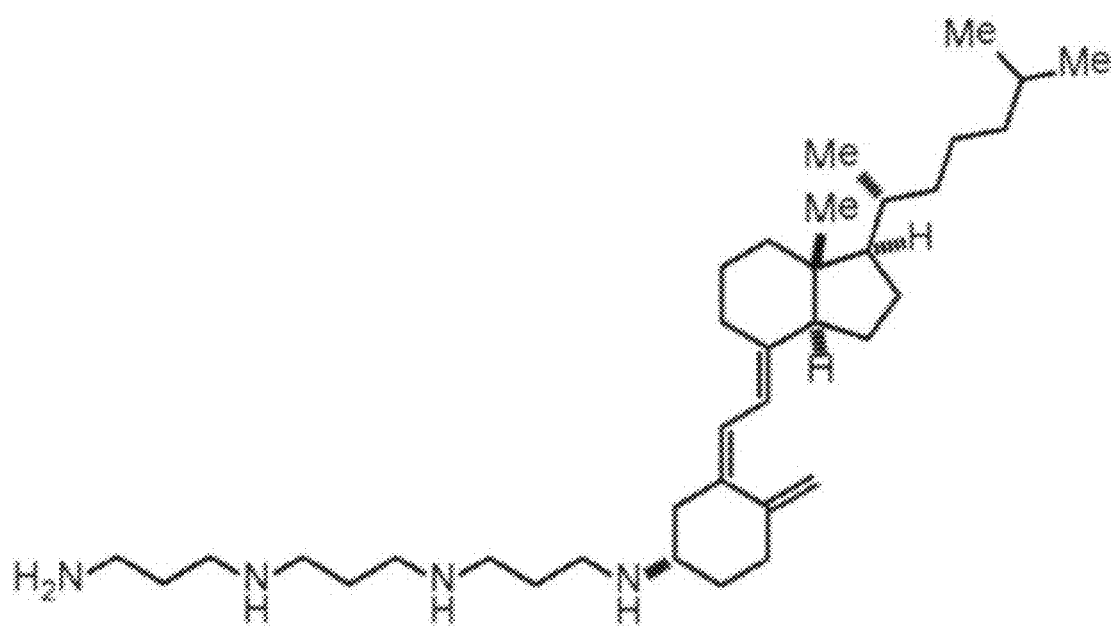

FIGS. 4A-4P show exemplary polyamine compounds comprising a benzene backbones. FIGS. 5A and 5B show exemplary polyamine compounds comprising an anthracene backbone. FIGS. 6A-6E show exemplary polyamine compounds comprising a Vitamin D backbone.

FIG. 7 through FIG. 10 show exemplary chemical synthesis strategies for preparing a variety of polyamine compounds according to certain aspects of the present invention.

In certain embodiments, the one or more polyamine moieties may have at least three amino groups separated by three atoms either in a straight chain or cyclic molecule. In some particular embodiments, the one or more polyamine moiety or moieties may comprise norspermidine (also known as N-(3-aminopropyl)propane-1,3-diamine), norspermine (N'-[3-(3-aminopropylamino)propyl]propane-1,3-diamine), or a combination thereof.

Exemplary compositions of the present invention may include a compound comprising a single polyamine chain or multiple polyamine chains attached to a base backbone compound to improve their antimicrobial activities or improve certain other features or aspects not present when polyamines are used alone such that the compositions may be designed for use in a specific application. Furthermore, it has been surprisingly discovered that by increasing the number of primary and secondary amines within a single molecule an increase in the antimicrobial activity of a compound may result. Furthermore, exemplary novel polyamines may be used in combination (e.g. formulated as a composition) with already approved, commercial antimicrobial products (e.g. chlorhexidine gluconate) to improve the dispersing or killing ability of such compositions.

In some aspects, the invention provides a compound or composition that comprises, consists essentially of, or consists of a polyamine compound or composition used in any of the embodiments or aspects of the methods described herein.

In some aspects, the invention provides a composition for treating (e.g., dispersing or killing) biofilms, the composition comprising a polyamine compound selected from:

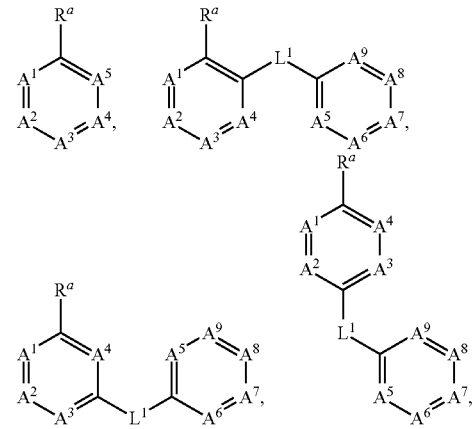

wherein:
each $R^a$ is a member independently selected from

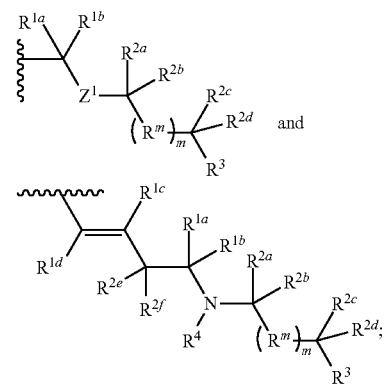

$A^1$, $A^2$, $A^3$, $A^4$, $A^5$, $A^6$, $A^7$, $A^8$, and $A^9$ are each an $A''$ member independently selected from N, $CR^a$, and $CR^5$; or, alternatively, a pair of adjacent $A''$ members join to form an additional, independently selected aryl, cycloalkyl, heterocyclyl, or heterocycloaryl ring that is fused with an $A''$ ring at the pair's $A''$ ring positions; wherein at least one $A''$ member and at most five $A''$ members are an independently selected $CR^a$;

each $R^{1a}$, $R^{1b}$, $R^{1c}$, and $R^{1d}$ is a member independently selected from hydrogen, fluoro, alkyl, and fluoroalkyl; or, alternatively, an $R^{1a}$ and an $R^{1b}$ join to form an oxo group; each $R^{2a}$, $R^{2b}$, $R^{2c}$, $R^{2d}$, $R^{2e}$, and $R^{2f}$ is a member independently selected from hydrogen, alkyl, fluoroalkyl, alkenyl, alkynyl, aryl, heteroaryl, arylalkyl, and heteroarylalkyl; alternatively, a pair of $R^2$ members from the same $R^a$ group independently selected from the group $R^{2a}$ and $R^{2b}$, $R^{2c}$ and $R^{2d}$, and $R^{2e}$ and $R^{2f}$ join to form a member independently selected from spirocycloalkyl, spiroheterocycyl, and oxo; or, alternatively, an $R^{2a}$ and an $R^{2c}$ from the same $R^a$ group join to form a ring independently selected from cycloalkyl and heterocycyl;

each $R^m$ is a member independently selected from —$CR^{2a}R^{2b}$—, —$CR^{2c}R^{2d}$—, —$C(R^{2a})$=$(R^{2b})$—, —CC—, and —$C(R^{2a})(R^{2b})$-$L^2$-$C(R^{2c})(R^{2d})$—; each m is an integer independently selected from 1 to 20;

each $L^1$ and $L^2$ is a member independently selected from a bond, —O—, —C(O)O—, —$NR^4$—, —$NR^4C(O)$—, and —$C(O)NR^4$—;

each $R^3$ is a member independently selected from —$Z^1$—$R^4$, —$Z^1$—$Y^1$—$R^4$, —$Z^1$—$Y^1$—$Y^2$—$R^4$, and —$Z^1$—$Y^1$—$Y^2$—$Y^3$—$R^4$;

each $R^4$ is a member independently selected from hydrogen, alkyl, fluoroalkyl, alkenyl, alkynyl, aryl, heteroaryl, arylalkyl, and heteroarylalkyl; or, alternatively, for a —$N(R^4)_2$ group, one of the two $R^4$ in the group is a member selected from —(CO)$OR^{6a}$—, (CO)$N(R^{6a})(R^{6b})$, and —$C(NR^{6a})N(R^{6b})(R^{6c})$; or, alternatively, for an —$N(R^4)_2$ group, the two $R^4$ groups join to form a heterocyclic ring;

each $R^5$ is a member independently selected from hydrogen, alkyl, hydroxyl, alkoxy, aminoalkoxy, alkylamino, alkylaminoalkoxy, alkenyl, alkynyl, aryl, aryloxy, arylamino, cycloalkyl, cycloalkoxy, cycloalkylalkoxy, cycloalkylamino, cycloalkylalkylamino, heterocyclyl, heterocycyloxy, heterocycylamino, halo, haloalkyl, fluoroalkyloxy, heteroaryl, heteroaryloxy, heteroarylamino, arylalkyl, arylalkyloxy, arylalkylamino, heteroarylalkyl, heteroarylalkyloxy, heteroarylalkylamino, hydroxyalkyl, aminoalkyl, and alkylaminoalkyl;

each $Y^1$, $Y^2$, and $Y^3$ is an independently selected group of Formula IA:

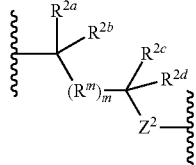

IA each $Z^1$ and $Z^2$ is a member independently selected from $NR^4$ and 0; and each $R^{6a}$, $R^{6b}$, and $R^{6c}$ is a member independently selected from hydrogen, alkyl, fluoroalkyl, alkenyl, alkynyl, aryl, heteroaryl, arylalkyl, cycloalkyl, and heteroarylalkyl; or, alternatively, two $R^{6n}$ members $R^{6a}$ and $R^{6b}$ or $R^{6a}$ and $R^{6c}$ join to form a heterocycyl ring;

wherein the polyamine compound comprises at least two primary or secondary amino groups.

In certain aspects, each $R^4$ is a member independently selected from hydrogen, alkyl, fluoroalkyl, alkenyl, alkynyl, aryl, heteroaryl, arylalkyl, and heteroarylalkyl; or, alternatively, for a —$N(R^4)_2$ group, one of the two $R^4$ in the group is a member selected from —(CO)$OR^{6a-}$, (CO)$N(R^{6a})(R^{6b})$, and —$C(NR^{6a})N(R^{6b})(R^{6c})$; and each $R^5$ is a member independently selected from hydrogen, alkyl, hydroxyl, alkoxy, alkylamino, alkenyl, alkynyl, aryl, aryloxy, arylamino, cycloalkyl, cycloalkoxy, cycloalkylamino, heterocyclyl, heterocycyloxy, heterocycylamino, halo, haloalkyl, fluoroalkyloxy, heteroaryl, heteroaryloxy, heteroarylamino, arylalkyl, arylalkyloxy, arylalkylamino, heteroarylalkyl, heteroarylalkyloxy, heteroarylalkylamino, hydroxyalkyl, aminoalkyl, and alkylaminoalkyl.

In another preferred aspect, the compounds or compositions of the embodiments and aspects described herein has the proviso that the polyamine compound is not of Formula IB:

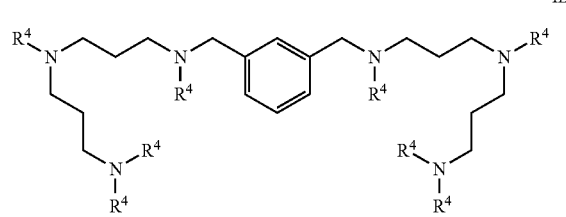

IB wherein the —$N(R^4)_2$ groups are tertiary amines.

In some aspects, the compounds or compositions of the embodiments and aspects described herein has the proviso that the polyamine compound is not:

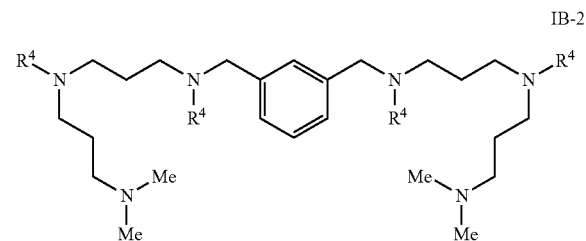

IB-2 wherein the —$R^4$ groups are hydrogen or methyl.

In a preferred aspect, the invention presents the compounds or compositions described herein with the proviso that the polyamine compound is not of Formula IB:

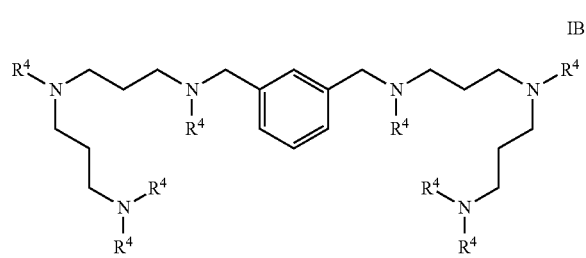

IB wherein the —$N(R^4)_2$ groups are tertiary amines; and with the proviso that the polyamine compound is not of Formula IC:

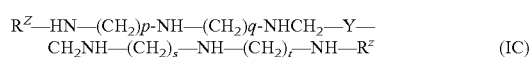

(IC)

or a salt thereof;

wherein Y is selected from anthracenyl, naphthyl, and phenyl;

wherein each $R^z$ is independently selected from hydrogen and alkyl; and wherein p, q, t, and s are each an integer independently selected from 3 and 4.

In some aspects, the composition comprises, consists essentially of, or consists of a polyamine compound of formula

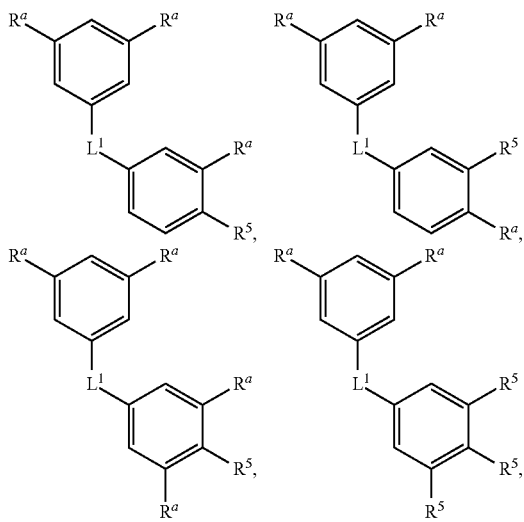

or a salt thereof;
wherein:
each $R^a$ is independently a group of Formula I:

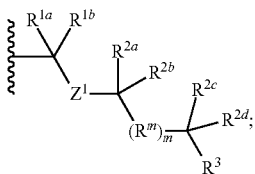

each $R^{1a}$ and $R^{1b}$ is a member independently selected from hydrogen, fluoro, alkyl, and fluoroalkyl;

each $R^{2a}$, $R^{2b}$, $R^{2c}$, and $R^{2d}$ is a member independently selected from hydrogen, alkyl, fluoroalkyl, aryl, and arylalkyl;

each $R^m$ is an independently selected $-CR^{2a}R^{2b}-$;

each m is an integer independently selected from 1 to 2;

each $L^1$ is a member independently selected from a bond and $-O-$;

each $R^3$ is an independently selected $-Z^1-Y^1-R^4$;

each $R^4$ is a member independently selected from hydrogen, alkyl, fluoroalkyl, alkenyl, and alkynyl; or, alternatively, for an $-N(R^4)_2$ group, one of the two $R^4$ in the group is a member selected from $-(CO)OR^{6a}-$, $-(CO)N(R^{6a})(R^{6b})$, and $-C(NR^{6a})N(R^{6b})(R^{6c})$; each $R^5$ is a member independently selected from hydrogen, alkyl, hydroxyl, alkoxy, halo, fluoroalkyl, fluoroalkyloxy, and hydroxyalkyl;

each $Y^1$ is an independently selected group of Formula IA:

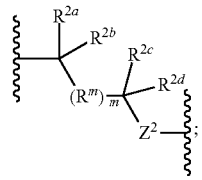

each $Z^1$ and $Z^2$ is an independently selected $NR^4$; and each $R^{6a}$, $R^{6b}$, and $R^{6c}$ is a member independently selected from hydrogen and alkyl;

wherein if $R^4$ is $-C(O)OR^{6a}$, $R^{6a}$ is alkyl; and wherein the polyamine compound comprises at least two primary or secondary amino groups.

In some aspects, each m is 1. In some aspects, at least one m is 1. In some aspects, each m is 2. In some aspects, at least one m is 2.

In some aspects, each $R^{2a}$, $R^{2b}$, $R^{2c}$, and $R^{2d}$ is a member independently selected from hydrogen, alkyl, and fluoroalkyl. In some aspects, each $R^{2a}$, $R^{2b}$, $R^{2c}$, and $R^{2d}$ is a member independently selected from hydrogen, alkyl, fluoroalkyl, and arylalkyl.

In some aspects, each $R^{1a}$ and $R^{1b}$ is a member independently selected from hydrogen and alkyl.

In some aspects, the polyamine compound is of formula

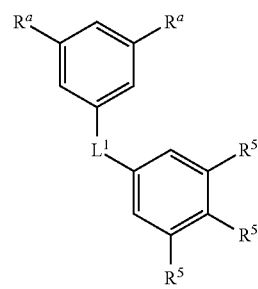

or a salt thereof.

In some aspects, $R^a$ is $-CH_2[NH(CH_2)_3]_2NH_2$. In some aspects, $R^a$ is an independently selected group of Formula VII:

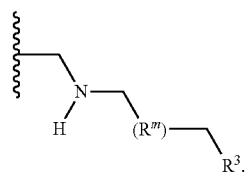

In some aspects, each m is 1.

In some aspects, $R^5$ is hydrogen.

In some aspects, each $R^4$ is a member independently selected from hydrogen and alkyl.

In some aspects, the polyamine compound is selected from

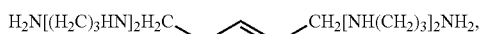

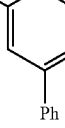

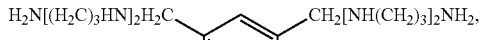

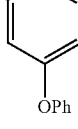

and a salt thereof.

In some aspects, $L^1$ is a bond.

In some aspects, $R^m$ is —CH$_2$—.

In some aspects, the polyamine compound is selected from

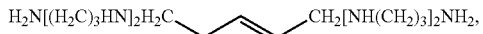

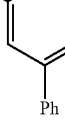

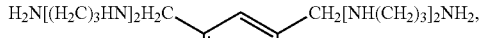

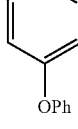

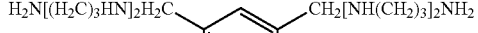

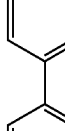

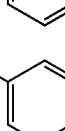

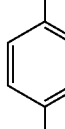

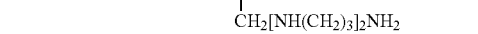

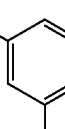

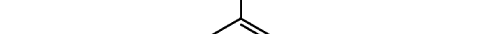

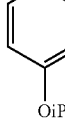

-continued

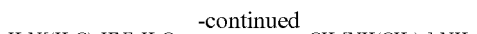

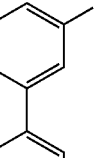

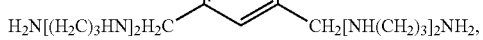

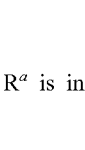

and a salt thereof.

In some aspects, each $R^a$ is independently a group of Formula II:

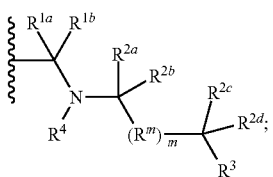

each of the A″ members is independently selected from $CR^a$ and $CR^5$; or, alternatively, a pair of adjacent A″ members join to form a cycloalkyl, aryl, heterocyclyl, or heterocycloaryl ring; wherein at least one A″ member and at most three A″ members are independently selected $CR^a$, each $R^{1a}$, $R^{1b}$, $R^{1c}$, and $R^{1d}$ is a member independently selected from hydrogen, fluoro, alkyl, and fluoroalkyl;

for each $R^a$ member, at most two $R^m$ of the $R^a$ member are selected from —C($R^{2a}$)=($R^{2b}$)—, —CC—, and —C($R^{2a}$)($R^{2b}$)-L$^2$-C($R^{2c}$)($R^{2d}$)—; and each m is an integer independently selected from 1 to 16.

In some aspects, the polyamine compound is selected from:

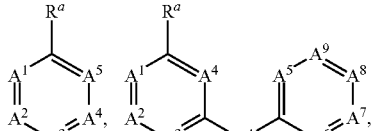

and a salt thereof;
wherein:
at least one A″ member and at most three A″ members are independently selected $CR^a$, each $R^{2a}$, $R^{2b}$, $R^{2c}$, $R^{2d}$, $R^{2e}$, and $R^{2f}$ is a member independently selected from hydrogen, alkyl, fluoroalkyl, alkenyl, alkynyl, aryl, heteroaryl, arylalkyl, and heteroarylalkyl; alternatively, a pair of $R^{2n}$ members from the $R^a$ group independently selected from the group $R^{2a}$ and $R^{2b}$, $R^{2c}$ and $R^{2d}$, and $R^{2e}$ and $R^{2f}$ join to form a ring independently selected from spirocycloalkyl and spiroheterocycyl; or, alternatively, the $R^{2a}$ and the $R^{2c}$ from the $R^a$ group join to form a ring independently selected from cycloalkyl and heterocycyl;

each m is an integer independently selected from 1 to 12;
each $R^3$ is a member independently selected from —$Z^1$—$Y^1$—$R^4$ and —$Z^1$—$Y^1$—$Y^2$—$R^4$; and
each $Z^1$ and $Z^2$ is an independently selected $NR^4$.

In some aspects, $A^1$, $A^2$, $A^3$, $A^4$, $A^5$, $A^6$, $A^7$, $A^8$, and $A^9$ are each an A″ member independently selected from $CR^a$, and $CR^5$; or, alternatively, a pair of adjacent $A''$ members join to form a cycloalkyl, aryl, heterocyclyl, or heterocycloaryl ring;

each $R^{2a}$, $R^{2b}$, $R^{2c}$, $R^{2d}$, $R^{2e}$, and $R^{2'}$ is a member independently selected from hydrogen, alkyl, fluoroalkyl, alkenyl, alkynyl, aryl, heteroaryl, arylalkyl, or heteroarylalkyl;

each m is an integer independently selected from 1 to 10;

each L and $L^2$ is a member independently selected from a bond, —O—, and —$NR^4$—; each $R^3$ is a member independently selected from —$Z^1$—$R^4$, —$Z^1$—$Y^1$—$R^4$, and —$Z^1$—$Y^1$—$Y^2$—$R^4$; and each $Z^1$ and $Z^2$ is an independently selected $NR^4$.

In some aspects, the invention provides the polyamine compound selected from:

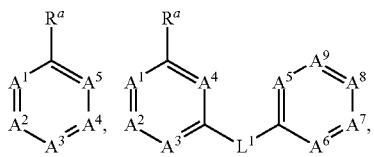

and a salt thereof;
wherein:
each $R^a$ is independently a group of Formula V:

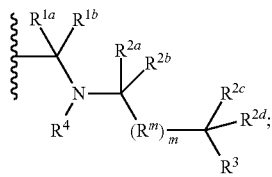

each of the $A''$ members is independently selected from $CR^a$ and $CR^5$; or, alternatively, a pair of adjacent $A''$ members join to form a cycloalkyl, aryl, heterocyclyl, or heterocycloaryl ring; wherein at least one $A''$ member and at most three $A''$ members are independently selected $CR^a$, each $R^{1a}$, $R^{1b}$, $R^{1c}$, and $R^{1d}$ is a member independently selected from hydrogen, fluoro, alkyl, and fluoroalkyl;

for each $R^a$ member, at most two $R^m$ of the $R^a$ member are selected from —$C(R^{2a})$=$(R^{2b})$—, —CC—, and —$C(R^{2a})(R^{2b})$-$L^2$-$C(R^{2c})(R^{2d})$—; and each $R^3$ is a member independently selected from —$Z^1$—$Y^1$—$R^4$ and —$Z^1$—$Y^1$—$Y^2$—$R^4$.

In some aspects, the polyamine compound comprises at least four primary or secondary amino groups. In some aspects, the polyamine compound comprises at least six primary or secondary amino groups.

In some aspects, the invention provides the polyamine compound selected from

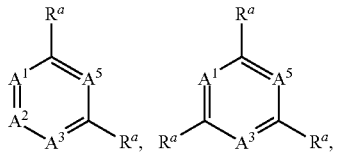

wherein each $A''$ member is an independently selected $CR^5$.

In some aspects, the invention provides the polyamine compound selected from

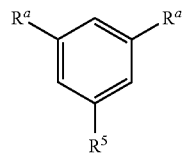

and a salt thereof, and
wherein $R^a$ is an independently selected group of Formula VII:

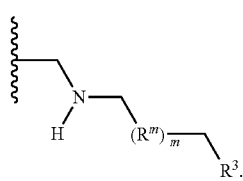

In some aspects, the invention provides the polyamine compound selected from

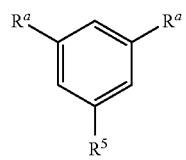

and a salt thereof, and
wherein $R^5$ is hydroxyl, alkoxy, cycloalkoxy, or arylalkyloxy.

In some aspects, $R^m$ is —$CH_2$—. In some aspects, $R^a$ is —$CH_2[NH(CH_2)_n]_pNH_2$; each n is an integer independently selected from 3 to 12; and each p is an integer independently selected from 1 to 3. In some aspects, m is 1. In some aspects, each m is 1. In some aspects, at least one m is 1. In some aspects, each m is 2. In some aspects, at least one m is 2. In some aspects, $R^5$ is selected from hydrogen, phenyl, and phenyloxy.

In some aspects, the polyamine compound is selected from

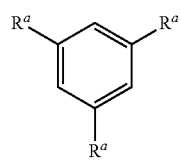

and a salt thereof.

In some aspects, the polyamine compound is selected from:

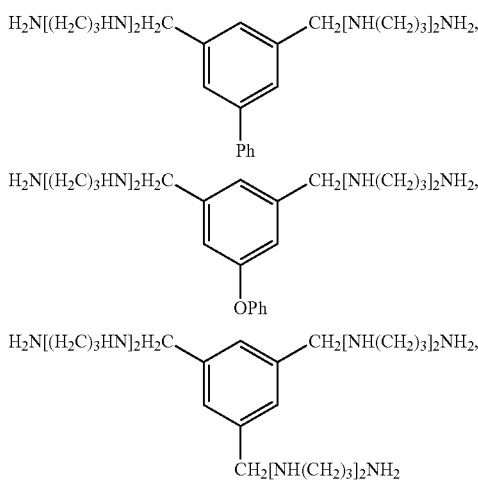

and a salt thereof.

In some aspects, the polyamine compound is selected from

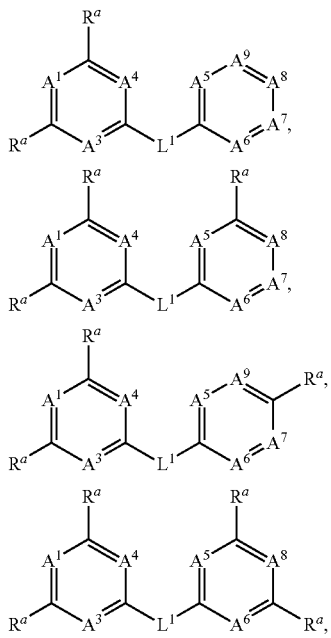

and a salt thereof;

wherein each $A^n$ member is an independently selected $CR^5$.

In some aspects, the polyamine compound is selected from

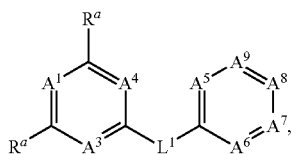

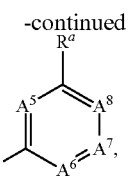

-continued and a salt thereof, wherein each $A^n$ member is an independently selected $CR^5$.

In some aspects, the polyamine compound is selected from

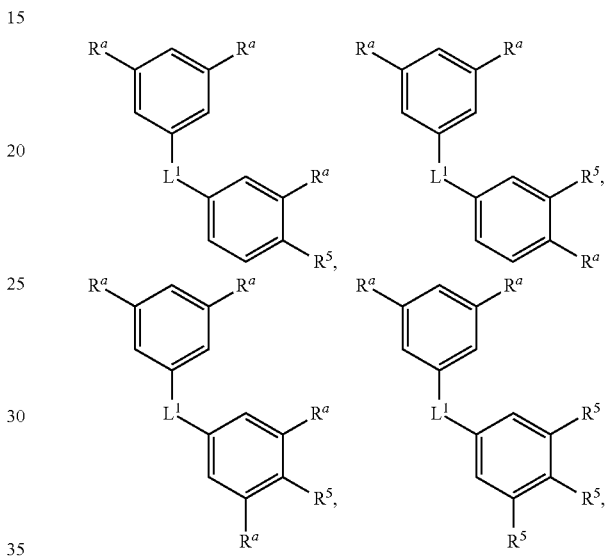

and a salt thereof.

In some aspects, $R^a$ is an independently selected group of Formula VII:

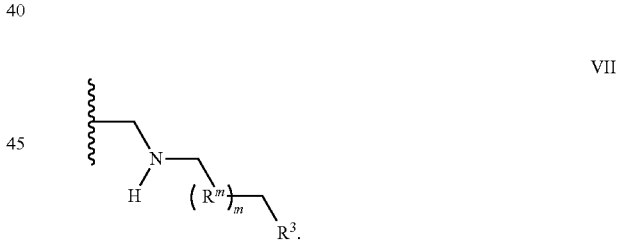

VII

In some aspects, $R^5$ is hydrogen. In some aspects, $L^1$ is selected from a bond and O. In some aspects, $R^m$ is —$CH_2$—. In some aspects, m is 1. In some aspects, each m is 1. In some aspects, at least one m is 1. In some aspects, each m is 2. In some aspects, at least one m is 2.

In some aspects, $R^a$ is —$CH_2[NH(CH_2)_n]_pNH_2$; each n is an integer independently selected from 3 to 12; and each p is an integer independently selected from 1 to 3.

In some aspects, $R^5$ is hydroxyl, alkoxy, cycloalkoxy, heterocycyloxy, aryloxy, arylalkyloxy, heteroaryloxy, or heteroarylalkyloxy. In some aspects, $R^5$ is hydroxyl, alkoxy, cycloalkoxy, heterocycyloxy, arylalkyloxy, heteroaryloxy, or heteroarylalkyloxy. In some aspects, $R^5$ is hydroxyl, alkoxy, cycloalkoxy, or arylalkyloxy. In some aspects, $R^5$ is hydroxyl, alkoxy, or cycloalkoxy. Preferably, $R^5$ is alkoxy.

In some aspects, $R^a$ is —$CH_2[NH(CH_2)_n]_pNHR^4$; each n is an integer independently selected from 3 to 12; and each p is an integer independently selected from 1 to 3. Preferably, $R^4$ is alkyl, cycloalkyl, or arylalkyl; more preferably, $R^4$ is alkyl.

In some aspects, $R^a$ is —$CH_2[NH(CH_2)_n]_pNHR^4$; each n is an integer independently selected from 3 to 12; and each p is an integer independently selected from 1 to 3. Preferably, n is 3. More preferably, $R^4$ is not hydrogen.

In some aspects, the polyamine compound is:

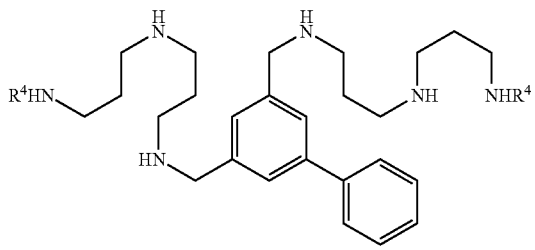

or a salt thereof. Preferably, $R^4$ is isobutyl.

In some aspects, the polyamine compound is selected from the group consisting of

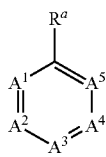

and a salt thereof;
wherein:
each $R^a$ is a member independently selected from the group consisting of

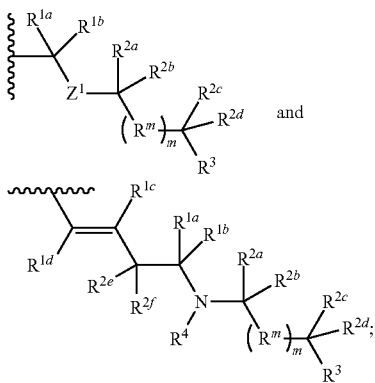

$A^1$, $A^2$, $A^3$, $A^4$ and $A^5$ are each an $A''$ member independently selected from the group consisting of N, $CR^a$, and $CR^5$; or, alternatively, a pair of adjacent $A''$ members join to form an additional, independently selected aryl, cycloalkyl, heterocyclyl, or heterocycloaryl ring; wherein at least one $A''$ member and at most three $A''$ members are each an independently selected $CR^a$;

each $R^{1a}$, $R^{1b}$, $R^{1c}$, and $R^{1d}$ is a member independently selected from the group consisting of hydrogen, fluoro, alkyl, and fluoroalkyl;

each $R^{2a}$, $R^{2b}$, $R^{2c}$, $R^{2d}$, $R^{2e}$, and $R^{2f}$ is a member independently selected from the group consisting of hydrogen, alkyl, fluoroalkyl, alkenyl, alkynyl, aryl, heteroaryl, arylalkyl, and heteroarylalkyl; alternatively, a pair of $R^2$ members from the same $R^a$ group independently selected from the group $R^{2a}$ and $R^{2b}$, $R^{2c}$ and $R^{2d}$, and $R^{2e}$ and $R^{2f}$ join to form a member independently selected from the group consisting of spirocycloalkyl, spiroheterocycyl, and oxo; or, alternatively, an $R^{2a}$ and an $R^{2c}$ from the same $R^a$ group join to form a ring that is independently selected from the group consisting of cycloalkyl and heterocycyl;

each $R^m$ is a member independently selected from the group consisting of —$CR^{2a}R^{2b}$—, —$C(R^{2a})$=$(R^{2b})$—, —CC—, and —$C(R^{2a})(R^{2b})$-L-$C(R^{2c})(R^{2d})$—;

each m is an integer independently selected from 1 to 16;

each L is a member independently selected from the group consisting of a bond, —O—, —C(O)O—, —$NR^4$—, —$NR^4C(O)$—, and —$C(O)NR^4$—;

each $R^3$ is a member independently selected from the group consisting of —$Z^1$—$R^4$, —$Z^1$—$Y^1$—$R^4$, —$Z^1$—$Y^1$—$Y^2$—$R^4$, and —$Z^1$—$Y^1$—$Y^2$—$Y^3$—$R^4$;

each $R^4$ is a member independently selected from the group consisting of hydrogen, alkyl, fluoroalkyl, alkenyl, alkynyl, aryl, cycloalkyl, heteroaryl, arylalkyl, cycloalkylalkyl, and heteroarylalkyl; or, alternatively, for an —$N(R^4)_2$ group, one of the two $R^4$ in the group is a member selected from the group consisting of —$(CO)OR^{6a}$—, —$(CO)N(R^{6a})(R^{6b})$, and —$C(NR^{6a})N(R^{6b})(R^{6c})$; or, alternatively, for an —$N(R^4)_2$ group, the two $R^4$ groups join to form a heterocyclic ring;

each $R^5$ is a member independently selected from the group consisting of hydrogen, alkyl, hydroxyl, alkoxy, aminoalkoxy, alkylamino, alkylaminoalkoxy, alkenyl, alkynyl, cycloalkyl, cycloalkoxy, cycloalkylalkoxy, cycloalkylamino, cycloalkylalkylamino, heterocyclyl, heterocycyloxy, heterocycylamino, halo, haloalkyl, fluoroalkyloxy, arylalkyl, arylalkyloxy, arylalkylamino, heteroaryl, heteroaryloxy, heteroarylalkyl, heteroarylalkyloxy, heteroarylalkylamino, hydroxyalkyl, aminoalkyl, and alkylaminoalkyl; wherein at least one $R^5$ is not hydrogen;

each $Y^1$, $Y^2$, and $Y^3$ is an independently selected group of Formula IA:

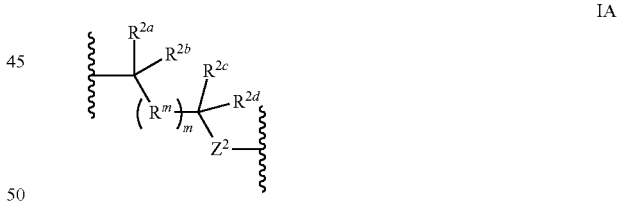

each $Z^1$ and $Z^2$ is a member independently selected from the group consisting of —$N(R^4)$— and —O—; and each $R^{6a}$, $R^{6b}$, and $R^{6c}$ is a member independently selected from the group consisting of hydrogen, alkyl, fluoroalkyl, alkenyl, alkynyl, aryl, heteroaryl, cycloalkyl, arylalkyl, heteroarylalkyl, and cycloalkylalkyl; or, alternatively, two $R^{6m}$ members $R^{6a}$ and $R^{6b}$ or $R^{6a}$ and $R^{6c}$ join to form a heterocycyl ring; wherein the polyamine compound comprises at least two primary or secondary amino groups.

In certain aspects, the $R^5$ heteroaryl group is n6m-heteroaryl. In certain aspects, the $R^5$ heteroaryloxy is n6m-heteroaryloxy.

In certain aspects, the polyamine compositions and methods have the proviso that they do not include the compounds claimed in U.S. Pat. No. 8,853,278. In certain aspects, the polyamine compositions and methods have the proviso that they do not include the compounds claimed in claim 14 of U.S. patent application Ser. No. 14/076,149 as filed on Nov. 8, 2013.

In certain aspects, the polyamine compositions and methods have the proviso that they do not include a compound of formula:

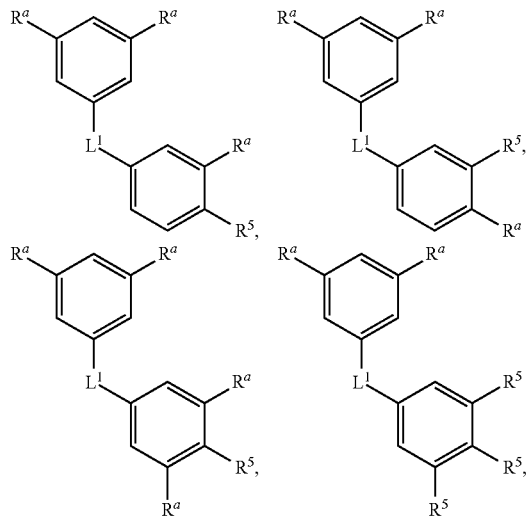

or a salt thereof,
wherein:
each $R^a$ is independently a group of Formula I:

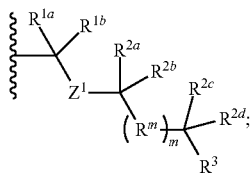

I each $R^{1a}$ and $R^{1b}$ is a member independently selected from the group consisting of hydrogen, fluoro, alkyl, and fluoroalkyl;

each $R^{2a}$, $R^{2b}$, $R^{2c}$, and $R^{2d}$ is a member independently selected from the group consisting of hydrogen, alkyl, fluoroalkyl, aryl, and arylalkyl;

each $R^m$ is an independently selected —$CR^{2a}R^{2b}$—;

each m is an integer independently selected from 1 to 2;

each $L^1$ is a member independently selected from the group consisting of a bond and —O—;

each $R^3$ is an independently selected —$Z^1$—$Y^1$—$R^4$;

each $R^4$ is a member independently selected from the group consisting of hydrogen, alkyl, fluoroalkyl, alkenyl, and alkynyl; or, alternatively, for a —$N(R^4)_2$ group, one of the two $R^4$ in the group is a member selected from the group consisting of —(CO)$OR^{6a}$—, —(CO)N($R^{6a}$)($R^{6b}$), and —C(N$R^{6a}$)N($R^{6b}$)($R^{6c}$);

each $R^5$ is a member independently selected from the group consisting of hydrogen, alkyl, hydroxyl, alkoxy, halo, fluoroalkyl, fluoroalkyloxy, hydroxyalkyl;

each $Y^1$ is an independently selected group of Formula IA:

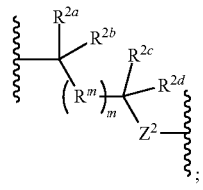

IA each $Z^1$ and $Z^2$ is an independently selected $NR^4$; and each $R^{6a}$, $R^{6b}$, and $R^{6c}$ is a member independently selected from the group consisting of hydrogen and alkyl; wherein if $R^4$ is —C(O)$OR^{6a}$, $R^{6a}$ is alkyl; and wherein the biocidal polyamine compound comprises at least two primary or secondary amino groups.

In certain aspects, the polyamine compound is selected from the group consisting of:

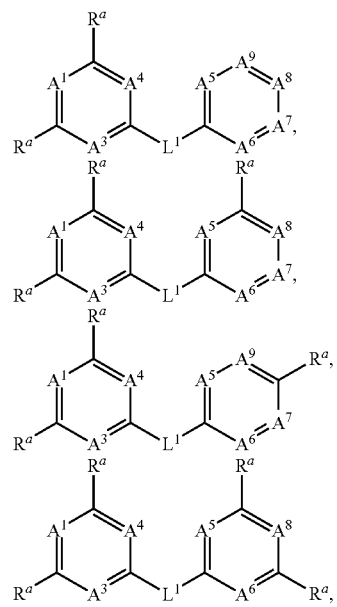

and a salt thereof;
wherein:
each $R^a$ is a member independently selected from the group consisting of

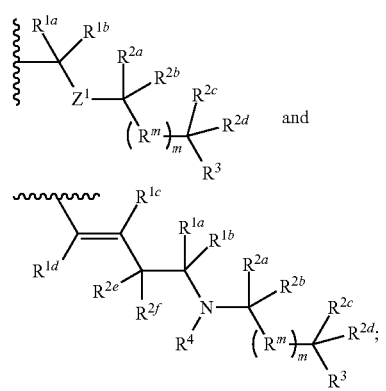

wherein each $A^n$ member is an independently selected $CR^5$;

each $R^{1a}$, $R^{1b}$, $R^{1c}$, and $R^{1d}$ is a member independently selected from the group consisting of hydrogen, fluoro, alkyl, and fluoroalkyl; or, alternatively, an $R^{1a}$ and an $R^{1b}$ join to form an oxo group;

each $R^{2a}$, $R^{2b}$, $R^{2c}$, $R^{2d}$, $R^{2e}$, and $R^{2f}$ is a member independently selected from the group consisting of hydrogen, alkyl, fluoroalkyl, alkenyl, alkynyl, aryl, heteroaryl, arylalkyl, or heteroarylalkyl; alternatively, a pair of $R^2$ members from the same $R^a$ group independently selected from the group $R^{2a}$ and $R^{2b}$, $R^{2c}$ and $R^{2d}$, and $R^{2e}$ and $R^{2f}$ join to form a member independently selected from the group consisting of spirocycloalkyl, spiroheterocycyl, and oxo; or, alternatively, an $R^{2a}$ and an $R^{2c}$ from the same $R^a$ group join to form a ring independently selected from the group consisting of cycloalkyl and heterocycyl;

each $R^m$ is a member independently selected from the group consisting of —$CR^{2a}R^{2b}$—, —$CR^{2c}R^{2d}$—, —$C(R^{2a})$=$(R^{2b})$—, —CC—, and —$C(R^{2a})(R^{2b})$-$L^2$-$C(R^{2c})(R^{2d})$—;

each m is an integer independently selected from 1 to 20;

each $L^1$ and $L^2$ is a member independently selected from the group consisting of a bond, —O—, —C(O)O—, —$NR^4$—, —$NR^4C(O)$—, and —$C(O)NR^4$—;

each $R^3$ is a member independently selected from the group consisting of —$Z^1$—$R^4$, —$Z^1$—$Y^1$—$R^4$, —$Z^1$—$Y^1$—$Y^2$—$R^4$, and —$Z^1$—$Y^1$—$Y^2$—$Y^3$—$R^4$;

each $R^4$ is a member independently selected from the group consisting of hydrogen, alkyl, fluoroalkyl, alkenyl, alkynyl, aryl, heteroaryl, arylalkyl, and heteroarylalkyl; or, alternatively, for a —$N(R^4)_2$ group, one of the two $R^4$ in the group is a member selected from the group consisting of —$(CO)OR^{6a}$—, $(CO)N(R^{6a})(R^{6b})$, and —$C(NR^{6a})N(R^{6b})(R^{6c})$;

each $R^5$ is a member independently selected from the group consisting of hydrogen, alkyl, hydroxyl, alkoxy, alkylamino, alkenyl, alkynyl, aryl, aryloxy, arylamino, cycloalkyl, cycloalkoxy, cycloalkylamino, heterocyclyl, heterocycyloxy, heterocycylamino, halo, haloalkyl, fluoroalkyloxy, heteroaryl, heteroaryloxy, heteroarylamino, arylalkyl, arylalkyloxy, arylalkylamino, heteroarylalkyl, heteroarylalkyloxy, heteroarylalkylamino; hydroxyalkyl, aminoalkyl, and alkylaminoalkyl;

each $Y^1$, $Y^2$, and $Y^3$ is an independently selected group of Formula IA:

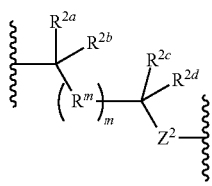

IA each $Z^1$ and $Z^2$ is a member independently selected from the group consisting of $NR^4$ and O; and each $R^{6a}$, $R^{6b}$, and $R^{6c}$ is a member independently selected from the group consisting of hydrogen, alkyl, fluoroalkyl, alkenyl, alkynyl, aryl, heteroaryl, arylalkyl, cycloalkyl, and heteroarylalkyl; or, alternatively, two $R^{6n}$ members $R^{6a}$ and $R^{6b}$ or $R^{6a}$ and $R^{6c}$ form a heterocycyl ring; wherein the biocidal polyamine compound comprises at least two primary or secondary amino groups. In certain aspects, the compositions and methods included herein have the proviso that they do not include such compounds.

In certain aspects, the polyamine compound comprises at least four primary or secondary amino groups. In some aspects, the polyamine compound comprises at least six primary or secondary amino groups. In some aspects, the polyamine compound comprises at least eight primary or secondary amino groups. In some aspects, the polyamine compound comprises at least nine primary or secondary amino groups.

In certain aspects, the polyamine compound is a hydrogen halide salt (e.g., a hydrochloride salt). In some aspects, the polyamine compound is a hydrochloride salt of

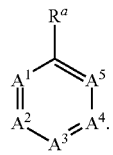

In certain aspects, the polyamine compound is selected from the group consisting of

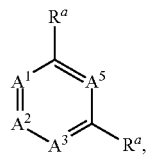 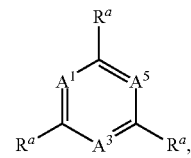

and a salt thereof,
wherein each $A^n$ member is an independently selected $CR^5$.

In certain aspects, each $R^a$ is independently a group of Formula II:

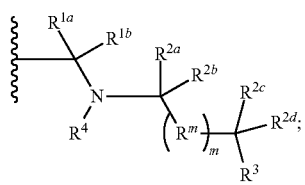

II each of the $A^n$ members is independently selected from the group consisting of $CR^a$ and $CR^5$; or, alternatively, a pair of adjacent $A^n$ members join to form an additional, independently selected cycloalkyl, aryl, heterocyclyl, or heterocycloaryl ring;

each $R^{1a}$, $R^{1b}$, $R^{1c}$, and $R^{1d}$ is a member independently selected from the group consisting of hydrogen, fluoro, alkyl, and fluoroalkyl; and for each $R^a$ member, at most two $R^m$ of the $R^a$ member are selected from the group consisting of —$C(R^{2a})$=$(R^{2b})$—, —CC—, and —$C(R^{2a})(R^{2b})$-L-C$(R^{2c})(R^{2d})$.

In certain aspects, each $R^{2a}$, $R^{2b}$, $R^{2c}$, $R^{2d}$, $R^{2e}$, and $R^{2f}$ is a member independently selected from the group consisting of hydrogen, alkyl, fluoroalkyl, alkenyl, alkynyl, aryl, heteroaryl, arylalkyl, and heteroarylalkyl; alternatively, a pair of $R^{2n}$ members from the $R^a$ group independently selected from the group $R^{2a}$ and $R^{2b}$, $R^{2c}$ and $R^{2d}$, and $R^{2e}$ and $R^{2f}$ join to form a ring independently selected from the group consisting of spirocycloalkyl and spiroheterocycyl; or, alternatively, the $R^{2a}$ and the $R^{2c}$ from the $R^a$ group join to form a ring independently selected from the group consisting of cycloalkyl and heterocycyl;

each m is an integer independently selected from 1 to 12;
each $R^3$ is a member independently selected from the group consisting of $-Z^1-Y^1-R^4$ and $-Z^1-Y^1-Y^2-R^4$; and
each $Z^1$ and $Z^2$ is an independently selected $NR^4$.

In certain aspects, $A^1$, $A^2$, $A^3$, $A^4$, and $A^5$ are each an $A''$ member independently selected from the group consisting of $CR^a$, and $CR^5$; or, alternatively, a pair of adjacent $A''$ members join to form an additional cycloalkyl, aryl, heterocyclyl, or heterocycloaryl ring;

each $R^{2a}$, $R^{2b}$, $R^{2c}$, $R^{2d}$, $R^{2e}$, and $R^{2f}$ is a member independently selected from the group consisting of hydrogen, alkyl, fluoroalkyl, alkenyl, alkynyl, aryl, heteroaryl, arylalkyl, or heteroarylalkyl;

each m is an integer independently selected from 1 to 10;
each L is a member independently selected from the group consisting of a bond, $-O-$, and $-NR^4-$;
each $R^3$ is a member independently selected from the group consisting of $-Z^1-R^4$, $-Z^1-Y^1-R^4$, and $-Z^1-Y^1-Y^2-R^4$; and
each $Z^1$ and $Z^2$ is an independently selected $NR^4$.

In certain aspects, each $R^a$ is independently a group of Formula V:

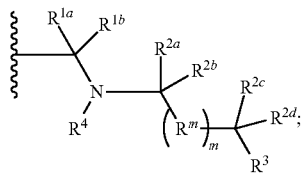

V each $R^{1a}$, $R^{1b}$, $R^{1c}$, and $R^{1d}$ is a member independently selected from the group consisting of hydrogen, fluoro, alkyl, and fluoroalkyl;

for each $R^a$ member, at most two $R^m$ of the $R^a$ member are selected from the group consisting of $-C(R^{2a})=(R^{2b})-$, $-CC-$, and $-C(R^{2a})(R^{2b})-L-C(R^{2c})(R^{2d})-$; and each $R^3$ is a member independently selected from the group consisting of $-Z^1-Y^1-R^4$ and $-Z^1-Y^1-Y^2-R^4$.

In certain aspects, $R^4$ is a member independently selected from the group consisting of hydrogen, alkyl, fluoroalkyl, alkenyl, alkynyl, aryl, cycloalkyl, heteroaryl, arylalkyl, cycloalkylalkyl, and heteroarylalkyl. In certain aspects, at least one $R^4$ is a member independently selected from the group consisting of alkyl, fluoroalkyl, alkenyl, alkynyl, aryl, cycloalkyl, heteroaryl, arylalkyl, cycloalkylalkyl, and heteroarylalkyl. In certain aspects, at least one $R^4$ is alkyl (e.g., lower alkyl; isobutyl; butyl; propyl; isopropyl). In certain aspects, at least one $R^4$ is alkenyl (e.g., allyl; methallyl). In certain aspects, at least one $R^4$ is alkynyl (e.g., propargyl). In certain aspects, at least one $R^4$ is cycloalkylalkyl (e.g., cyclohexylmethyl). In certain aspects, at least one $R^4$ is arylalkyl. In certain aspects, at least one $R^4$ is heteroarylalkyl.

In certain aspects, for an $-N(R^4)_2$ group, one of the two $R^4$ in the group is a member selected from the group consisting of $-(CO)OR^{6a}-$, $-(CO)N(R^{6a})(R^{6b})$, and $-C(NR^{6a})N(R^{6b})(R^{6c})$. In certain aspects, $R^{6a}$ is alkyl. In certain aspects, $R^{6a}$ and $R^{6b}$ are alkyl.

In certain aspects, for an $-N(R^4)_2$ group, the two $R^4$ groups join to form a heterocyclic ring.

In certain aspects, at least one $R^5$ is a member independently selected from the group consisting of alkyl, hydroxyl, alkoxy, aminoalkoxy, alkylamino, alkylaminoalkoxy, cycloalkyl, cycloalkoxy, cycloalkylalkoxy, halo, fluoroalkyl, fluoroalkyloxy, arylalkyl, arylalkyloxy, heteroaryl, heteroaryloxy, heteroarylalkyloxy, hydroxyalkyl, aminoalkyl, and alkylaminoalkyl. In certain aspects, at least one $R^5$ is a member independently selected from hydroxyl, alkoxy, aminoalkoxy, alkylaminoalkoxy, cycloalkoxy, cycloalkylalkoxy, fluoroalkyloxy, arylalkyloxy, heteroaryloxy, heteroarylalkyloxy, hydroxyalkyl, aminoalkyl, and alkylaminoalkyl. In certain aspects, at least one $R^5$ is a member independently selected from the group consisting of alkyl, hydroxyl, alkoxy, halo, fluoroalkyl, and fluoroalkyloxy.

In certain aspects, at least one $R^5$ is a member independently selected from the group consisting of hydroxyl, alkoxy, and fluoroalkyloxy. In certain aspects, at least one $R^5$ is hydroxy. In certain aspects, at least one $R^5$ is alkoxy. In certain aspects, at least one $R^5$ is fluoroalkyloxy. In certain aspects, at least one $R^5$ is a member independently selected from the group consisting of aminoalkoxy and alkylaminoalkoxy. In certain aspects, at least one $R^5$ is aminoalkoxy. In certain aspects, at least one $R^5$ is alkylaminoalkoxy.

In certain aspects, at least one $R^5$ is a member independently selected from the group consisting of cycloalkoxy and cycloalkylalkoxy. In certain aspects, at least one $R^5$ is cycloalkoxy. In certain aspects, at least one $R^5$ is cycloalkylalkoxy. In certain aspects, at least one $R^5$ is arylalkyloxy. In certain aspects, at least one $R^5$ is a member independently selected from the group consisting of heteroaryloxy and heteroarylalkyloxy. In certain aspects, at least one $R^5$ is heteroaryloxy. In certain aspects, at least one $R^5$ is heteroarylalkyloxy.

In certain aspects, at least one $R^5$ is a member independently selected from the group consisting of hydroxyalkyl, aminoalkyl, and alkylaminoalkyl. In certain aspects, at least one $R^5$ is hydroxyalkyl. In certain aspects, at least one $R^5$ is aminoalkyl or alkylaminoalkyl. In certain aspects, at least one $R^5$ is aminoalkyl. In certain aspects, at least one $R^5$ is alkylaminoalkyl.

In certain aspects, each $Z^1$ and $Z^2$ is an independently selected $-N(R^4)-$; and each $R^{6a}$, $R^{6b}$, and $R^{6c}$ is a member independently selected from the group consisting of hydrogen and alkyl.

In certain aspects, each $R^{1a}$, $R^{1b}$, $R^{1c}$, and $R^{1d}$ is hydrogen; each $R^{2a}$, $R^{2b}$, $R^{2c}$, $R^{2d}$, $R^{2e}$, and $R^{2f}$ is hydrogen; each $R^3$ is an independently selected $-Z^1-Y^1-R^4$; and each L is a member independently selected from the group consisting of a bond and $-O-$.

In certain aspects, at least one $R^4$ is a member independently selected from the group consisting of alkyl, arylalkyl, and cycloalkylalkyl. In certain aspects, at least one $R^4$ is alkyl (e.g., isobutyl). In certain aspects, at least one $R^4$ is arylalkyl. In certain aspects, at least one $R^4$ is cycloalkylalkyl (e.g., cyclohexylmethyl).

In certain aspects, at least one $R^4$ is a member independently selected from the group consisting of alkyl, arylalkyl, and cycloalkylalkyl.

In certain aspects, $R^a$ is an independently selected group of Formula VII:

VII

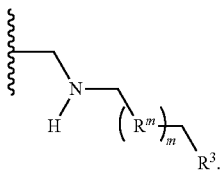

In certain aspects, $R^a$ is —CH$_2$[NH(CH$_2$)$_3$]$_2$NH(R$^4$)

In certain aspects, $R^a$ is —CH$_2$[NH(CH$_2$)$_n$]$_p$NR$^4$; wherein each n is an integer independently selected from 3 to 12; and wherein each p is an integer independently selected from 1 to 3. In certain aspects, n is 3 or 4. In certain aspects, $R^4$ is isobutyl. In certain aspects, n is 3 or 4, and $R^4$ is isobutyl.

In certain aspects, each $R^{2a}$, $R^{2b}$, $R^{2c}$, and $R^{2d}$ is a member independently selected from the group consisting of hydrogen, alkyl, and fluoroalkyl; and the polyamine compound comprises at least four primary or secondary amino groups.

In certain aspects, m is 1 or 2. In certain aspects, L is a bond. In certain aspects, m is 1 or 2, and L is a bond.

In certain aspects, the invention provides a polyamine composition for treatment of biofilms, the composition comprising, consisting essentially of, or consisting of a polyamine compound of formula

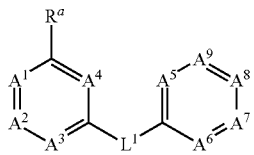

or a salt thereof;
wherein:
each $R^a$ is an independently selected group of Formula I:

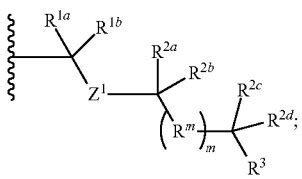

I $A^1$, $A^2$, $A^3$, $A^4$, $A^5$, $A^6$, $A^7$, $A^8$, and $A^9$ are each an $A''$ member independently selected from N, CR$^a$, and CR$^5$; wherein at least one $A''$ member and at most five $A''$ members are independently selected CR$^a$;

each $R^{1a}$ and $R^{1b}$ is a member independently selected from hydrogen, fluoro, alkyl, and fluoroalkyl;

each $R^{2a}$, $R^{2b}$, $R^{2c}$, and $R^{2d}$ is a member independently selected from hydrogen, alkyl, fluoroalkyl, aryl, and arylalkyl;

each $R^m$ is a member independently selected from —CR$^{2a}$R$^{2b}$— and —C(R$^{2a}$)(R$^{2b}$)-L$^2$-C(R$^{2c}$)(R$^{2d}$)—;

each m is an integer independently selected from 1 to 20;

each $L^1$ is a member independently selected from a bond and —O—;

each $L^2$ is a member independently selected from a bond, —O—, and —NR$^4$—;

each $R^3$ is a member independently selected from —Z$^1$—R$^4$, —Z$^1$—Y$^1$—R$^4$, and —Z$^1$—Y$^1$—Y$^2$—R$^4$;

each $R^4$ is a member independently selected from hydrogen, alkyl, fluoroalkyl, alkenyl, alkynyl, aryl, and arylalkyl; or, alternatively, for a —N(R$^4$)$_2$ group, one of the two R$^4$ in the group is a member selected from —(CO)OR$^{6a}$—, —(CO)N(R$^{6a}$)(R$^{6b}$), and —C(NR$^{6a}$)N(R$^{6b}$)(R$^{6c}$);

each $R^5$ is a member independently selected from hydrogen, alkyl, hydroxyl, alkoxy, alkylamino, aryl, aryloxy, heterocyclyl, halo, fluoroalkyl, fluoroalkyloxy, heteroaryl, arylalkyl, arylalkyloxy, hydroxyalkyl, aminoalkyl, and alkylaminoalkyl;

each $Y^1$ and $Y^2$ is an independently selected group of Formula IA:

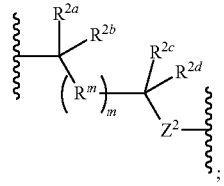

IA each $Z^1$ and $Z^2$ is a member independently selected from NR$^4$ and O;

each $R^{6a}$, $R^{6b}$, and $R^{6c}$ is a member independently selected from hydrogen and alkyl; wherein if $R^4$ is —C(O)OR$^{6a}$, $R^{6a}$ is alkyl; and wherein the biocidal polyamine compound comprises at least two primary or secondary amino groups.

In some aspects, the composition comprises a polyamine compound of formula

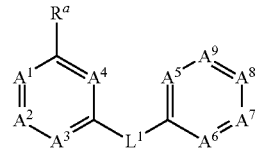

or a salt thereof.

In some aspects, each $A^1$, $A^2$, $A^3$, $A^4$, $A^5$, $A^6$, $A^7$, $A^8$, and $A^9$ are each an $A''$ member independently selected from N, CR$^a$, and CR$^5$; wherein at least one $A''$ member and at most five $A''$ members are independently selected CR$^a$.

In some aspects, each $R^{1a}$ and $R^{1b}$ is a member independently selected from hydrogen, fluoro, alkyl, and fluoroalkyl.

In some aspects, each $R^{2a}$, $R^{2b}$, $R^{2c}$, and $R^{2d}$ is a member independently selected from hydrogen, alkyl, fluoroalkyl, aryl, and arylalkyl.

In some aspects, each $R^m$ is a member independently selected from —CR$^{2a}$R$^{2b}$— and —C(R$^{2a}$)(R$^{2b}$)-L$^2$-C(R$^{2c}$)(R$^{2d}$)—.

In some aspects, each $R^{6a}$, $R^{6b}$, and $R^{6c}$ is a member independently selected from hydrogen and alkyl; wherein if $R^4$ is —C(O)OR$^{6a}$, $R^{6a}$ is alkyl.

In some aspects, each $L^1$ is a member independently selected from a bond and —O—; and each $L^2$ is a member independently selected from a bond, —O—, and —NR$^4$—.

In some aspects, each $R^5$ is a member independently selected from hydrogen, alkyl, hydroxyl, alkoxy, alkylamino, aryl, aryloxy, heterocyclyl, halo, fluoroalkyl, fluoroalkyloxy, heteroaryl, arylalkyl, arylalkyloxy, hydroxyalkyl, aminoalkyl, and alkylaminoalkyl.

In some aspects, each $R^{6a}$, $R^{6b}$, and $R^{6c}$ is a member independently selected from hydrogen and alkyl; wherein if $R^4$ is —C(O)O$R^{6a}$, $R^{6a}$ is alkyl.

In some aspects, the invention provides a polyamine compound selected from:

(a) a compound of Formula IC:

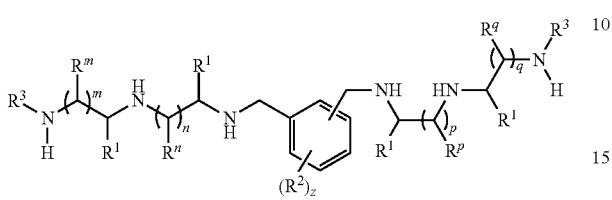

or a salt thereof, and (b) a compound of Formula ID:

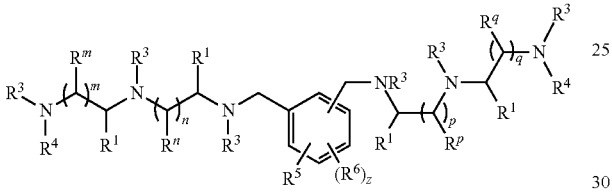

or a salt thereof;

wherein:
  each $R^l$, $R^m$, $R^n$, $R^p$, and $R^q$ is independently a substituent independently selected from hydrogen, alkyl, alkenyl, alkynyl, aryl, heteroaryl, arylalkyl, and heteroarylalkyl;
  each $R^2$ is independently a substituent independently selected from hydrogen, alkyl, alkoxy, alkylamino, alkenyl, alkynyl, aryl, aryloxy, arylamino, halo, haloalkyl, heteroaryl, heteroaryloxy, heteroarylamino, arylalkyl, alkylaryloxy, alkylarylamino, heteroarylalkyl, heteroalkylaryloxy, heteroalkylarylamino,

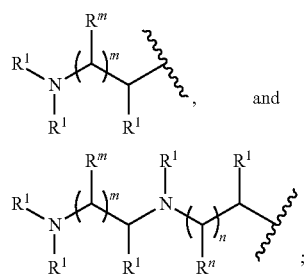

each z is independently an integer independently selected from 1 to 3;

each m, n, p, and q is independently an integer independently selected from 1 to 20;

each $R^3$ is independently a substituent independently selected from hydrogen,

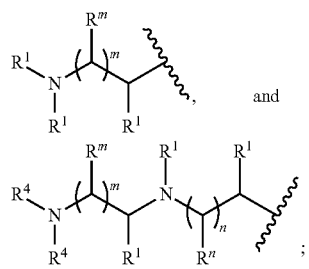

each $R^4$ is independently a substituent independently selected from hydrogen, alkyl, alkenyl, alkynyl, aryl, heteroaryl, arylalkyl, heteroarylalkyl,

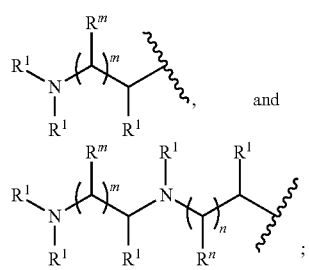

and each $R^5$ is independently a substituent independently selected from alkyl, alkoxy, alkylamino, alkenyl, alkynyl, aryl, aryloxy, arylamino, halo, haloalkyl, heteroaryl, heteroaryloxy, heteroarylamino, arylalkyl, alkylaryloxy, alkylarylamino, heteroarylalkyl, heteroalkylaryloxy, heteroalkylarylamino,

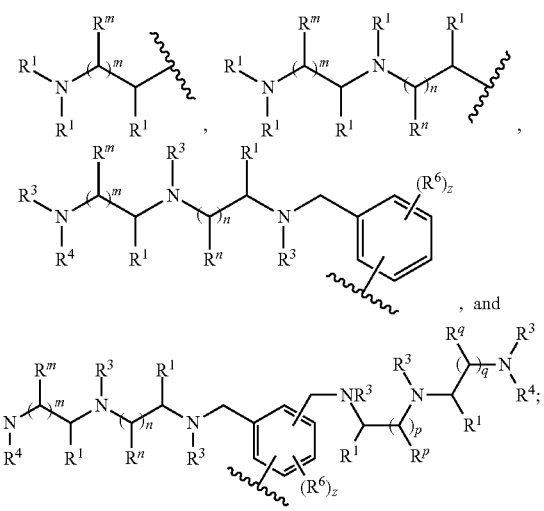

and each $R^6$ is independently a substituent independently selected from hydrogen, alkyl, alkoxy, alkylamino, alkenyl, alkynyl, aryl, aryloxy, arylamino, halo, haloalkyl, heteroaryl, heteroaryloxy, heteroarylamino, arylalkyl, alkylaryloxy, alkylarylamino, heteroarylalkyl, heteroalkylaryloxy, and heteroalkylarylamino.

In some aspects, the polyamine compound is selected from:

(a) a compound of Formula IE:

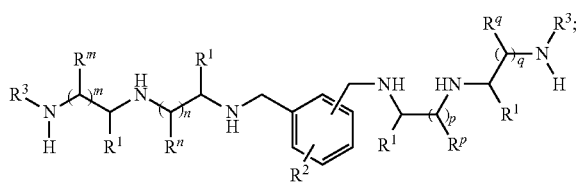

and (b) a compound of Formula IF:

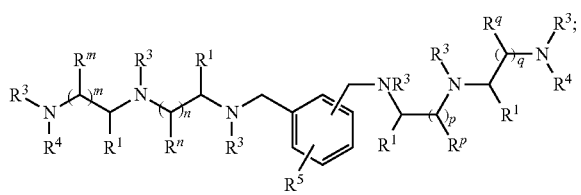

wherein:

each $R^l$, $R^m$, $R^n$, $R^p$, and $R^q$ is independently a substituent independently selected from hydrogen, alkyl, alkenyl, alkynyl, aryl, heteroaryl, arylalkyl, and heteroarylalkyl;

each $R^2$ is independently a substituent independently selected from hydrogen, alkyl, alkoxy, alkylamino, alkenyl, alkynyl, aryl, aryloxy, arylamino, heteroaryl, heteroaryloxy, heteroarylamino, arylalkyl, alkylaryloxy, alkylarylamino, heteroarylalkyl, heteroalkylaryloxy, heteroalkylarylamino,

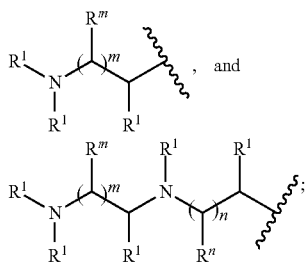

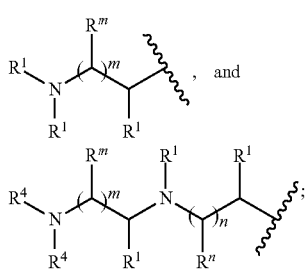

each m, n, p, and q is independently an integer independently selected from 1 to 20;

each $R^3$ is independently a substituent independently selected from hydrogen,

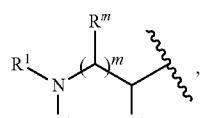

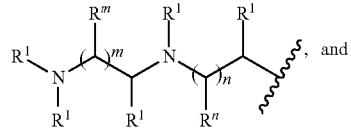

each $R^4$ is independently a substituent independently selected from hydrogen, alkyl, alkenyl, alkynyl, aryl, heteroaryl, arylalkyl, heteroarylalkyl,

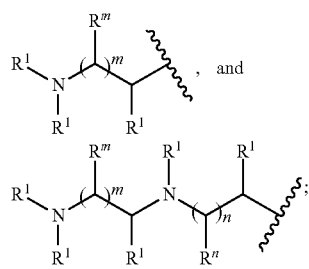

each $R^5$ is independently a substituent independently selected from alkyl, alkoxy, alkylamino, alkenyl, alkynyl, aryl, aryloxy, arylamino, heteroaryl, heteroaryloxy, heteroarylamino, arylalkyl, alkylaryloxy, alkylarylamino, heteroarylalkyl, heteroalkylaryloxy, heteroalkylarylamino,

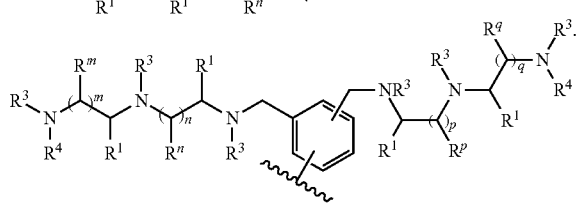

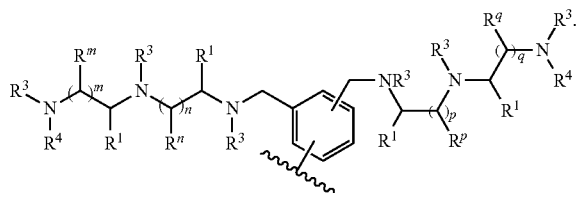

In still some aspects, $R^2$ is hydrogen.
In yet some aspects, $R^5$ is aryl or aryloxy.
In still yet some aspects, $R^5$ is In some aspects, the polyamine compound is

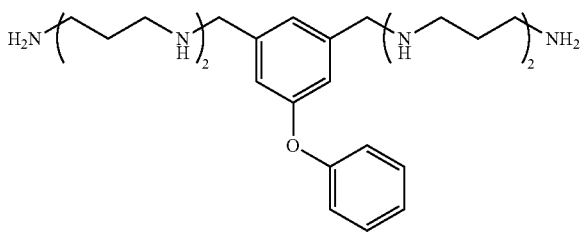

or a salt thereof.

In some aspects, the invention provides a polyamine compound of Formula I-P or a salt thereof:

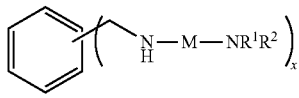

I-P wherein:

M is selected from:

(a) a $C_1$-$C_{13}$ alkyl, alkenyl or alkynyl group, and (b) -(L-NH)$_z$-L-, where L is a $C_3$-$C_{13}$ alkyl, alkenyl or alkynyl group, and where z is an integer from zero to 6;

x is an integer from 1 to 6; and $R^1$ and $R^2$ each is independently selected from hydrogen and $C_1$-$C_{13}$ alkyl group.

In some aspects, the polyamine compound of Formula I-P may comprise a hydrophobic phenyl group and up to six hydrophilic polyamine chains. Each of the hydrophilic polyamine chains may be the same, or some of the hydrophilic polyamine chains may be same, or none of the hydrophilic polyamine may be the same. Additionally, each hydrophilic polyamine chain may comprise a neutral amine, a cationic ammonium salt, or both.

In some aspects, the polyamine compound may comprise a compound of Formula II-P or a salt thereof, wherein n is an integer from 1 to 13, x is an integer from 1 to 6, and P and $R^2$ each may independently be hydrogen or a $C_1$-$C_{13}$ alkyl group.

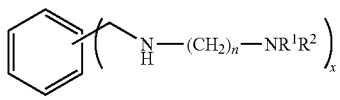

II-P

In some aspects, the polyamine compound may comprise a compound of Formula III-P or a salt thereof, wherein n is an integer from 1 to 13, and the hydrophobic phenyl group is substituted with two hydrophilic polyamine chains at the ortho-, meta-, or para-position.

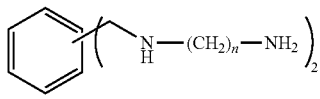

III-P

In yet some aspects, the polyamine compound may comprise a compound of Formula IV-P or a salt thereof, wherein each m and n is an independently selected integer from 1 to 13.

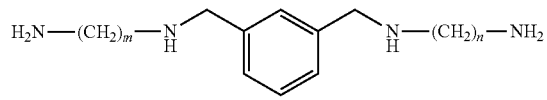

IV-P

In some aspects, m is 12 (i.e., compound IV-1 or a salt thereof). In some alternative aspects, m is 6 (i.e., compound IV-2 or a salt thereof).

In some aspects, the polyamine compound may comprise a compound of Formula V-P or a salt thereof, wherein n is an integer from 1 to 13, and the three hydrophilic polyamine chains may be at any position on the hydrophobic phenyl group.

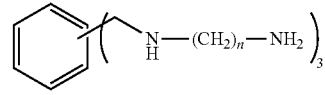

V-P

In some aspects, the polyamine compound may comprise a compound of Formula VI-P or a salt thereof, wherein each m, n and p is an independently selected integer from 1 to 13: and each $R^1$ and $R^2$ may independently be hydrogen or a $C_1$-$C_{13}$ alkyl group.

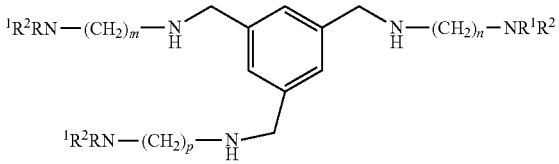

VI-P

In some aspects, m, p, and n are 3 (e.g., compound VI-1). In some aspects, m, p, and n are 6 (e.g., compound VI-2).

In some aspects, the polyamine compound may comprise a compound of Formula VII-P or a salt thereof:

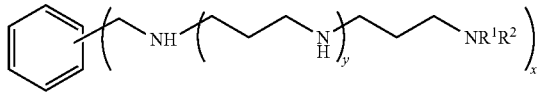

VII-P wherein:

x is an integer from 1 to 6, y is an integer from zero to 6, each $R^1$ and $R^2$ is independently selected from hydrogen and $C_1$-$C_{13}$ alkyl; and wherein the substituted hydrophilic polyamine chains may be at any position of the hydrophobic phenyl group.

In some aspects, the polyamine compound may comprise a compound of Formula VII-1 or a salt thereof, wherein y is an integer from zero to 6, and the two hydrophilic polyamine chains may be at the ortho-, meta-, or para-position of the hydrophobic phenyl group.

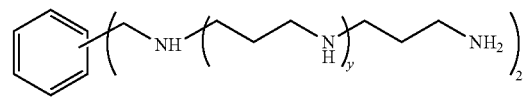

VII-1

In some aspects, the polyamine compound may comprise a compound of Formula VII-3 or a salt thereof, wherein y is an integer from zero to 6, and the three hydrophilic polyamine chains may be at any position of the hydrophobic phenyl group.

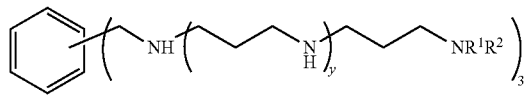

VII-3

In yet some aspects, the polyamine compound is a compound of Formula VII-4 or a salt thereof, wherein f, g and h are each an independently selected integer from zero to 6.

chains may be the same, or some of the hydrophilic polyamine chains may be same, or none of the hydrophilic polyamine chain may be the same. Additionally, each hydrophilic polyamine chain may comprise a neutral amine, a cationic ammonium salt, or both.

In some aspects, the polyamine compound is a compound of Formula VIII-1 or a salt thereof, wherein n is an integer from 3 to 13, and the two hydrophilic polyamine chains may be at the ortho-, meta- or para-position of the hydrophobic phenyl group.

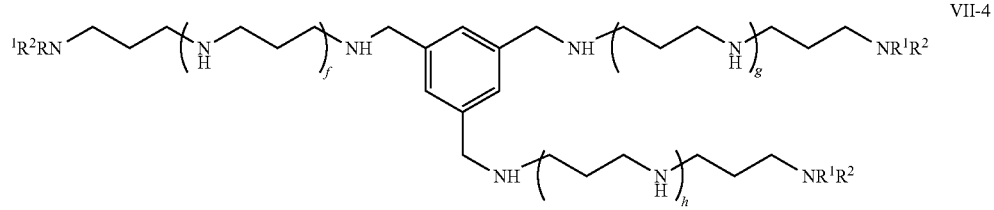

VII-4

In some aspects, the polyamine compound is a compound of Formula VII-5 or a salt thereof:

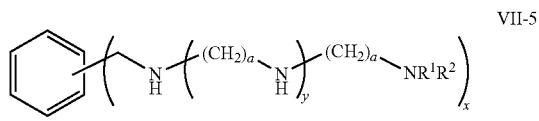

VII-5 wherein:
a is an independently selected integer from 2 to 13,
x is an independently selected integer from 1 to 6,
y is an independently selected integer from zero to 6,
each $R^1$ and $R^2$ is independently selected from hydrogen and $C_1$-$C_{13}$ alkyl, and
the substituted hydrophilic polyamine chains may be at any position of the hydrophobic phenyl group.

In some aspects, the polyamine compound is a compound of Formula VIII-P or a salt thereof:

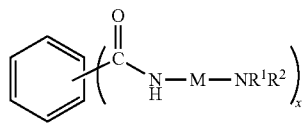

VIII-P wherein:
M may be selected from:
(a) $C_1$-$C_{13}$ alkyl, alkenyl or alkynyl group,
(b) -(L-NH)$_z$-L-group, wherein L is $C_3$-$C_{13}$ alkyl, alkenyl or alkynyl group, and z is an integer from zero to 6;
x is an integer from 1 to 6; and
$R^1$ and $R^2$ each may independently be hydrogen or a $C_1$-$C_{13}$ alkyl group.

The polyamine compound of general Formula VIII-P may comprise a hydrophobic phenyl group and up to six hydrophilic polyamine chains, each of the hydrophilic polyamine chains connecting to the hydrophobic phenyl group via an amide functional group. Each of the hydrophilic polyamine

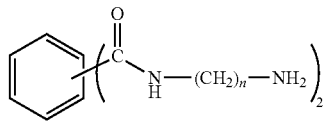

VIII-1

In some aspects, the polyamine compound is a compound of Formula VIII-2 or a salt thereof, wherein y is an integer from zero to 6, and the two hydrophilic polyamine chains may be at the ortho-, meta-, or para-position of the hydrophobic phenyl group.

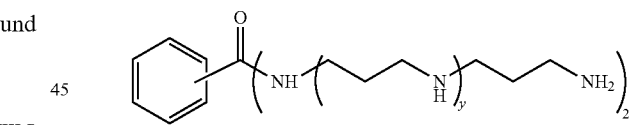

VIII-2

In some aspects, the polyamine compound is a compound of Formula VIII-3 or a salt thereof.

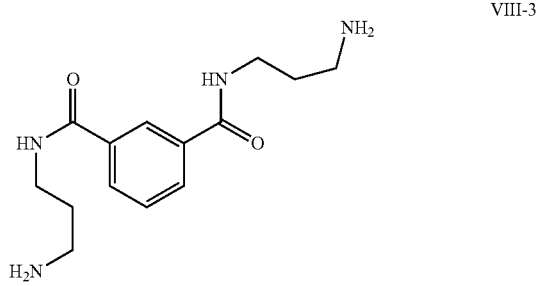 [SMILES: NCCCNC(=O)c1cccc(C(=O)NCCCN)c1]

VIII-3

In some aspects, the polyamine compound is a compound of Formula VIII-4 or a salt thereof:

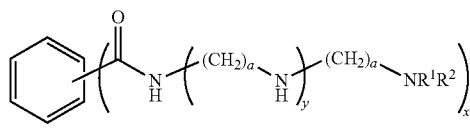

VIII-4 wherein:
a is an integer from 2 to 13,
x is an integer from 1 to 6,
y is an integer from zero to 6,
each $R^1$ and $R^2$ is independently selected from the group hydrogen and a $C_1$-$C_{13}$ alkyl group, and
the substituted hydrophilic polyamine chains may be at any position of the hydrophobic phenyl group.

In some aspects, the polyamine compound is a compound of Formula I-P, Formula VIII-P, or a salt thereof, wherein M, $R^1$ and $R^2$ are as described herein, and x is an integer from 1 to 6. The polyamine compound comprises a hydrophobic phenyl group and at least one hydrophilic polyamine chain.

In certain aspects, the compounds of the present invention are antimicrobial and provide triple action against bacteria and biofilms. Advantageously, the antimicrobial compounds of the present invention have specific activity against biofilms.

Figure 23:
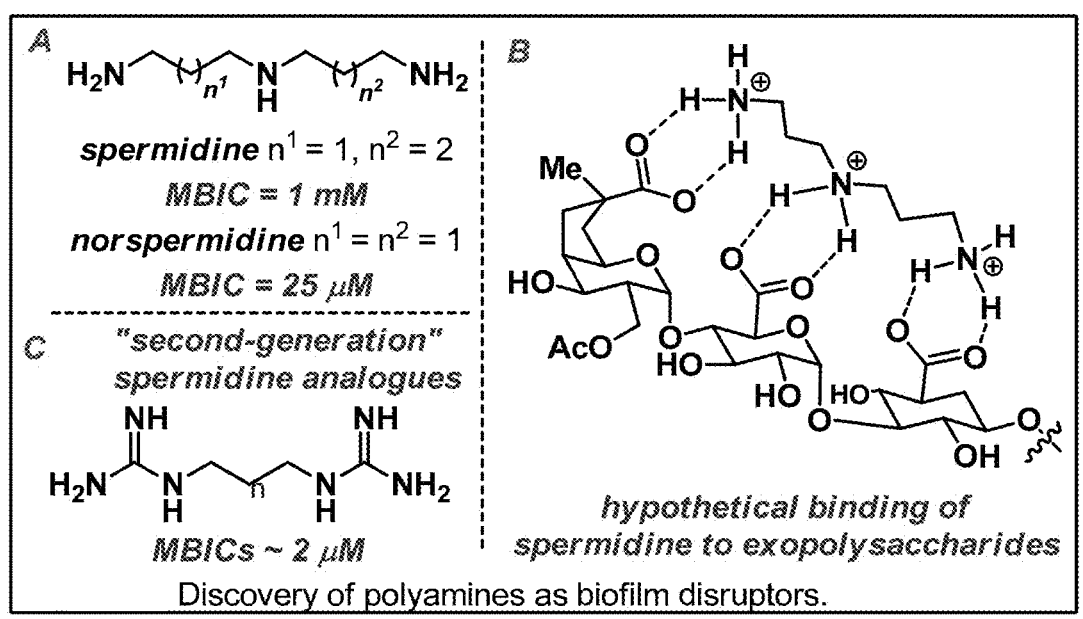
FIG. 23 shows a hypothetical mode of binding of spermidine to an exopolysaccharide.

Organisms residing in biofilms present a complex extracellular matrix of polysaccharides (exopolysaccharides) and proteins. As a result of this complex matrix, nutrient-limiting conditions exist that alter the normal or planktonic metabolic state. These conditions reduce the efficacy of traditional antibiotic agents, rendering them up to 1,000× less active against biofilms. A hallmark of these exopolysaccharides is the presentation of acidic residues from repeated glucoronic acid motifs and pyruvate derived acetals. A recent study by Losick and co-workers demonstrated that the simple polyamines spermine and norspermidine (FIG. 23A) were naturally occurring inhibitors of biofilm formation, endogenously produced at high concentrations (50-80 µM) in response to nutrient limiting conditions and waste accumulation in mature pellicles (Kolodkin-Gal, I. et al., A self-produced trigger for biofilm disassemby that targets exopolysaccharide. Cell 149 (2012)). In this study, they were able to demonstrate that norspermidine could inhibit biofilm formation at 25 µM and showed that, at similar concentrations, it could disperse the exopolysaccharide component of the matrix but not the protein component. Interestingly, spermidine was only active at much higher concentrations (~1 mM) leading them to propose a rationale for this activity in the ability of the polyamines to engage the acidic residues in the matrix at regular intervals (FIG. 23B).

Figure 26:
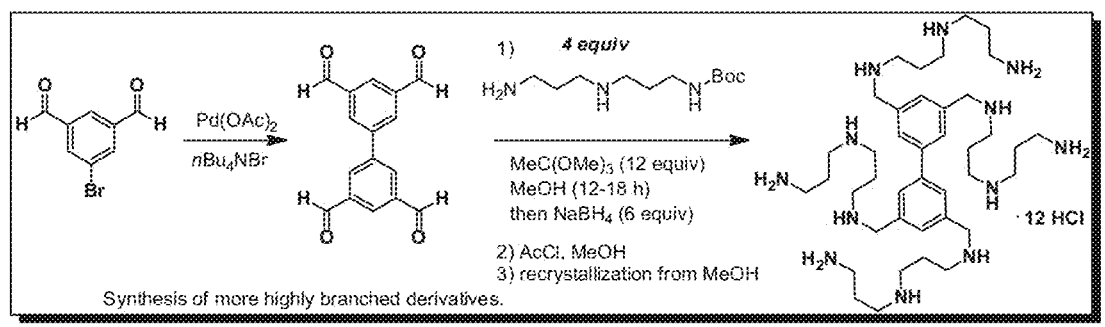
FIG. 26 shows a method for making yet another embodiment of the polyamine compound.

In certain aspects, compounds of the present invention having increased numbers of chains, produce a more effective compound against A. baumannii. For example, compounds with four polyamine chains can be generated with Pd(II) mediated dimerization of 5-bromoisopthalaldehyde followed by reductive amination (FIG. 26).

Figure 27:
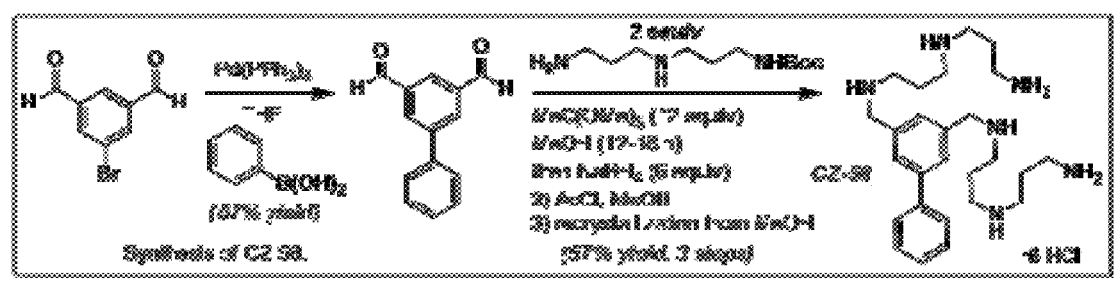
FIG. 27 shows a method for making still another embodiment of the polyamine compound.
Figure 28:
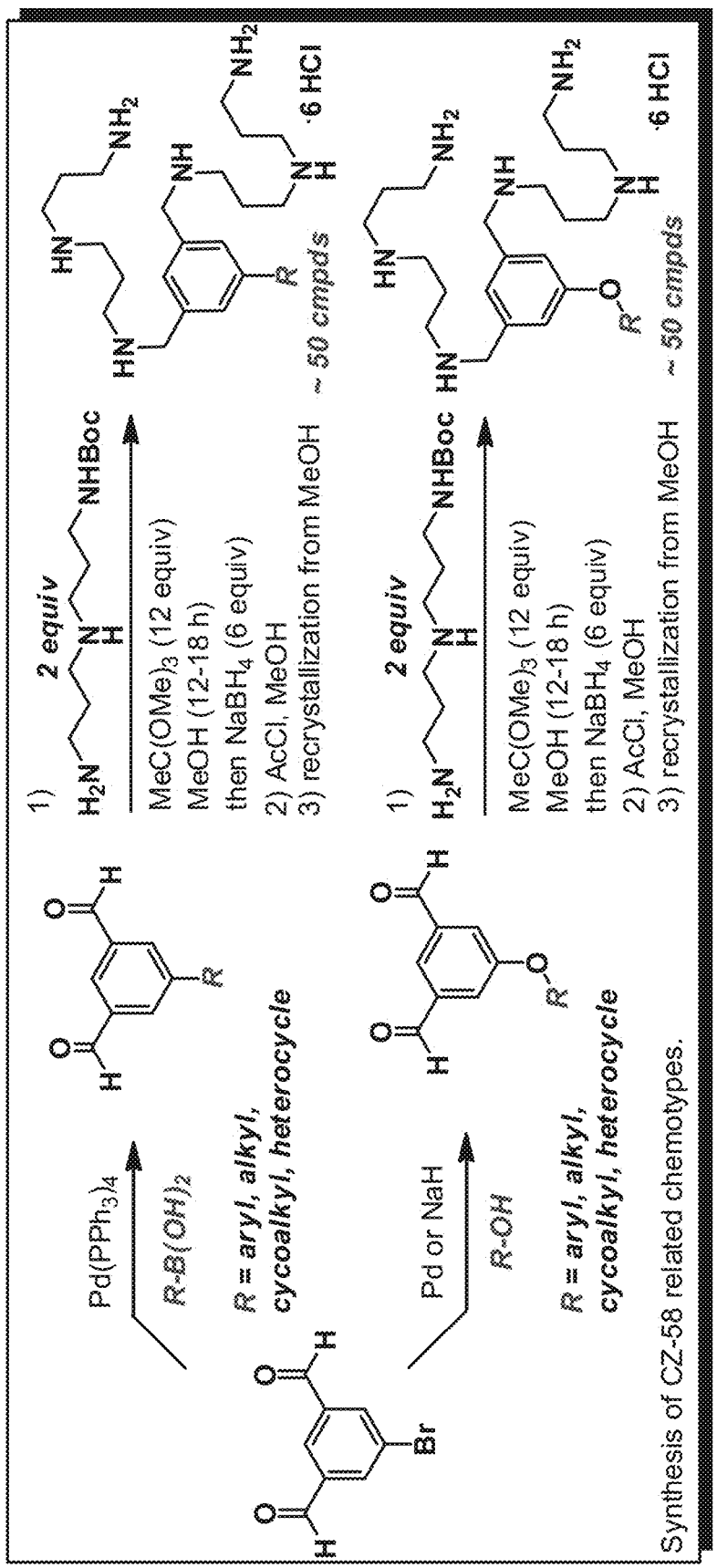
FIG. 28 shows a method for making several other embodiments of the polyamine compound.
Figure 29:
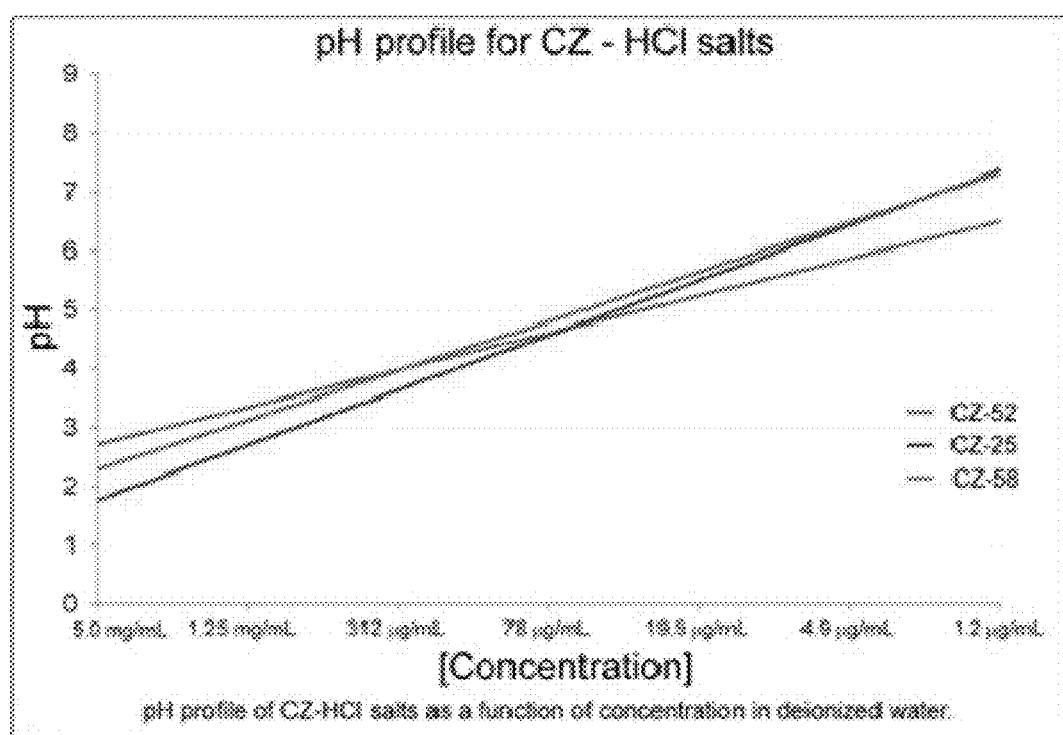
FIG. 29 shows a pH profile of selected polyamine compounds' hydrochloride salts in deionized water.

In certain aspects, the compounds of present invention combine a hydrophobic backbone with a cationic tail that have the functionality to inhibit biofilm formation, disrupt established biofilms, and kill the emerging planktonic bacteria. Certain of the compounds of the invention are set forth in FIGS. 27 and 28.

In a particular embodiment, the polyamine compound may comprise a hydrophobic moiety head and at least one hydrophilic moiety tail comprising a polyamine group. When the polyamine compound comprises more than one hydrophilic moiety tails, the hydrophilic moiety tails may be the same, or alternatively, the hydrophilic moiety tails may be different.

As discussed above, the exemplary polyamine compounds shown herein are not intended to be limiting.

Synthesis

Figure 25:
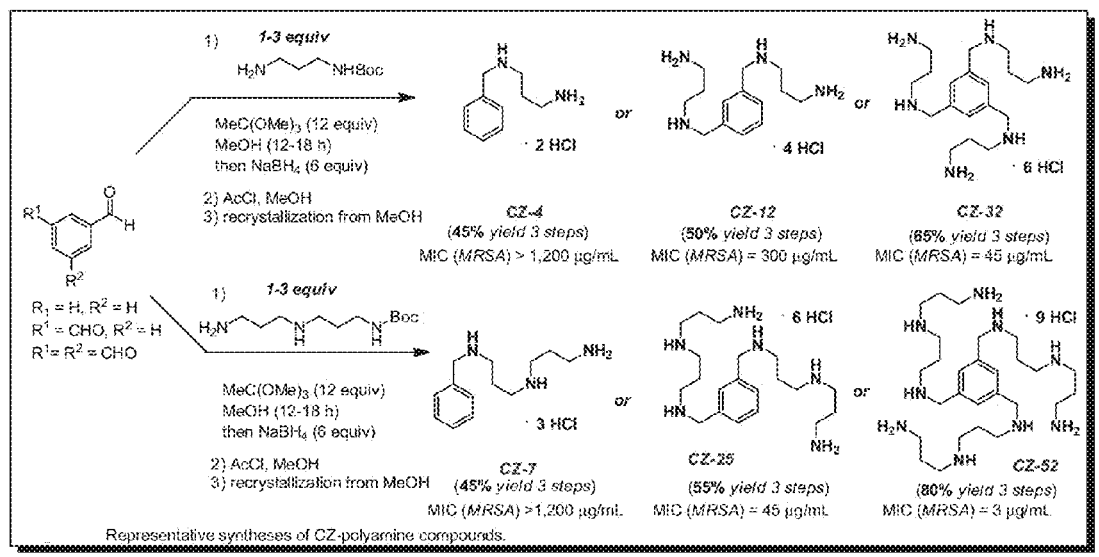
FIG. 25 shows a method for making several embodiments of the polyamine compound.

The synthesis of diaminopropane substituted backbones is straightforward and results in CZ-4, 12, 32 (FIG. 25) from the known mono-Boc protected diaminopropane and commercially available aldehydes (benzaldehyde, isopthalaldehyde or 1,3,5-benzenetricarboxaldehyde). This three-step synthetic procedure proceeds via reductive amination (Baxter, E. W. & Reitz, A. B. Reductive Aminations of Carbonyl Compounds with Borohydride and Borane Reducing Agents. Org Reac 1, 59 (2004)) and acidic removal of the Boc group. The norspermidine series (e.g., CZ-7, CZ-25, and CZ-52) can be prepared in a similar manner from the mono-Boc protected norspermidine (FIG. 25). No purification is required until a final recrystallization of the HCl salt, which has allowed easy preparation of these compounds on larger scale.

In some embodiments, the polyamine compound may be produced by the reductive amination method of General Synthetic Scheme 1.

General Synthetic Scheme 1

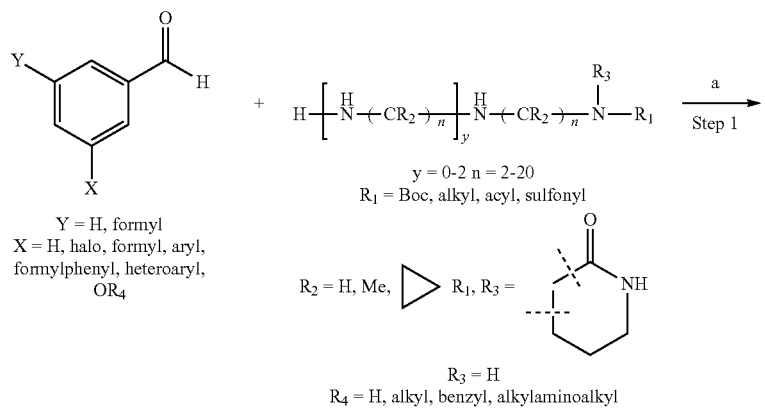

-continued

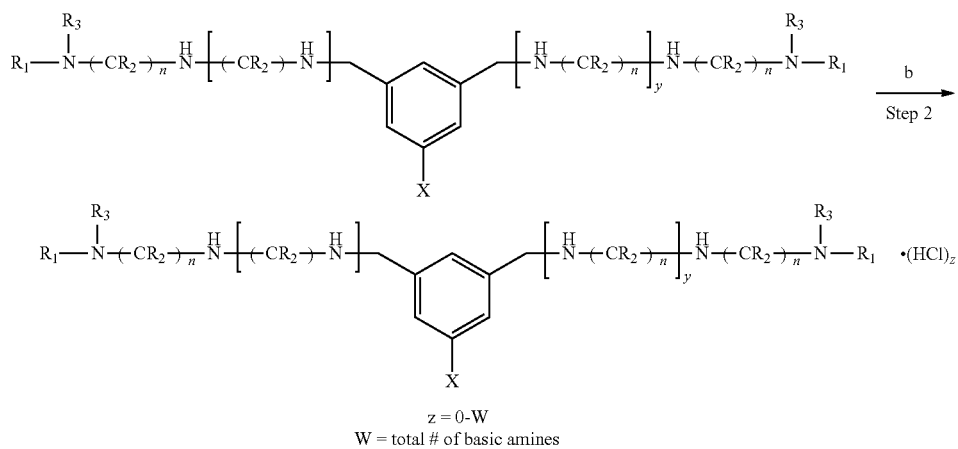

z = 0-W
W = total # of basic amines

Reagents: (a) MeOH, 3 Å molecular sieves, rt, 1-28 h; NaBH$_4$; (b) HCl, MeOH, rt 1-4 h.

The General Synthetic Schemes included herein set forth methods of preparing some compounds within the aspects and embodiments disclosed herein. In some alternative aspects, these methods can be used to produce a compound of the one of the aspects and embodiments disclosed herein. In some alternative aspects, these methods can be used to produce a precursor or starting material for producing such a compound.

In General Synthetic Schemes 1, 2, 3, and 5, "CR$_2$" indicates a methylene with two substituents, which may be hydrogen, methyl (or, alternatively, lower alkyl), or spirocyclopropane (i.e., the two substituents are the spirocyclic ring).

In some embodiments, the polyamine compound may be produced by the acylation method of General Synthetic Scheme 2

General Synthetic Scheme 2

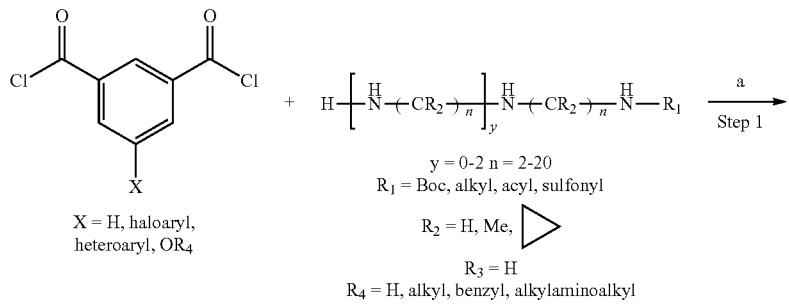

X = H, haloaryl, heteroaryl, OR$_4$ y = 0-2  n = 2-20
R$_1$ = Boc, alkyl, acyl, sulfonyl
R$_2$ = H, Me, △
R$_3$ = H
R$_4$ = H, alkyl, benzyl, alkylaminoalkyl

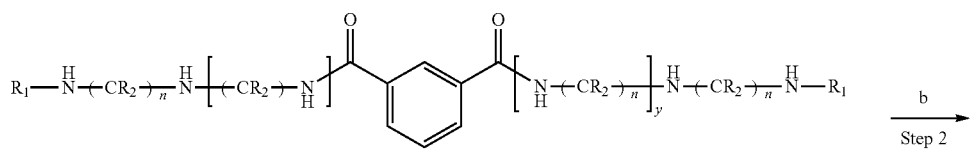

z = 0-W
W = total # of basic amines

Reagents: (a) TEA, CH$_2$Cl$_2$, rt, 1-28 h; (b) HCl, MeOH, rt 1-4 h.

In some embodiments, the polyamine compound may be produced by the reductive amination method of General Synthetic Scheme 3.
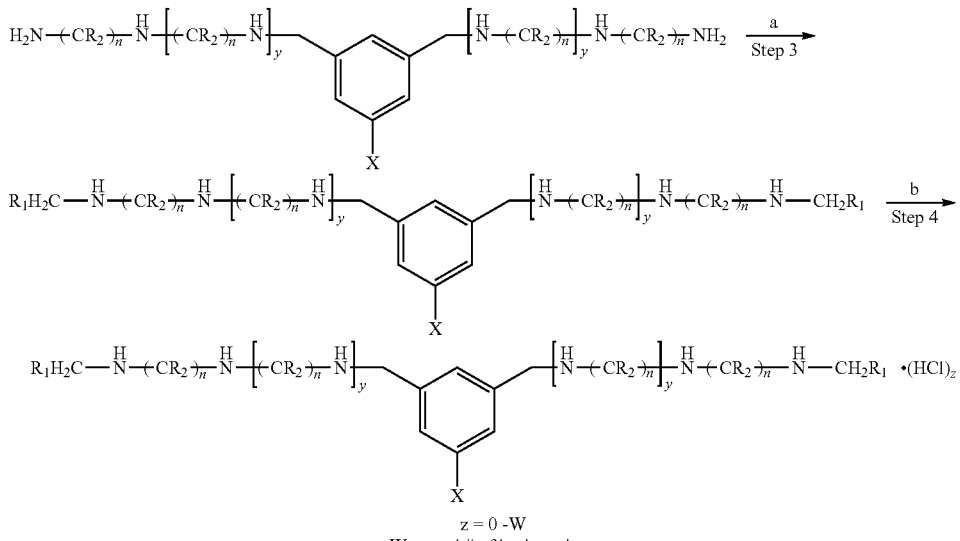
Reagents: (a) R₁CHO, Meoh, 3 Å molecular sieves, rt, 1-28 h; NaBH₄; (b) HCl, MeOH, rt 1-4 h.
In some embodiments, the polyamine compound may be produced by the reductive amination method of General Synthetic Scheme 4.
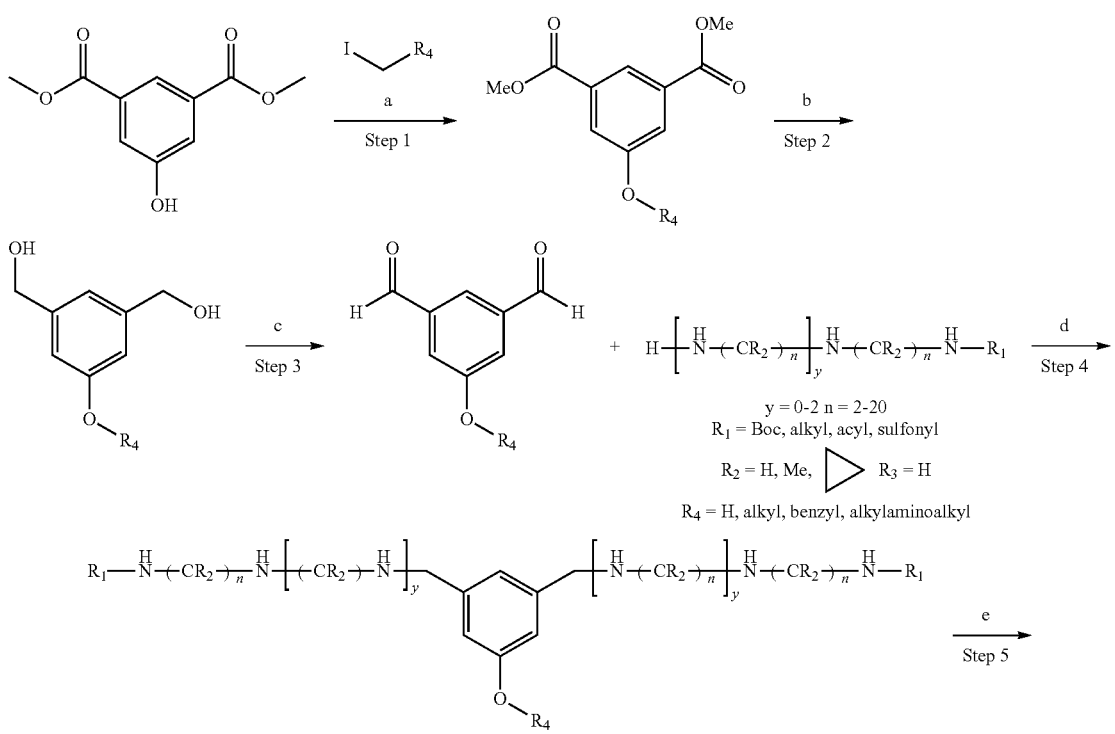

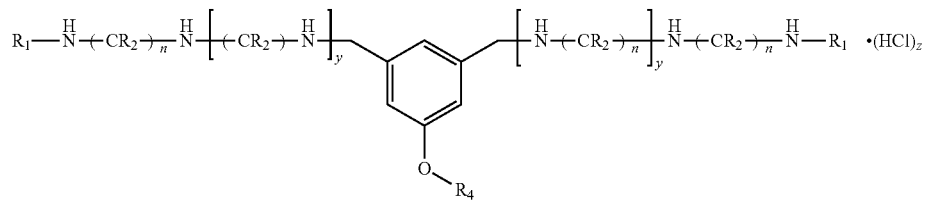

Z = 0-W
W = total # of basic amines

Reagents: (a) CH₃CN, Cs₂CO₃, rt, 16 h; (b) THF, LiAlH₄, rt, 8 h; (c) PCC, CH₂Cl₂, rt 1-4 h; (d) MeOH, 3 Å molecular sieves, rt, 1-28 h; NaBH₄; (e) HCl, MeOH, rt 1-4 h.

In some aspects, the $R_4CH_2I$ can include a different leaving group for the nucleophilic substitution reaction of (a). Other leaving groups useful for phenol alkylation include Br, Cl, tosylate, mesylate, triflate, and the like.

The precursor compounds shown below were made by the method of Steps 1 to 3 in the General Synthetic Scheme 4 above.

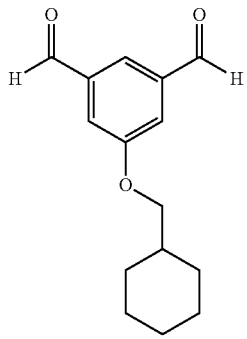 [SMILES: O=Cc1cc(C=O)cc(OCC2CCCCC2)c1]

5-(Cyclohexylmethoxy)isophthalaldehyde: ¹H NMR (300 MHz, CDCl₃) δ ppm 10.02 (s, 2H), 7.91 (s, 1H), 7.61 (s, 2H), 3.84 (d, J=6.0 Hz, 2H), 1.87-1.67 (m, 6H), 1.31-1.03 (m, 5H). ¹³C NMR (75 MHz, CDCl₃) δ ppm 191.4, 160.9, 138.6, 124.3, 120.2, 74.6, 37.9, 30.1, 26.7, 26.0.

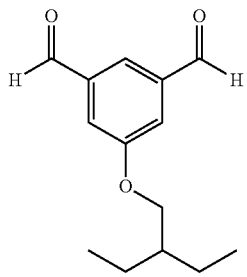 [SMILES: CCC(CC)COc1cc(C=O)cc(C=O)c1]

5-(2-Ethylbutoxy)isophthalaldehyde: ¹H NMR (500 MHz, CDCl₃) δ ppm 10.01 (s, 2H), 7.90 (s, 1H), 7.62 (s, 2H), 3.94 (d, J=5.5 Hz, 2H), 1.68 (hept, J=6.5 Hz, 1H), 1.46 (dec, J=6.5 Hz, 4H), 0.91 (t, J=7.5 Hz, 6H). ¹³C NMR (125 MHz, CDCl₃) δ ppm 191.1, 160.7, 138.5, 124.1, 120.0, 71.1, 40.9, 23.5, 11.3.

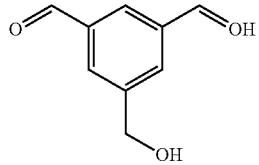 [SMILES: O=Cc1cc(C=O)cc(CO)c1]

5-(Hydroxymethyl)isophthalaldehyde: ¹H NMR (500 MHz, CDCl₃) δ ppm 10.09 (s, 2H), 8.27 (s, 1H), 8.15 (s, 2H), 4.88 (s, 2H), 2.54 (br s, 1H). ¹³C NMR (125 MHz, CDCl₃) δ ppm 191.4, 143.7, 137.4, 132.8, 130.3, 63.9.

In some embodiments, the polyamine compound may be produced by the method of Scheme 5, wherein $R^1$ may be hydrogen or a $C_1$-$C_{13}$ alkyl group.

Scheme 5

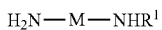

[1]

-continued

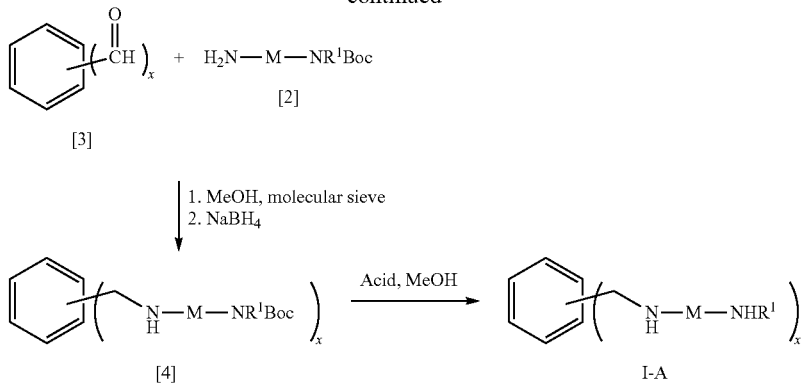

The method of Scheme 6 may include reacting a polyamine of Formula [1] with di-t-butyldicarbonate compound [(Boc)$_2$O] to protect at least one terminal amine group of the polyamine [1], while leaving at least one terminal amine group of the polyamine [1] unprotected. The resulting polyamine of Formula [2] having at least one Boc-protected terminal amine is reacted with a substituted benzaldehyde of Formula [3]. Then, the resulting product is reduced, such as by a hydride reducing agent (e.g., NaBH$_4$ or LiAlH$_4$) to provide a corresponding polyamine conjugate of Formula [4] having the terminal amine group on at least one hydrophilic polyamine chain Boc-protected. The Boc-protected terminal amine group is then deprotected, such as by acid hydrolysis, to provide the polyamine compound of Formula I-A comprising a hydrophobic phenyl group and at least one hydrophilic polyamine chain.

In some embodiments, the polyamine compound of Formula VIII-P may be produced by the method of Scheme 6, wherein R$^1$ may independently be hydrogen or C$_1$-C$_{13}$ alkyl group.

Scheme 6

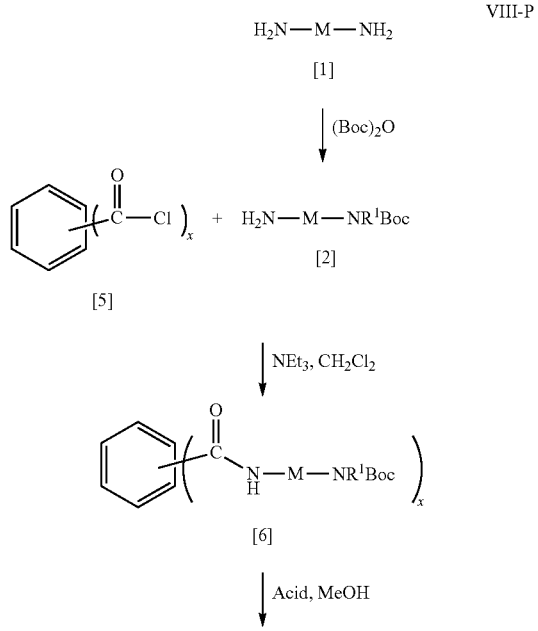

-continued

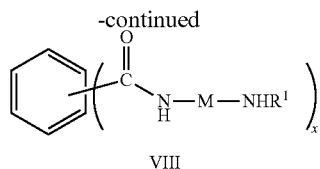

The method of Scheme 7 may include reacting the substituted benzoyl chloride of Formula [5] with a polyamine of Formula [2] having at least one terminal amine group protected with a Boc-protecting group, in a presence of base such as triethylamine (NEt$_3$) to provide a corresponding substituted benzyl amide of Formula [6]. The compound of Formula [6] comprises a hydrophobic phenyl group and at least one hydrophilic polyamine chain having a Boc-protected terminal amine group. Then, the Boc-protected terminal amine group of the hydrophilic polyamine chain is deprotected, such as by acid hydrolysis, to provide the polyamine compound of Formula VIII-P.

The polyamine compounds exhibit unexpectedly superior ability in treating biofilms, compared to most known antimicrobial compounds. The microorganisms in the biofilm community may be eradicated effectively and rapidly such that they have minimum, if any, opportunity to upregulate their defense mechanism and develop resistance against the polyamine compound. Without being bound by any theory, it is believed that the unexpectedly superior biofilms treatment is due to the beneficial synergistic of hydrophobicity and hydrophilicity of the polyamine compound. It is believed that the hydrophobic moiety of the polyamine compound facilitates the dispersion of the microorganisms in biofilms, while the hydrophilic polyamine moiety provides an antimicrobial effect on the dispersed microorganisms.

The polyamine compounds may eradicate the biofilms, reduce the formation of biofilms, or inhibit the formation of biofilms. The hydrophobicity and hydrophilicity of the polyamine compounds may be designed by tailoring the hydrophobic moieties and hydrophilic moieties of the polyamine compounds such that the desired level of antimicrobial effect on the biofilms may be achieved. One skilled in the arts recognizes the parameters controlling the hydrophobicity/hydrophilicity effect, and, therefore, may readily modify the teachings of present disclosure to produce various polyamine compounds without departing from the scope of present disclosure. As non-limiting examples, the hydrophilicity effect of the polyamine compound may be modified by varying numbers of the hydrophilic polyamine chains in the polyamine compound, numbers of amine groups in the hydrophilic polyamine chains, numbers of carbons between amine groups in the hydrophilic polyamine chains, etc. As non-limiting examples, the hydrophobicity effect of the polyamine compound may be modified by varying positions of the hydrophilic polyamine chains on the hydrophobic groups, altering chemical structures of the hydrophobic groups to other known non-polar functional group, etc.

The polyamine compounds may exhibit enhanced antimicrobial effect on biofilms comprised of Gram-negative or Gram-positive bacteria. The polyamine compounds may exhibit enhanced antimicrobial effect on biofilms consisting of mycobacteria.

In one embodiment, the antimicrobial composition may comprise a polyamine compound and at least one additive. Various additives may be used for the antimicrobial composition. By way of non-limiting examples, the additives may further enhance the dispersion of microorganisms in biofilms, impart the antimicrobial effect against the dispersed microorganisms, facilitate the application/administration of the antimicrobial composition to the biofilms, improve the stability of the antimicrobial composition, control the release/application rate of the antimicrobial composition to the biofilms, etc. Non-limiting examples of additives for further enhancing the antimicrobial effect may be biocide and other bactericide. By way of non-limiting examples, the additives for facilitating the administration of the antimicrobial composition may include a pharmaceutically acceptable carrier typically used for medical or pharmaceutical applications, an emulsifier or dispersant typically used for industrial applications.

The antimicrobial composition may be formulated to provide the desired level of antimicrobial effect on the biofilms by selecting a polyamine compound and other additives as well as by adjusting the amount of each component in the antimicrobial composition. In some embodiments, the antimicrobial composition may be formulated to inhibit the formation of biofilms. In some embodiment, the antimicrobial composition may be formulated to disrupt the biofilms. In still other embodiments, the antimicrobial composition may be formulated to eradicate substantially all microorganisms in the biofilms.

Any suitable amount of polyamine can be used in the compositions and methods of the invention. In general, the polyamines are used in concentrations ranging from about 1 ppm to about 100,000 ppm, or higher. The concentration of a polyamine used in a composition or method of the invention can be, for example, from about 1 to about 100,000 ppm, or from about 10 to about 10,000 ppm, or from about 100 to about 1,000 ppm, or from about 1 to about 100 ppm, or from about 1,000 to about 10,000 ppm, or from about 10,000 to about 100,000 ppm. The concentration of a polyamine can be about 1; 2; 3; 4; 5; 6; 7; 8; 9; 10; 15; 20; 25; 30; 35; 40; 45; 50; 55; 60; 65; 70; 75; 80; 85; 90; 95; 100; 125; 150; 175; 200; 225; 250; 275; 300; 325; 350; 375; 400; 425; 450; 475; 500; 525; 550; 575; 600; 625; 650; 675; 700; 725; 750; 775; 800; 825; 850; 875; 900; 925; 950; 975; 1000; 1500; 2000; 2500; 3000; 3500; 4000; 4500; 5000; 5500; 6000; 6500; 7000; 7500; 8000; 8500; 9000; 9500; 10,000; 12,500; 15,000; 17,500; 20,000; 22,500; 25,000; 27,500; 30,000; 32,500; 35,000; 37,500; 40,000; 42,500; 45,000; 47,500; 50,000; 52,500; 55,000; 57,500; 60,000; 62,500; 65,000; 67,500; 70,000; 72,500; 75,000; 77,500; 80,000; 82,500; 85,000; 87,500; 90,000; 92,500; 95,000; 97,500; or about 100,000 ppm. Other concentrations of polyamines can be useful in the compositions and methods of the invention, depending in part on factors including the specific polyamine used, the presence of potentiating agents if any, or the species of microorganisms that are targeted.

In certain aspects, increasing number of polyamine chains on the hydrophobic backbone systematically increase the antimicrobial activity. For example, it is demonstrated herein that with a single chain of diaminopropane added to a benzyl backbone (CZ-4, FIG. 25), the MIC (as defined by the Clinical and Laboratory Standards Institute (CLSI)) against MRSA is greater than 1,200 µg/mL, whereas two chains decrease the MIC to 300 µg/mL (CZ-12) and three chains reduce it further to 45 µg/mL (CZ-32). Similarly, with a single chain of norspermidine attached to a benzyl backbone (CZ-7, FIG. 25), the MIC against MRSA is greater than 1,200 µg/mL. By adding a second chain of norspermidine (CZ-25), the MIC is 45 µg/mL. With a third chain of norspermidine attached (CZ-52), the MIC becomes 3 µg/mL (FIG. 25).

This trend of enhancing antimicrobial activity by increasing the number of polyamine chains attached to a backbone is effective for treating MRSA, but modulating this trend with increased hydrophobicity enhances the activity of CZ compounds against *A. baumannii*. Interestingly, CZ-52, with three norspermidine chains, has greater activity against MRSA biofilms than against *A. baumannii*, whereas CZ-58 (FIG. 27) has greater activity (10-fold increase) against *A. baumannii* biofilms than MRSA biofilms (see Table 4 below).

Applications

As described herein, biofilms can also affect a wide variety of biological, medical, and processing operations. Methods and treatments using a polyamine compound, or a combination of a polyamine compound with another compound, may include killing, dispersing, treating, reducing biofilms or preventing or inhibiting biofilm formation.

In one embodiment, the invention provides a method for dispersing or killing a biofilm, the method comprising a step of treating the biofilm with an anti-biofilm composition, thereby effectively dispersing or killing the biofilm; wherein the method comprises, consists essentially of, or consists of using a polyamine compound or composition as set forth in any of the embodiments or aspects described herein.

In some aspects, the step of treating the biofilm with an anti-biofilm composition effectively disperses the biofilm.

In another embodiment, the invention provides a method for inhibiting formation of a biofilm, the method comprising a step of treating planktonic bacteria with a polyamine composition as set forth in any of the embodiments or aspects herein, thereby inhibiting incorporation of the planktonic bacteria into the biofilm.

In certain aspects, the method of killing, dispersing, dislodging, treating, or reducing biofilms, or preventing or inhibiting biofilm formation, includes contacting the biofilm with an effective amount of a composition of the present invention.

In some aspects, the formation of a biofilm is inhibited. In other aspects, a previously formed biofilm is dispersed. In still other aspects, substantially all of the cells comprising a biofilm are killed.

In some embodiments, the invention provides a method of killing, dispersing, treating, or reducing biofilms, or preventing or inhibiting biofilm formation, the method comprising contacting a biofilm or a surface having a biofilm disposed thereon with an effective amount of a polyamine compound.

In some aspects, a surface comprises a medical device, a wound dressing, a contact lens, or an oral device. In some aspects, the medical device is selected from a clamp, forceps, scissors, skin hook, tubing, needle, retractor, scaler, drill, chisel, rasp, saw, catheter, orthopedic device, artificial heart valve, prosthetic joint, voice prosthetic, stent, shunt, pacemaker, surgical pin, respirator, ventilator, and an endoscope and combinations thereof.

In some aspects, the method described herein comprises, consists essentially of, or consists of using the polyamine compound or composition described in any of the embodiments or aspects herein.

In some aspects, the invention provides a method that comprises, consists essentially of, or consists of using a polyamine compound or composition from any of the embodiments or aspects described herein.

In some embodiments, the invention provides a method for dispersing or killing a biofilm, the method comprising a step of treating the biofilm with an anti-biofilm composition, thereby effectively dispersing or killing the biofilm;

wherein the anti-biofilm composition comprises, consists essentially of, or consists of a polyamine compound selected from any of the embodiments or aspects described herein.

In some embodiments, the polyamine compound or combination of a polyamine compound and at least one other composition may be used to treat Gram negative and Gram positive bacteria (including strains that are resistant to conventional antibiotics), mycobacteria (including *Mycobacterium tuberculosis*), enveloped viruses, fungi and even transformed or cancerous cells.

In some embodiments, the polyamine compounds of the present invention are used for the treatment of cancer. The method comprises administering to a subject a composition comprising a polyamine compound as described herein in an amount effective to reduce cancer cell proliferation or differentiation. In some embodiments, the cancer is breast cancer, a leukemia, or a melanoma. In some embodiments, the method includes administering to the subject an effective amount of a composition comprising a polyamine compound as described herein and a chemotherapeutic agent. The polyamine compounds and compositions can be administered according to known methods. Such methods are described, for example, in International Patent Application No. PCT/US2013/031166, which is incorporated herein by reference in its entirety.

The compounds, compositions, and methods described herein can be used to kill, disperse, treat, reduce biofilms, or prevent or inhibit biofilm formation. In exemplary methods, the biofilms are formed by biofilm-forming bacteria. The bacteria can be a gram-negative bacterial species or a gram-positive bacterial species. Nonlimiting examples of such bacteria include a member of the genus *Actinobacillus* (such as *Actinobacillus actinomycetemcomitans*), a member of the genus *Acinetobacter* (such as *Acinetobacter baumannii*), a member of the genus *Aeromonas*, a member of the genus *Bordetella* (such as *Bordetella pertussis, Bordetella bronchiseptica*, or *Bordetella parapertussis*), a member of the genus *Brevibacillus*, a member of the genus *Brucella*, a member of the genus *Bacteroides* (such as *Bacteroidesfragilis*), a member of the genus *Burkholderia* (such as *Burkholderia cepacia* or *Burkholderia pseudomallei*), a member of the genus *Borelia* (such as *Borelia burgdorferi*), a member of the genus *Bacillus* (such as *Bacillus anthracis* or *Bacillus subtilis*), a member of the genus *Campylobacter* (such as *Campylobacter jejuni*), a member of the genus *Capnocytophaga*, a member of the genus *Cardiobacterium* (such as *Cardiobacterium hominis*), a member of the genus *Citrobacter*, a member of the genus *Clostridium* (such as *Clostridium tetani* or *Clostridium dificile*), a member of the genus *Chlamydia* (such as *Chlamydia trachomatis, Chlamydia pneumoniae*, or *Chlamydia psiffaci*), a member of the genus *Eikenella* (such as *Eikenella corrodens*), a member of the genus *Enterobacter*, a member of the genus *Escherichia* (such as *Escherichia coli*), a member of the genus *Francisella* (such as *Francisella tularensis*), a member of the genus *Fusobacterium*, a member of the genus *Flavobacterium*, a member of the genus *Haemophilus* (such as *Haemophilus ducreyi* or *Haemophilus influenzae*), a member of the genus *Helicobacter* (such as *Helicobacter pylori*), a member of the genus *Kingella* (such as *Kingella kingae*), a member of the genus *Klebsiella* (such as *Klebsiella pneumoniae*), a member of the genus *Legionella* (such as *Legionella pneumophila*), a member of the genus *Listeria* (such as *Listeria monocytogenes*), a member of the genus *Leptospirae*, a member of the genus *Moraxella* (such as *Moraxella catarrhalis*), a member of the genus *Morganella*, a member of the genus *Mycoplasma* (such as *Mycoplasma hominis* or *Mycoplasma pneumoniae*), a member of the genus *Mycobacterium* (such as *Mycobacterium tuberculosis* or *Mycobacterium leprae*), a member of the genus *Neisseria* (such as *Neisseria gonorrhoeae* or *Neisseria meningitidis*), a member of the genus *Pasteurella* (such as *Pasteurella multocida*), a member of the genus *Proteus* (such as *Proteus vulgaris* or *Proteus mirablis*), a member of the genus *Prevotella*, a member of the genus *Plesiomonas* (such as *Plesiomonas shigelloides*), a member of the genus *Pseudomonas* (such as *Pseudomonas aeruginosa*), a member of the genus *Providencia*, a member of the genus *Rickettsia* (such as *Rickettsia rickettsii* or *Rickettsia typhi*), a member of the genus *Stenotrophomonas* (such as *Stenotrophomonas maltophila*), a member of the genus *Staphylococcus* (such as *Staphylococcus aureus* or *Staphylococcus epidermidis*), a member of the genus *Streptococcus* (such as *Streptococcus viridans, Streptococcus pyogenes* (group A), *Streptococcus agalactiae* (group B), *Streptococcus bovis*, or *Streptococcus pneumoniae*), a member of the genus *Streptomyces* (such as *Streptomyces hygroscopicus*), a member of the genus *Salmonella* (such as *Salmonella enteriditis, Salmonella typhi*, or *Salmonella typhimurium*), a member of the genus *Serratia* (such as *Serratia marcescens*), a member of the genus *Shigella*, a member of the genus *Spirillum* (such as *Spirillum minus*), a member of the genus *Treponema* (such as *Treponema pallidum*), a member of the genus *Veillonella*, a member of the genus *Vibrio* (such as *Vibrio cholerae, Vibrio parahaemolyticus*, or *Vibrio vulnificus*), a member of the genus *Yersinia* (such as *Yersinia enter ocolitica, Yersinia pestis*, or *Yersinia pseudotuberculosis*), and a member of the genus *Xanthomonas* (such as *Xanthomonas maltophilia*).

In some embodiments, the biofilm exposed to the compounds, compositions, or methods of the present invention may comprise Gram-negative or Gram-positive bacteria. In some embodiments, the bacteria are mycobacteria.

In some aspects, the biofilm comprises an antibiotic-resistant bacterial species.

The antimicrobial compounds, compositions, and methods comprising a polyamine compound may be used to control, prevent or kill biofilms in various environments. In some embodiments, they may be used for treating biofilms in subjects that include human or other animals. In some embodiments, they may be used for treating biofilms in medical applications such as medical devices, wound dressings, contact lens, oral devices, etc. In some embodiments, they may be used for treating or preventing a biofilm-related disorder. In some embodiments, they may be used for treating biofilms in industrial applications such as oil pipelines, water pipelines, water treatment at manufacturing sites, industrial flush solution, industrial wash water, industrial coatings, etc. In some embodiments, they may be used for household and hygiene applications. In some embodiments, they may be used for agricultural applications, such as water remediation, crop treatment, etc. In some embodiments, they may be used for food preparation applications, such as meat sprays, fruit and vegetable sanitizers.

In some aspects, the method comprises a step of coating an object with the anti-biofilm composition. In some aspects, the method comprises a step of treating a contact lens with the anti-biofilm composition.

In some embodiments, the polyamine compound or combination of a polyamine compound and at least one other composition are directed for use in industrial applications, for example oil pipelines, water treatment, water pipelines, fracking water sanitation, milk production facility pipeline flush solution, oil fields, paper and pulp production, machining fluids, ship coatings, shipping, paint, handrail sanitizers, water filtration, biofouling and biocorrosion, natural gas pipeline treatment, HVAC units, etc.

In some embodiments, the polyamine compound or combination of a polyamine compound and at least one other composition are directed for use in household applications, for example, sanitizing wipes, cleansers, toilet bowl inserts, baby care products, toys, etc.

In some embodiments, the polyamine compound or combination of a polyamine compound and at least one other composition are directed for use in environmental applications, for example, agriculture, water remediation, water treatment, crop treatment, etc.

In some aspects, the method comprises a step of treating a pipe with the anti-biofilm composition. In some aspects, the method comprises a step of treating a heating or cooling tower with the anti-biofilm composition.

In some embodiments, the polyamine compound or combination of a polyamine compound and at least one other composition are directed for use in food production, for example, fruit and vegetable sanitizers, water systems in food production facilities, meat sprays, cooling system sanitizers, air filtration units, feed, packaging, etc.

In some aspects, the anti-biofilm composition is a paint.

In some aspects, the method comprises a step of treating a patient with a biofilm-related disorder.

Some aspects of this disclosure is directed to methods of treating a biofilm-related disorder in a subject in need thereof, the method comprising administering to the subject an effective amount of a polyamine compound of the present invention.

In some embodiments, the composition is administered to a surface of the subject selected from the group of dermal and mucosal surfaces and combinations thereof. In other embodiments, the surface is an oral surface, a skin surface, a urinary tract surface, a vaginal tract surface, or a lung surface.

In some embodiments, the composition is administered to the subject via subcutaneous, intra-muscular, intra-peritoneal, intravenous, oral, nasal, or topical administration, and a combination thereof.

In some aspects, a subject is treated. A subject can be a mammal including, but not limited to, a primate (e.g., a monkey, such as a cynomolgous monkey, a chimpanzee, and a human). A subject can be a non-human animal such as a bird (e.g., a quail, chicken, or turkey), a farm animal (e.g., a cow, goat, horse, pig, or sheep), a pet (e.g., a cat, dog, or guinea pig, rat, or mouse), or laboratory animal (e.g., an animal model for a disorder). Non-limiting representative subjects can be a human infant, a pre-adolescent child, an adolescent, an adult, or a senior/elderly adult.

In some embodiments, the subject is a human.

In some instances, a subject in need of treatment can be one afflicted with one or more of the infections or disorders described herein. In some aspects, the subject is at risk of developing a biofilm on or in a biologically relevant surface, or already has developed such a biofilm. Such a subject at risk can be a candidate for treatment with a polyamine compound, or combination of a polyamine compound with another compound, in order to inhibit the development or onset of a biofilm-production-related disorder/condition or prevent the recurrence, onset, or development of one or more symptoms of a biofilm-related disorder or condition. Such a subject can be harboring an immature biofilm that is clinically evident or detectable to the skilled artisan, but that has not yet fully formed. A subject at risk of developing a biofilm can also be one in which implantation of an indwelling device, such as a medical device, is scheduled. The risk of developing a biofilm can also be due to a propensity of developing a biofilm-related disease (such as the presence of a channel transporter mutation associated with cystic fibrosis). In such subjects, a biofilm-related disorder can be at an early stage, e.g., no bacterial infection or biofilm formation is yet detected.

In certain embodiments a biofilm-related disorder is selected from pneumonia, cystic fibrosis, otitis media, chronic obstructive pulmonary disease, and a urinary tract infection and combinations thereof. In other embodiments, the biofilm-related disorder is a medical device-related infection. In further embodiments, the biofilm-related disorder is a periodontal disease, such as gingivitis, periodontitis or breath malodor. In still further embodiments, the biofilm-related disorder is caused by bacteria. In some embodiments, the bacteria are Gram-negative or Gram-positive bacteria. In still other embodiments, the bacteria are of the genus *Actinobacillus, Acinetobacter, Aeromonas, Bordetella, Brevibacillus, Brucella, Bacteroides, Burkholderia, Borelia, Bacillus, Campylobacter, Capnocytophaga, Cardiobacterium, Citrobacter, Clostridium, Chlamydia, Eikenella, Enterobacter, Escherichia, Entembacter, Francisella, Fusobacterium, Flavobacterium, Haemophilus, Helicobacter, Kingella, Klebsiella, Legionella, Listeria, Leptospirae, Moraxella, Morganella, Mycoplasma, Mycobacterium, Neisseria, Pasteurella, Proteus, Prevotella, Plesiomonas, Pseudomonas, Providencia, Rickettsia, Stenotrophomonas, Staphylococcus, Streptococcus, Streptomyces, Salmonella, Serratia, Shigella, Spirillum, Treponema, Veillonella, Vibrio, Yersinia,* or *Xanthomonas*.

Non-limiting examples of biofilm-related disorders include otitis media, prostatitis, cystitis, bronchiectasis, bacterial endocarditis, osteomyelitis, dental caries, periodontal disease, infectious kidney stones, acne, Legionnaire's disease, chronic obstructive pulmonary disease (COPD), and cystic fibrosis. In one specific example, subjects with cystic fibrosis display an accumulation of biofilm in the lungs and digestive tract. Subjects afflicted with COPD, such as emphysema and chronic bronchitis, display a characteristic inflammation of the airways wherein airflow through such airways, and subsequently out of the lungs, is chronically obstructed.

Biofilm-related disorders can also encompass infections derived from implanted/inserted devices, medical device-related infections, such as infections from biliary stents, orthopedic implant infections, and catheter-related infections (kidney, vascular, peritoneal). An infection can also originate from sites where the integrity of the skin or soft tissue has been compromised. Non-limiting examples include dermatitis, ulcers from peripheral vascular disease, a burn injury, and trauma. For example, a Gram-positive bacterium, such as *S. pneumoniae*, can cause opportunistic infections in such tissues. The ability of *S. pneumoniae* to infect burn wound sites, e.g., is enhanced due to the breakdown of the skin, burn-related immune defects, and antibiotic selection.

In yet other embodiments, a biofilm-related disorder is pneumonia, cystic fibrosis, otitis media, chronic obstructive pulmonary disease, or a urinary tract infection. In some embodiments, the biofilm-related disorder is a medical device-related infection.

In other aspects, this disclosure features compounds, compositions, or methods, such as industrial, therapeutic or pharmaceutical compositions, comprising polyamine compounds in combination with one or more additional active compositions.

In some instances a polyamine compound can be administered alone or in combination with a second agent, e.g. a biocide, an antibiotic, or an antimicrobial agent, to thereby kill, disperse, treat, reduce prevent, or inhibit bacterial biofilms. An antibiotic can be co-administered with the polyamine compound either sequentially or simultaneously.

The antibiotic can be any compound known to one of ordinary skill in the art that can inhibit the growth of, or kill, bacteria. Useful, non-limiting examples of antibiotics include lincosamides (clindomycin); chloramphenicols; tetracyclines (such as tetracycline, chlortetracycline, demeclocycline, methacycline, doxycycline, minocycline); aminoglycosides (such as gentamicin, tobramycin, netilmicin, smikacin, kanamycin, streptomycin, neomycin); beta-lactams (such as penicillins, cephalosporins, imipenem, aztreonam); glycopeptide antibiotics (such as vancomycin); polypeptide antibiotics (such as bacitracin); macrolides (erythromycins), amphotericins; sulfonamides (such as sulfanilamide, sulfamethoxazole, sulfacetamide, sulfadiazine, sulfisoxazole, sulfacytine, sulfadoxine, mafenide, p-aminobenzoic acid, trimethoprim-sulfamethoxazole); methenamin; nitrofurantoin; phenazopyridine; trimethoprim; rifampicins; metronidazoles; cefazolins; lincomycin; spectinomycin; mupirocins; quinolones (such as nalidixic acid, cinoxacin, norfloxacin, ciprofloxacin, perfloxacin, ofloxacin, enoxacin, fleroxacin, levofloxacin); novobiocins; polymixins; gramicidins; and antipseudomonals (such as carbenicillin, carbenicillin indanyl, ticarcillin, azlocillin, mezlocillin, piperacillin) or any salts or variants thereof. Such antibiotics are commercially available, e.g., from Daiichi Sankyo, Inc. (Parsipanny, N.J.), Merck (Whitehouse Station, N.J.), Pfizer (New York, N.Y.), Glaxo Smith Kline (Research Triangle Park, N.C.), Johnson & Johnson (New Brunswick, N.J.), AstraZeneca (Wilmington, Del.), Novartis (East Hanover, N.J.), and Sanofi-Aventis (Bridgewater, N.J.). The antibiotic used will depend on the type of bacterial infection.

Additional known biocides include biguanide, chlorhexidine, triclosan, chlorine dioxide, and the like.

Useful examples of antimicrobial agents include, but are not limited to, Pyrithiones, especially the zinc complex (ZPT); Octopirox®; dimethyldimethylol hydantoin (Glydant®); methylchloroisothiazolinone/methylisothiazolinone (Kathon CG®); sodium sulfite; sodium bisulfite; imidazolidinyl urea (Germall 115®), diazolidinyl urea (Germaill II®); benzyl alcohol; 2-bromo-2-nitropropane-1,3-diol (Bronopol®); formalin (formaldehyde); iodopropenyl butyl-carbamate (Polyphase PI 00®); chloroacetamide; methanamine; methyldibromonitrile glutaronitrile (1,2-dibromo-2,4-dicyanobutane or Tektamer®); glutaraldehyde; 5-bromo-5-nitro-1,3-dioxane (Bronidox®); phenethyl alcohol; o-phenylphenol/sodium o-phenylphenol; sodium hydroxymethylglycinate (Suttocide A®); polymethoxy bicyclic oxazolidine (Nuosept C®); dimethoxane; thimersal; dichlorobenzyl alcohol; captan; chlorphenenesin; dichlorophene; chlorbutanol; glyceryl laurate; halogenated diphenyl ethers; 2,4,4'-trichloro-2'-hydroxy-diphenyl ether (Triclosan®. or TCS); 2,2'-dihydroxy-5,5'-dibromo-diphenyl ether; phenolic compounds; phenol; 2-methylphenol; 3-methylphenol; 4-methylphenol; 4-ethylphenol; 2,4-dimethylphenol; 2,5-dimethylphenol; 3,4-dimethylphenol; 2,6-dimethylphenol; 4-n-propylphenol; 4-n-butylphenol; 4-n-amylphenol; 4-tert-amylphenol; 4-n-hexylphenol; 4-n-heptylphenol; mono- and poly-alkyl and aromatic halophenols; p-chlorophenol; methyl p-chlorophenol; ethyl p-chlorophenol; n-propyl p-chlorophenol; n-butyl p-chlorophenol; n-amyl p-chlorophenol; sec-amyl p-chlorophenol; cyclohexyl p-chlorophenol; n-heptyl p-chlorophenol; n-octyl p-chlorophenol; o-chlorophenol; methyl o-chlorophenol; ethyl o-chlorophenol; n-propyl o-chlorophenol; n-butyl o-chlorophenol; n-amyl o-chlorophenol; tert-amyl o-chlorophenol; n-hexyl o-chlorophenol; n-heptyl o-chlorophenol; o-benzyl p-chlorophenol; o-benzyl-m-methyl p-chlorophenol; o-benzyl-m,m-dimethyl-p-chlorophenol; o-phenylethyl-p-chlorophenol; o-phenylethyl-m-methyl p-chlorophenol; 3-methyl p-chlorophenol; 3,5-dimethyl p-chlorophenol; 6-ethyl-3-methyl p-chlorophenol; 6-n-propyl-3-methyl-p-chlorophenol; 6-isopropyl-3-methyl-p-chlorophenol; 2-ethyl-3,5-dimethyl p-chlorophenol; 6-sec-butyl-3-methyl p-chlorophenol; 2-isopropyl-3, 5-dimethyl p-chlorophenol; 6-diethylmethyl-3-methyl p-chlorophenol; 6-isopropyl-2-ethyl-3-methyl p-chlorophenol; 2-sec-amyl-3, 5-dimethyl p-chlorophenol; 2-diethylmethyl-3, 5-dimethyl p-chlorophenol; 6-sec-octyl-3-methyl p-chlorophenol; p-chloro-m-cresol: p-bromophenol; methyl p-bromophenol; ethyl p-bromophenol; n-propyl p-bromophenol; n-butyl p-bromophenol; n-amyl p-bromophenol; sec-amyl p-bromophenol; n-hexyl p-bromophenol; cyclohexyl p-bromophenol; o-bromophenol; tert-amyl o-bromophenol; n-hexyl o-bromophenol; n-propyl-m,m-dimethyl-o-bromophenol; 2-phenylphenol; 4-chloro-2-methylphenol; 4-chloro-3-methyl phenol; 4-chloro-3,5-dimethyl phenol; 2,4-dichloro-3,5-dimethylphenol; 3,4,5,6-tetrabromo-2-methyl-phenol; 5-methyl-2-pentylphenol; 4-isopropyl-3-methylphenol; p-chloro-m-xylenol (PCMX); chlorothymol; phenoxyethanol; phenoxyisopropanol; 5-chloro-2-hydroxydiphenylmethane; resorcinol and its derivatives; resorcinol; methyl resorcinol; ethyl resorcinol; n-propyl resorcinol; n-butyl resorcinol; n-amyl resorcinol; n-hexyl resorcinol; n-heptyl resorcinol; n-octyl resorcinol; n-nonyl resorcinol; phenyl resorcinol; benzyl resorcinol; phenylethyl resorcinol; phenylpropyl resorcinol; p-chlorobenzyl resorcinol; 5-chloro 2,4-dihydroxydiphenyl methane; 4'-chloro 2,4-dihydroxydiphenyl methane; 5-bromo 2,4-dihydroxydiphenyl methane; 4'-bromo 2,4-dihydroxydiphenyl methane; bisphenolic compounds; 2,2'-methylene bis-(4-chlorophenol); 2,2'-methylene bis-(3,4,6-trichlorophenol); 2,2'-methylene bis(4-chloro-6-bromophenol); bis(2-hydroxy-3,5-dichlorophenyl) sulfide; bis(2-hydroxy-5-chlorobenzyl)sulfide; benzoic esters (parabens); methylparaben; propylparaben; butylparaben; ethylparaben; isopropylparaben; isobutylparaben; benzylparaben; sodium methylparaben; sodium propylparaben; halogenated carbanilides; 3,4,4'-trichlorocarbanilides (e.g., Triclocarban® or TCC); 3-trifluoromethyl-4,4'-dichlorocarbanilide; 3,3',4-trichlorocarbanilide; chlorohexidine and its digluconate; diacetate and dihydrochloride; undecenoic acid; thiabendazole, hexetidine; and poly(hexamethylenebiguanide) hydrochloride (Cosmocil®).

In some embodiments of any methods described herein, the method further comprises administering a biocide. In some embodiments, the biocide is an antibiotic.

In instances where a polyamine compound, or combination of a polyamine compound with another compound, is to be administered to a subject, the compound or composition herein can be incorporated into pharmaceutical compositions. The polyamine compound, or combination of a polyamine compound with another compound, can be incorporated into pharmaceutical compositions as pharmaceutically acceptable salts or derivatives. Some pharmaceutically acceptable derivatives of the polyamine compounds of the present invention may include a chemical group, which increases aqueous solubility. As used herein, a "pharmaceutically acceptable carrier" means a carrier that can be administered to a subject together with a polyamine compound, or combination of a polyamine compound with another compound, described herein, which does not destroy the pharmacological activity thereof. Pharmaceutically acceptable carriers include, for example, solvents, binders, dispersion media, coatings, preservatives, colorants, isotonic and absorption delaying agents, and the like, compatible with pharmaceutical administration. Supplementary active compounds can also be incorporated into the compositions.

Non-limiting examples of pharmaceutically acceptable carriers that can be used include poly(ethylene-co-vinyl acetate), PVA, partially hydrolyzed poly(ethylene-co-vinyl acetate), poly(ethylene-co-vinyl acetate-co-vinyl alcohol), a cross-linked poly(ethylene-co-vinyl acetate), a cross-linked partially hydrolyzed poly(ethylene-co-vinyl acetate), a cross-linked poly(ethylene-co-vinyl acetate-co-vinyl alcohol), poly-D,L-lactic acid, poly-L-lactic acid, polyglycolic acid, PGA, copolymers of lactic acid and glycolic acid (PLGA), polycaprolactone, polyvalerolactone, poly (anhydrides), copolymers of polycaprolactone with polyethylene glycol, copolymers of polylactic acid with polyethylene glycol, polyethylene glycol; and combinations and blends thereof.

Other carriers include, e.g., an aqueous gelatin, an aqueous protein, a polymeric carrier, a cross-linking agent, or a combination thereof. In other instances, the carrier is a matrix. In yet another instances, the carrier includes water, a pharmaceutically acceptable buffer salt, a pharmaceutically acceptable buffer solution, a pharmaceutically acceptable antioxidant, ascorbic acid, one or more low molecular weight pharmaceutically acceptable polypeptides, a peptide comprising about 2 to about 10 amino acid residues, one or more pharmaceutically acceptable proteins, one or more pharmaceutically acceptable amino acids, an essential-to-human amino acid, one or more pharmaceutically acceptable carbohydrates, one or more pharmaceutically acceptable carbohydrate-derived materials, a non-reducing sugar, glucose, sucrose, sorbitol, trehalose, mannitol, maltodextrin, dextrins, cyclodextrin, a pharmaceutically acceptable chelating agent, EDTA, DTPA, a chelating agent for a divalent metal ion, a chelating agent for a trivalent metal ion, glutathione, pharmaceutically acceptable nonspecific serum albumin, or combinations thereof.

In other embodiments, the compositions can also comprise a pharmaceutically acceptable carrier. In still other embodiments the effective amount is an amount effective to treat or prevent a biofilm-related disorder. In some embodiments, an effective amount comprises and amount effective to treat or prevent a biofilm on a surface.

In some embodiments, the compositions discussed herein further comprises an agent suitable for application to the surface. In other embodiments, the composition is formulated as a wash solution, a dressing, a wound gel, or a synthetic tissue. In further embodiments, the composition is formulated as tablets, pills, troches, capsules, aerosol spray, solutions, suspensions, gels, pastes, creams, or foams. In some embodiments, the composition is formulated for parenteral (e.g., intravenous), intradermal, subcutaneous, oral (e.g., inhalation), transdermal (topical), transmucosal, vaginal, or rectal administration.

Another aspect of this disclosure is directed to biofilm resistant medical devices, comprising a surface likely to contact a biological fluid and a polyamine compound. In some embodiments, the medical device further comprises a polyamine compound, or combinations of a polyamine compound and at least one other composition, that is coated on or impregnated into said surface.

In some embodiments, the polyamine compound or combination of a polyamine compound and at least one other composition is formulated as a slow-release formulation.

In some embodiments, the polyamine compound or combination of a polyamine compound and at least one other composition are directed for use in medical applications, for example, active release or passive antimicrobial coatings for medical devices, lavage solutions for open wounds, oral mouthwashes, toothpaste additives, hand sanitizers, systemic prophylactic antibiotics, lock solutions for catheters, eye drop solutions for irrigation and contact lens cleaners, prophylactic dental inserts, high level disinfectants, gastrointestinal (GI) tract oral medications for the treatment of infections such as those caused by *Shigella, Cryptosporidium, Vibrio cholerae*, or *Clostridium difficile*, cancer treatment including multiple myeloma, osteosarcoma, lymphoma or other forms of cancer, topical ointments to treat dermatological complications including infection, canker sores, psoriasis, herpes, chronic wounds, diaper rash, onychomycosis (athletes foot), tinea unguium (toenail fungus), ulcers, or acne, etc.

In some embodiments, the base is selected from a liquid, gel, paste, or powder. In further embodiments, the composition is selected from shampoos, bath additives, hair care preparations, soaps, lotions, creams, deodorants, skin-care preparations, cosmetic personal care preparations, intimate hygiene preparations, foot care preparations, light protective preparations, skin tanning preparations, insect repellants, antiperspirants, shaving preparations, hair removal preparations, fragrance preparations, dental care, denture care and mouth care preparations and combinations thereof.

A pharmaceutical composition containing a polyamine compound, or combination of a polyamine compound with another compound, can be formulated to be compatible with its intended route of administration as known by those of ordinary skill in the art. Nonlimiting examples of routes of administration include parenteral, e.g., intravenous, intradermal, subcutaneous, oral {e.g., inhalation), transdermal (topical), transmucosal, vaginal and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition can be sterile and can be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. It may be desirable to include isotonic agents, for example, sugars, polyalcohols such as mannitol, sorbitol, or sodium chloride in the composition. Prolonged absorption of the injectable compositions can be accomplished by including in the composition an agent that delays absorption, for example, aluminum monostearate and gelatin (see, e.g., Remington: The Science and Practice of Pharmacy, 21st edition, Lippincott Williams & Wilkins, Gennaro, ed. (2006)).

Sterile injectable solutions can be prepared by incorporating a polyamine compound, or combination of a polyamine compound with another compound, in the required amount in an appropriate solvent with one or a combination of ingredients enumerated above, as required, followed by filtered sterilization. Generally, dispersions are prepared by incorporating an active compound into a sterile vehicle that contains a basic dispersion medium and the required other ingredients from those enumerated above. In the case of sterile powders for the preparation of sterile injectable solutions, the methods of preparation include, without limitation, vacuum drying and freeze-drying which yields a powder of the active ingredient plus any additional desired ingredient from a previously sterile-filtered solution thereof.

Oral compositions may include an inert diluent or an edible carrier or binders. For the purpose of oral therapeutic administration, a polyamine, or a combination of a polyamine compound, or combination of a polyamine compound with another compound, can be incorporated with excipients and used in the form of tablets, pills, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, polyamine compound, or combination of a polyamine compound with another compound, can be delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, but are not limited to, for example, for transmucosal administration, detergents, bile salts, and fusidic acid derivatives. Transmucosal administration can be accomplished through the use of nasal sprays or suppositories. For transdermal administration, the active compounds and compositions are formulated into pharmaceutically acceptable formulation embodiments, such as ointments, salves, gels, or creams as generally known in the art.

For treatment of acute or chronic wounds, polyamine compound, or combination of a polyamine compound with another compound, can be formulated as a dressing, a wash solution, gel, or a synthetic tissue, etc.

The pharmaceutical compositions containing a polyamine compound, or combination of a polyamine compound with another compound, can also be prepared in the form of suppositories (e.g., with conventional suppository bases such as cocoa butter and other glycerides) or retention enemas for rectal delivery.

Some pharmaceutical compositions containing a polyamine compound, or combination of a polyamine compound with another compound, can be prepared with a carrier that protects the polyamine compound, or combination of a polyamine compound with another compound, against rapid elimination from the body, such as a controlled release formulation, including implants and microencapsulated delivery systems as described, e.g., in Tan et al., Pharm. Res. 24:2297-2308 (2007).

Additionally, biodegradable, biocompatible polymers can be used, such as ethylene vinyl acetate, polyanhydrides, polyglycolic acid, collagen, polyorthoesters, and polylactic acid. Methods for preparation of such formulations are apparent to those skilled in the art. The materials can also be obtained commercially (e.g., from Alza Corp., Mountain View, Calif.). Liposomal suspensions (including liposomes targeted to particular cells with monoclonal antibodies to cell surface antigens) can also be used as pharmaceutically acceptable carriers. These can be prepared according to methods known to those skilled in the art, e.g., as described in U.S. Pat. No. 4,522,811.

Toxicity and therapeutic efficacy of such compounds and compositions can be determined by standard pharmaceutical procedures in cell cultures or experimental animals, e.g., for determining the $LD_{50}$ (the dose lethal to 50%> of the population) and the $ED_{50}$ (the dose therapeutically effective in 50% of the population). The dose ratio between toxic and therapeutic effects is the therapeutic index and it can be expressed as the ratio $LD_{50}/ED_{50}$. While compounds and compositions that exhibit toxic side effects can be used, care should be taken to design a delivery system that targets active components to the site of affected tissue in order to minimize potential damage to normal cells and, thereby, reduce side effects.

The data obtained from the cell culture assays and animal studies can be used in formulating a range of dosage for use in humans. The dosage of such compounds and compositions lies generally within a range of circulating concentrations that include the $ED_{50}$ with little or no toxicity. The dosage can vary within this range depending upon the dosage form employed and the route of administration utilized. For any compounds or compositions used in the methods described herein, the therapeutically effective dose can be estimated initially from cell culture assays. A dose can be formulated in animal models to achieve a circulating plasma concentration range that includes the $IC_{50}$ (i.e., the concentration of the test compound or composition that achieves a half-maximal inhibition of symptoms) as determined in cell culture. Such information can be used to more accurately determine useful doses in humans. Levels in plasma can be measured, for example, by high performance liquid chromatography. Information for preparing and testing such compositions are known in the art. See, e.g., Remington: The Science and Practice of Pharmacy, 21st ed., Lippincott Williams & Wilkins, Gennaro, ed. (2006).

A physician will appreciate that certain factors may influence the dosage required to effectively treat a subject, including but not limited to the severity of the disease or disorder, previous treatments, the general health or age of the subject, and other diseases present. Moreover, treatment of a subject with a therapeutically effective amount of a polyamine compound, or combination of a polyamine compound with another compound, can include a single treatment or a series of treatments.

The compounds or pharmaceutical compositions can be included in a container, pack, or dispenser together with instructions for administration. A person of ordinary skill in the art will appreciate that the compounds or pharmaceutical compositions described herein can be formulated as single-dose vials.

Polyamine compounds, or combination of a polyamine compound with another compound, may be suitable as antibiofilm active substances in personal care preparations, for example shampoos, bath additives, hair care preparations, liquid and solid soaps (based on synthetic surfactants and salts of saturated or unsaturated fatty acids), lotions and creams, deodorants, other aqueous or alcoholic solutions, e.g. cleansing solutions for the skin, moist cleaning cloths, oils or powders.

Any suitable amount of polyamine can be used in the compositions and methods of the invention. In general, the polyamines are used in concentrations ranging from about 1 ppm to about 100,000 ppm, or higher. The concentration of a polyamine used in a composition or method of the invention can be, for example, from about 1 to about 100,000 ppm, or from about 10 to about 10,000 ppm, or from about 100 to about 1,000 ppm, or from about 1 to about 100 ppm, or from about 1,000 to about 10,000 ppm, or from about 10,000 to about 100,000 ppm. The concentration of a polyamine can be about 1; 2; 3; 4; 5; 6; 7; 8; 9; 10; 15; 20; 25; 30; 35; 40; 45; 50; 55; 60; 65; 70; 75; 80; 85; 90; 95; 100; 125; 150; 175; 200; 225; 250; 275; 300; 325; 350; 375; 400; 425; 450; 475; 500; 525; 550; 575; 600; 625; 650; 675; 700; 725; 750; 775; 800; 825; 850; 875; 900; 925; 950; 975; 1000; 1500; 2000; 2500; 3000; 3500; 4000; 4500; 5000; 5500; 6000; 6500; 7000; 7500; 8000; 8500; 9000; 9500; 10,000; 12,500; 15,000; 17,500; 20,000; 22,500; 25,000; 27,500; 30,000; 32,500; 35,000; 37,500; 40,000; 42,500; 45,000; 47,500; 50,000; 52,500; 55,000; 57,500; 60,000; 62,500; 65,000; 67,500; 70,000; 72,500; 75,000; 77,500; 80,000; 82,500; 85,000; 87,500; 90,000; 92,500; 95,000; 97,500; or about 100,000 ppm. Other concentrations of polyamines can be useful in the compositions and methods of the invention, depending in part on factors including the specific polyamine used, the presence of other active agents if any, or the species of microorganisms that are targeted.

There is thus disclosed compounds, compositions, or methods comprising novel polyamine compounds, or combinations of polyamine compounds with other compounds, that have antimicrobial activity and dispersing activity against a variety of bacterial strains capable of forming biofilms, and methods of using the same.

EXAMPLES

The following examples serve to explain embodiments of the present disclosure in more detail. These examples should not be construed as being exhaustive or exclusive as to the scope of this disclosure.

The following material and methods were used.
Bacterial strains.

A clinical strain of MRSA, isolated from a patient who underwent arthroscopic knee surgery and characterized by ARUP Laboratories, Salt Lake City, Utah, was used for this study in addition to *Pseudomonas aeruginosa* ATCC 27853 and *Alcanivorax borkumensis* ATCC 700651. Both ATCC strains were purchased as freeze-dried pellets from ATCC. *P. aeruginosa* was resuspended in BHI broth, grown overnight at 37° C. and transferred to fresh BHI with 30% glycerol for storage at −80° C. The MRSA isolate was likewise stored in BHI with 30% glycerol at −80° C. Notably, the clinical MRSA isolate was not passaged more than three times prior to or during the study. Prior to performing MIC analysis and biofilm experiments, the frozen stocks of MRSA and *P. aeruginosa* were streaked onto Columbia blood agar plates and grown overnight at 37° C. *A. borkumensis* ATCC 700651 was resuspended from a lyophilized pellet into marine broth, grown overnight at 30° C. and passaged on marine agar plates prior to experimentation.

Example 1

MIC Determination.

To determine the MIC of the polyamine chains alone and the synthesized compounds against MRSA and *P. aeruginosa* ATCC 27853, a modified protocol from the Clinical and Laboratory Standards Institute (CLSI) guideline M26-A was used. Consistent with this guideline, the MIC was defined as the concentration of antimicrobial that was required to reduce approximately $5 \times 10^5$ cells per mL to approximately $5 \times 10^2$ per mL in a 24-hour period. Each MIC experiment was performed n=10 times for each antimicrobial. All data was collected using cation adjusted MHB for standardization.

As mentioned, MRSA and *P. aeruginosa* ATCC 27853 were grown on Columbia blood agar plates prior to experimentation. From the blood agar plates, a 0.5 McFarland standard was made of each isolate. This equated to approximately $5 \times 10^7$ cells/mL for the MRSA isolate and approximately $3 \times 10^7$ cells/mL for the *P. aeruginosa* ATCC 27853 isolate. Of the 0.5 McFarland stock solution, 50 µL were added to MHB. All of the antimicrobials were kept in PBS stock solutions at 10 mg/mL and diluted in the MHB to reach the desired concentration that would determine the MIC value. All tests were performed such that a final volume of 5 mL of MHB were obtained. This provided a final bacterial concentration of approximately $5 \times 10^5$ cells/mL.

Each sample was incubated in glass test tubes at 37° C. for 24 hours, then plated in duplicate on tryptic soy agar (TSA) using a 10-fold dilution series. TSA plates were further incubated 24 hours at 37° C. The number of colony forming units (CFU) that grew were counted in order to calculate the number of bacteria that were present per mL in the original MHB solution. The concentration of compound that resulted in a reduction of approximately $5\times10^5$ cells/mL to approximately $5\times10^2$ cells/mL in a 24-hour period was defined as the MIC.

Figure 7:
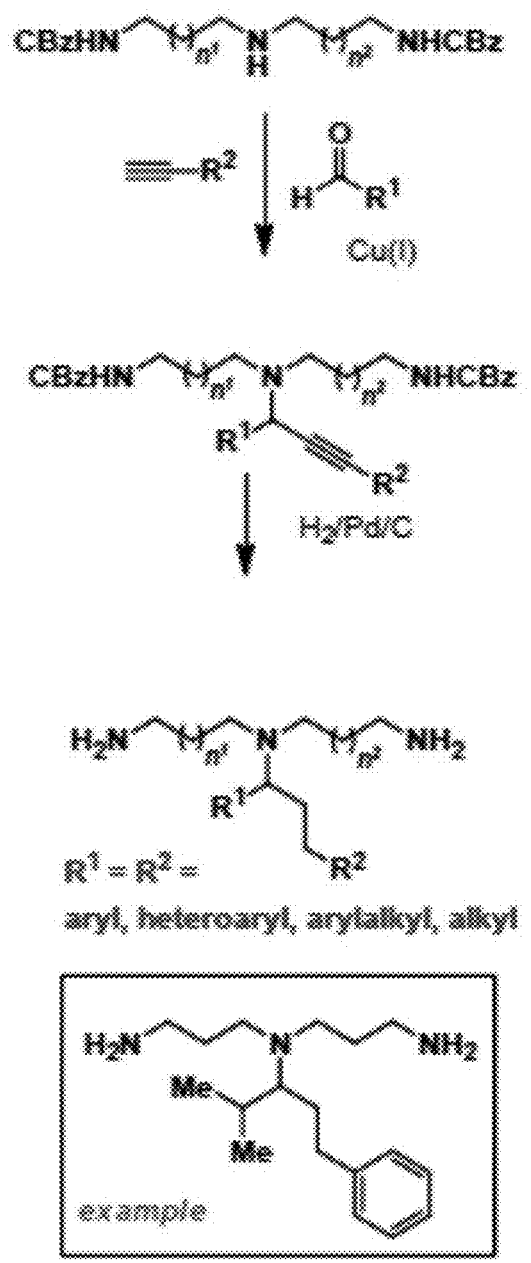
FIG. 7 shows an exemplary synthesis strategy to produce polyamine compounds according to certain aspects of the present invention.
Figure 8:
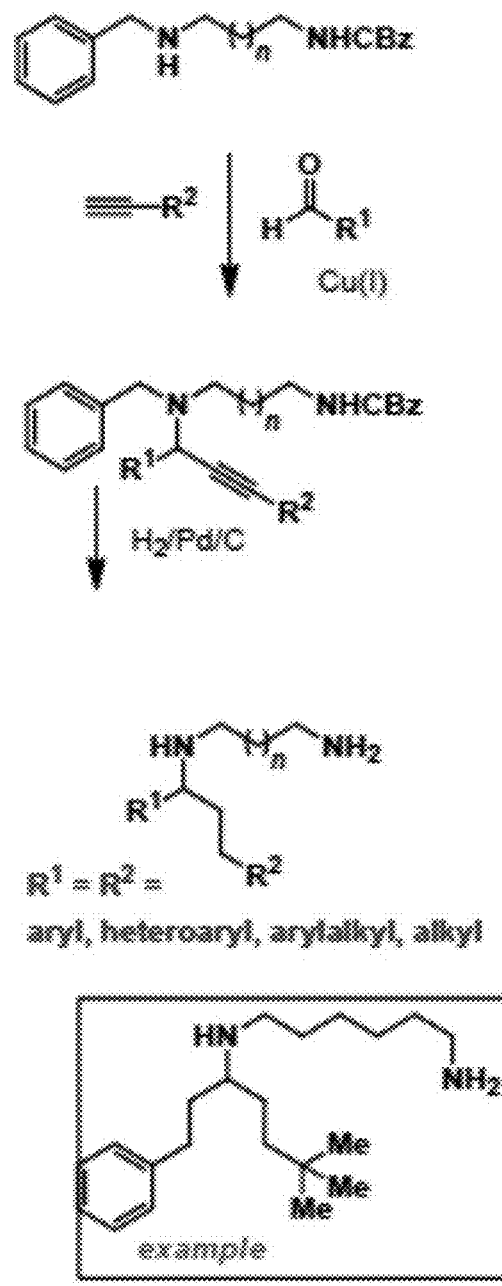
FIG. 8 shows another exemplary synthesis strategy to produce polyamine compounds according to certain aspects of the present invention.
Figure 9:
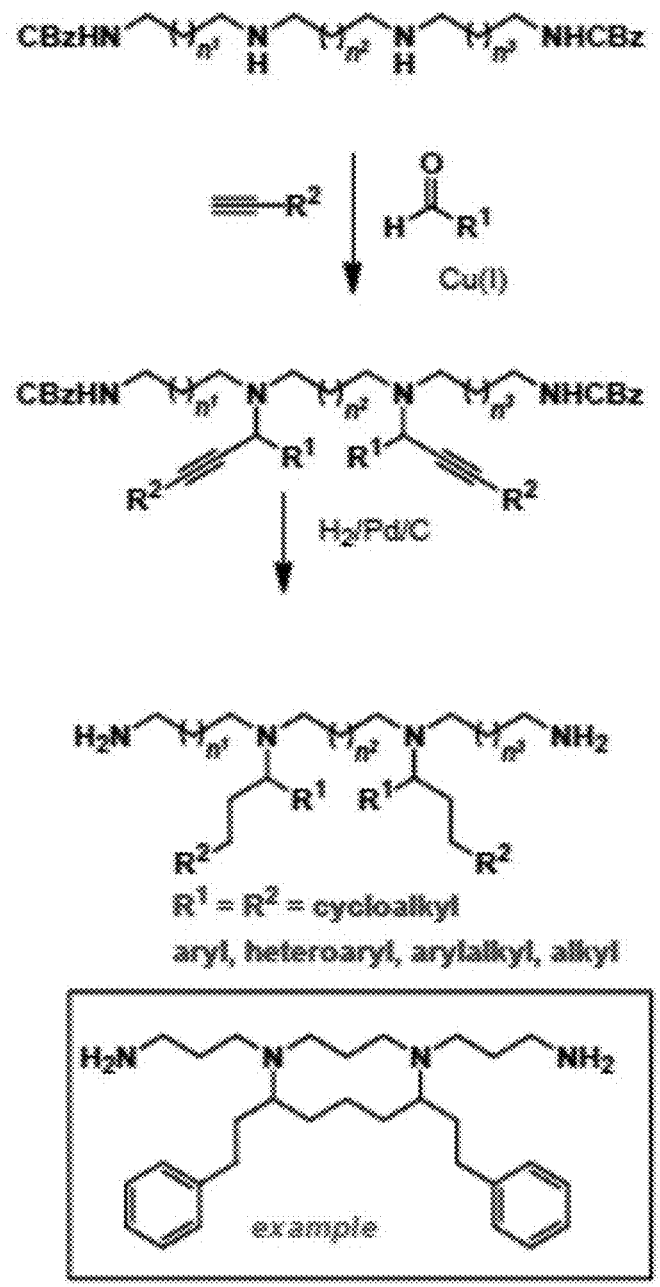
FIG. 9 shows still another exemplary synthesis strategy to produce polyamine compounds according to certain aspects of the present invention.
Figure 10:
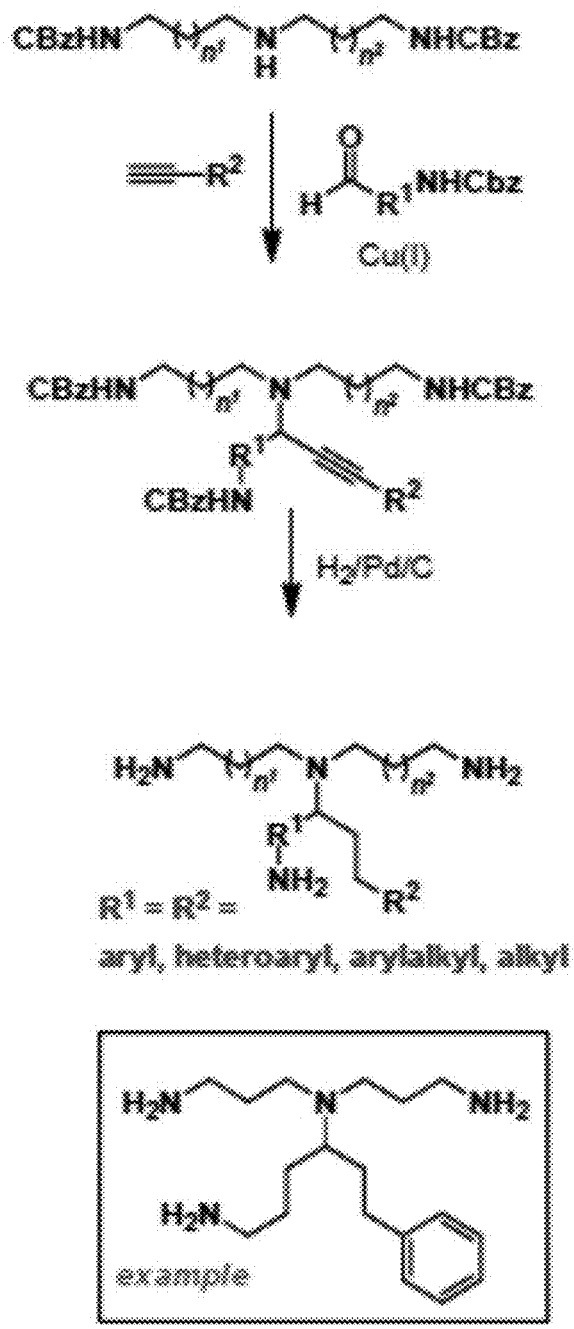
FIG. 10 shows yet another exemplary synthesis strategy to produce polyamine compounds according to certain aspects of the present invention.
Figure 11:
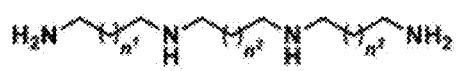
FIG. 11 shows the minimum inhibitory concentration ("MIC") of polyamines and novel polyamine compounds according to certain aspects of the present invention.
Figure 11:
Figure 11:
Figure 11:
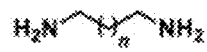
Figure 11:
Figure 11:
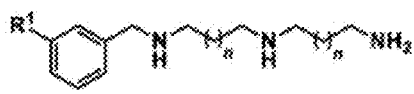
Figure 11:
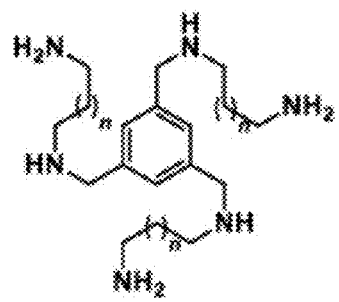

For comparison to a current standard of care, the MICs of vancomycin against the MRSA isolate and tobramycin against the *P. aeruginosa* ATCC 27853 isolate were also determined. MIC results for various compounds are shown in FIG. 7.

MRSA and *P. aeruginosa* Biofilm Eradication.

Biofilms of MRSA and *P. aeruginosa* ATCC 27853 were grown on the surface of PEEK membranes using a membrane biofilm reactor. Data demonstrating the design and repeatability of this reactor have been published previously. Williams et al., *In Vivo Efficacy of a Silicone—Cationic Steroid Antimicrobial Coating to Prevent Implant-Related Infection*, Biomaterials 33, 8641-8656 (2012); Williams et al., *Use of delrin plastic in a modified CDC biofilm reactor*, Res J Microbiol 6, 425-429 (2011); Williams et al, *Experimental model of biofilm implant-related osteomyelitis to test combination biomaterials using biofilms as initial inocula*, J Biomed Mat Res A 100, 1888-1900 (2012); Williams et al., *A modified CDC biofilm reactor to produce mature biofilms on the surface of PEEK membranes for an in vivo animal model application*, Curr Microbiol 62, 1657-1663 (2011). Prior to growing the biofilms, PEEK membranes were first sonicated for 10 min in medical grade detergent, rinsed with running reverse osmosis water for 10 min, sonicated in reverse osmosis water for 10 min and rinsed once again using 70% ethanol.

Four guillotine-like holders were designed to hold eight PEEK membranes (two per holder). All components were washed, assembled and the reactor autoclaved prior to each use. Following American Society for Testing and Materials (ASTM) standard E2562-07, the modified reactor was run under the following conditions: approximately $5\times10^7$ bacterial cells were inoculated into 500 mL of BHI in the biofilm reactor. A paddle in the base of the reactor was stirred at 130 rpm. The unit was placed on a hot plate set at 33° C. for 24 hrs. A 10% BHI broth solution was then flowed through the reactor at 6.94 mL/min for an additional 24 hrs.

Following the 48-hour growth period, six of the PEEK membranes were aseptically removed and placed into 5 mL of MHB that contained varying concentrations of the synthesized compounds. For comparison, vancomycin was also tested against MRSA biofilms and tobramycin was tested against *P. aeruginosa* ATCC 27853 biofilms. The membranes and broth were incubated in glass test tubes at 37° C. for 24 hours. The test tubes containing membranes were vortexed for 1 minute, sonicated at 42 kHz for 10 minutes and plated in duplicate on TSA using a 10-fold dilution series and incubated at 37° C. for 24 hours. This process allowed for the determination of what was defined as the effective biofilm eradication concentration (EBEC) of the selected compounds. In this case, the EBEC was defined as the concentration of compound required to reduce the number of cells in the biofilms from approximately $10^9$ cells/PEEK membrane to $10^5$ cells/membrane. A level of $10^9$ bacteria in the biofilms represented an amount of bacteria that may be present in one gram of soil in a natural ecosystem. See, e.g., Bakken, *Separation and Purification of Bacteria from Soil*, Appl Environ Microbiol 49, 1482-1487 (1985); Torsvik et al., *High Diversity in DNA of Soil Bacteria*, Applied and Environmental Microbiology 56, 782-787 (1990).

Figure 12A:
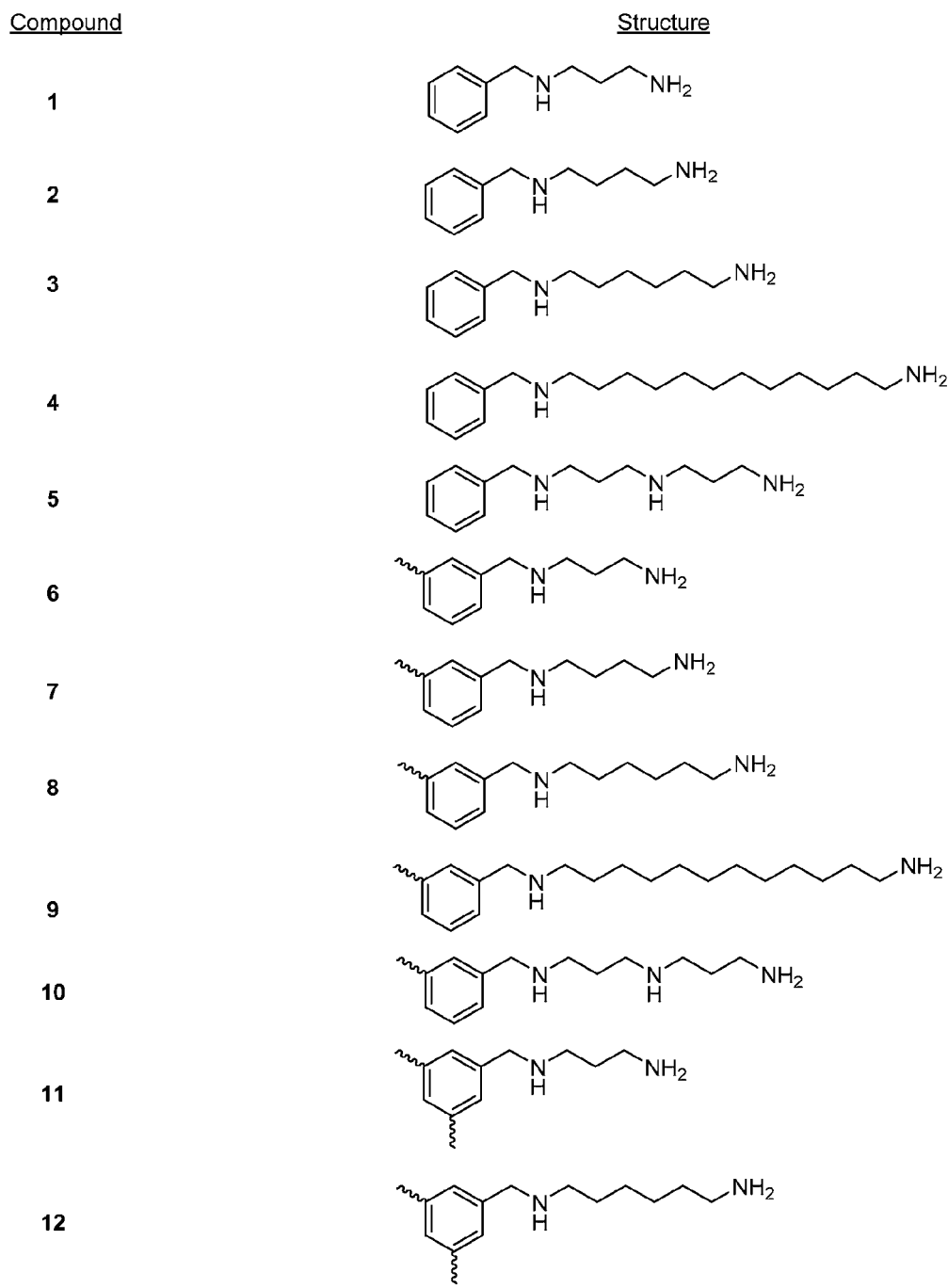
FIG. 12A is a table showing certain polyamine compounds according to certain aspects of the present invention.

Two membranes from each run of the reactor were aseptically removed and quantified to serve as positive controls of biofilm growth. All of the biofilm eradication studies were repeated n=5 times. EBEC results are summarized in FIGS. 12A and 12B.

Model Oil Pipeline Contamination Using *Alcanivorax borkumensis*.

Figure 13:
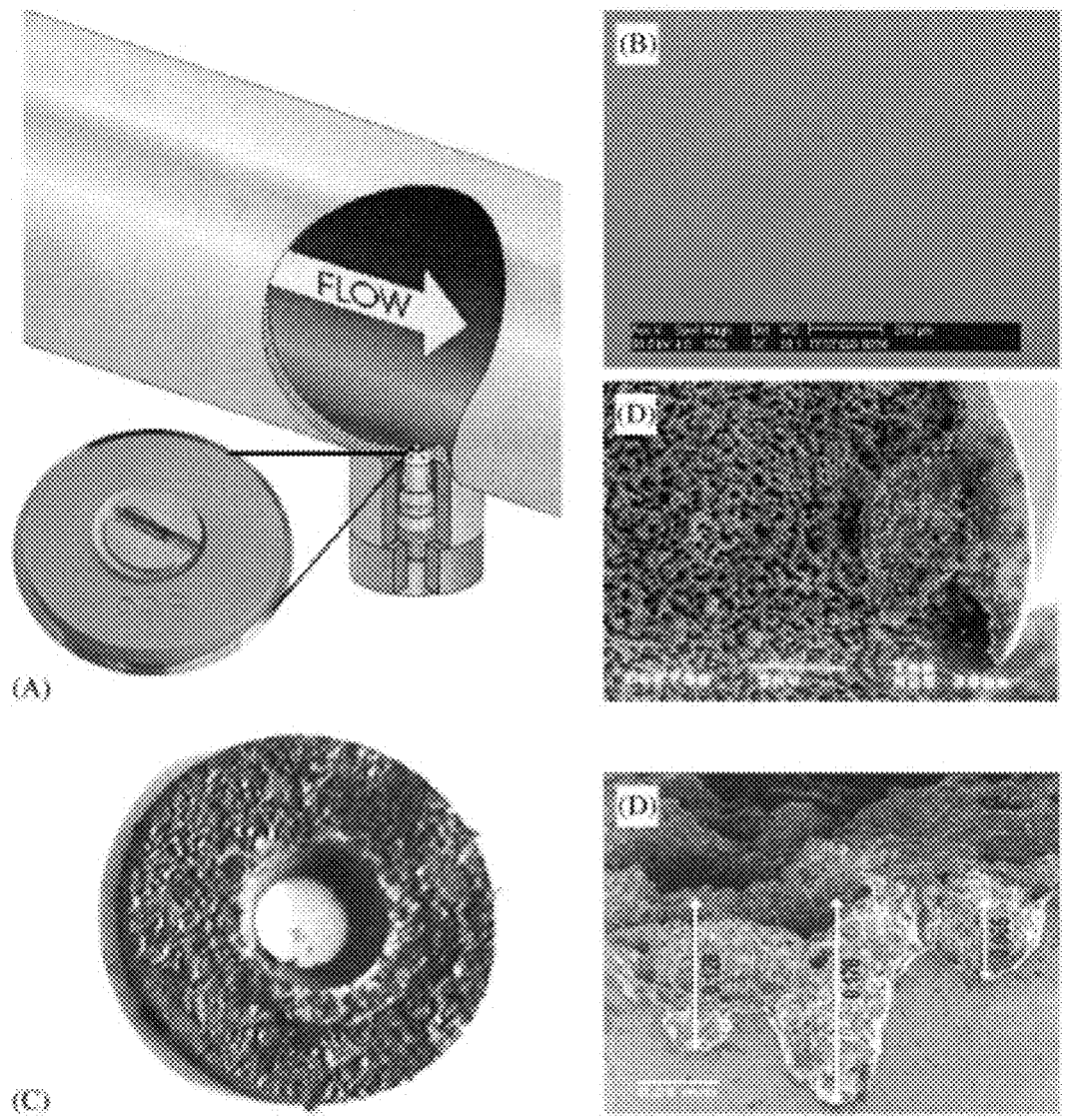
FIG. 13 shows an example of microbial contamination in the oil and gas industry.

FIG. 13 shows an example of microbial contamination in the oil and gas industry. To test the ability and efficacy of the novel synthesized compounds to disperse and kill biofilms that may exist in a variety of settings, a model oil pipeline system was prepared to grow biofilms of *A. borkumensis*, a gram-negative organism that metabolizes alkane chains. In cases of oil spills, this organism may be beneficial for bioremediation, but in this instance, it was used to represent bacteria in an oil field or pipeline that may have adverse or unwanted effects of oil degradation.

Figure 14A:
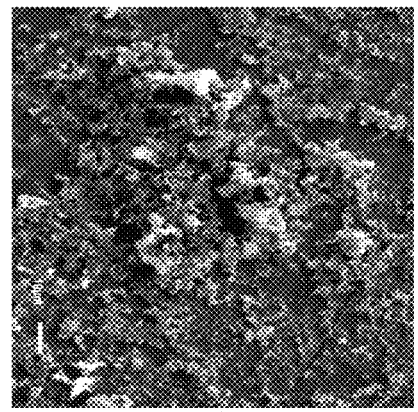
FIG. 14A shows a representative bacteria biofilm.
Figure 14B:
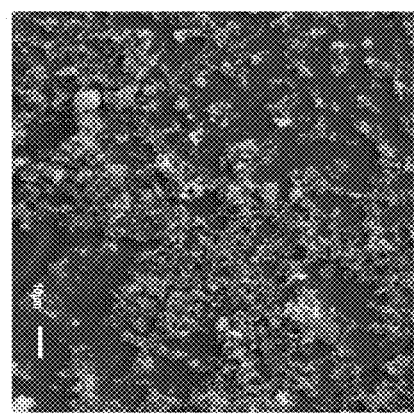
FIG. 14B shows a representative bacteria biofilm, such as the biofilm shown in FIG. 10A, treated according to certain standards in the oil and gas industry.
Figure 14C:
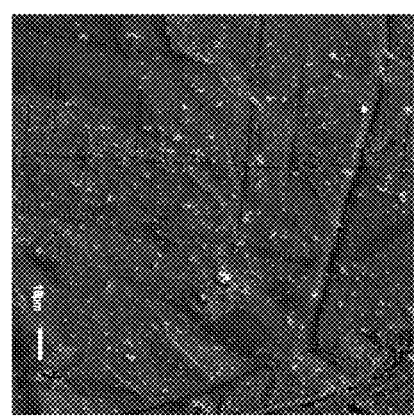
FIG. 14C shows a representative bacteria biofilm, such as the biofilm shown in FIG. 10A, treated with a polyamine compound of the present invention.

FIG. 14B shows a representative bacteria biofilm, such as the biofilm shown in FIG. 14A, treated according to certain standards in the oil and gas industry. The biofilm shown in FIG. 14B was treated with a solution comprising 0.25% glutaraldehyde. A similar representative biofilm was treated with a solution comprising 0.5% of a polyamine compound described herein, and is shown in FIG. 14C.

Figure 15:
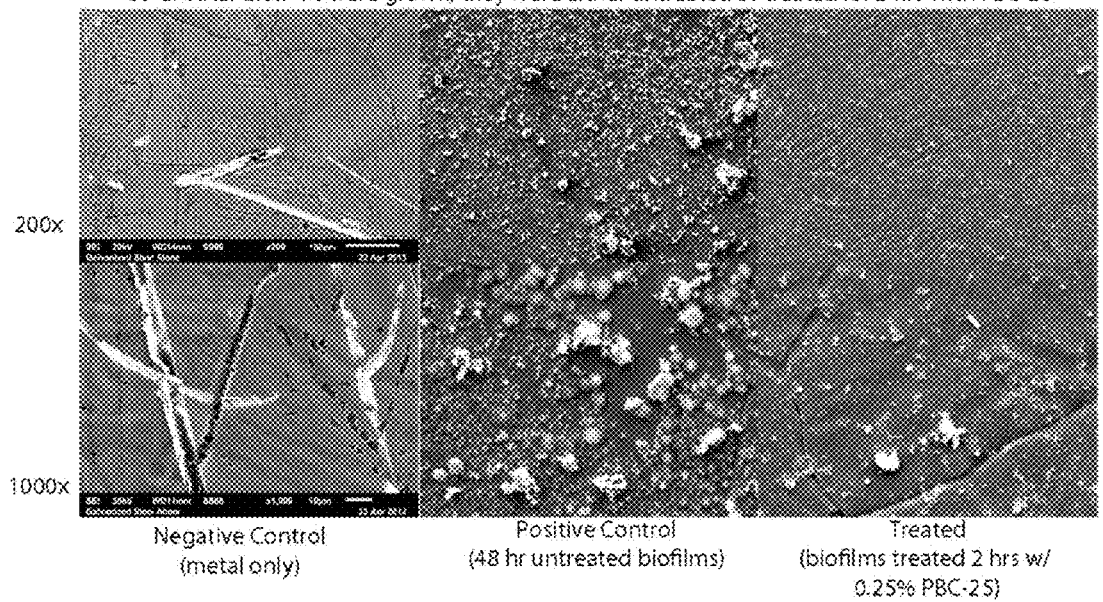
FIG. 15 shows the results of treating biofilms of *Alcanivorax borkumensis* grown on the surface of galvanized steel with a polyamine compound of the present invention.

FIG. 15 shows the results of treating biofilms of *Alcanivorax borkumensis* grown on the surface of galvanized steel with a solution comprising 0.25% of a polyamine compound of the present invention.

Combination Treatment.

Data collected with benzylnorspermidine (CZ-7; PBC-7) at 0.25% mixed with chlorhexidine gluconate at 0.25% has shown significant dispersal of a biofilm of MRSA that consisted of $10^{11}$ cells within one hour.

Example 2

A compound was screened for its ability to create zones of inhibition on cation adjusted Mueller Hinton agar. It is believed that the compound of Example 2 may be represented by the structure disclosed in FIG. 4H. To perform this test, lawns of methicillin-resistant *Staphylococcus aureus* (MRSA) or *Pseudomonas aeruginosa* ATCC 27853 were made on cation adjusted Mueller Hinton agar using standard microbiological techniques. Immediately after plating bacteria on agar, a 50 µL drop of the compound was placed onto the agar surface. The compound was tested in duplicate at 100 µg/mL, 50 µg/mL, 25 µg/mL and 10 µg/mL. All plates were incubated at 37° C. for 24 hours. Results indicated that total clearing was seen against MRSA at 10 µg/mL. Partial clearing was seen against *P. aeruginosa* at 25 µg/mL and total clearing at 50 µg/mL.

The second test determined the minimum inhibitory concentration (MIC) of the compound against MRSA and *P. aeruginosa* ATCC 27853. In this instance, the MIC was defined as the amount of antimicrobial required to reduce $10^5$ cells/mL to $10^2$ cells/mL in a 24-hour period. This definition was consistent with the Clinical and Laboratory Standards Institute (CLSI). More specifically, the microdilution method as outlined in the M26-A CLSI guideline was used. All tests were performed with cation adjusted Mueller Hinton broth. MIC data are presented in Table 1.

In addition to determining the MIC, the minimum biofilm eradication concentration (MBEC) of PBC-51 was also determined. The MBEC was determined using the MBEC assay, formerly known as the Calgary Biofilm Device, developed by Innovotech. In this instance, the MBEC was defined as the amount of antimicrobial required to eradicate 100% of detectable biofilm after being grown in the MBEC device. To grow the biofilms within this device, 150 μL of solution containing a concentration of $10^5$ cells/mL were inoculated into each well of a 96-well plate. A lid containing 96 pegs was placed onto the plate and incubated for 24 hours at 37° C. while being shaken at 110 rpm. Biofilms developed on the surface of the polystyrene pegs within the 96-well plate. After 24 hours, each peg contained between $10^5$ and $10^6$ cells in well-established biofilms. The lid with pegs was transferred to a 96-well plate that contained 200 μL of varying concentrations of the compound and was incubated at 37° C. for an additional 24 hours. The plate was then sonicated, and the biofilms quantified using a 10-fold dilution series to determine the MBEC. Data are presented in Table 1.

TABLE 1

MIC, MBEC and EBEC of PBC-51 Against MRSA and P. aeruginosa ATCC 27853. Data are presented in μg/mL and μM concentrations.

| Organism | MIC (μg/mL/μM) | MBEC (μg/mL/μM) | EBEC (μg/mL/μM) |
|---|---|---|---|
| MRSA | ~1/~1.88 | <25/<47 | ~250/~470.88 |
| P. aeruginosa | ~6/~11.30 | ~35/~65.92 | <100/<188.33 |

The fourth test that was performed was the effective biofilm eradication concentration (EBEC). To determine the EBEC, biofilms of MRSA and P. aeruginosa ATCC 27853 were grown on the surface of PEEK membranes using a previously established protocol. Briefly, 500 mL of brain heart infusion (BHI) broth were inoculated with 105 cells/mL of MRSA or P. aeruginosa. BHI broth was placed into a membrane biofilm reactor and placed on a hot plate set at 34° C. for 24 hours with a stir bar rotating at 130 rpm. Following the initial 24-hour growth period, a 10% BHI broth solution was flowed through the reactor at a rate of 6.944 mL/min for another 24 hours. After 48 hours of growth, each PEEK membrane had biofilm growth on it. In this experiment, there were ~$2\times10^{11}$ cells of MRSA per PEEK membrane and ~$2\times10^{10}$ cells of P. aeruginosa per PEEK membrane. The EBEC was defined as the concentration of the compound that was required to eradicate all detectable amounts (100%) of bacteria within the biofilms. Data are presented in Table 1.

In addition to determining the antimicrobial efficacy of the compound, an initial test was performed to determine its hemolytic nature. To do so, the compound was suspended in concentrations of 100 μg/mL, 50 μg/mL and 25 μg/mL. Twenty L of each concentration was placed onto the surface of Columbia blood agar and incubated at 37° C. for 24 hours. Results indicated that none of these concentrations displayed hemolytic activity.

Initial tests based on visual observation were performed to determine the ability of the compound to disperse biofilms. This was done by observing the biofilms of MRSA and P. aeruginosa that had grown on the surface of PEEK membranes after they had been placed in three separate concentrations of the compound (300 μg/mL, 200 μg/mL and 100 μg/mL). Biofilms were observed every 30 minutes to see if they separated from the PEEK membrane. Within 2 hours, biofilms began to separate from the PEEK membranes, by 4 hours approximately half of the biofilms had separated and by 24 hours, all detectable amounts of biofilm had separated from the PEEK membrane. For comparison, it is the understanding of the inventors hereof that this dispersal effect is not seen with other antimicrobials such as chlorhexidine gluconate, glutaraldehyde, or benzethonium chloride.

The MIC, MBEC and EBEC of vancomycin were also determined for comparison, and the results are presented in Table 2.

TABLE 2

MIC, MBEC and EBEC of Vancomycin Against MRSA.

| Organism | MIC (μg/mL/μM) | MBEC (μg/mL/μM) | EBEC (μg/mL/μM) |
|---|---|---|---|
| MRSA | 10/6.73 | >500/>336.50 | >20,000/>13,460 |

Example 3

MIC Analysis

To determine the MIC of polyamine compounds, the protocol described herein was used. The MIC is defined as being the concentration of antimicrobial (in μg/mL) required to reduce the number of bacteria in a solution from $10^5$ colony forming units (CFU)/mL to $10^2$ CFU/mL in a 24-hour period.

In brief, a 0.5 McFarland of each bacterial isolate was made. A 0.5 McFarland is a measure of turbidity in a liquid sample that contains approximately $1\times10^{\wedge 8}$ CFU/mL. The 0.5 McFarland standard was diluted in cation adjusted Mueller Hinton Broth (CAMHB), and 50 μL of broth were added to a well of a 96-well plate. In addition, 50 μL of CAMHB that contained a desired concentration of antimicrobial were also added to the well for a final volume of 100 μL and a final concentration of approximately $5\times10^4$ CFU/well (which equated to approximately $5\times10^5$ CFU/mL). Each well contained a desired amount of polyamine compound in order to experimentally determine the MIC. Each 96-well plate was incubated at 37° C. for 24 hours. The contents of each well were plated on tryptic soy agar (TSA). TSA plates were incubated for 37° C. for 24 hours after which the number of CFU were counted and used to calculate the CFU/mL that remained after exposure to varying concentrations of compound. This procedure was repeated n=8 times for each concentration of antimicrobial. The concentration of polyamine compound that reduced bacteria from $10^5$ CFU/mL to $10^2$ CFU/mL in 24 hours was considered the MIC.

MICs from representative polyamine compounds as well as select antibiotics are provided in Table 3A and 3B. Consistent with what was mentioned previously, these data indicate that with an increase in the number of polyamine chains attached to a lipophilic backbone, the MIC is lowered, indicating it has greater antimicrobial potential. CZ-7 has one chain of norspermidine attached, CZ-25 has two chains of norspermidine and CZ-51 and CZ-52 have three chains attached.

TABLE 3A

MICs of Polyamine Compounds and Select Traditional Antibiotics (µg/mL)

| Compound | MRSA | P. aeruginosa | A. baumannii | MRSA | P. aeruginosa |
|---|---|---|---|---|---|
| CZ-7 | >500 | >500 | >500 | >500 | >5,000 |
| CZ-25 | 40 | 500 | 150 | 25 | >500 |
| CZ-52 | 3 | 17 | ~25 | 20 | 400 |
| Vancomycin | 10 | — | — | >500 | — |
| Tobramycin | —* | 2 | — | — | 100 |
| Polymyxin B sulfate | — | — | 2 | — | — |

\* Not yet determined
\*\*No change

TABLE 3B

MICs of Polyamine Compounds and Select Traditional Antibiotics (µg/mL) II

| Compound | A. baumannii | MRSA | P. aeruginosa | A. baumannii |
|---|---|---|---|---|
| CZ-7 | >500 | >5,000 | >5,000 | >5,000 |
| CZ-25 | 450 | >5,000 | >5,000 | >5,000 |
| CZ-52 | 300 | 250 | >5,000 | >5,000 |
| Vancomycin | — | >25,000 | — | — |
| Tobramycin | — | — | 2,000 | — |
| Polymyxin B sulfate | 50 | — | — | 1,000 |

\*Not yet determined
\*\*No change

To determine the MBEC of each polyamine compound, the MBEC Inoculation Tray by Innovotech, formerly known as the Calgary biofilm device, was used. Within this device, biofilms grow on the surface of polystyrene pegs, 96 of which are attached to a lid. These pegs are inserted into a flat bottom 96-well plate. In this instance, the MBEC of a molecule was defined as the concentration of compound (in µg/mL) required to reduce $10^5$ or $10^6$ CFU/peg (biofilm levels varied by isolate) to $10^2$ CFU/peg in a 24-hour period.

Following the manufacturer's guidelines, biofilms were grown on the surface of each peg by first making a 0.5 McFarland of each isolate. The 0.5 McFarland was diluted 1:100 in CAMHB. Into each well of a flat bottom 96-well plate, 150 µL of broth were pipetted. The plate was shaken at 100 rpm for 24 hours (P. aeruginosa and A. baumannii) or 48 hours (MRSA). The pegs were then placed into a separate flat bottom 96-well plate for 10 seconds with 200 µL of phosphate buffered saline (PBS) in each well to remove nonadherent cells. The lid was then placed into a 96-well plate that contained varying concentrations of antimicrobial with 200 µL per well. The plate was incubated for 24 hours at 37° C. after which time 100 µL of broth were plated on TSA. TSA plates were incubated 24 hours at 37° C. and the number of CFU counted to calculate the CFU/peg. In this instance, the MBEC was defined as the concentration of antimicrobial required to reduce $10^5$ or $10^6$ CFU/peg to $10^2$ CFU/peg in a 24 hour period.

MBEC data are presented in Table 4. Similar to the MIC data, the trend of increasing antimicrobial activity by increasing the number of polyamine chains attached to a backbone was confirmed against low number biofilms.

EBEC Analysis

In addition to determining the MIC and the MBEC of polyamine compounds against planktonic bacteria and low number biofilms, our group wanted to determine the efficacy of polyamine compounds against high number biofilms. To do so, biofilms were grown on the surface of polyetherketone (PEEK) membranes using a membrane biofilm reactor. This reactor is similar to the CDC biofilm reactor, but rather than growing biofilms on coupon surfaces, the reactor was modified to hold PEEK membranes. In short, to grow biofilms within this system, 500 mL of brain heart infusion (BHI) broth were inoculated with 1 mL of a 0.5 McFarland. The reactor was placed on a hot plate set at 34° C. and the bacteria were grown under batch conditions for 24 hours. Following this protocol, biofilms typically grow to $10^9$ CFU/PEEK membrane. each PEEK membrane has high number biofilms A solution of 10% BHI was then flowed through the reactor at a rate of 6.94 mL/min for an additional 24 hours. PEEK membranes were then removed and placed into 2 mL of CAMHB that contained a desired concentration of polyamine compound or antibiotic. The EBEC was defined as the concentration of antimicrobial required to reduce a biofilm from approximately $10^9$ CFU/PEEK membrane to approximately $10^2$ CFU/PEEK membrane in a 24-hour period.

EBEC data are presented in Table 4. One of the most striking results was the difference in efficacy between CZ-52 and vancomycin. At 25,000 µg/mL, vancomycin did not have the ability to reduce biofilms of MRSA by even 1 $\log_{10}$ unit. In contrast, at 250 rµg/mL CZ-52 was able to reduce MRSA biofilms by greater than 7 $\log_{10}$ units in a 24-hour period.

Example 4

Release of Polyamine Compounds from Carrier Products

To collect proof-of-concept/preliminary data that carrier(s) will release these products in sufficient amounts to have antimicrobial efficacy, a polytherapy formula was prepared. A Vanicream-based cream from the University of Utah compounding pharmacy was used as the formulation base, and active ingredients were added to create a cream with final concentrations of 0.25% CZ-52, 0.25% CZ-25 and 0.1% Polymyxin B sulfate. To test its efficacy, 0.5 McFarland standards of MRSA, P. aeruginosa, and A. baumannii were made, and a lawn of each isolate was spread on Columbia blood agar. Approximately 20 mg of cream was placed in the center of each lawn. The plates were incubated 24 hours at 37° C.

Figure 16:
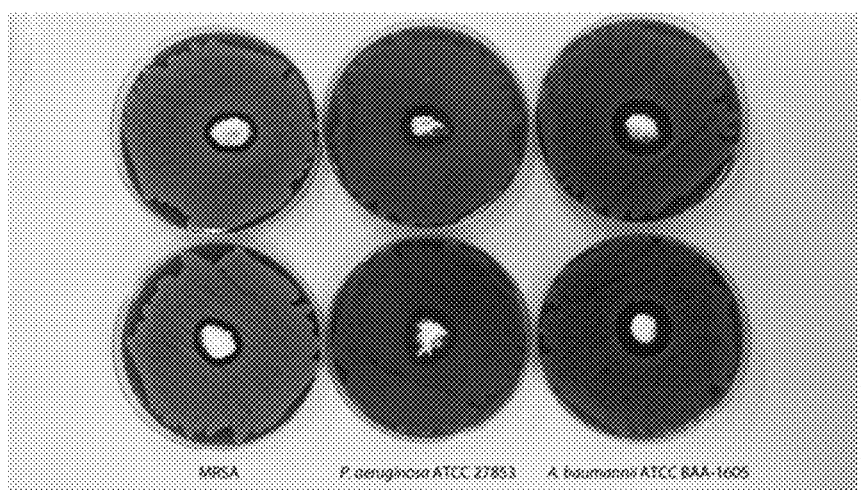
FIG. 16 shows a photograph demonstrating the ability of Vanicream-based cream to elute compounds CZ-25, CZ-52, and polymyxin B polytherapy formula and to eradicate bacteria as indicated by zones of clearing around the cream. The second row of plates is from a duplicate test of the same cream.

Zones of clearing in each experiment provided a preliminary indication that the antimicrobials will elute out of the cream in sufficient quantities to eradicate each bacterial isolate (FIG. 16). Notably, the cream alone (negative control) created no zones of inhibition, and polyamine compounds used alone in the cream likewise created zones of clearing. In broth samples, the polytherapy composition has shown similar results by eradicating all detectable amounts of each bacterial isolate after they had been grown as biofilms on PEEK membranes with approximately $10^9$ CFU/PEEK membrane. In short, these data indicate that the polytherapy antimicrobial agents will elute out of carrier product(s) and eradicate bacteria, including those in biofilms.

Example 5

Biofilm Dispersion

CZ-25 and CZ-52 were tested for their ability to disperse biofilms of MRSA and *P. aeruginosa*. To test for dispersion, biofilms of each isolate were grown on the surface of commercially pure titanium (Ti) coupons (½" diameter×⅛" height) in a CDC biofilm reactor. The growth conditions for this reactor were the same as those for the membrane biofilm reactor. After biofilms were grown for 48 hours, each Ti coupon was aseptically removed and placed into 2 mL of CAMHB for 2 hours. The CAMHB had a final concentration of 0.25% (2.5 mg/mL) CZ-25 or CZ-52. Each compound was tested n=3 times.

Following the 2-hour exposure, each coupon was fixed in 0.25% glutaraldehyde for 24 hours, dehydrated using ascending concentrations of ethanol (70%, 95%, 100%) with 3×10 min. changes and desiccated. One side of each coupon was carbon coated and imaged using a JEOL JSM-6610 SEM to directly observe the surface of the coupons and determine the ability of polyamine compounds to disperse biofilms compared to positive controls that had no treatment.

When compared to untreated controls, data have indicated that CZ-25 and CZ-52 have the ability to disperse biofilms from the surface of a material (FIG. 17) such that a monolayer of cells or reduced communities remain.

The MRSA biofilms were grown on the surface of titanium (Ti) coupons using a CDC biofilm reactor. For this reactor, an initial inoculum of ~5×10^5 cells/mL were put into 500 mL of brain heart infusion (BHI) broth. The reactor was placed on a hot plate set at 34 C for 24 hours and the bacteria were allowed to grow in batch culture. For an additional 24 hours, 10% BHI broth was flowed through the reactor at a rate of 6.94 mL/min. After the 48-hour growth period, the coupons were aseptically removed and placed into 2 mL of cation adjusted Mueller Hinton broth (CAMHB) for 2 hours. Digital images of the biofilm dispersion process were collected after 30 minutes of exposure to polyamine compounds. After 2 hours, the same procedure as above was used to fix the biofilms and image them by SEM.

Figure 18:
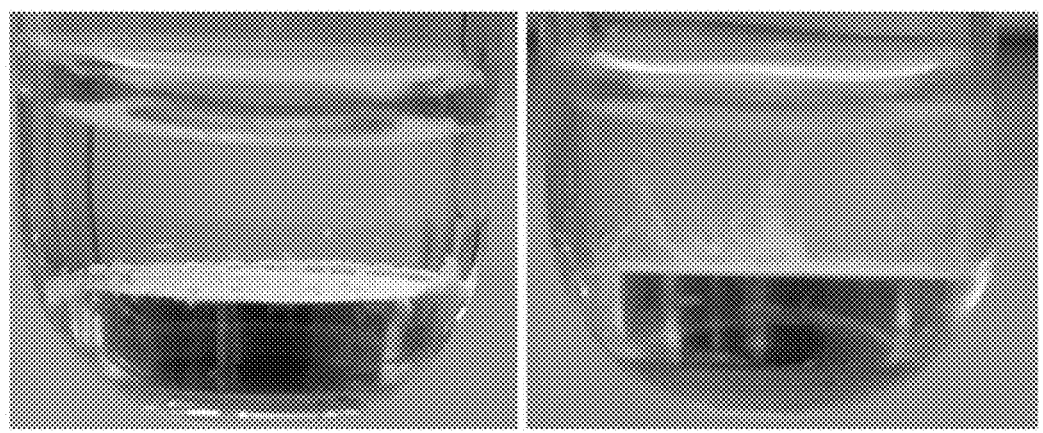
FIG. 18 shows photographs of MRSA biofilms being dispersed by the compound CZ-25. (Left) Biofilms of MRSA grown on the surface of Ti coupons in a CDC biofilm reactor exposed to water for 2 hours. (Right) Biofilms of MRSA grown on the surface of Ti coupons exposed to the compound CZ-25 in water for 2 hours. Note the strings of biofilm dispersing from the surface of the metal.

Digital images of MRSA biofilms being dispersed from the surface of the Ti coupon also help to highlight the dispersive ability of CZ-25 (FIG. 18).

Figure 19:
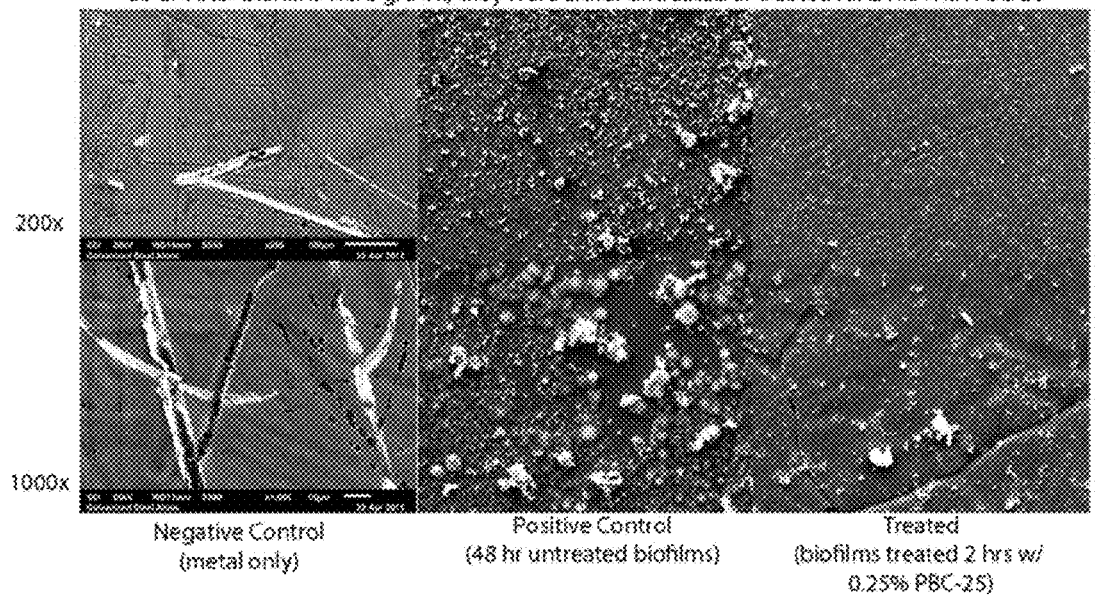
FIG. 19 shows SEM images of biofilms of *Alcanivorax borkumensis* grown on the surface of galvanized steel in a flow system, then exposed to the compound CZ-25 (also known as PBC-25).
Figure 20:
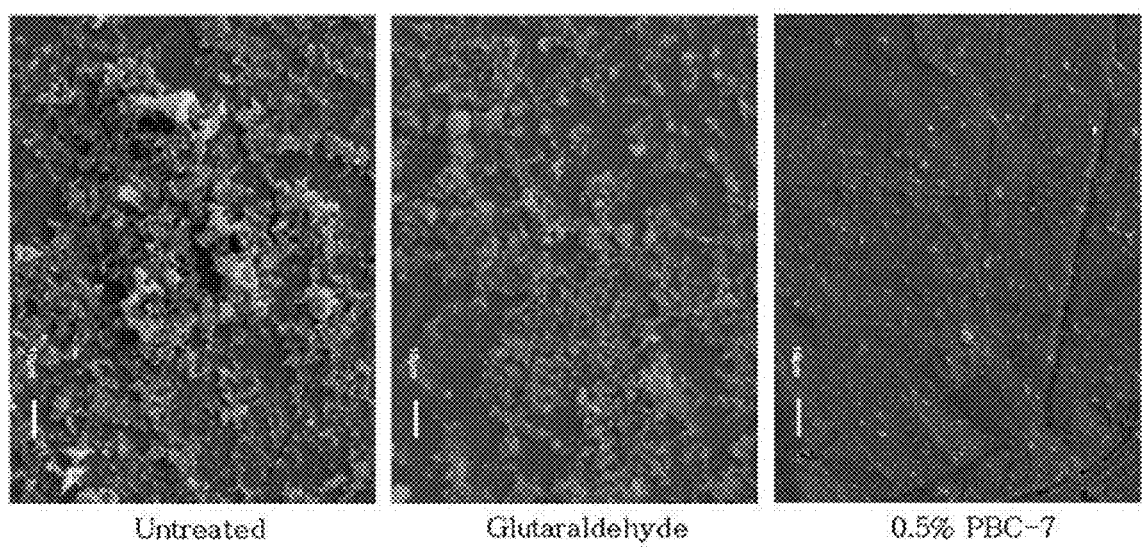
FIG. 20 shows photographs SEM images of biofilms of *Alcanivorax borkumensis* grown on the surface of galvanized steel in a flow system, then exposed to the compound CZ-7 (also known as PBC-7). Glutaraldehyde, the standard of treatment in oil and gas facilities, was compared as a control.

Data has also been collected to determine the dispersive capacity of polyamine compounds against *Alcanivorax borkumensis*, an oil-eating bacterium (FIGS. 19 and 20).

For the dispersal data with the *Alcanivorax borkumensis*, ½ inch diameter galvanized steel pipe that was approximately 6 inches long was purchased. Two strips of galvanized sheet metal were cut into ½ cm×2 cm strips, and two of those were placed into the pipe. The pipe was connected to silicone tubing, and marine broth was run through the pipes with an inoculum of 5×10=cells/mL. The broth was flowed through the pipes at a rate of 6.94 mL/min using a peristaltic pump. Biofilms were grown on the surface of the galvanized steel for 48 hours, then exposed to polyamine compounds or glutaraldehyde for two hours. The strips of galvanized steel were then removed, fixed in 0.25% glutaraldehyde for 2 hours (those that had already been exposed to glutaraldehyde were not fixed twice), and dehydrated in ascending concentrations of ethanol (70%, 95%, 100%) with 3×10 minute exchanges of each. Lastly, the strips were carbon-coated and were imaged using a JEOL JSM-6610 scanning electron microscope (SEM) with a lanthanum hexaboride ($LaB_6$) filament.

Example 6

One of the most promising aspects of polyamine compounds is that preliminary data suggests that these compounds address the characteristics of biofilms that have made them resistant to antibiotic treatment. Specifically, polyamine compounds have potent antimicrobial activity against very high inocula of bacteria and kill bacteria in a rapid fashion. Without meaning to be bound by theory, initial characterization suggests that polyamine compounds are membrane-active, meaning they are nonspecific in nature. This nonspecific action reduces the potential for bacteria to upregulate their defense mechanisms and reduces the risk of resistance development. From the data collected to date, it does not appear that polyamine compounds are limited to eradicating bacteria that are in log-phase growth as indicated by their activity against bacteria in the biofilm phenotype. Bacteria in a biofilm have reduced metabolic activity, which is one of the primary contributing factors that allows biofilms to resist traditional antibiotic therapy. Typically, antibiotics affect bacteria in log-phase growth. Finally, polyamine compounds have the ability to disperse biofilms while demonstrating antimicrobial kill. By dispersing and killing bacteria in a biofilm, it is hypothesized that polyamine compounds interrupt water channels and the community as a whole, allowing for distribution of polyamine compounds to a greater number, if not all, of the cells within a biofilm.

A key aspect of polyamine compounds is the process by which they are synthesized to provide triple action against bacteria and biofilms. The ability to synthesize antimicrobial compounds with specific activity against biofilms is significant. Traditional approaches to discovering or developing antibiotics has primarily been done through cumbersome, high-throughput screening methods with limited results wherein perhaps 1 in 1,000 compounds may be of interest. Using the below method, our group was able to produce a lead product after synthesizing approximately 20 compounds.

Organisms residing in biofilms present a complex extracellular matrix of polysaccharides (exopolysaccharides) and proteins. As a result of this complex matrix, nutrient limiting conditions may exist that alter the normal or planktonic metabolic state. As stated above, this produces to a reduced efficacy of traditional antibiotic agents, rendering them up to 1,000 times less active. A hallmark of these exopolysaccharides is the presentation of acidic residues from repeated glucoronic acid motifs and pyruvate derived acetals. A recent study by Losick and co-workers demonstrated that the simple polyamines spermine and norspermidine were naturally occurring inhibitors of biofilm formation, endogenously produced at high concentrations (50-80 µM) in response to nutrient limiting conditions and waste accumulation in mature pellicles. In this study they were able to demonstrate that norspermidine could inhibit biofilm formation at 25 µM and showed that at similar concentrations it could disperse the exopolysaccharide component of the matrix but not the protein component. This does suggest, however, that these agents might be capable of disassembling established biofilms. Interestingly, spermidine was only active at much higher concentrations (~1 mM) leading them to propose a rationale for this activity in the ability of the polyamines to engage the acidic residues in the matrix at regular intervals.

Figure 24:
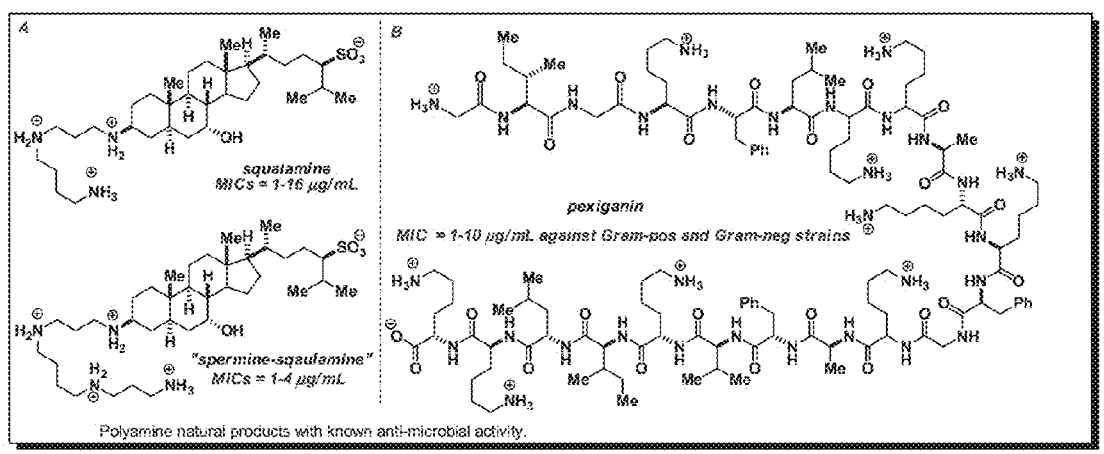
FIG. 24 shows several polyamine-containing natural products with antimicrobial activity.

Given the lack of activity for spermidine vs. norspermidine, it is interesting to note that many secondary metabolites containing the polyamine frameworks have been identified as potent antimicrobials against planktonic bacteria. Most notably squalamine, which contains a spermidine tail, and the related natural product incorporating a spermine tail show potent antimicrobial activity against Gram-positive and Gram-negative bacteria (FIG. 24). Lysine-rich cationic peptides such as magainin and pexiganin are also potent anti-microbials against a wide range of organisms and have been developed as topical antimicrobials for the treatment of diabetic foot ulcers.

Of note is the incorporation of hydrophobic and cationic residues that are present in these antimicrobial "kill" compounds, without adhering to the strict hydrogen bond donor-acceptor pattern of the biofilm disruptors. Thus, an initial study was made to investigate the utility of combining a simplified hydrophobic backbone with a cationic tail that might impart molecules with the ability to inhibit biofilm formation, disrupt established biofilms and kill the emerging planktonic bacteria. The study began with the synthesis of benzylic substituted polyamines (FIG. 25). The synthesis of diaminopropane substituted backbones is straightforward to provide CZ-4,12,32 from the known mono-Boc protected diaminopropane and the commercially available aldehydes (benzaldehyde, isopthalaldehyde or 1,3,5-benzenetricarboxaldehyde). This three-step synthetic procedure proceeds via reductive amination and acidic removal of the Boc group. Of note is that no purification is required until a final recrystallization of the HCl salt. The norspermidine series (CZ-7, 25,52) can be prepared in a similar manner from the mono-Boc protected norspermidine. Of note is that no purification is required until a final recrystallization of the HCl salt, which allows easy preparation of these compounds on at least a ~10 g scale.

In some cases, increasing number of polyamine chains on the hydrophobic backbone systematically increases activity. For example, with a single chain of diaminopropane added to a benzyl backbone (CZ-4, FIG. 25), the minimum inhibitory concentration (MIC; as defined by the Clinical and Laboratory Standards Institute (CLSI)) against MRSA is greater than 1,200 µg/mL, whereas two chains decrease the MIC to 300 µg/mL (CZ-12) and three chains reduce it further to 45 µg/mL (CZ-32). Similarly, with a single chain of norspermidine attached to a benzyl backbone (CZ-7, FIG. 25), the MIC against MRSA is greater than 1,200 µg/mL. By adding a second chain of norspermidine (CZ-25), the MIC is 45 µg/mL. With a third chain of norspermidine attached (CZ-52), the MIC becomes 3 µg/mL.

Concurrently to the other goals of this project, a focused synthetic effort will continue to exploit this trend and generate related chemotypes with increased efficacy (e.g., compounds with four polyamine chains). This is expected to be accomplished, for example, via Pd(II) mediated dimerization of 5-bromoisopthalaldehyde followed by reductive amination (FIG. 26).

Example 7

Evaluation of Biofilm Remediation and Removal Chemistries

A series of experiments is conducted to investigate the impact of biofilm remediation and removal chemistries on mimetic multispecies biofilms commonly associated with anthropogenic heating and cooling water systems.

The criteria for success is to demonstrate that these chemistries:

(1) Remove a multispecies biofilm from a copper, mild steel, galvanized steel, and stainless steel substrate to a greater extent than that which can be achieved by the existing water treatment chemistries.

(2) Do not aggressively corrode the metal substrates when used in an optimum concentration.

(3) Avoid material compatibility issues with the existing treatment chemicals used to minimize scale formation and prevent corrosion of the metal parts of the anthropogenic heating and cooling system.

Biofilm Generation on the Metal Coupons

Normally, monoculture bacteria belonging to the *Pseudomonas* genus have been used to investigate the physical and mechanical properties of biofilm on different heat exchanger surfaces and substrates under changing flow conditions. However, to more accurately represent conditions that would be found in the real environment, a mixture of *Pseudomonas fluorescens* and *Pseudomonas putida* together with a 0.1% mixture of NCH 3010 *Bacillus subtilis*, NCH 3032 *Bacillus subtilis*, NCH 3016 *Bacillus licheniformis*, and NCH 3040 *Bacillus thuringiensis* all of which are naturally occurring soil bacteria is used. The microorganisms will be provided in pellet form from Eco-Bionics, and each pellet contains a starter culture and appropriate nutrients that produce actively growing bacteria with the addition of water.

Figure 21:
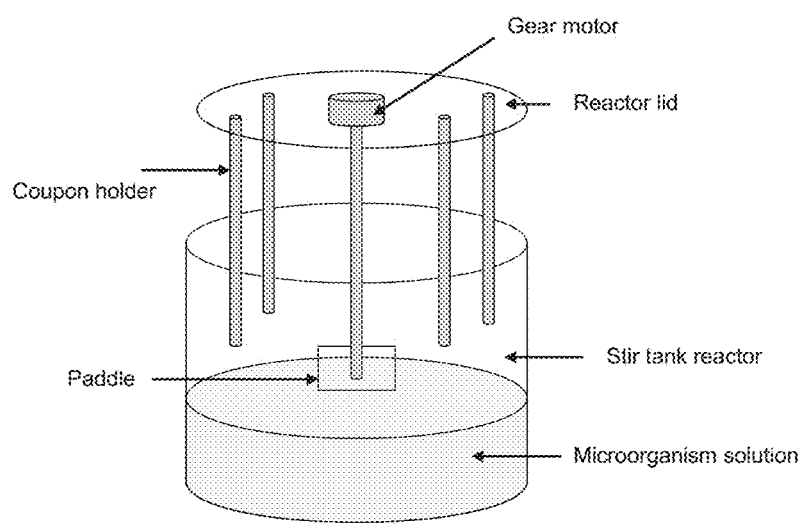
FIG. 21 shows a schematic of the stir tank biofilm reactor.
Figure 22:
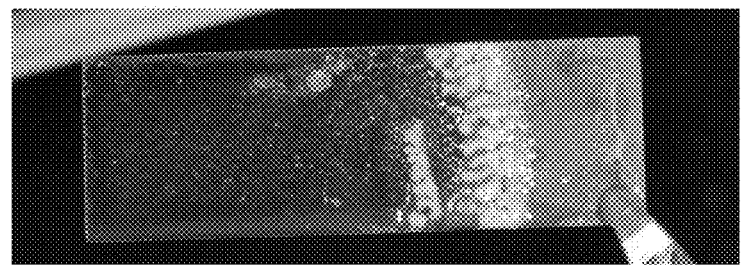
FIG. 22 shows a photograph of a glass slide removed after 6 days in the stir tank bioreactor.

The experimental test procedure is a modified version of the single tube method. Biofilm are grown on the metal coupons using a biofilm reactor designed around a continuous stir tank reactor (FIG. 21). Prior to operation the reaction chamber and the individual components are disassembled, soaked in a 10% bleach solution, then scrubbed in hot soapy water and rinsed in distilled water. Once cleaned, the stir tank reactor is charged with 2 liters of DI water, and 20 g of the Free Flow pellets will be added to the water. Coupons are placed onto the coupon holding rods, which is then inserted into the Free Flow pellet solution. The reactor runs for 6 days with the Free Flow solution being replaced every 2 days.

Biofilm growth is visually observed and documented photographically. To quantify the presence of viable microorganisms within the biofilm structure formed on the metal coupons (see FIG. 17 for an example of the typical biofilm formed on the substrate) the biofilm covered coupons is removed from the reactor and lightly rinsed with sterile buffer to remove any loose debris from the surface. The coupons are then transferred to a container with 40 ml of Phosphate buffer solution (PBS) and vortexed for 30 sec then placed in a sonication bath (Branson model 3200) for 30 sec. After sonication, the container with the buffer and coupon is removed and vortexed again for 30 sec before being returned to the sonication bath for an additional 30 sec of processing. A third and final vortexing step ensures that the adhered biofilm will be thoroughly removed. After processing to remove the biofilm the PBS solution will be serially diluted onto tryptic soy agar (TSA) plates which will be incubated at 30° C. for up to 36 hours before being enumerated.

The biofilm coupons are exposed to a high, medium, and low concentration of the product (based on the recommended dosing rates) for a prescribed time. After treatment, the coupons are removed, and the eluant and treatment solutions are assayed to enumerate viable bacteria A standard dispersant used for biofilm removal, together with a standard biocide (oxidizing and non-oxidizing) used at the recommended label use concentrations, are used as controls.

Corrosion Testing

Treatment solution of the same concentrations used in the experiments above is prepared with standard corrosion inhibitor products and calcium deposit products in regular tap water and tested in a standard corrosion test. The solution is added to a treatment tank that is stirred continually for two weeks, after which the coupons are removed and analyzed for corrosion using standard corrosion test methods. Corrosion rates of less than 3.0 mpy for mild steel and 0.2 mpy for copper are considered non corrosive. A standard dispersant used for biofilm removal together with a standard biocide (oxidizing and non-oxidizing) used at the recommended label use concentrations are used as controls.

Conclusions

We have been able to determine minimum amounts of our polyamine compounds that will have activity against biofilms of *P. aeruginosa*. In general, the polyamine compounds do better against Bacilli than *P. aeruginosa*, so what is active against *P. aeruginosa* is likely active against Bacilli.

These formulas are made in PBS, water or broth.

Example 8

Methods for MIC, MBEC and EBEC Analysis

To determine the MIC of the compounds of the present invention the following procedure was used.

A 0.5 McFarland of *A. baumannii* is made. A 0.5 McFarland is a measure of turbidity in a liquid sample that contains approximately $7.5\times10^7$ CFU/mL. The 0.5 McFarland standard is diluted in CAMHB and 50 μL of broth is added to a well of a 96-well plate. In addition, 50 μL of CAMHB that contains a desired concentration of antimicrobial is added to the well for a final volume of 100 μL and a final concentration of approximately $5\times10^4$ CFU/well (which equates to approximately $5\times10^5$ CFU/mL). Each well contains a desired amount of CZ compound in order to experimentally determine the MIC. Each 96-well plate is incubated at 37° C. for 24 hours. The contents of each well is plated on tryptic soy agar (TSA). TSA plates is incubated at 37° C. for 24 hours after which the number of CFUs is counted and used to calculate the CFU/mL that remain after exposure to varying concentrations of compound. This procedure is repeated n=8 times for each concentration of antimicrobial. The concentration of CZ compound that reduces bacteria from $10^5$ CFU/mL to $10^2$ CFU/mL in 24 hours is considered the MIC.

To determine the MBEC, the MBEC Inoculation Tray by Innovotech, formerly known as the Calgary biofilm device, is used. Within this device, biofilms grow on the surface of polystyrene pegs, 96 of which are attached to a lid. These pegs are inserted into a flat bottom 96-well plate. In this instance, the MBEC of a molecule is defined as the concentration of compound required to reduce approximately $10^6$ CFU/peg to approximately $10^2$ CFU/peg in a 24-hour period.

Following the manufacturer's guidelines, biofilms are grown on the surface of each peg by first making a 0.5 McFarland of *A. baumannii*. The 0.5 McFarland is diluted 1:100 in CAMHB broth. Into each well of a flat bottom 96-well plate, 150 μL of broth is pipetted. The plate is shaken at 100 rpm for 24 hours. The pegs are placed into a separate flat bottom 96-well plate for 10 seconds with 200 μL of phosphate buffered saline (PBS) in each well to remove nonadherent cells. The lid is placed into a 96-well plate that contains varying concentrations of antimicrobial with 200 μL of broth per well. The plate is incubated for 24 hours at 37° C. after which time 100 μL of broth is plated on TSA. TSA plates is incubated 24 hours at 37° C. and the number of CFU counted to calculate the CFU/peg.

In addition to determining the MIC and the MBEC of compounds against planktonic bacteria and low number biofilms, the efficacy of the compounds of the invention against high number biofilms is determined. To do so, biofilms are grown on the surface of PEEK membranes using a membrane biofilm reactor (Williams, D. L., Haymond, B. S. & Bloebaum, R. D. Use of delrin plastic in a modified CDC biofilm reactor. *Res J Microbiol* 6, 425-429 (2011); Williams, D. L., Woodbury, K. L., Haymond, B. S., Parker, A. E. & Bloebaum, R. D. A modified CDC biofilm reactor to produce mature biofilms on the surface of PEEK membranes for an in vivo animal model application. *Curr Microbiol* 62, 1657-1663 (2011); Williams, D. L. et al., In Vivo Efficacy of a Silicone—Cationic Steroid Antimicrobial Coating to Prevent Implant-Related Infection. *Biomaterials* 33, 8641-8656 (2012); Williams, D. L. et al., Experimental model of biofilm implant-related osteomyelitis to test combination biomaterials using biofilms as initial inocula. *J Biomed Mat Res A* 100, 1888-1900 (2012)). This reactor is similar to the CDC biofilm reactor, but rather than growing biofilms on coupon surfaces, the reactor was modified to hold PEEK membranes. In short, to grow biofilms within this system, 500 mL of brain heart infusion (BHI) broth is inoculated with 1 mL of a 0.5 McFarland. The reactor is placed on a hot plate set at 34° C. and the bacteria grown under batch conditions for 24 hours. A solution of 10% BHI will then be flowed through the reactor at a rate of 6.94 mL/min for an additional 24 hours. Following this protocol, biofilms typically grow to $10^9$ CFU/PEEK membrane. PEEK membranes is removed and placed into 2 mL of CAMHB that contain a desired concentration of the test compound. The EBEC is defined as the concentration of antimicrobial required to reduce a biofilm from approximately $10^9$ CFU/PEEK membrane to approximately $10^2$ CFU/PEEK membrane in a 24-hour period.

MIC, MBEC and EBEC Analysis

To determine the MIC of the test compounds and traditional antibiotics, a protocol which defines the MIC as being the concentration of antimicrobial required to reduce the number of bacteria in a solution from $10^5$ colony forming units (CFU)/mL to $10^2$ CFU/mL in a 24-hour period. MICs for tests compounds as well as for select antibiotics are provided in Table 4. Consistent with what was mentioned previously, these data indicate that, with an increase in the number of polyamine chains attached to a lipophilic backbone, the MIC is lowered, indicating it has greater antimicrobial potential. CZ-7 has one chain of norspermidine attached, CZ-25 has two chains of norspermidine, and CZ-52 has three chains attached (FIG. 25).

The trend of increasing antimicrobial activity by increasing the number of polyamine chains attached to a backbone while also modulating the hydrophobicity of that backbone shows promising activity against *A. baumannii*, more specifically in the case of CZ-58 (FIG. 27). The analysis below shows that compounds of the invention have increased efficacy relative to current therapies (e.g., polymyxin B).

MBEC data were collected using the MBEC Inoculation Tray by Innovotech. The MBEC was defined in these preliminary results as the concentration of antimicrobial required to reduce $10^5$ or $10^6$ CFU/peg to $10^2$ CFU/peg in a 24-hour period. MBEC data are presented in Table 4.

TABLE 4

MICs, MBECs and EBECs of CZ compounds and traditional antibiotics. Data reported in μg/mL and μM concentrations.

| Compound | MIC μg/mL (μM) | | MBEC μg/mL (μM) | | EBEC μg/mL (μM) | |
|---|---|---|---|---|---|---|
| | MRSA | A. baumannii | MRSA | A. baumannii | MRSA | A. baumannii |
| CZ-7 | >500 (>2,259) | >500 (>2,259) | >500 (>2,259) | >500 (>2,259) | >5,000 (>22,590) | >10,000 (>45,180) |
| CZ-25 | 40 (110) | 150 (411) | 25 (69) | 450 (1234) | >5,000 (13,715) | ~7,500 |
| CZ-52 | 3 (6) | 400 (800) | 20 (40) | >500 (995) | 250 (500) | ~7,000 (~14,000) |
| CZ-58 | 6 (13.6) | 30 (68) | 30 (68) | >50 (>113) | 1,500 (3,403) | 400 (908) |
| Vancomycin | 10 (6.9) | — | >500 (>345) | — | >>25,000 (>>17,225) | — |
| Polymyxin B sulfate | — | 1 (0.7) | — | 50 (36) | — | 1,000 (722) |

EBEC data were collected to determine the efficacy of CZ-52, CZ-58 and traditional antibiotics against high number biofilms containing approximately $10^9$ CFU grown on the surface of a polyetheretherketone (PEEK) membrane. Results are shown in Table 4. EBEC data showed striking differences in efficacy between CZ-52 and vancomycin (Table 4). At 25,000 μg/mL, vancomycin did not have the ability to reduce biofilms of MRSA by even 1 $\log_{10}$ unit. In contrast, at 250 μg/mL CZ-52 was able to reduce MRSA biofilms by greater than 7 $\log_{10}$ units in a 24-hour period. Although the MIC of CZ-58 was lower against MRSA compared to A. baumannii, CZ-58 had greater activity against biofilms of A. baumannii than against MRSA biofilms in the EBEC assay. The EBEC of polymyxin B against A. baumannii was 1,000× greater than the MIC, whereas the EBEC for CZ-58 was only ~13× greater than the MIC. Although the MIC of CZ-58 was "high" compared to MICs of traditional antibiotics, the efficacy against biofilms was promising.

Table 5 provides MIC results for a variety of compounds against MRSA, *Pseudomonas aeruginosa*, and *Acinetobacter baumannii*.

TABLE 5

MICs of CZ compounds.

| CZ No. | Compound | MIC (MRSA) | MIC (P. aeruginosa) | MIC (A. bumannii) |
|---|---|---|---|---|
| CZ-3 | Benzyl-NH-(CH₂)₄-NH₂ · 2 HCl | + | | + |
| CZ-4 | Benzyl-NH-(CH₂)₃-NH₂ · 2 HCl | + | | + |
| CZ-5 | Benzyl-NH-(CH₂)₁₀-NH₂ · 2 HCl | + | | |
| CZ-6 | Benzyl-NH-(CH₂)₃-NH-(CH₂)₃-N(Me)₂ · 3 HCl | + | | |

TABLE 5-continued

MICs of CZ compounds.

| CZ No. | Compound | MIC (MRSA) | MIC (P. aeruginosa) | MIC (A. bumannii) |
|---|---|---|---|---|
| CZ-7 | benzyl-NH-(CH2)3-NH-(CH2)3-NH2 · 3 HCl | + | + | |
| CZ-8 | benzyl-NH-(CH2)10-NH2 | + | | |
| CZ-9 | benzyl-NH-(CH2)4-NH2 · 2 HCl | + | | |
| CZ-10 | benzyl-N(Me)-(CH2)10-N(Me)2 · 2 HCl | + | | |
| CZ-11 | benzyl-NH-(CH2)10-NH-benzyl · 2 HCl | + | | |
| CZ-12 | H2N-(CH2)3-NH-CH2-(m-C6H4)-CH2-NH-(CH2)3-NH2 · 4 HCl | + | ++ | |
| CZ-13 | (3-MeO-benzyl)-NH-(CH2)10-NH2 · 2 HCl | + | | |
| CZ-14 | H2N-(CH2)3-NH-CH2-(m-C6H4)-CH2-NH-(CH2)3-NH2 | + | | |
| CZ-15 | benzyl-NH-(CH2)3-NH-(CH2)3-NH2 | + | | |

TABLE 5-continued

MICs of CZ compounds.

| CZ No. | Compound | MIC (MRSA) | MIC (*P. aeruginosa*) | MIC (*A. bumannii*) |
|---|---|---|---|---|
| CZ-16 | (structure) .4HCl | + | | |
| CZ-19 | (structure) .4HCl | + | | |
| CZ-21 | (structure) | +++ | | + |
| CZ-22 | (structure) .3HCl | ++ | | |
| CZ-24 | (structure) | | | |
| CZ-25 | (structure) .6 HCl | +++ | + | + |
| CZ-25 (Bz) | (structure) .6 HOBz | +++ | | |

TABLE 5-continued
MICs of CZ compounds.
| CZ No. | Compound | MIC (MRSA) | MIC (P. aeruginosa) | MIC (A. bumannii) |
|---|---|---|---|---|
| CZ-26 | 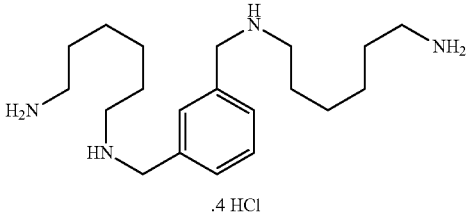 [SMILES: NCCCCCCNCc1cccc(CNCCCCCCN)c1] .4 HCl | ++ | + | |
| CZ-27 | 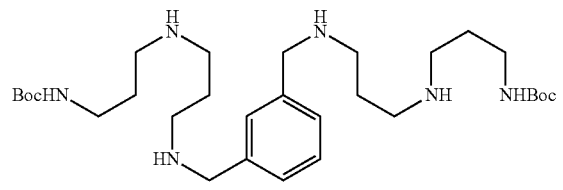 [SMILES: CC(C)(C)OC(=O)NCCCNCCCNCc1cccc(CNCCCNCCCNC(=O)OC(C)(C)C)c1] | + | | |
| CZ-32 | 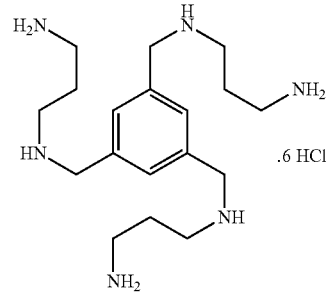 [SMILES: NCCCNCc1cc(CNCCCN)cc(CNCCCN)c1] .6 HCl | ++ | ++ | |
| CZ-33 | 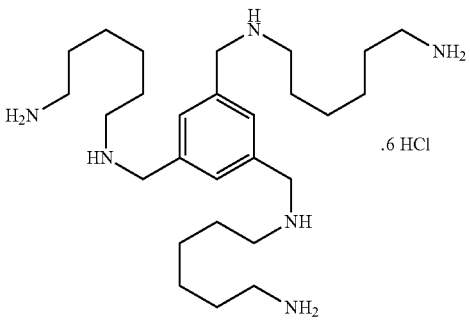 [SMILES: NCCCCCCNCc1cc(CNCCCCCCN)cc(CNCCCCCCN)c1] .6 HCl | ++ | + | |
| CZ-40 | 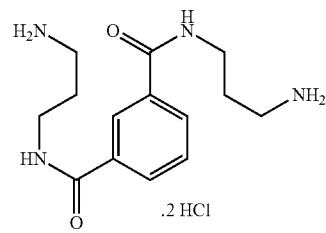 [SMILES: NCCCNC(=O)c1cccc(C(=O)NCCCN)c1] .2 HCl | + | + | |
| CZ-41 | 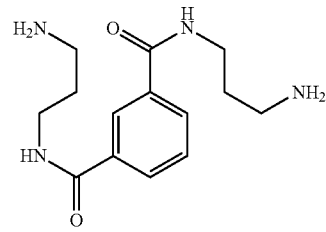 [SMILES: NCCCNC(=O)c1cccc(C(=O)NCCCN)c1] | + | | |

TABLE 5-continued

MICs of CZ compounds.

| CZ No. | Compound | MIC (MRSA) | MIC (P. aeruginosa) | MIC (A. bumannii) |
|---|---|---|---|---|
| CZ-42 | (structure) | ++ | ++ | |
| CZ-43 | (structure) .6 HCl | + | + | |
| CZ-46 | (structure) | | | |
| CZ-51 | (structure) .9 HCl mixture of mono/di/tri-Boc | +++ | +++ | |

TABLE 5-continued
MICs of CZ compounds.
| CZ No. | Compound | MIC (MRSA) | MIC (P. aeruginosa) | MIC (A. bumannii) |
|---|---|---|---|---|
| CZ-52 | 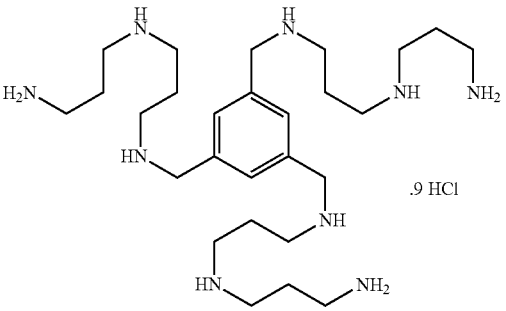 [SMILES: NCCCNCCCNCc1cc(CNCCCNCCCN)cc(CNCCCNCCCN)c1] .9 HCl | +++ | +++ | + |
| CZ-53 | 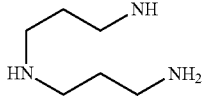 .6 HCl | +++ | ++ to +++ | |
| CZ-54 | 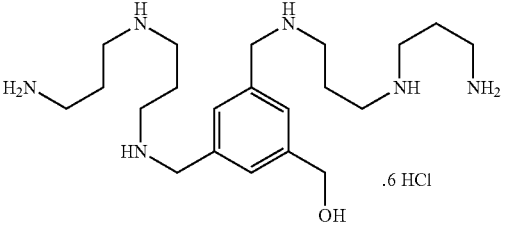 [SMILES: NCCCNCCCNCc1cc(CO)cc(CNCCCNCCCN)c1] .8 HCl | +++ | +++ | |
| CZ-55 | 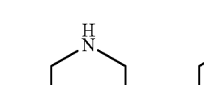 .x HOBz | +++ | +++ | + |
| CZ-56 | 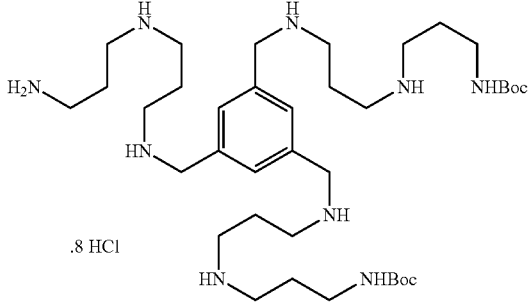 [SMILES: CC(C)(C)OC(=O)NCCCNCCCNCc1cc(CNCCCNCCCN)cc(CNCCCNCCCNC(=O)OC(C)(C)C)c1] .x decanoic acid | | | |

TABLE 5-continued
MICs of CZ compounds.
| CZ No. | Compound | MIC (MRSA) | MIC (*P. aeruginosa*) | MIC (*A. bumannii*) |
|---|---|---|---|---|
| CZ-57 | 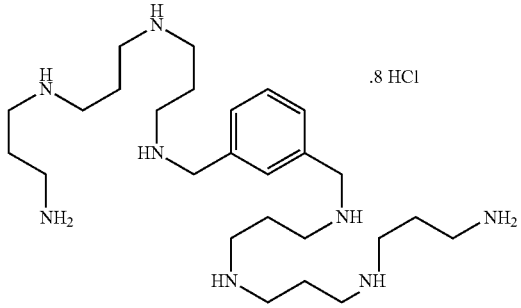 [SMILES: NCCCNCCCNCCCNCc1cccc(CNCCCNCCCNCCCN)c1] .8 HCl | +++ | + | |
| CZ-58 | 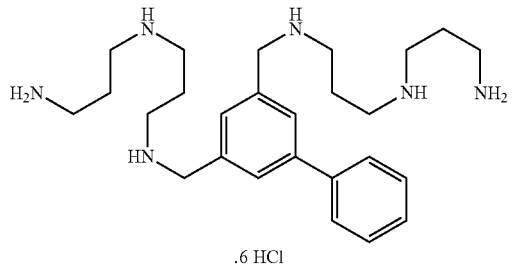 [SMILES: NCCCNCCCNCc1cc(CNCCCNCCCN)cc(-c2ccccc2)c1] .6 HCl | +++ | ++ to +++ | ++ |
| CZ-60 | 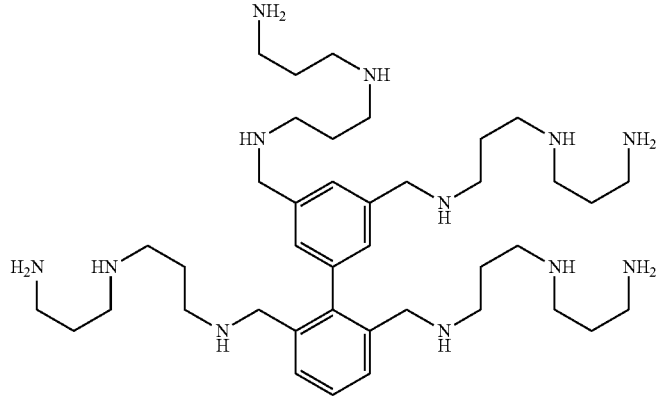 [SMILES: NCCCNCCCNCc1cc(CNCCCNCCCN)cc(-c2c(CNCCCNCCCN)cccc2CNCCCNCCCN)c1] | +++ | + | + |
| CZ-61 | 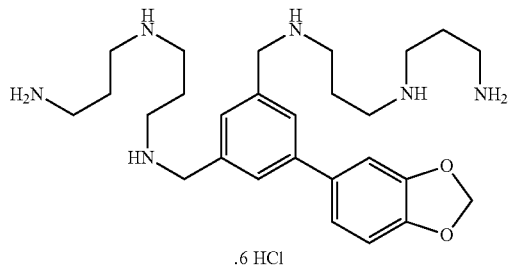 [SMILES: NCCCNCCCNCc1cc(CNCCCNCCCN)cc(-c2ccc3c(c2)OCO3)c1] .6 HCl | +++ | +++ | +++ |

TABLE 5-continued

MICs of CZ compounds.

| CZ No. | Compound | MIC (MRSA) | MIC (*P. aeruginosa*) | MIC (*A. bumannii*) |
|---|---|---|---|---|
| CZ-62 | (structure) .9 HCl | +++ | +++ | +++ |
| CZ-63 | (structure) .6 HCl | +++ | +++ | +++ |
| CZ-64 | (structure) .6 HCl | | | |
| CZ-65 | (structure) .9 HCl | +++ | +++ | +++ |
| CZ-66 | (structure) .9 HCl | +++ | +++ | |

TABLE 5-continued
MICs of CZ compounds.
| CZ No. | Compound | MIC (MRSA) | MIC (*P. aeruginosa*) | MIC (*A. bumannii*) |
|---|---|---|---|---|
| CZ-67 | 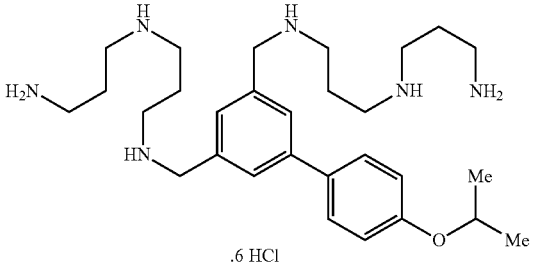 [SMILES: CC(C)Oc1ccc(-c2cc(CNCCCNCCCN)cc(CNCCCNCCCN)c2)cc1] | | | |
| CZ-68 | 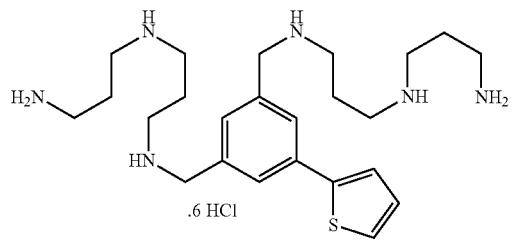 [SMILES: NCCCNCCCNCc1cc(CNCCCNCCCN)cc(-c2cccs2)c1] | | | |
| CZ-69 | 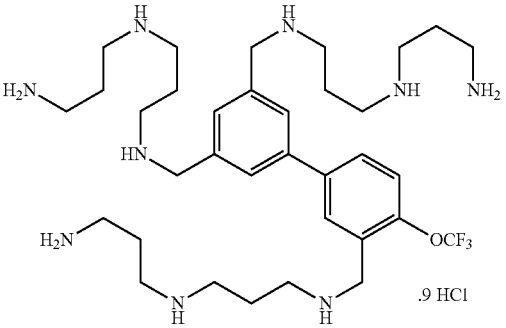 [SMILES: NCCCNCCCNCc1cc(CNCCCNCCCN)cc(-c2ccc(OC(F)(F)F)c(CNCCCNCCCN)c2)c1] | +++ | +++ | |
| CZ-70 | 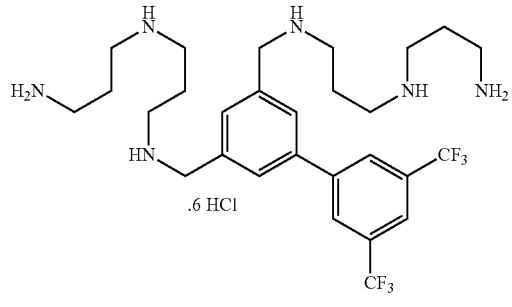 [SMILES: NCCCNCCCNCc1cc(CNCCCNCCCN)cc(-c2cc(C(F)(F)F)cc(C(F)(F)F)c2)c1] | +++ | +++ | |
| CZ-71 | 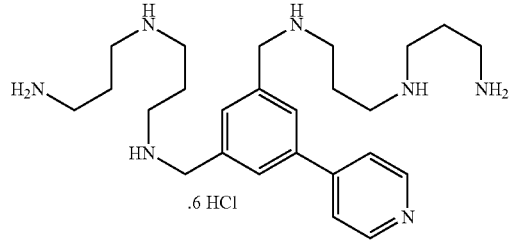 [SMILES: NCCCNCCCNCc1cc(CNCCCNCCCN)cc(-c2ccncc2)c1] | +++ | + | |

TABLE 5-continued
MICs of CZ compounds.
| CZ No. | Compound | MIC (MRSA) | MIC (P. aeruginosa) | MIC (A. bumannii) |
|---|---|---|---|---|
| CZ-72 | 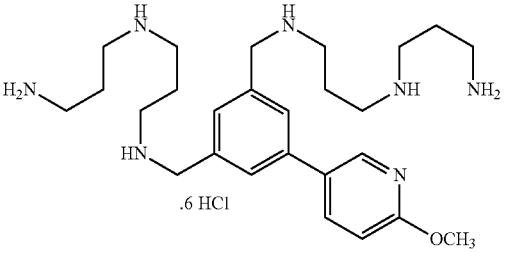 [SMILES: COc1ccc(-c2cc(CNCCCNCCCN)cc(CNCCCNCCCN)c2)cn1] | +++ | +++ | |
| CZ-73 | 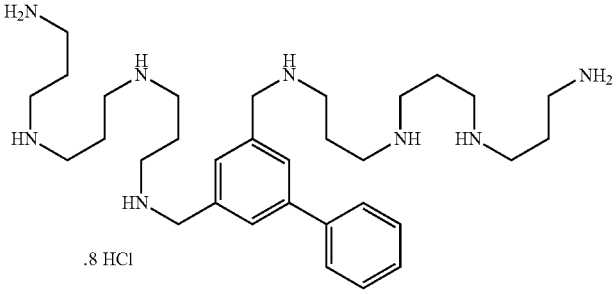 [SMILES: NCCCNCCCNCCCNCc1cc(CNCCCNCCCNCCCN)cc(-c2ccccc2)c1] | +++ | +++ | ++ |
| CZ-74 | 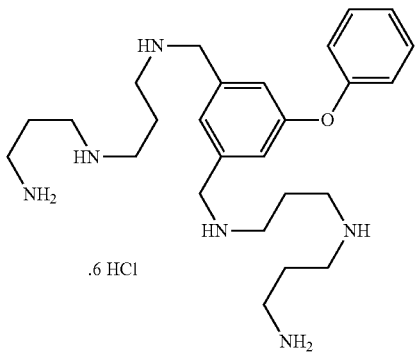 [SMILES: NCCCNCCCNCc1cc(CNCCCNCCCN)cc(Oc2ccccc2)c1] | +++ | +++ | |
| CZ-75 | 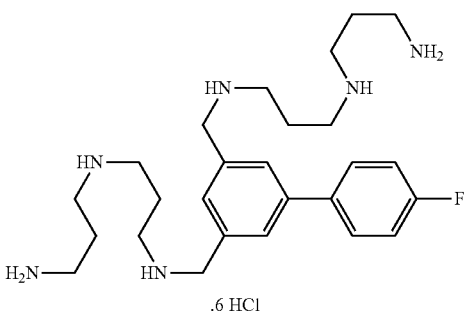 [SMILES: NCCCNCCCNCc1cc(CNCCCNCCCN)cc(-c2ccc(F)cc2)c1] | +++ | +++ | |
| CZ-76 | 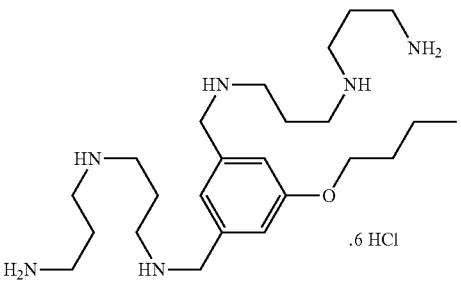 [SMILES: CCCCOc1cc(CNCCCNCCCN)cc(CNCCCNCCCN)c1] | +++ | ++ | |

TABLE 5-continued
MICs of CZ compounds.
| CZ No. | Compound | MIC (MRSA) | MIC (P. aeruginosa) | MIC (A. bumannii) |
|---|---|---|---|---|
| CZ-77 | 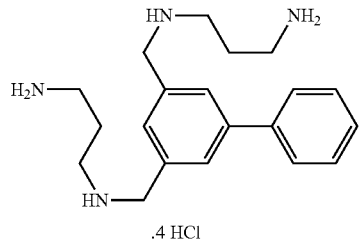 [SMILES: NCCCNCc1cc(CNCCCN)cc(-c2ccccc2)c1] .4 HCl | +++ | +++ | |
| CZ-81 | 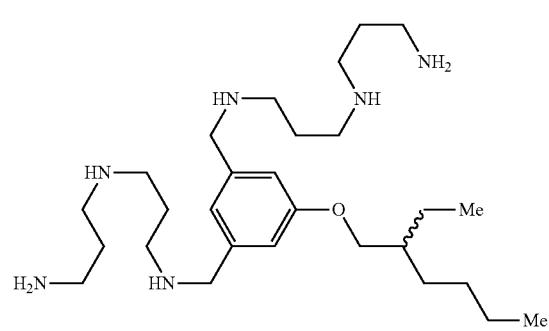 .6 HCl | +++ | +++ | +++ |
| CZ-83 | 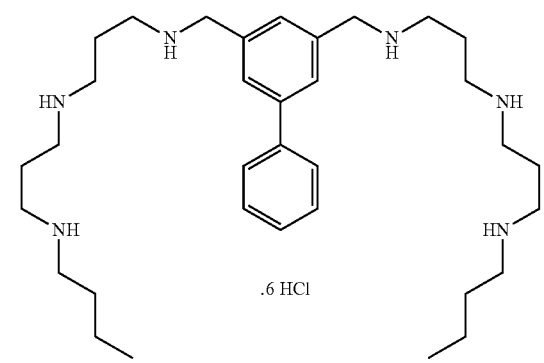 [SMILES: CCCCNCCCNCCCNCc1cc(CNCCCNCCCNCCCC)cc(-c2ccccc2)c1] .6 HCl | +++ | +++ | +++ |
| CZ-84 | 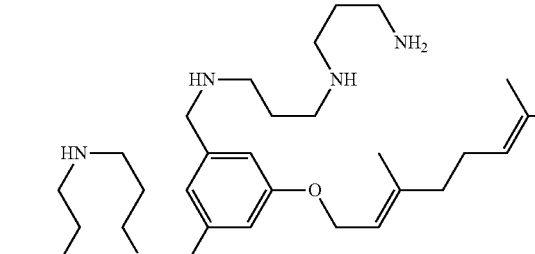 | | | |

TABLE 5-continued
MICs of CZ compounds.
| CZ No. | Compound | MIC (MRSA) | MIC (*P. aeruginosa*) | MIC (*A. bumannii*) |
|---|---|---|---|---|
| CZ-86 | 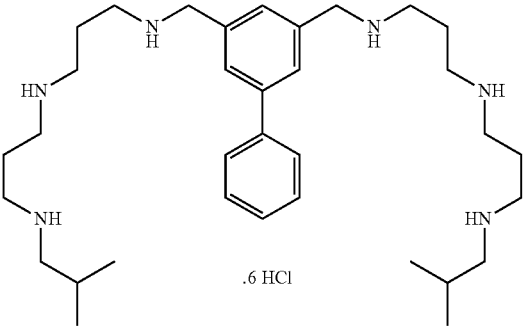 [SMILES: CC(C)CNCCCNCCCNCc1cc(CNCCCNCCCNCC(C)C)cc(-c2ccccc2)c1] .6 HCl | +++ | ++ to +++ | +++ |
| CZ-86 Free Base | 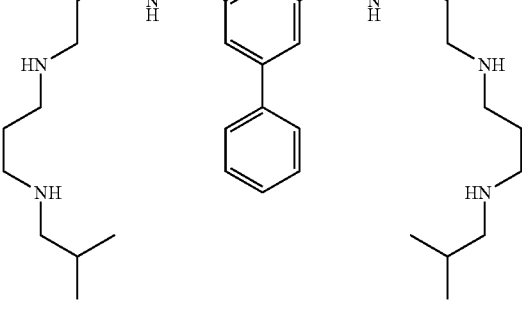 | | | |
| CZ-87 | 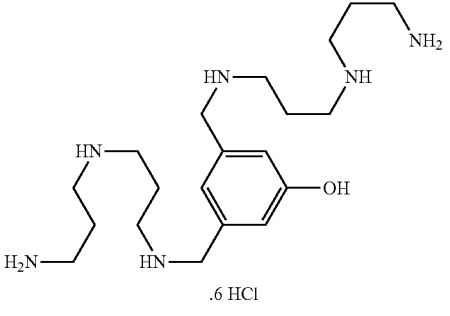 [SMILES: NCCCNCCCNCc1cc(O)cc(CNCCCNCCCN)c1] .6 HCl | +++ | +++ | |
| CZ-88 | 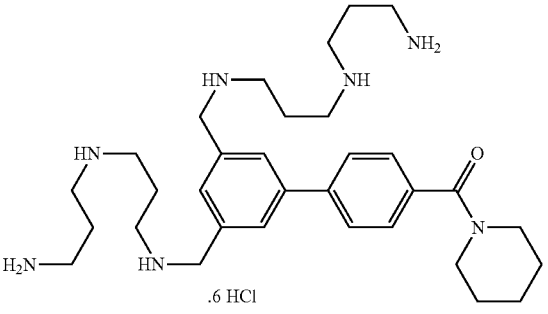 [SMILES: NCCCNCCCNCc1cc(CNCCCNCCCN)cc(-c2ccc(C(=O)N3CCCCC3)cc2)c1] .6 HCl | +++ | +++ | |

TABLE 5-continued
MICs of CZ compounds.
| CZ No. | Compound | MIC (MRSA) | MIC (*P. aeruginosa*) | MIC (*A. bumannii*) |
|---|---|---|---|---|
| CZ-89 | 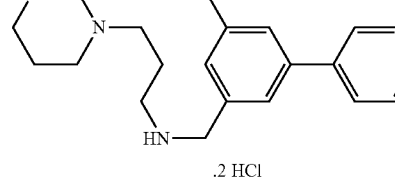 .2 HCl | +++ | +++ | |
| CZ-90 | 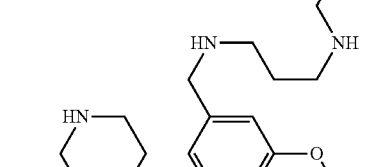 .6 HCl | +++ | +++ | |
| CZ-91 | 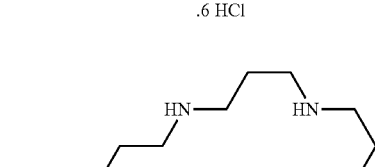 .6 HCl | +++ | +++ | |
| CZ-92 | 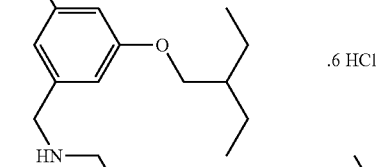 .6 HCl | +++ | +++ | |

TABLE 5-continued
MICs of CZ compounds.
| CZ No. | Compound | MIC (MRSA) | MIC (P. aeruginosa) | MIC (A. bumannii) |
|---|---|---|---|---|
| CZ-93 | 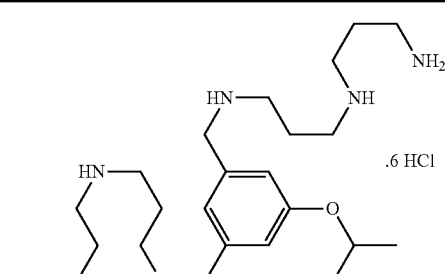 .6 HCl | +++ | +++ | |
| CZ-94 | 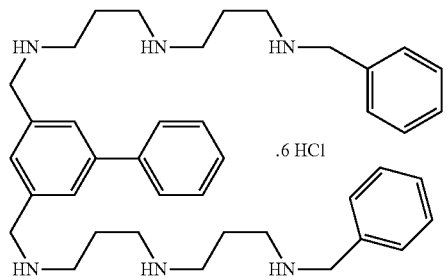 [SMILES: c1ccc(CNCCCNCCCNCc2cc(CNCCCNCCCNCc3ccccc3)cc(-c3ccccc3)c2)cc1] .6 HCl | +++ | +++ | |
| CZ-95 | 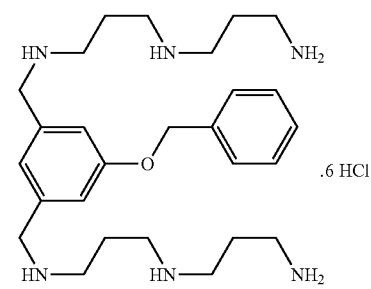 [SMILES: NCCCNCCCNCc1cc(CNCCCNCCCN)cc(OCc2ccccc2)c1] .6 HCl | +++ | +++ | |
| CZ-96 | 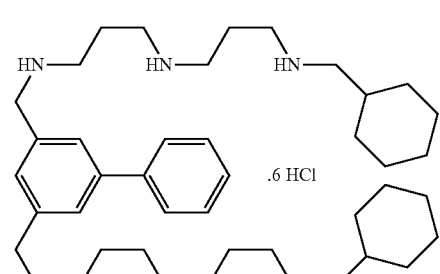 .6 HCl | +++ | +++ | |

TABLE 5-continued
MICs of CZ compounds.
| CZ No. | Compound | MIC (MRSA) | MIC (*P. aeruginosa*) | MIC (*A. bumannii*) |
|---|---|---|---|---|
| CZ-97 | 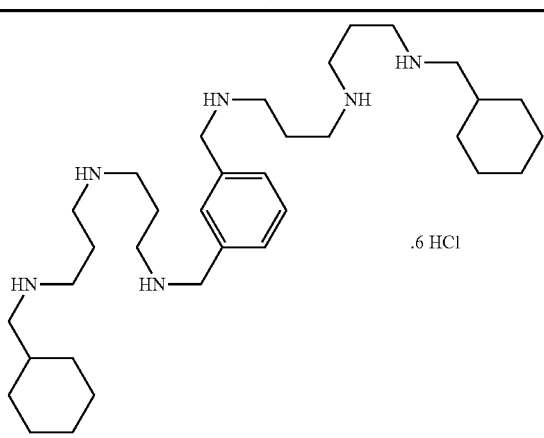 .6 HCl | +++ | +++ | |
| CZ-98 | 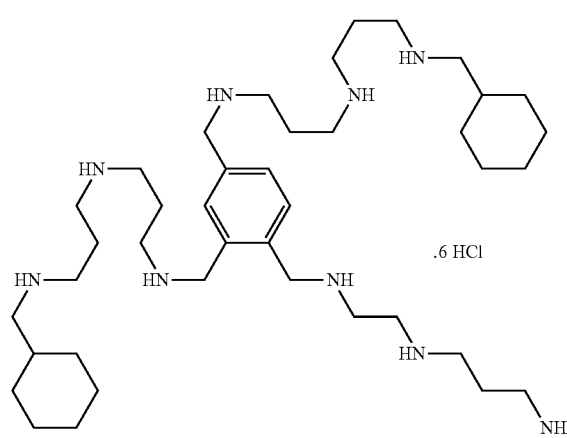 .6 HCl | | | |
| CZ-99 | 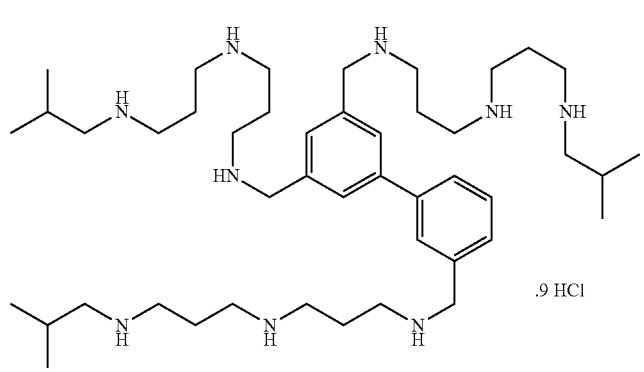 [SMILES: CC(C)CNCCCNCCCNCc1cccc(-c2cc(CNCCCNCCCNCC(C)C)cc(CNCCCNCCCNCC(C)C)c2)c1] .9 HCl | +++ | ++ to +++ | |
| CZ-100 | 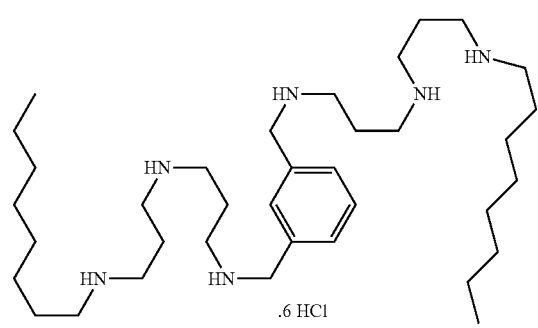 [SMILES: CCCCCCCCNCCCNCCCNCc1cccc(CNCCCNCCCNCCCCCCCC)c1] .6 HCl | +++ | +++ | +++ |

TABLE 5-continued
MICs of CZ compounds.
| CZ No. | Compound | MIC (MRSA) | MIC (P. aeruginosa) | MIC (A. bumannii) |
|---|---|---|---|---|
| CZ-101 | 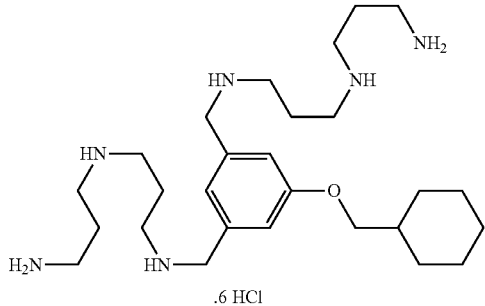 [SMILES: NCCCNCCCNCc1cc(CNCCCNCCCN)cc(OCC2CCCCC2)c1] .6 HCl | +++ | +++ | |
| CZ-102 | 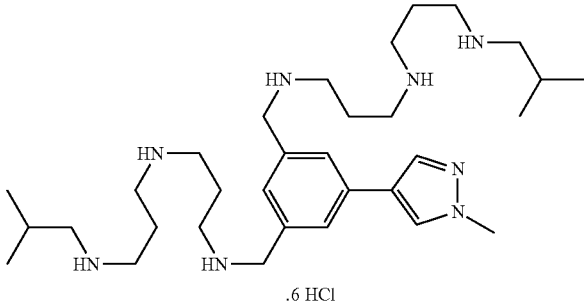 [SMILES: CC(C)CNCCCNCCCNCc1cc(CNCCCNCCCNCC(C)C)cc(-c2cnn(C)c2)c1] .6 HCl | +++ | ++ | |
| CZ-103 | 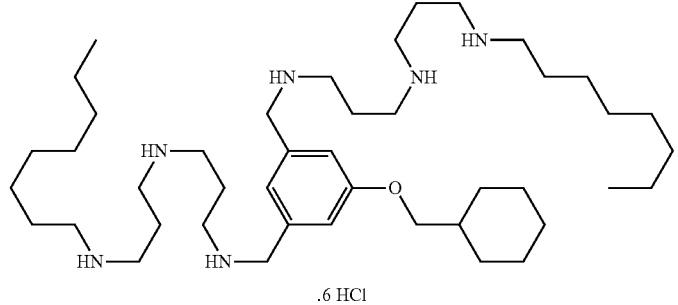 [SMILES: CCCCCCCCNCCCNCCCNCc1cc(CNCCCNCCCNCCCCCCCC)cc(OCC2CCCCC2)c1] .6 HCl | +++ | +++ | +++ |
| CZ-104 | 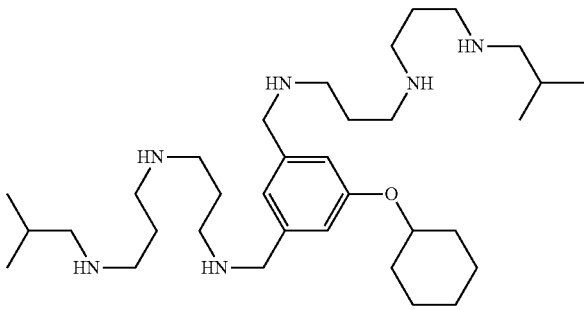 [SMILES: CC(C)CNCCCNCCCNCc1cc(CNCCCNCCCNCC(C)C)cc(OC2CCCCC2)c1] | +++ | ++ to +++ | |

TABLE 5-continued
| | MICs of CZ compounds. | | | |
|---|---|---|---|---|
| CZ No. | Compound | MIC (MRSA) | MIC (P. aeruginosa) | MIC (A. bumannii) |
| CZ-105 | 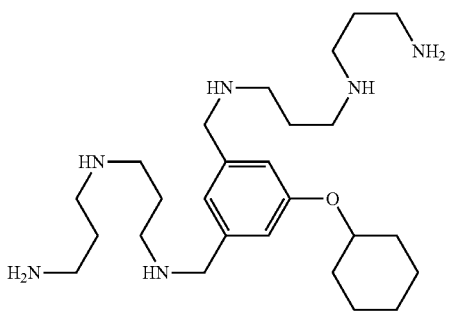 .6 HCl | +++ | ++ | |
| CZ-106 | 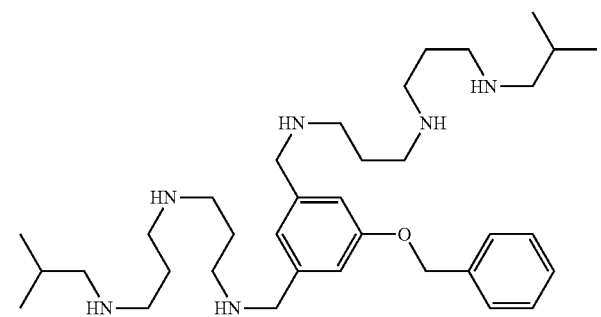 .6 HCl | +++ | ++ | |
| CZ-107 | 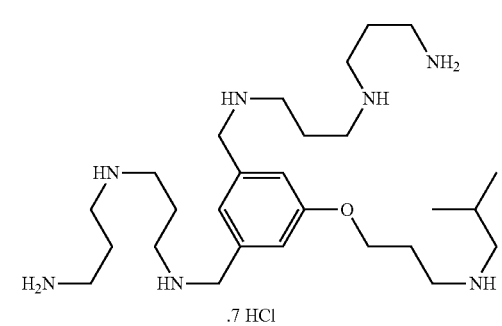 [SMILES: CC(C)CNCCCOc1cc(CNCCCNCCCN)cc(CNCCCNCCCN)c1] .7 HCl | +++ | ++ | |
| CZ-108 | 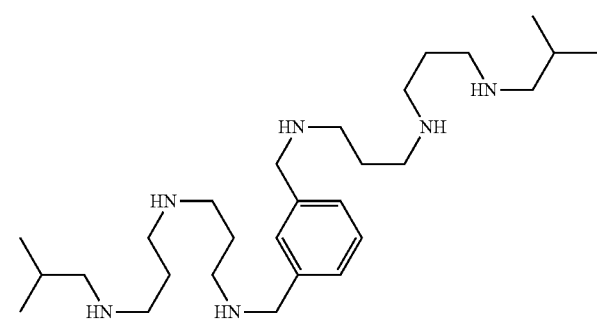 .6 HCl | +++ | +++ | |

TABLE 5-continued
MICs of CZ compounds.
| CZ No. | Compound | MIC (MRSA) | MIC (P. aeruginosa) | MIC (A. bumannii) |
|---|---|---|---|---|
| CZ-109 | 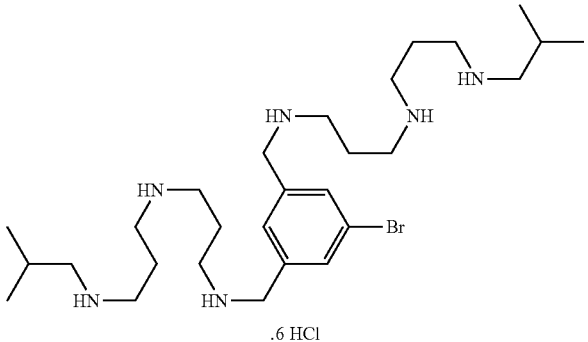 [SMILES: CC(C)CNCCCNCCCNCc1cc(Br)cc(CNCCCNCCCNCC(C)C)c1] .6 HCl | +++ | +++ | |
| CZ-110 | 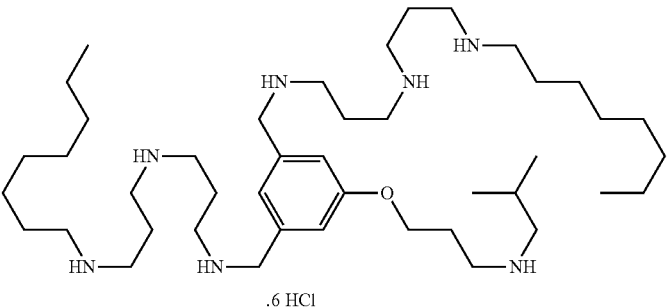 [SMILES: CCCCCCCCNCCCNCCCNCc1cc(CNCCCNCCCNCCCCCCCC)cc(OCCCNCC(C)C)c1] .6 HCl | +++ | +++ | +++ |
| CZ-111 | 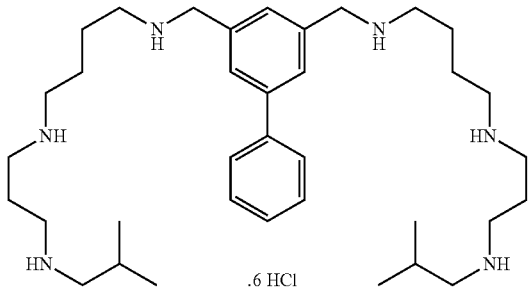 [SMILES: CC(C)CNCCCNCCCCNCc1cc(CNCCCCNCCCNCC(C)C)cc(-c2ccccc2)c1] .6 HCl | +++ | +++ | |
| CZ-112 | 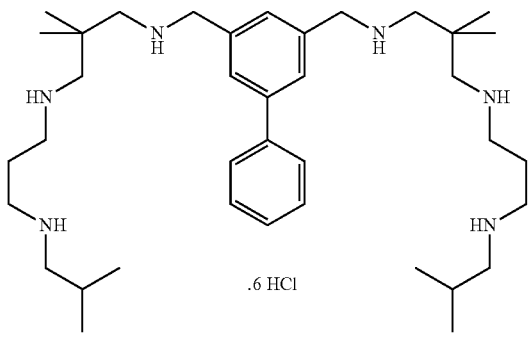 [SMILES: CC(C)CNCCCNCC(C)(C)CNCc1cc(CNCC(C)(C)CNCCCNCC(C)C)cc(-c2ccccc2)c1] .6 HCl | +++ | +++ | |

TABLE 5-continued
MICs of CZ compounds.
| CZ No. | Compound | MIC (MRSA) | MIC (*P. aeruginosa*) | MIC (*A. bumannii*) |
|---|---|---|---|---|
| CZ-113 | 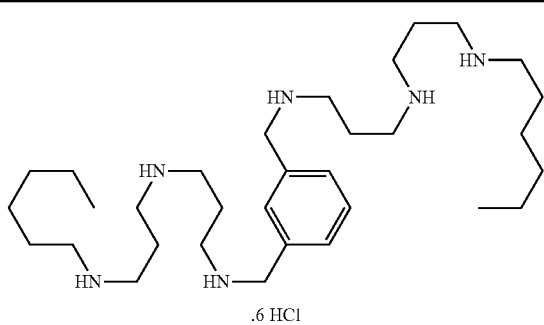 .6 HCl | +++ | +++ | |
| CZ-114 | 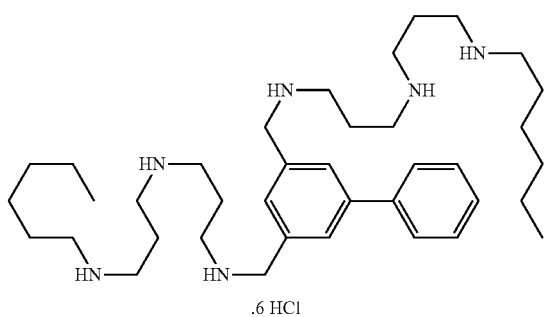 [SMILES: CCCCCCNCCCNCCCNCc1cc(CNCCCNCCCNCCCCCC)cc(-c2ccccc2)c1] .6 HCl | +++ | +++ | |
| CZ-115 | 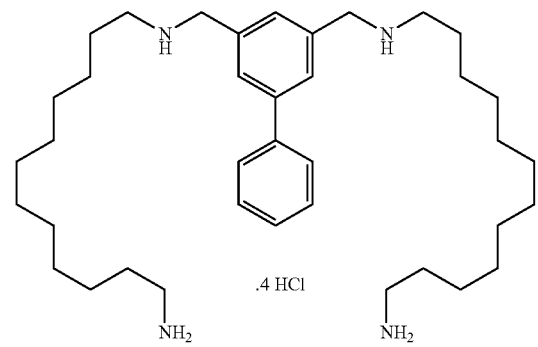 [SMILES: NCCCCCCCCCCCCNCc1cc(CNCCCCCCCCCCCCN)cc(-c2ccccc2)c1] .4 HCl | +++ | +++ | |
| CZ-116 | 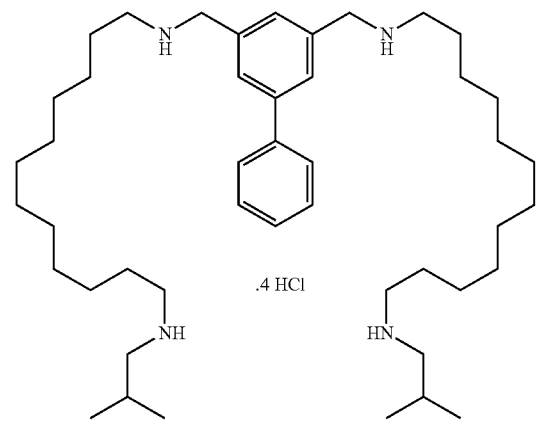 [SMILES: CC(C)CNCCCCCCCCCCCCNCc1cc(CNCCCCCCCCCCCCNCC(C)C)cc(-c2ccccc2)c1] .4 HCl | +++ | +++ | |

TABLE 5-continued
MICs of CZ compounds.
| CZ No. | Compound | MIC (MRSA) | MIC (P. aeruginosa) | MIC (A. bumannii) |
|---|---|---|---|---|
| CZ-117 | 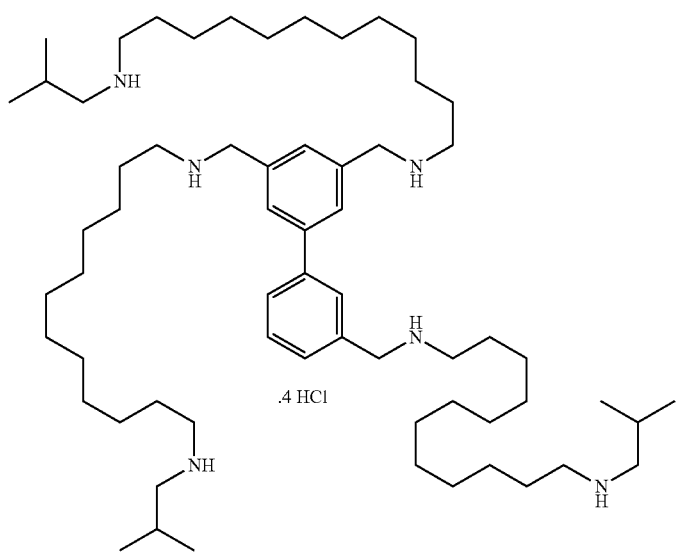 [SMILES: CC(C)CNCCCCCCCCCCCCNCc1cccc(-c2cc(CNCCCCCCCCCCCCNCC(C)C)cc(CNCCCCCCCCCCCCNCC(C)C)c2)c1] .4 HCl | +++ | +++ | |
| CZ-118 | 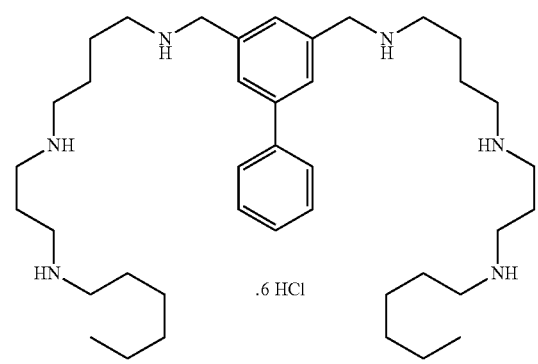 [SMILES: CCCCCCNCCCNCCCCNCc1cc(CNCCCCNCCCNCCCCCC)cc(-c2ccccc2)c1] .6 HCl | +++ | +++ | |
| CZ-119 | 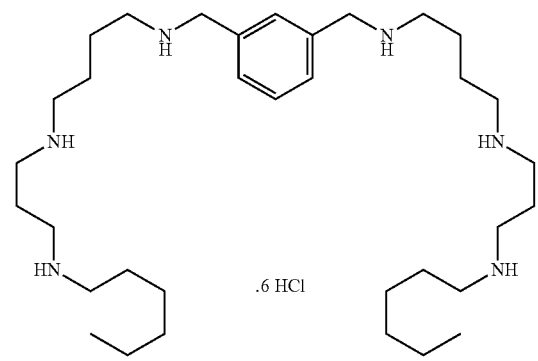 [SMILES: CCCCCCNCCCNCCCCNCc1cccc(CNCCCCNCCCNCCCCCC)c1] .6 HCl | +++ | +++ | |

TABLE 5-continued

MICs of CZ compounds.

| CZ No. | Compound | MIC (MRSA) | MIC (P. aeruginosa) | MIC (A. bumannii) |
|---|---|---|---|---|
| CZ-120 | .6 HCl | | | |
| CZ-121 | .7 HCl | | | |
| CZ-122 | .7 HCl | | | |
| CZ-123 | .3 HCl | | | |

TABLE 5-continued

MICs of CZ compounds.

| CZ No. | Compound | MIC (MRSA) | MIC (*P. aeruginosa*) | MIC (*A. bumannii*) |
|---|---|---|---|---|
| CZ-124 | .6 HCl | | | |
| CZ-125 | .6 HCl | | | |
| CZ-126 | .9 HCl | | | |

TABLE 5-continued
MICs of CZ compounds.
| CZ No. | Compound | MIC (MRSA) | MIC (*P. aeruginosa*) | MIC (*A. bumannii*) |
| --- | --- | --- | --- | --- |
CZ-127
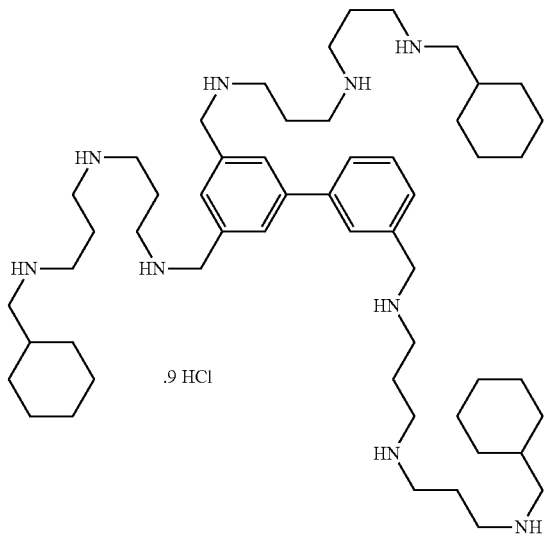 [SMILES: c1cc(CNCCCNCCCNCC2CCCCC2)cc(-c2cc(CNCCCNCCCNCC3CCCCC3)cc(CNCCCNCCCNCC3CCCCC3)c2)c1]
.9 HCl
CZ-128
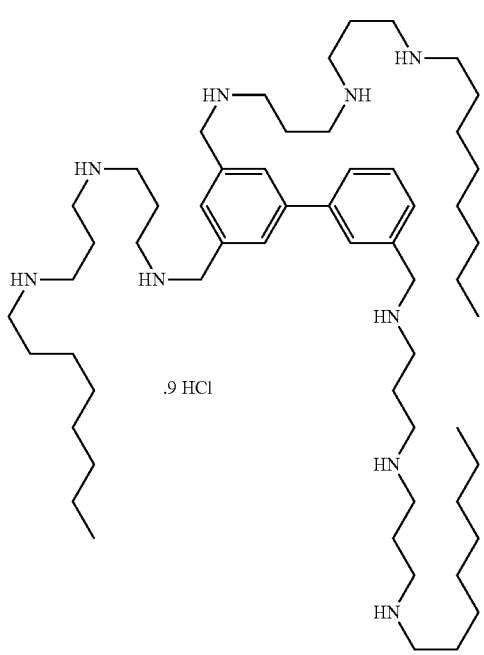 [SMILES: CCCCCCCCNCCCNCCCNCc1cccc(-c2cc(CNCCCNCCCNCCCCCCCC)cc(CNCCCNCCCNCCCCCCCC)c2)c1]
.9 HCl TABLE 5-continued
MICs of CZ compounds.
| CZ No. | Compound | MIC (MRSA) | MIC (*P. aeruginosa*) | MIC (*A. bumannii*) |
|---|---|---|---|---|
| CZ-129 | 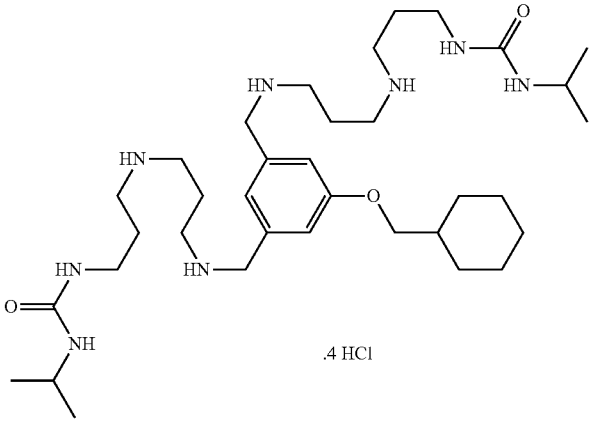 [SMILES: CC(C)NC(=O)NCCCNCCCNCc1cc(CNCCCNCCCNC(=O)NC(C)C)cc(OCC2CCCCC2)c1] .4 HCl | | | |
| CZ-130 | 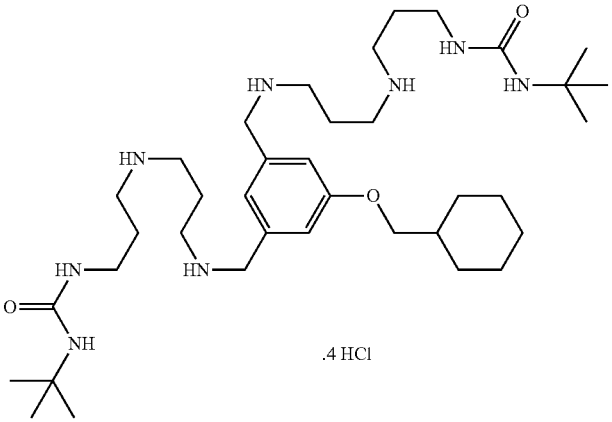 [SMILES: CC(C)(C)NC(=O)NCCCNCCCNCc1cc(CNCCCNCCCNC(=O)NC(C)(C)C)cc(OCC2CCCCC2)c1] .4 HCl | | | |
| CZ-131 | 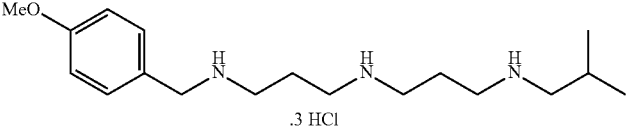 [SMILES: COc1ccc(CNCCCNCCCNCC(C)C)cc1] .3 HCl | | | |
| CZ-133 | 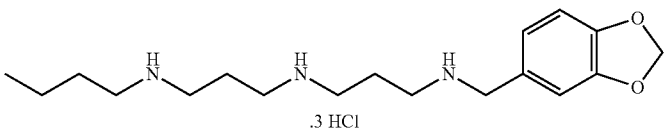 [SMILES: CCCCNCCCNCCCNCc1ccc2c(c1)OCO2] .3 HCl | | | |
| CZ-134 | 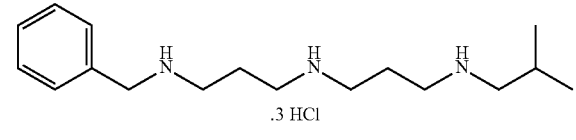 [SMILES: CC(C)CNCCCNCCCNCc1ccccc1] .3 HCl | | | |
| CZ-135 | 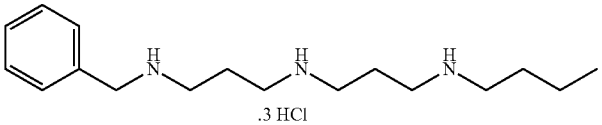 [SMILES: CCCCNCCCNCCCNCc1ccccc1] .3 HCl | | | |

TABLE 5-continued
MICs of CZ compounds.
| CZ No. | Compound | MIC (MRSA) | MIC (*P. aeruginosa*) | MIC (*A. bumannii*) |
|---|---|---|---|---|
| CZ-136 | 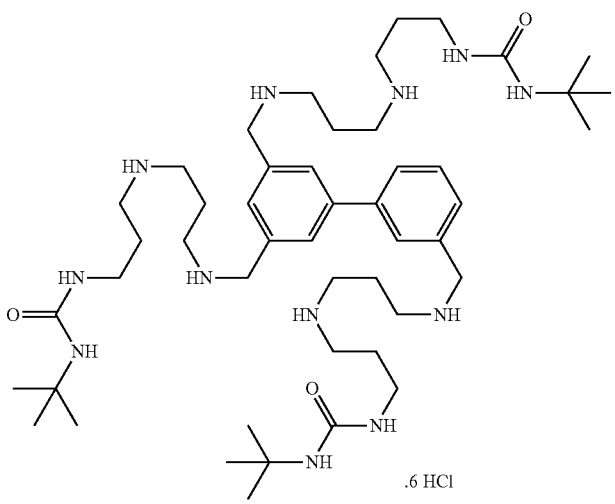 [SMILES: CC(C)(C)NC(=O)NCCCNCCCNCc1cccc(-c2cc(CNCCCNCCCNC(=O)NC(C)(C)C)cc(CNCCCNCCCNC(=O)NC(C)(C)C)c2)c1] .6 HCl | | | |
| CZ-137 | 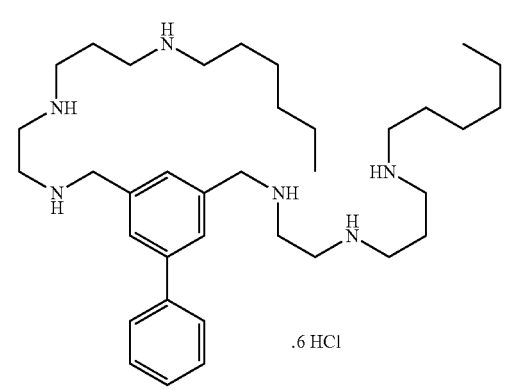 [SMILES: CCCCCCNCCCNCCNCc1cc(CNCCNCCCNCCCCCC)cc(-c2ccccc2)c1] .6 HCl | | | |
| CZ-138 | 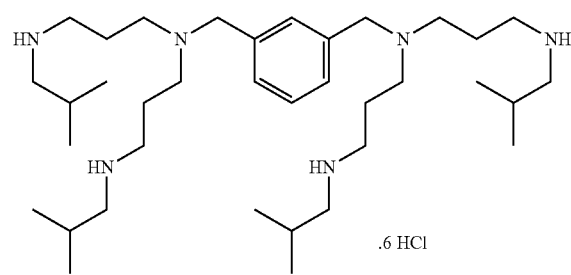 [SMILES: CC(C)CNCCCN(CCCNCC(C)C)Cc1cccc(CN(CCCNCC(C)C)CCCNCC(C)C)c1] .6 HCl | | | |

TABLE 5-continued
MICs of CZ compounds.
| CZ No. | Compound | MIC (MRSA) | MIC (P. aeruginosa) | MIC (A. bumannii) |
|---|---|---|---|---|
| CZ-139 | 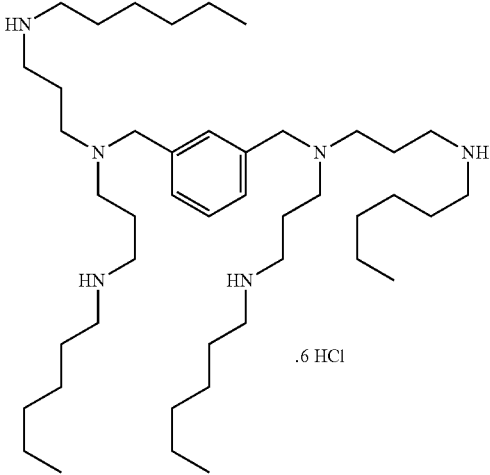 [SMILES: CCCCCCNCCCN(CCCNCCCCCC)Cc1cccc(CN(CCCNCCCCCC)CCCNCCCCCC)c1] .6 HCl | | | |
| CZ-140 | 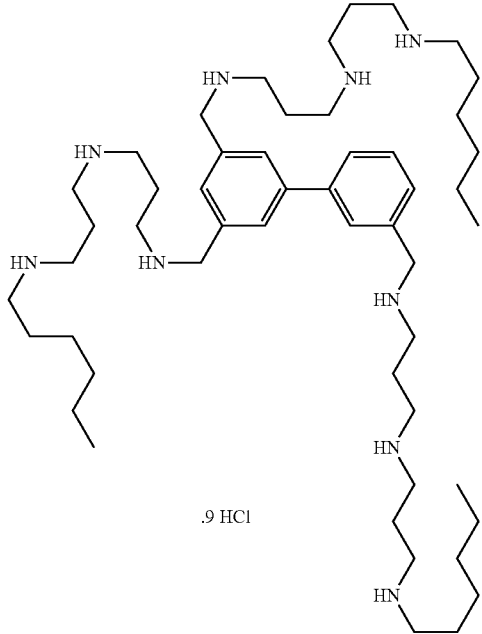 [SMILES: CCCCCCNCCCNCCCNCc1cccc(-c2cc(CNCCCNCCCNCCCCCC)cc(CNCCCNCCCNCCCCCC)c2)c1] .9 HCl | | | |
| CZ-141 | 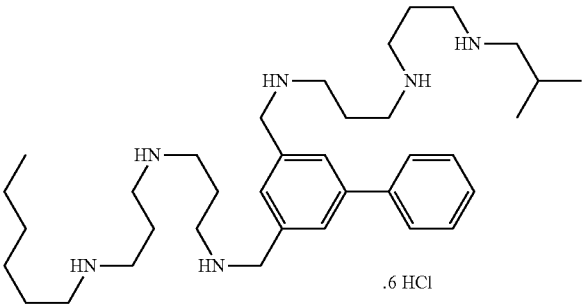 [SMILES: CCCCCCNCCCNCCCNCc1cc(CNCCCNCCCNCC(C)C)cc(-c2ccccc2)c1] .6 HCl | | | |

TABLE 5-continued
MICs of CZ compounds.
| CZ No. | Compound | MIC (MRSA) | MIC (*P. aeruginosa*) | MIC (*A. bumannii*) |
|---|---|---|---|---|
| CZ-142 | 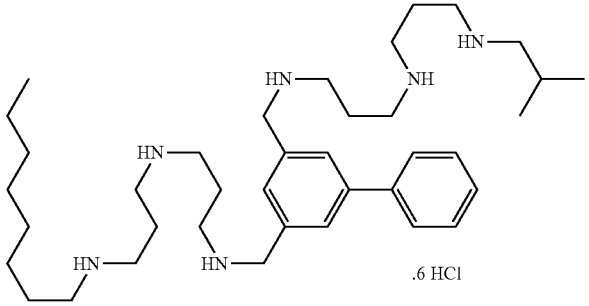 [SMILES: CCCCCCCCNCCCNCCCNCc1cc(CNCCCNCCCNCC(C)C)cc(-c2ccccc2)c1] .6 HCl | | | |
| CZ-143 | 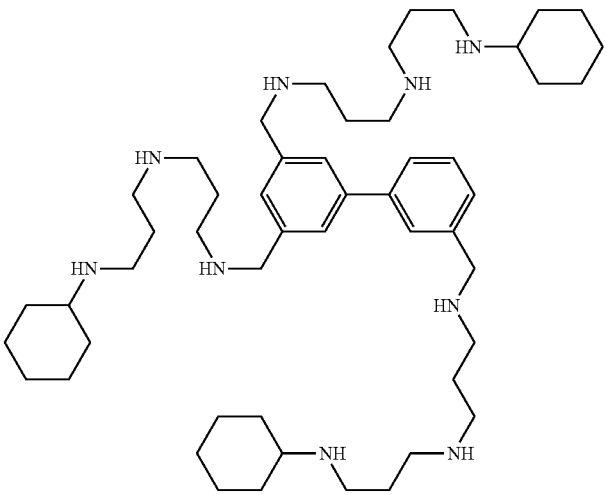 [SMILES: c1cc(CNCCCNCCCNC2CCCCC2)cc(-c2cc(CNCCCNCCCNC3CCCCC3)cc(CNCCCNCCCNC3CCCCC3)c2)c1] | | | |
| CZ-144 | 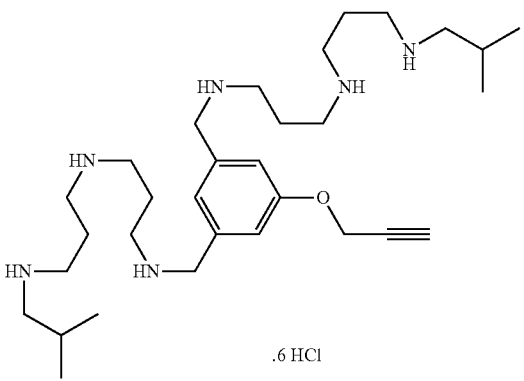 [SMILES: C#CCOc1cc(CNCCCNCCCNCC(C)C)cc(CNCCCNCCCNCC(C)C)c1] .6 HCl | | | |

TABLE 5-continued

MICs of CZ compounds.

| CZ No. | Compound | MIC (MRSA) | MIC (P. aeruginosa) | MIC (A. bumannii) |
|---|---|---|---|---|
| CZ-145 | 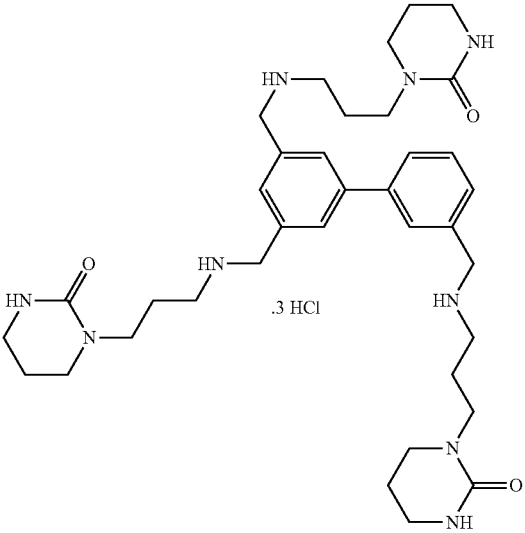 [SMILES: O=C1NCCCN1CCCNCc1cccc(-c2cc(CNCCCN3CCCNC3=O)cc(CNCCCN3CCCNC3=O)c2)c1] .3 HCl | | | |
| CZ-146 | 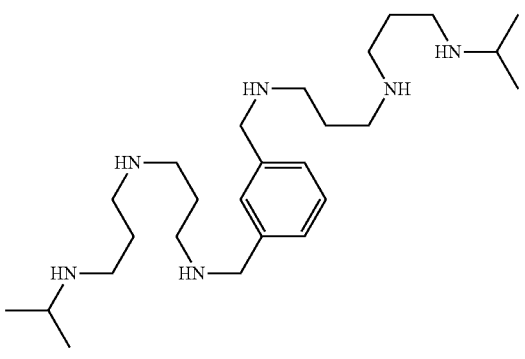 .6 HCl | | | |
| CZ-147 | 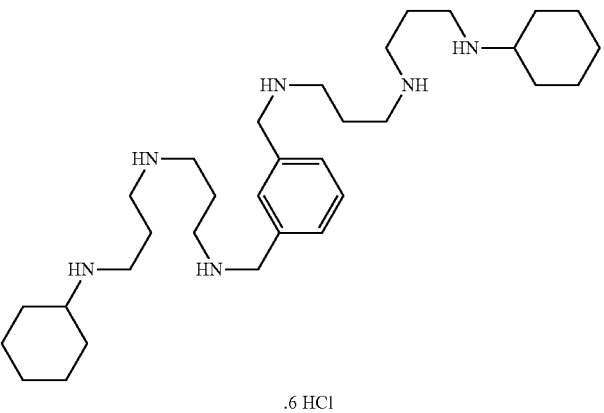 [SMILES: c1cc(CNCCCNCCCNC2CCCCC2)cc(CNCCCNCCCNC2CCCCC2)c1] .6 HCl | | | |

+ = MIC >100 μM.
++ = 100 μM ≥ MIC ≥ 50 μM. MIC results of ">n μM" or "<n μM" will also be designated as ++ if 100 ≥ n ≥ 50.
+++ = 50 μM > MIC. MIC results of ">n μM" or "<n μM" will also be designated as +++ if n <50.

Example 9

Biofilm Dispersion

The compounds of the present invention such as CZ 25, CS-58 and CS-52 have excellent dispersal characteristics. To test for dispersion, biofilms of each isolate were grown on the surface of commercially pure titanium (Ti) coupons (½" diameter×⅛" height) in a CDC biofilm reactor. The growth conditions for this reactor were the same as those for the membrane biofilm reactor. After biofilms were grown for 48 hours, each Ti coupon was aseptically removed and placed into 2 mL of cation adjusted Mueller Hinton broth (CAMHB) for 2 hours. The CAMHB had a final concentration of 0.25% (2.5 mg/mL) CZ-25 or CZ-52. Each compound was tested n=3 times.

Following the 2-hour exposure, each coupon was fixed in 0.25% glutaraldehyde for 24 hours, dehydrated using ascending concentrations of ethanol (70%, 95%, 100%) with 3×10 min. changes and desiccated. One side of each coupon was carbon coated and imaged using a JEOL JSM-6610 SEM to directly observe the surface of the coupons and determine the ability of CZ compounds to disperse biofilms compared to positive controls that had no treatment. When compared to untreated controls, data have indicated that CZ-25, CZ-52 and CZ-58 have the ability to disperse Norspermidine was reacted with di-t-butyl dicarbonate compound to provide N-Boc protected norspermidine using the following procedure: To a solution of norspermidine (27.2 g, 207.7 mmol, 3.0 equiv.) in THF solvent (1000 mL) at 0° C. was added di-t-butyl dicarbonate (18.1 g, 83.1 mmol, 1 equiv.) dropwise over a period of two hours. During the period of addition, the solution went from clear to a cloudy white. Following addition, the reaction mixture was allowed to stir at room temperature for a period of 12 hours. The THF solvent was evaporated, and the residue was dissolved in $CH_2Cl_2$ (250 mL) and washed with water (250 mL). The resultant aqueous layer was washed with $CH_2Cl_2$ (4×100 mL). The organic layer was dried with $Na_2SO_4$ and evaporated to afford the Boc-protected amine as a clear viscous liquid.

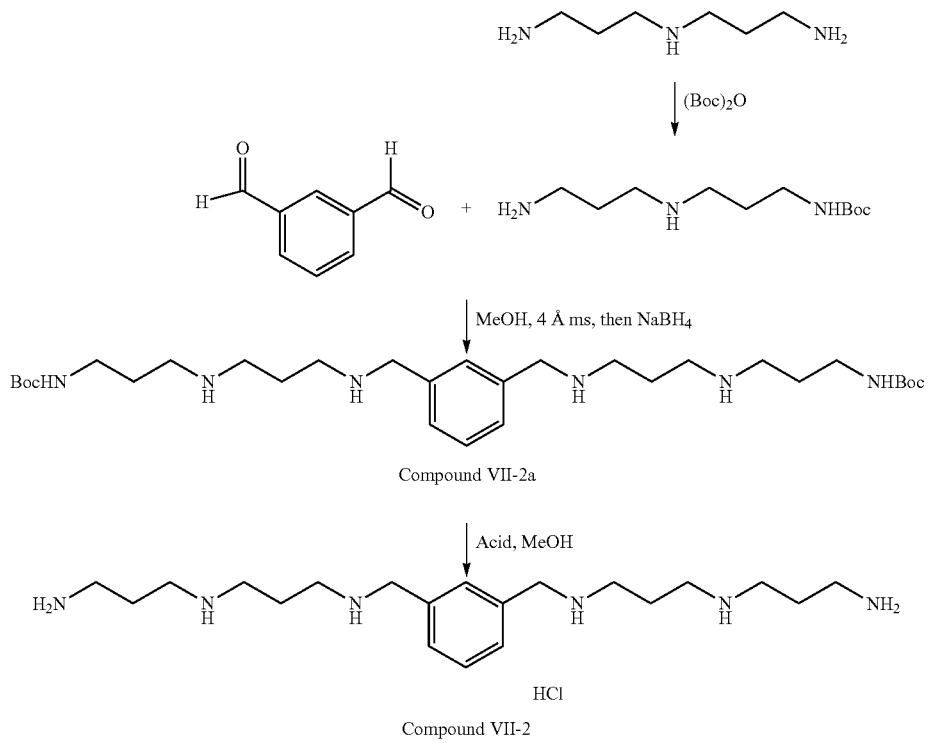

biofilms from the surface of a material (FIG. 17) such that a monolayer of cells or reduced communities remain.

Figure 17:
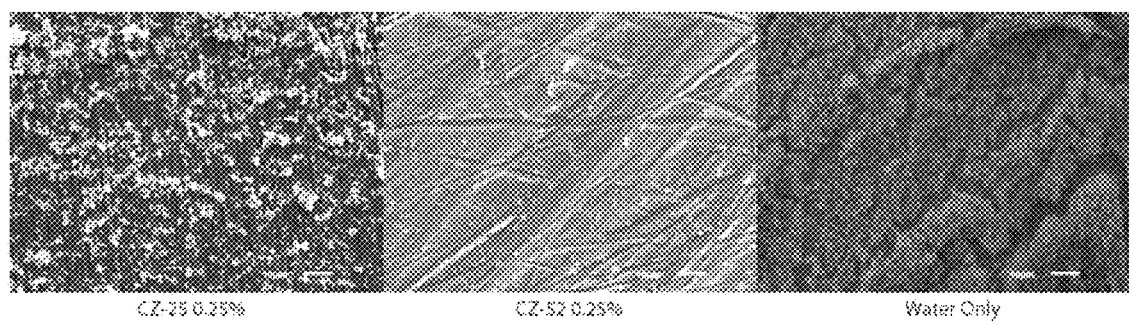
FIG. 17 shows scanning electron microscopy (SEM) images of Ti coupons with MRSA biofilms exposed to CZ-25 (left), CZ-52 (middle), or water only (right). The compounds CZ-25 and CZ-52 demonstrated the ability to disperse the majority of biofilms such that a monolayer of cells remained on the surface of the Ti. Those samples treated with water only had biofilm communities that remained in all areas of the coupons.

FIG. 17 provides SEM images of Ti coupons with MRSA biofilms exposed to CZ-25 (left), CZ-52 (middle) or water only (right). CZ-25 and CZ-52 demonstrated the ability to disperse the majority of biofilms such that a monolayer of cells remained on the surface of the Ti. Those samples treated with water only had biofilm communities that remained in all areas of the coupons.

Example 10

Preparation of $N^1,N^{1'}$-(1,3-phenylenebis(methylene))bis($N^3$-(3-aminopropyl)propane-1,3-diamine), hydrochloride salt[Compound VII-2]

The polyamine compound (VII-2) may be synthesized as shown in Scheme 7.

Benzene-1,3-dicarboxyaldehyde was reacted with at least two equivalents of the N-Boc protected norspermidine in the presence of molecular sieve and methanol solvent to provide a corresponding polyamide product, which was then reduced by sodium borohydride ($NaBH_4$) to produce the N-Boc protected polyamine compound VII-2a using following procedure: To a stirring solution of 4 Å molecular sieve (100 mg) in MeOH solvent (25 mL) was added benzene-1,3-dicarboxyaldehyde (0.78 g, 5.87 mmol, 1 equiv.) followed by the Boc-protected amine (2.71 g, 11.74 mmol, 2 equiv.). The solution was stirred for 12 hours at room temperature. The newly formed imine was quenched at room temperature by the addition of $NaBH_4$ (0.89 g, 23.48 mmol, 4 equiv.) after which the solution was stirred for an additional one hour. The solution was filtered through a pad of celite, and the solvent evaporated in vacuo to afford brown oil. The crude mixture was dissolved in EtOAc (100 mL) and washed with 10% NaOH (100 mL): The resulting NaOH was further washed with EtOAc (50 mL×1). The organic layer was dried with Na$_2$SO$_4$ and concentrated under reduced pressure to provide a crude Boc-protected product.

The Boc-protecting group on the terminal amine of the polyamine compound VII-2a was deprotected by subjecting compound VII-2a to acid hydrolysis to produce the polyamine compound (VII-2) using the following procedure: The crude Boc-protected product was added to a stirring solution of HCl in MeOH (100 mL) and left for one hours. The solvent was evaporated in vacuo to yield a white to off-white solid which was recrystallized from MeOH to provide the polyamine compound (VII-2) as white solid to off-white solid (30% yield). $^1$H NMR (500 MHz, D$_2$O): 7.60 (s, 4H), 4.33 (s, 4H), 3.26-3.18 (m, 12H), 3.12 (t, J=8 Hz, 4H), 2.21-2.08 (m, 8H).

4 equiv.) after which the solution was stirred for an additional one hour. The solution was filtered through a pad of celite, and the solvent evaporated in vacuo to afford brown oil. The crude mixture was dissolved in EtOAc (100 mL) and washed with 10% NaOH (100 mL). The resulting NaOH solution was further washed with EtOAc (50 mL×1). The organic layer was dried with Na$_2$SO$_4$ and concentrated under reduced pressure to provide the polyamine compound VII-2B.

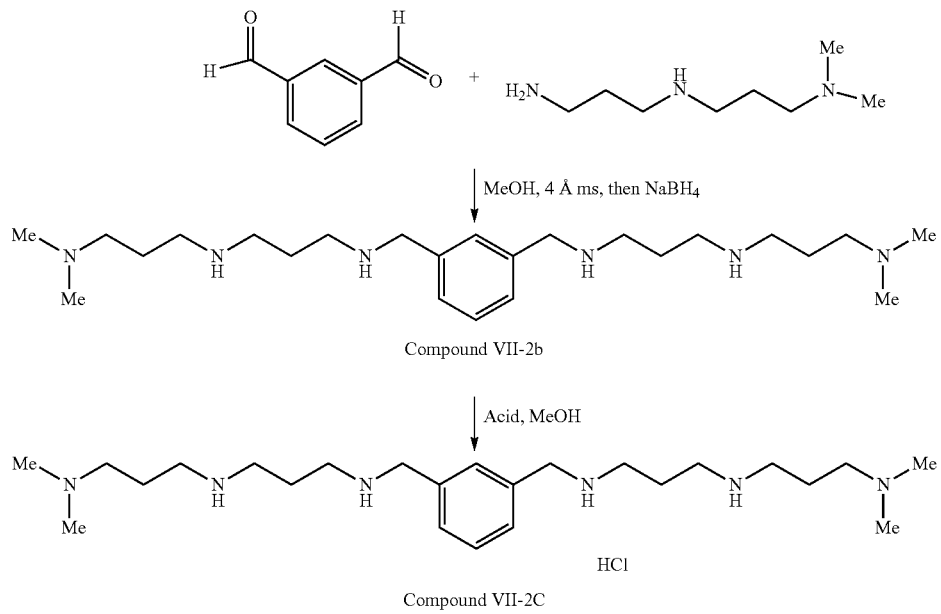

Compound VII-2b

Compound VII-2C

The crude the polyamine compound VII-2B was added to a stirring solution of HCl in MeOH solvent (100 mL) and left for one hour. The solvent was evaporated in vacuo to yield a white to off-white solid, which was recrystallized from MeOH to afford the polyamine compound VII-2C at about 30% yield as white solid to off-white solid. $^1$H NMR (500 MHz, D$_2$O): 7.59 (s, 4H), 4.24 (s, 4H), 3.29-3.15 (m, 16H), 2.91 (s, 12H), 2.21-2.15 (m, 8H).

Example 11

Preparation of N$^1$,N$^{1'}$-(((1,3-phenylenebis(methylene))bis(azanediyl))bis(propane-3,1-diyl))bis(N$^3$,N$^3$-dimethylpropane-1,3-diamine), hydrochloride salt [Compound VII-2C]

The polyamine compound (VII-2C) may be synthesized as shown in Scheme 8. Benzene-1,3-dicarboxyaldehyde was reacted with at least two equivalents of N, N-dimethylnorspermidine in the presence of molecular sieve and methanol solvent to provide a corresponding polyamide product, which was then reduced by sodium borohydride (NaBH$_4$) to produce the polyamine compound VII-2B using the following procedure: To a stirring solution of 4 Å molecular sieve (100 mg) in MeOH solvent (25 mL) was added benzene-1,3-dicarboxyaldehyde (0.78 g, 5.87 mmol, 1 equiv.) followed by N, N-dimethylnorspermidine (2.71 g, 11.74 mmol, 2 equiv). The solution was stirred for 12 hours at room temperature. The newly formed imine was quenched at room temperature by the addition of NaBH$_4$ (0.89 g, 23.48 mmol, Example 12

Preparation of N-benzyl-1,12-dodecyldiamine (V-1)

The polyamine compound (V-1) may be synthesized as shown in Scheme 9 from 1,12-dodecyldiamine, either via synthetic route [A] or [B].

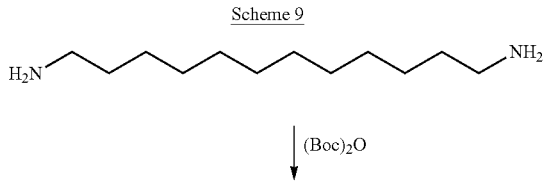

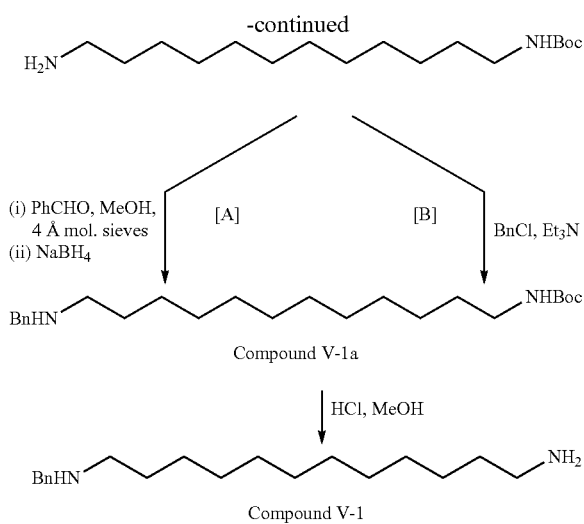

Compound V-1a

Compound V-1

In the synthetic route [A], N-Boc protected-1,12-dodecyldiamine was reacted with benzyl chloride in the presence of base and solvent to provide a corresponding polyamide compound V-1a. In the synthetic route [B], N-Boc protected-1,12-dodecyldiamine, prepared as described in Example 10 as following: To a solution of amine (27.2 g, 207.7 mmol, 3.0 equiv.) in THF solvent (1000 mL) at 0° C. was added di-tert-butyl dicarbonate (18.1 g, 83.1 mmol, 1 equiv.) dropwise over a period of two hours. During the period of addition, the solution went from clear to a cloudy white. Following addition, the reaction mixture was allowed to stir at room temperature for a period of 12 hours. The THF solvent was evaporated, and the residue was dissolved in $CH_2Cl_2$ (250 mL) and washed with water (250 mL). The resultant aqueous layer was washed with $CH_2Cl_2$ (4×100 mL). The organic layer was dried with $Na_2SO_4$ and evaporated to afford the N-Boc protected-1,12-dodecyldiamine amine as a clear viscous liquid.

The N-Boc protected-1,12-dodecyldiamine was reacted with benzaldehyde in the presence of molecular sieve and methanol solvent to provide a corresponding polyamide product, which was then reduced by sodium borohydride ($NaBH_4$) to produce the N-Boc protected polyamine compound V-1a using the following procedure: To a stirring solution of 4 Å molecular sieve (100 mg) in MeOH solvent (25 mL) was added the benzaldehyde (0.78 g, 5.87 mmol, 1 equiv.) followed by the N-Boc protected-1,12-dodecyldiamine (1.36 g, 5.87 mmol, 1 equiv.). The solution was stirred for 12 hours at room temperature. The newly formed imine was quenched at room temperature by the addition of $NaBH_4$ (0.89 g, 23.48 mmol, 4 equiv.) after which the solution was stirred for an additional one hour. The solution was filtered through a pad of celite, and the solvent evaporated in vacuo to afford brown oil. The crude mixture was dissolved in EtOAc (100 mL) and washed with 10% NaOH (100 mL). The resulting NaOH solution was further washed with EtOAc (50 mL×1). The organic layer was dried with $Na_2SO_4$ and concentrated under reduced pressure to provide the N-Boc protected polyamine compound V-1a.

The Boc protecting group on the terminal amine of the polyamine compound V-1a was deprotected by treating compound V-1a with acid to produce the polyamine compound (V-1) using following procedure: The crude N-Boc protected polyamine compound V-1a was added to a stirring solution of HCl in MeOH solvent (100 mL) and left for one hour. The solvent was evaporated in vacuo to yield a white to off-white solid, which was recrystallized from MeOH to afford the polyamine compound (V-1) at about 30% yield as a white solid to off-white solid. $^1$H NMR (500 MHz, $D_2O$): 7.42 (s, 5H), 4.15 (s, 2H), 3.26 (p, J=1.5 Hz, 2H), 2.96-2.89 (m, 4H), 1.63-1.56 (m, 4H), 1.28-1.21 (m, 14H).

Example 13

Preparation of 1,3,5-tris-[N-(3-aminopropyl)-methylamine]-benzene (VI-1)

The polyamine compound (VI-1) may be synthesized as shown in Scheme 10.

Scheme 10

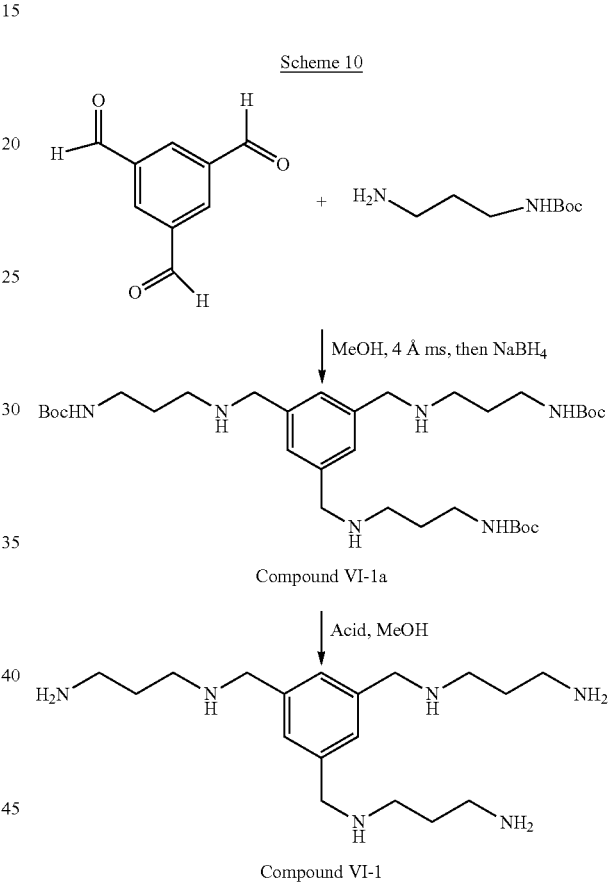

Compound VI-1a

Compound VI-1

1,3-Diaminopropane was reacted with di-t-butyldicarbonate compound to provide N-Boc-1,3-diaminopropane using following procedure: To a solution of amine (27.2 g, 207.7 mmol, 3.0 equiv.) in THF solvent (1000 mL) at 0° C. was added di-tert-butyl dicarbonate (18.1 g, 83.1 mmol, 1 equiv.) dropwise over a period of two hours. During the period of addition, the solution went from clear to a cloudy white. Following addition, the reaction mixture was allowed to stir at room temperature for a period of 12 hours. The THF solvent was evaporated, and the residue was dissolved in $CH_2Cl_2$ (250 mL) and washed with water (250 mL). The resultant aqueous layer was backwashed with $CH_2Cl_2$ (4×100 mL). The organic layer was dried with $Na_2SO_4$ and evaporated to afford the N-Boc-1,3-diaminopropane as a clear viscous liquid.

Benzene-1,3,5-tricarboxyaldehyde was reacted with at least three equivalents of three equivalents of the N-Boc protected 1,3-diaminopropane in the presence of molecular sieve and methanol solvent to provide a corresponding polyamide product, which was then reduced by sodium borohydride (NaBH$_4$) to produce the N-Boc protected polyamine compound VI-1a using following procedure: To a stirring solution of 4 Å molecular sieve (100 mg) in MeOH solvent (20 mL) was added benzene-1,3,5-tricarboxyaldehyde (64 mg, 0.39 mmol, 1 equiv.) followed by N-Boc protected 1,3-diaminopropane (222 mg, 1.19 mmol, 3 equiv.). The solution was stirred for 12 hours at room temperature. The newly formed imine was quenched at room temperature by the addition of NaBH$_4$ (90 mg, 2.38 mmol, 6 equiv.) after which the solution was stirred for an additional one hour. The solution was filtered through a pad of celite, and the solvent evaporated in vacuo to afford brown oil. The crude mixture was dissolved in EtOAc (100 mL) and washed with 10% NaOH (100 mL). The resulting NaOH was further backwashed with EtOAc (50 mL×1). The organic layer was dried with Na$_2$SO$_4$ and concentrated under reduced pressure to provide the N-Boc protected polyamine compound VI-1a.

The Boc protecting group on the terminal amine of the polyamine compound VI-1a was deprotected by treating compound VI-1a with acid to produce the polyamine compound (VI-1) using following procedure: The crude polyamine compound VI-1a was added to a stirring solution of HCl in MeOH solvent (100 mL) and left for one hour. The solvent was evaporated in vacuo to yield a white to off-white solid, which was recrystallized from MeOH solvent to afford the polyamine compound VI-1 at about 30% yield as white solid to off-white solid.

Example 14

Preparation of N$^1$,N$^{1'}$,N$^{1''}$-(benzene-1,3,5-triyltris (methylene))tris(N$^3$-isopropylpropane-1,3-diamine) (HCl) (VII-4C)

The polyamine compound (VII-4C) may be synthesized as shown in Scheme 11.

Scheme 11

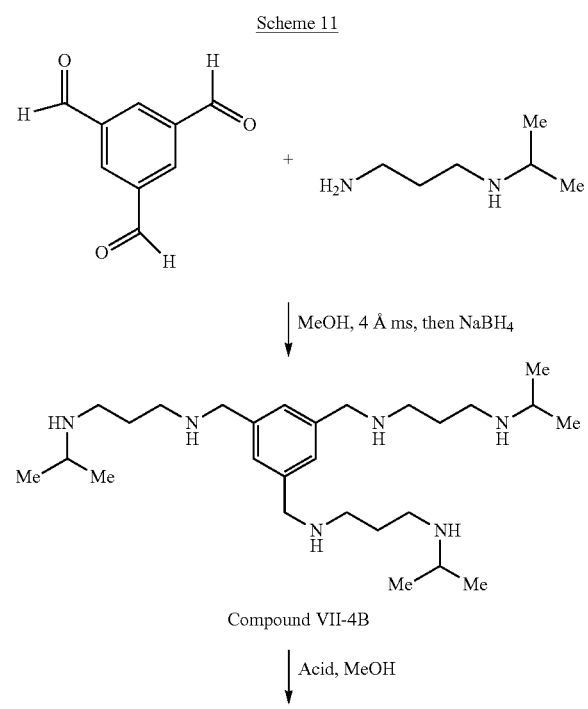

Compound VII-4B

Acid, MeOH

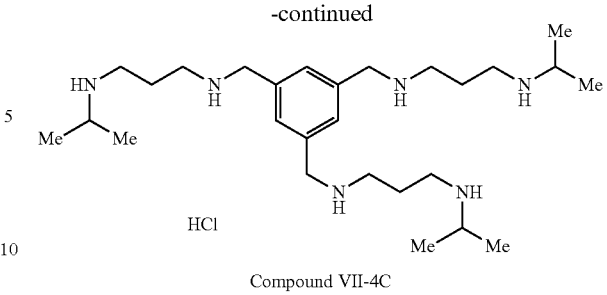

Compound VII-4C

Benzene-1,3,5-tricarboxyaldehyde was reacted with at least three equivalents of N,N-dimethylnorspermidine in the presence of molecular sieve and methanol solvent to provide a corresponding polyamide product, which was then reduced by sodium borohydride (NaBH$_4$) to produce the N-Boc protected polyamine compound VII-4B using the following procedure: To a stirring solution of 4 Å molecular sieve (100 mg) in MeOH solvent (20 mL) was added benzene-1,3,5-tricarboxyaldehyde (64 mg, 0.39 mmol, 1 equiv.) followed by N, N-dimethylnorspermidine (222 mg, 1.19 mmol, 3 equiv.). The solution was stirred for 12 hours at room temperature. The newly formed imine was quenched at room temperature by the addition of NaBH$_4$ (90 mg, 2.38 mmol, 6 equiv.) after which the solution was stirred for an additional one hour. The solution was filtered through a pad of celite, and the solvent evaporated in vacuo to afford brown oil. The crude mixture was dissolved in EtOAc (100 mL) and washed with 10% NaOH (100 mL). The resulting NaOH was further backwashed with EtOAc (50 mL×1). The organic layer was dried with Na$_2$SO$_4$ and concentrated under reduced pressure to provide the crude N-Boc protected polyamine compound VII-4B.

The polyamine compound VII-4B was added to a stirring solution of HCl in MeOH solvent (100 mL) and left for one hour. The solvent was evaporated in vacuo to afford the polyamine compound VII-4C as viscous liquid at about 30% yield. $^1$H NMR (500 MHz, D$_2$O): 7.68 (s, 3H), 4.35 (s, 6H), 3.41 (p, J=6.5 Hz, 3H), 3.23 (t, J=7.5 Hz, 6H), 3.14-3.07 (m, 6H), 2.14-2.11 (m, 6H), 1.30 (d, J=6.5 Hz, 18H).

Example 15

Preparation of 1,3-bis-[N—(N'-3-aminopropyl)propyl-3-amine)-methylamine]-benzene (VII-2)

The polyamine compound (VII-2) may be synthesized as shown in Scheme 12. N-(3-Aminopropyl)propane-1,3-diamine (i.e., norspermidine) was reacted with di-t-butyldicarbonate compound to provide a N-Boc protected norspermidine compound. Benzene-1,3,5-tricarboxyaldehyde was reacted with at least three equivalents of three equivalents of the N-Boc protected norspermidine compound in the presence of molecular sieve and methanol solvent to provide a corresponding polyamide product, which was then reduced by sodium borohydride (NaBH$_4$) to produce the N-Boc protected polyamine compound VII-2a. using the following procedure: To a stirring solution of 4 Å molecular sieve (100 mg) in MeOH solvent (20 mL) was added benzene-1,3,5-tricarboxyaldehyde (64 mg, 0.39 mmol, 1 equiv.) followed by the N-Boc protected norspermidine compound (222 mg, 1.19 mmol, 3 equiv.). The solution was stirred for 12 hours at room temperature. The newly formed imine was quenched at room temperature by the addition of NaBH$_4$ (90 mg, 2.38 mmol, 6 equiv.) after which the solution was stirred for an additional one hour. The solution was filtered through a pad of celite, and the solvent evaporated in vacuo to afford brown oil. The crude mixture was dissolved in EtOAc (100 mL) and washed with 10% NaOH (100 mL). The resulting NaOH was further backwashed with EtOAc (50 mL×1). The organic layer was dried with Na$_2$SO$_4$ and concentrated under reduced pressure to provide the crude N-Boc protected polyamine compound VII-2a.

Scheme 13

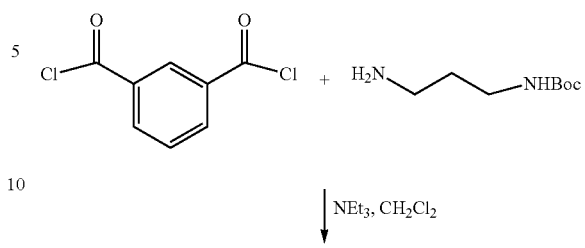

Scheme 12

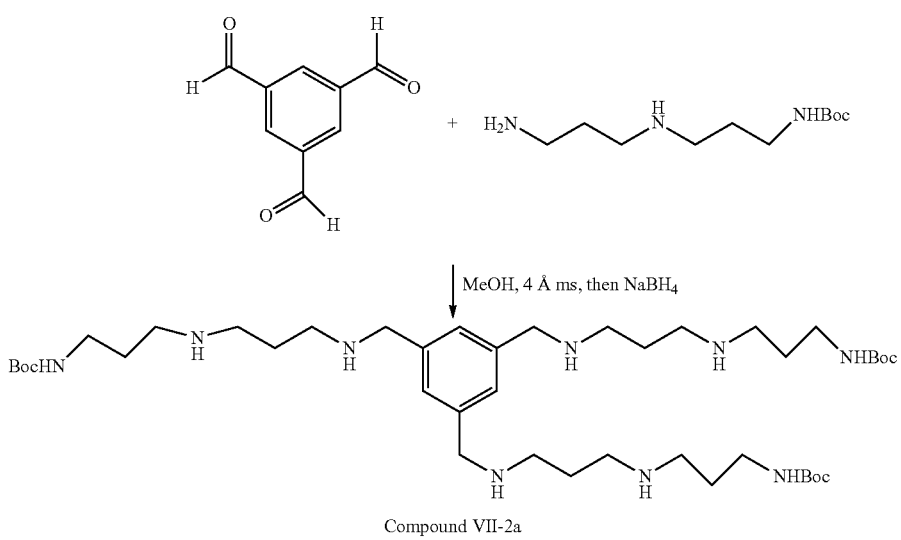

Compound VII-2a

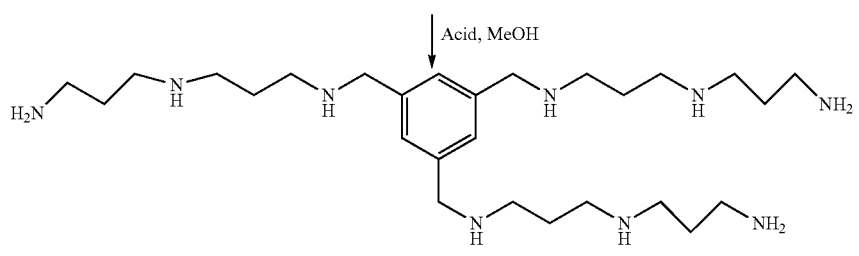

Compound VII-2

The Boc protecting group on the terminal amine of the polyamine compound VII-2a was deprotected by treating compound VII-2a with acid to produce the polyamine compound (VII-2) using following procedure: The crude polyamine compound VII-2a was added to a stirring solution of HCl in MeOH solvent (100 mL) and left for one hour. The solvent was evaporated in vacuo to yield a white to off-white solid, which was recrystallized from MeOH to afford the polyamine compound VII-2 as white solid to off-white solid at 30% yield.

Example 16

Preparation of 1,3-bis-[N-3-aminopropyl]benzenediamide (VIII-3)

The polyamine compound (VIII-3) may be synthesized as shown in Scheme 13.

-continued

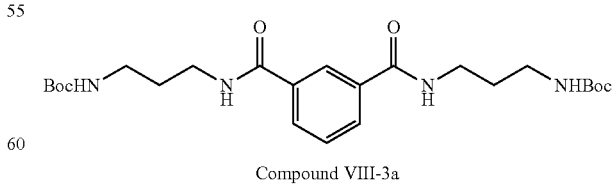

Compound VIII-3a

147

-continued

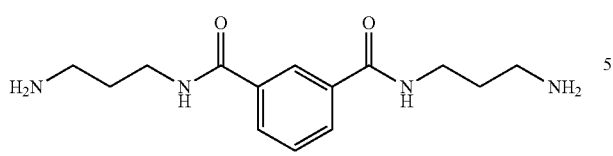

Compound VIII-3

Benzene-1,3-dicarbonylchloride was reacted with at least two equivalents of the N-Boc protected 1,3-diaminopropane (prepared as described in Example 4) in the presence of triethylamine (NEt₃) and dichloromethane solvent to provide a corresponding N-Boc protected polyamide compound VIII-3a. The Boc protecting group on the terminal amine of the polyamine compound VIII-3a was deprotected by treating compound VIII-3a with acid, such as acetyl chloride, in methanol to produce the polyamine compound (VIII-3).

Example 17

General Method for Preparation of Dialdehyde Aryl Starting Material

An aldehyde precursor to the polyamine compound may be produced by the palladium coupling method of General Synthetic Scheme 14.

General Synthetic Scheme 14

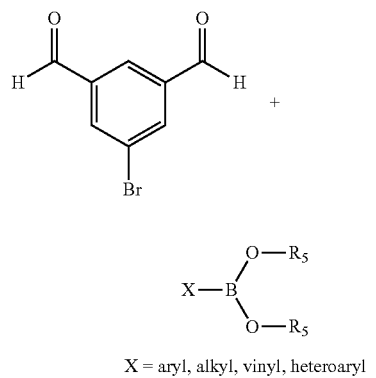

X = aryl, alkyl, vinyl, heteroaryl

Reagents: (a) 5:1 DME/H₂O, Pd(PPh₃)₄, K₂CO₃

Specific examples of this method are set forth in the following Examples, such as Example 68.

148

Example 18

Preparation of $N^1,N^{1'}$-(1,3-phenylenebis(methylene))bis(N3-(3-ammoniopropyl)propane-1,3-diaminium) chloride (CZ-25)

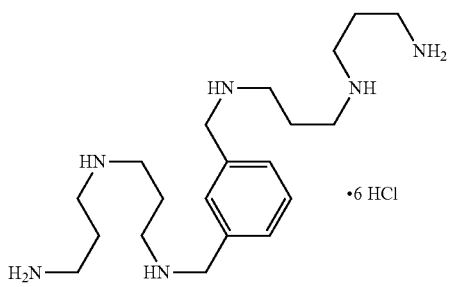 [SMILES: NCCCNCCCNCc1cccc(CNCCCNCCCN)c1]

Step 1: Di-tert-butyl (((((1,3-phenylenebis(methylene))bis(azanediyl))bis(propane-3,1-diyl))bis(azanediyl))bis(propane-3,1-diyl))dicarbamate Isophthalaldehyde (1.07 g, 7.99 mmol) and MeOH (50 mL) were added to a round-bottom flask. To the solution was added tert-butyl (3-((3-aminopropyl)amino)propyl)carbamate (3.69 g, 16.0 mmol) and the reaction mixture was stirred for 24 h. Sodium borohydride (1.21 g, 32.0 mmol) was added portionwise and stirred for 1 h. The reaction mixture was concentrated under reduced pressure, and aq. NaOH (10%, 150 mL) and EtOAc (150 mL) were added. The layers were separated, and the aqueous layer was extracted with EtOAc (150 mL). The organic layers were combined, dried over Na₂SO₄, filtered, and concentrated under reduced pressure to afford the desired product as a clear oil. The intermediate was carried forward without further purification.

Step 2: $N^1,N^{1'}$-(1,3-Phenylenebis(methylene))bis($N^3$-(3-aminopropyl)propane-1,3-diamine)

To the crude di-tert-butyl (((((1,3-phenylenebis(methylene))bis(azanediyl))-bis(propane-3,1-diyl))bis(azanediyl))bis(propane-3,1-diyl))dicarbamate from Step 1 was added methanolic HCl (150 mL, 1.0 M). The reaction mixture was stirred for 2 h and concentrated under reduced pressure. The solid was collected by vacuum filtration, and it was washed with Et₂O (30 mL) and hot MeOH (30 mL) to afford the desired product (1.1 g, 56%) as a white solid. ¹H NMR (500 MHz, D₂O) δ ppm 7.62 (s, 4H), 4.36 (s, 4H), 3.28-3.21 (m, 12H), 3.15 (t, J=8.0 Hz, 4H), 2.23-2.11 (m, 8H). ¹³C NMR (125 MHz, D₂O) 131.4, 131.3, 131.1, 130.2, 50.8, 44.7, 44.6, 44.1, 36.5, 23.6, 22.6. LRMS [M+H]⁺ 365.3.

Example 19

Preparation of $N^1$-benzylbutane-1,4-diaminium chloride (CZ-3)

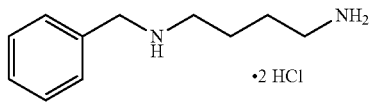 [SMILES: NCCCCNCc1ccccc1]

Example 19 was prepared in a similar fashion to Example 18 (CZ-25) from benzaldehyde and tert-butyl (4-aminobutyl)carbamate. $^1$H NMR (500 MHz, D$_2$O) δ 7.52 (s, 5H), 4.26 (s, 2H), 3.15 (t, J=8 Hz, 2H), 3.07 (t, J=7.5 Hz, 2H), 1.86-1.74 (m, 4H). $^{13}$C NMR (125 MHz, D$_2$O) 130.6, 129.9, 129.7, 129.2, 51.0, 46.3, 38.8, 23.9, 22.7. LRMS [M+H]$^+$ 179.2.

Example 20

Preparation of N$^1$-benzylpropane-1,3-diamine (CZ-4)

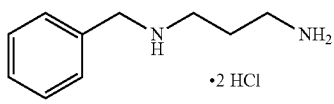 [SMILES: NCCCNCc1ccccc1]

Example 20 was prepared in a similar fashion to Example 18 (CZ-25) from benzaldehyde and tert-butyl (3-aminopropyl)carbamate. $^1$H NMR (500 MHz, D$_2$O) δ 7.49 (quint, J=3 Hz, 5H), 4.26 (s, 2H), 3.17 (t, J=8 Hz, 2H), 3.07 (t, J=8 Hz, 2H), 2.09 (quint, J=7.5 Hz, 2H). $^{13}$C NMR (125 MHz, D$_2$O) δ 130.6, 129.9, 129.8, 129.4, 51.4, 44.1, 36.7, 23.9. LRMS [M+H]$^+$ 291.3.

Example 21

Preparation of N$^1$-benzyldodecane-1,12-diamine, hydrochloride salt (CZ-5)

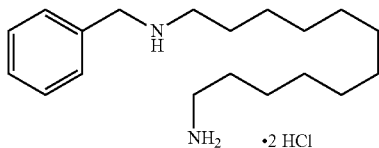 [SMILES: NCCCCCCCCCCCCNCc1ccccc1]

Example 21 was prepared in a similar fashion to Example 18 (CZ-25) from benzaldehyde and tert-butyl (12-aminododecyl)carbamate.

Example 22

Preparation of N$^1$-(3-(benzylamino)propyl)-N$^3$,N$^3$-dimethylpropane-1,3-diamine, hydrochloride salt (CZ-6)

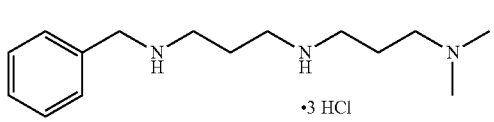 [SMILES: CN(C)CCCNCCCNCc1ccccc1]

Example 22 was prepared in a similar fashion to Example 18 (CZ-25) from benzaldehyde and N$^1$-(3-aminopropyl)-N$^3$,N$^3$-dimethylpropane-1,3-diamine. $^1$H NMR (500 MHz, D$_2$O) δ 7.41 (s, 5H), 4.18 (s, 2H), 3.20-3.08 (m, 8H), 2.83 (s, 6H), 2.15-2.03 (m, 4H). $^{13}$C NMR (125 MHz, D$_2$O) 131.0, 130.5, 130.4, 129.9, 54.8, 51.8, 45.3, 45.1, 44.5, 43.5, 23.2, 21.8.

Example 23

Preparation of N$^1$-(3-aminopropyl)-N$^3$-benzylpropane-1,3-diamine, hydrochloride salt (CZ-7)

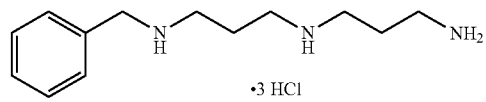 [SMILES: NCCCNCCCNCc1ccccc1]

Example 23 was prepared in a similar fashion to Example 18 (CZ-25) from benzaldehyde and tert-butyl (3-((3-aminopropyl)amino)propyl)carbamate. $^1$H NMR (500 MHz, D$_2$O) δ 7.49 (s, 5H), 4.25 (s, 2H), 3.20-3.15 (m, 6H), 3.11 (t, J=8 Hz, 2H), 2.17-2.07 (m, 4H). $^{13}$C NMR (125 MHz, D$_2$O) δ 130.3, 129.8, 129.7, 129.2, 51.2, 44.6, 44.6, 43.8, 36.5, 23.7, 22.6. LRMS [M+H]$^+$ 222.2.

Example 24

Preparation of N$^1$-benzylhexane-1,6-diamine, hydrochloride salt (CZ-9)

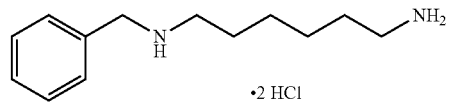 [SMILES: NCCCCCCNCc1ccccc1]

Example 24 was prepared in a similar fashion to Example 18 (CZ-25) from benzaldehyde and tert-butyl (6-aminohexyl)carbamate.

Example 25

Preparation of N$^1$-Benzyl-N$^1$,N$^{12}$,N$^{12}$-trimethyldodecane-1,12-diamine, hydrochloride salt (CZ-10)

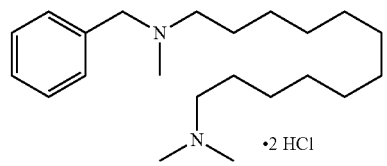 [SMILES: CN(C)CCCCCCCCCCCCN(C)Cc1ccccc1]

Example 25 was prepared in a similar fashion to Example 18 (CZ-25) from benzaldehyde and N$^1$,N$^1$,N$^{12}$-trimethyldodecane-1,12-diamine.

Example 26

Preparation of N¹-benzyl-N¹,N¹²,N¹²-trimethyldodecane-1,12-diamine, hydrochloride salt (CZ-11)

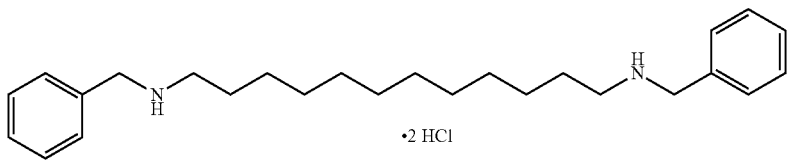 [SMILES: c1ccc(CNCCCCCCCCCCCCNCc2ccccc2)cc1]

Example 26 was prepared in a similar fashion to Example 18 (CZ-25) from benzaldehyde and dodecane-1,12-diamine. $^1$H NMR (500 MHz, D$_2$O+CD$_3$OD) δ 7.53 (s, 10H), 4.24 (s, 4H), 3.04 (t, J=8.5 Hz, 4H), 1.77-1.70 (m, 4H), 1.42-1.28 (m, 16H). $^{13}$C NMR (125 MHz, D$_2$O+CD$_3$OD) δ 131.0, 129.8, 129.6, 129.3, 50.9, 47.0, 29.2, 29.1, 28.7, 26.2, 25.7.

Example 27

Preparation of N¹-benzyl-N¹,N¹²,N¹²-trimethyldodecane-1,12-diamine, hydrochloride salt (CZ-12)

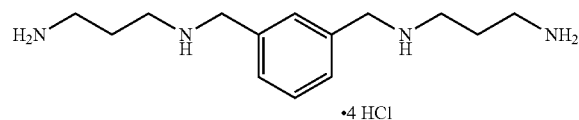 [SMILES: NCCCNCc1cccc(CNCCCN)c1]

Example 27 was prepared in a similar fashion to Example 18 (CZ-25) from isophthalaldehyde and tert-butyl (3-aminopropyl)carbamate.

Example 28

Preparation of N¹-(3-methoxybenzyl)dodecane-1,12-diamine, hydrochloride salt (CZ-13)

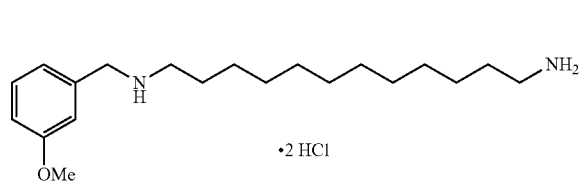 [SMILES: COc1cccc(CNCCCCCCCCCCCCN)c1]

Example 28 was prepared in a similar fashion to Example 18 (CZ-25) from 3-methoxybenzaldehyde and tert-butyl (12-aminododecyl)carbamate. $^1$H NMR (500 MHz, D$_2$O) δ 7.40 (t, J=8.0 Hz, 1H), 7.06 (s, 1H), 7.05 (s, 1H), 7.03 (s, 1H), 4.16 (s, 2H), 3.82 (s, 3H), 3.00-2.93 (m, 4H). 1.66-1.58 (m, 4H), 1.32-1.22 (m, 16H). $^{13}$C NMR (125 MHz, D$_2$O) δ 158.4, 131.5, 129.8, 121.6, 114.5, 114.3, 54.7, 49.8, 46.1, 38.7, 27.8, 27.7, 27.4, 25.9, 24.8, 24.5.

Example 29

Preparation of N¹-(3-aminopropyl)-N³-(3-(benzylamino)propyl)propane-1,3-diamine, hydrochloride salt (CZ-16)

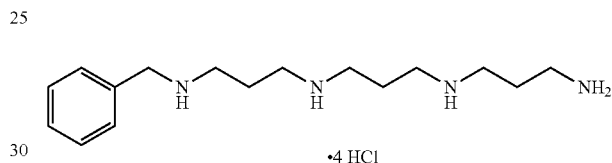

Example 29 was prepared in a similar fashion to Example 18 (CZ-25) from benzaldehyde and tert-butyl (3-((3-((3-aminopropyl)amino)propyl)amino)propyl)carbamate. $^1$H NMR (500 MHz, D$_2$O) δ 7.49 (s, 5H), 4.27 (s, 2H), 3.51-3.49 (m, 6H), 3.27-3.14 (m, 6H), 3.12 (t, J=8.0 Hz, 2H), 2.21-2.10 (m, 4H). $^{13}$C NMR (125 MHz, D$_2$O) δ 130.5, 130.0, 130.0, 129.5, 51.4, 45.3, 45.2, 43.9, 43.2, 36.6, 27.8, 23.9, 22.8.

Example 30

Preparation of N¹,N¹'-((2,4,6-trimethyl-1,3-phenylene)bis(methylene))bis(propane-1,3-diaminium) chloride (CZ-19)

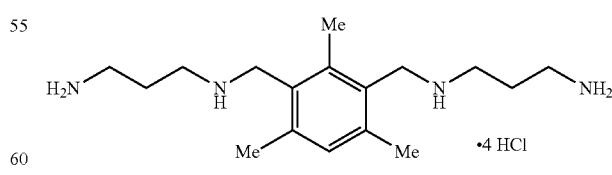

Example 30 was prepared in a similar fashion to Example 18 (CZ-25) from 2,4-bis(bromomethyl)-1,3,5-trimethylbenzene tert-butyl (3-aminopropyl)carbamate.

Example 31

Preparation of N¹,N¹'-(1,3-phenylenebis(methylene))bis(dodecane-1,12-diamine), hydrochloride salt (CZ-21)

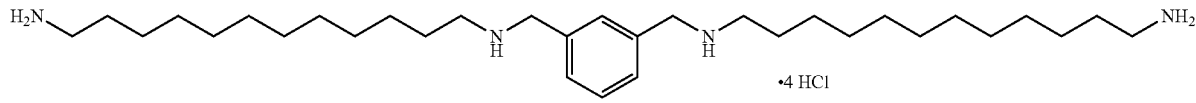 [SMILES: NCCCCCCCCCCCCNCc1cccc(CNCCCCCCCCCCCCN)c1]

Example 31 was prepared in a similar fashion to Example 18 (CZ-25) from isophthalaldehyde and tert-butyl (12-aminododecyl)carbamate. $^1$H NMR (500 MHz, D$_2$O) δ 7.65 (s, 3H), 4.36 (s, 4H), 3.11 (t, J=8.0 Hz, 4H), 3.06 (t, J=7.5 Hz, 4H), 1.77-1.68 (m, 8H), 1.47-1.33 (m, 32H). $^{13}$C NMR (125 MHz, D$_2$O) δ 130.4, 129.9, 129.7, 128.9, 49.0, 45.6, 38.2, 27.3, 27.3, 27.2, 27.1, 26.9, 26.8, 25.4, 24.4, 24.3, 24.0. LRMS [M+H]$^+$ 503.5.

Example 32

Preparation of (3-(((3-((3-aminopropyl)amino)propyl)amino)methyl)phenyl)methanol, hydrochloride salt (CZ-22)

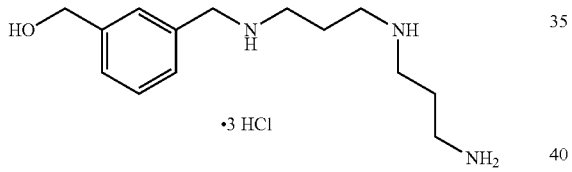

Example 32 was prepared in a similar fashion to Example 18 (CZ-25) from isophthalaldehyde and N¹,N¹-dimethylpropane-1,3-diamine.

Example 33

Preparation of N¹,N¹'-(1,3-phenylenebis(methylene))bis(hexane-1,6-diamine), hydrochloride salt (CZ-26)

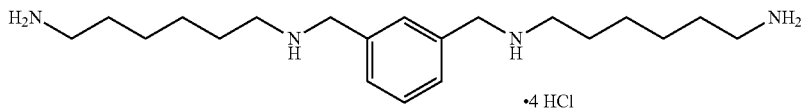 [SMILES: NCCCCCCNCc1cccc(CNCCCCCCN)c1]

Example 33 was prepared in a similar fashion to Example 18 (CZ-25) from isophthalaldehyde and tert-butyl (6-aminohexyl)carbamate.

Example 34

Preparation of di-tert-butyl (((((1,3-phenylenebis(methylene))bis(azanediyl))bis(propane-3,1-diyl))bis(azanediyl))bis(propane-3,1-diyl))dicarbamate (CZ-27)

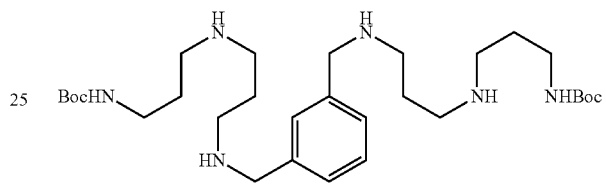

Example 34 was prepared in a similar fashion to Example 18 (CZ-25) from benzaldehyde and tert-butyl (3-((3-aminopropyl)amino)propyl)carbamate.

Example 35

Preparation of N¹,N¹',N¹''-(benzene-1,3,5-triyltris(methylene))tris(propane-1,3-diamine) hydrochloride salt (CZ-32)

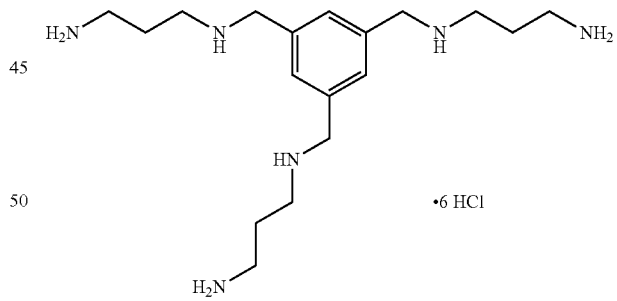

Example 35 was prepared in a similar fashion to Example 18 (CZ-25) from benzene-1,3,5-tricarbaldehyde and tert-butyl (3-aminopropyl)carbamate.

Example 36

Preparation of N¹,N¹',N¹''-(benzene-1,3,5-triyltris(methylene))tris(hexane-1,6-diamine), hydrochloride salt (CZ-33)

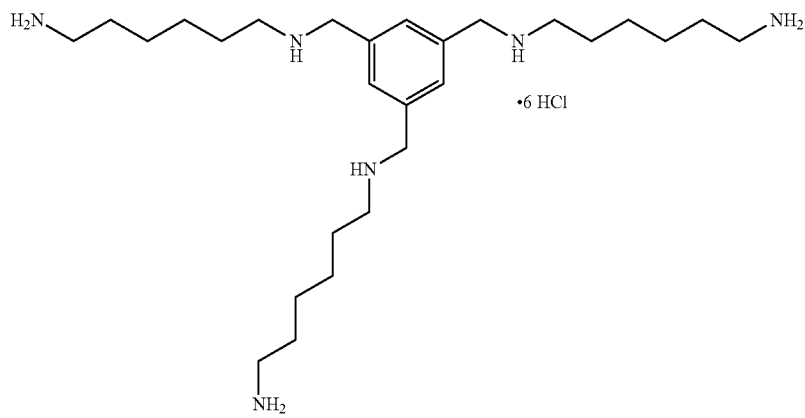 [SMILES: NCCCCCCNCc1cc(CNCCCCCCN)cc(CNCCCCCCN)c1]

Example 36 was prepared in a similar fashion to Example 18 (CZ-25) from benzene-1,3,5-tricarbaldehyde and tert-butyl (6-aminohexyl)carbamate.

Example 37

Preparation of N¹,N¹'-(((1,3-phenylenebis(methylene))bis(azanediyl))bis(propane-3,1-diyl))bis(N³,N³-dimethylpropane-1,3-diamine), hydrochloride salt (CZ-43)

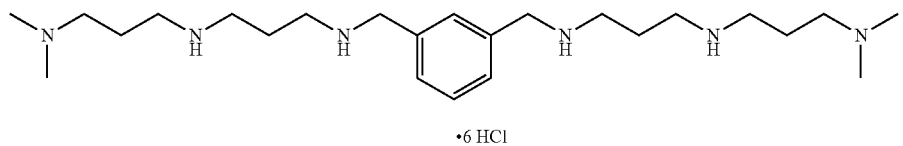

Example 37 was prepared in a similar fashion to Example 18 (CZ-25) from isophthalaldehyde and N¹-(3-aminopropyl)-N³,N³-dimethylpropane-1,3-diamine. $^1$H NMR (500 MHz, D$_2$O) δ 7.57 (s, 4H), 4.31 (s, 4H), 3.28-3.14 (m, 16H), 2.91 (s, 12H), 2.20-2.10 (m, 8H). $^{13}$C NMR (125 MHz, D$_2$O) δ 132.1, 131.9, 131.8, 130.9, 54.8, 51.5, 45.3, 45.1, 44.8, 43.5, 23.3, 21.9.

Example 38

Preparation of N¹,N¹',N¹''-(benzene-1,3,5-triyltris(methylene))tris(N³,N³-dimethylpropane-1,3-diamine), hydrochloride salt (CZ-46)

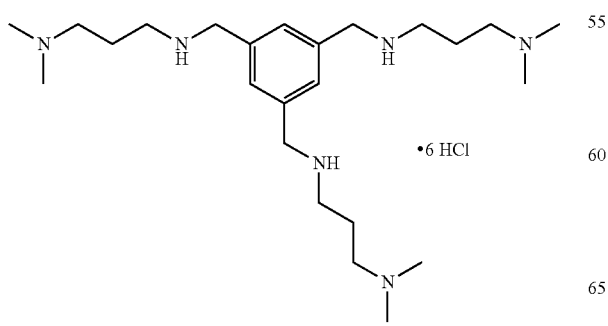

Example 38 was prepared in a similar fashion to Example 18 (CZ-25) from benzene-1,3,5-tricarbaldehyde and $N^1,N^1$-dimethylpropane-1,3-diamine.

Example 39

Preparation of (3,5-bis(((3-((3-aminopropyl)amino) propyl)amino)methyl)phenyl)-methanol, hydrochloride salt (CZ-53)

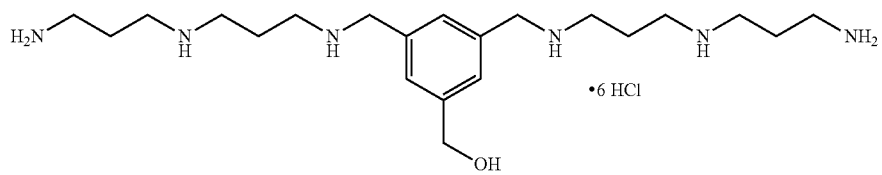 [SMILES: NCCCNCCCNCc1cc(CO)cc(CNCCCNCCCN)c1]

Example 3 was prepared in a similar fashion to Example 18 (CZ-25) from 5-(hydroxymethyl)isophthalaldehyde and tert-butyl (3-((3-aminopropyl)amino)propyl)carbamate. $^1$H NMR (500 MHz, D$_2$O) δ 7.57 (s, 2H), 7.55 (s, 1H), 4.72 (s, 2H), 4.35 (s, 4H), 3.26-3.19 (m, 12H), 3.13 (t, J=7.5 Hz, 4H), 2.21-2.09 (m, 8H). $^{13}$C NMR (125 MHz, D$_2$O) δ 142.8, 132.0, 130.7, 130.0, 63.2, 51.0, 44.9, 44.8, 44.4, 36.7, 23.9, 22.9.

Example 40

Preparation of tri-tert-butyl-(((((benzene-1,3,5-triyl-tris(methylene))tris(azanediyl))tris-(propane-3,1-diyl))tris(azanediyl))tris(propane-3,1-diyl))tricarbamate, hydrochloride salt (CZ-54)

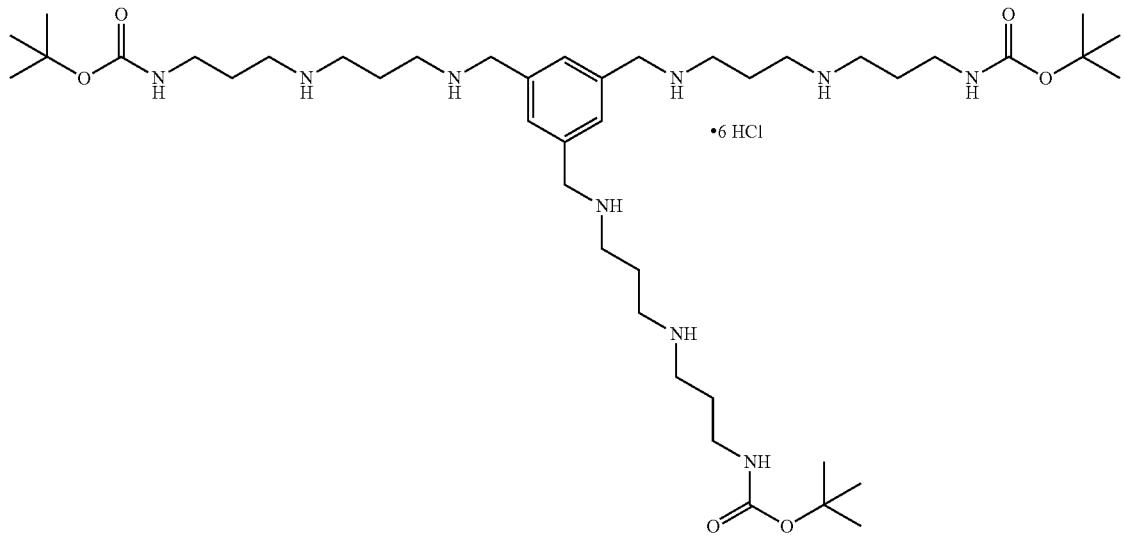 [SMILES: CC(C)(C)OC(=O)NCCCNCCCNCc1cc(CNCCCNCCCNC(=O)OC(C)(C)C)cc(CNCCCNCCCNC(=O)OC(C)(C)C)c1]

Example 40 was prepared in a similar fashion to Example 18 (CZ-25) from benzene-1,3,5-tricarbaldehyde and tert-butyl (3-((3-aminopropyl)amino)propyl)carbamate.

Example 41

Preparation of N¹,N¹'-(1,3-phenylenebis(methylene))bis(N³-(3-((3-aminopropyl)amino)propyl)propane-1,3-diamine), hydrochloride salt (CZ-57)

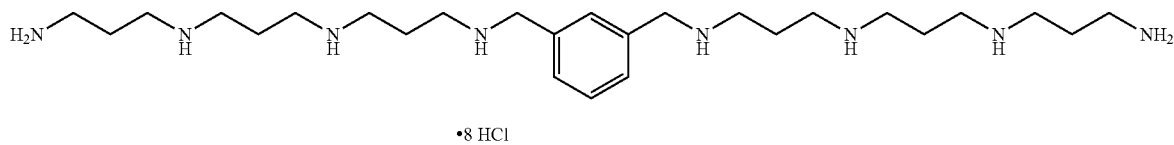 [SMILES: NCCCNCCCNCCCNCc1cccc(CNCCCNCCCNCCCN)c1]

•8 HCl

Example 41 was prepared in a similar fashion to Example 18 (CZ-25) from isophthalaldehyde and tert-butyl (3-((3-((3-aminopropyl)amino)propyl)amino)propyl)-carbamate.

Example 42

Preparation of 3,3'-(isophthaloylbis(azanediyl))bis(propan-1-aminium) chloride (CZ-40)

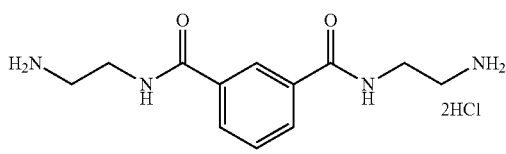 [SMILES: NCCNC(=O)c1cccc(C(=O)NCCN)c1]

Step 1: tert-Butyl(5-(3-((3-((tert-butoxycarbonyl)amino)propyl)carbamoyl)phenyl)-5-oxopentyl)carbamate Isophthaloyl chloride (344 mg, 1.70 mmol), triethylamine (343 mg, 3.41 mmol), and $CH_2Cl_2$ (10 mL) were added to a round-bottom flask. To the solution was added tert-butyl (3-aminopropyl)carbamate (593 mg, 3.41 mmol), and the reaction mixture was stirred for 16 h. The mixture was washed with aq. NaOH (10%, 50 mL) and the layers separated. The aqueous layer was extracted with $CH_2Cl_2$ (2×50 mL) and organic layers were combined, dried over $Na_2SO_4$, filtered, and concentrated under reduced pressure. Purification by column chromatography (hexanes/EtOAc) afforded the desired product, which was used without further purification.

Step 2: 3,3'-(Isophthaloylbis(azanediyl))bis(propan-1-aminium) chloride

To the crude tert-butyl(5-(3-((3-((tert-butoxycarbonyl)amino)propyl)carbamoyl)phenyl)-5-oxopentyl)carbamate from Step 1 was added methanolic HCl (150 mL, 1.0 M). The reaction mixture was stirred for 2 h and concentrated under reduced pressure. The solid was collected by vacuum filtration and washed with $Et_2O$ (30 mL) and hot MeOH (30 mL) to afford the desired product (0.388 g, 56%) as a white solid.

Example 43

Preparation of N¹,N¹',N¹''-(benzene-1,3,5-triyltris(methylene))tris(N³-(3-aminopropyl)propane-1,3-diamine), hydrochloride salt (CZ-52)

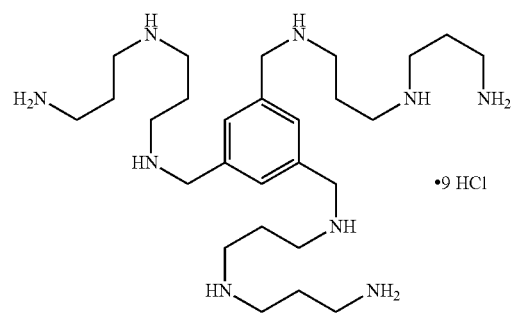 [SMILES: NCCCNCCCNCc1cc(CNCCCNCCCN)cc(CNCCCNCCCN)c1]

•9 HCl

Step 1: Tri-tert-butyl (((((benzene-1,3,5-triyltris(methylene))tris(azanediyl))-tris(propane-3,1-diyl))tris(azanediyl))tris(propane-3,1-diyl))tricarbamate Benzene-1,3,5-tricarbaldehyde (1.80 g, 11.04 mmol) and MeOH (50 mL) were added to a round-bottom flask. To the solution was added trimethyl orthoformate (165.6 g, 17.6 mmol) and tert-butyl (3-((3-aminopropyl)amino)propyl)carbamate (7.66 g, 33.1 mmol) and the reaction mixture was stirred for 24 h. Sodium borohydride (1.67 g, 44.2 mmol) was added portionwise and stirred for 1 h. The reaction mixture was concentrated under reduced pressure and aq. NaOH (10%, 150 mL) and EtOAc (150 mL) were added. The layers were separated and the aqueous layer was extracted with EtOAc (150 mL). The organic layers combined, dried over $Na_2SO_4$, filtered, and concentrated under reduced pressure to afford the desired product as a clear oil. The intermediate was carried forward without further purification.

Step 2: N¹,N¹',N¹''-(Benzene-1,3,5-triyltris(methylene))tris(N³-(3-aminopropyl)propane-1,3-diamine), hydrochloride salt To the crude tri-tert-butyl (((((benzene-1,3,5-triyltris(methylene))tris(azanediyl))tris(propane-3,1-diyl))tris(azanediyl))tris(propane-3,1-diyl))tricarbamate from Step 1 was added methanolic HCl (150 mL, 1.0 M). The reaction mixture was stirred for 2 h and concentrated under reduced pressure. The solid was collected by vacuum filtration and washed with Et$_2$O (30 mL) and hot MeOH (30 mL) to afford the desired product (5.6 g, 61%) as a white solid. LRMS [M+H]$^+$ 508.5.

Example 44

Preparation of tert-butyl (3-((3-((3,5-bis(((3-((3-aminopropyl)amino)propyl)amino)methyl)-benzyl)amino)propyl)amino)propyl)carbamate (CZ-51)

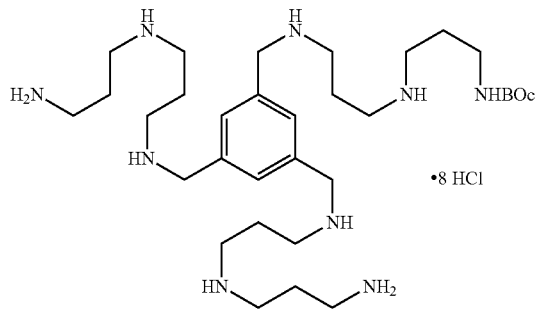

Example 44 was prepared in a similar fashion to Example 43 (CZ-52) from benzene-1,3,5-tricarbaldehyde and tert-butyl (3-((3-aminopropyl)amino)propyl)carbamate.

Example 45

Preparation of N$^1$,N$^{1'}$-([1,1'-biphenyl]-3,5-diylbis(methylene))bis(N$^3$-(3-ammoniopropyl)propane-1,3-diaminium) chloride (CZ-58)

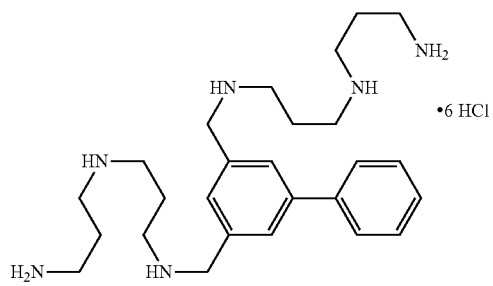 [SMILES: NCCCNCCCNCc1cc(CNCCCNCCCN)cc(-c2ccccc2)c1]

Step 1: [1,1'-Biphenyl]-3,5-dicarbaldehyde

A solution of 5-bromoisophthaldehyde (40.0 g, 187.8 mmol) (*Med. Chem. Commun.*, 2012, 3, 763-770), phenylboronic acid (22.9 g, 187.8 mmol) and potassium carbonate (64.8 g, 469.5 mmol) in DME/H$_2$O (5:1, 600 mL) was purged with N$_2$ for 5 min. Tetrakispalladium triphenylphosphine (1.1 g, 0.9 mmol) was added, and the reaction mixture was heated to 90° C. and stirred for 16 h. The reaction mixture was cooled to rt, filtered through a pad of Celite diatomaceous earth, and the solvent evaporated under reduced pressure. Purification by column chromatography (10% EtOAc/hexanes) afforded the desired product (74%, 29.1 g) as an off-white solid. $^1$H NMR (300 MHz, CDCl$_3$) δ ppm 10.18 (s, 2H), 8.37 (d, J=1.2 Hz, 2H), 8.35 (t, J=1.5 Hz, 1H), 7.70-7.66 (m, 2H), 7.55-7.43 (m, 3H).

Step 2: Di-tert-butyl (((((([1,1'-biphenyl]-3,5-diylbis(methylene))bis(azanediyl))bis-(propane-3,1-diyl))bis(azanediyl))bis(propane-3,1-diyl))dicarbamate

[1,1'-Biphenyl]-3,5-dicarbaldehyde (3.62 g, 17.24 mmol) and MeOH (100 mL) were added to a round-bottom flask. To the solution was added tert-butyl (3-((3-aminopropyl)amino)propyl)carbamate (7.96 g, 34.4 mmol), and the reaction mixture was stirred for 24 h. Sodium borohydride (2.62 g, 69.0 mmol) was added, and the mixture was stirred for 1 h. The solvent was removed under reduced pressure to afford a white solid. Aqueous NaOH (10%, 200 mL) was added, and the solution was extracted with EtOAc (200 mL). The organic layer was separated, and the aqueous layer was extracted with EtOAc (200 mL). The organic layers were combined, dried over Na$_2$SO$_4$, filtered, and concentrated under reduced pressure to afford the desired product as a clear oil that was used without further purification.

Step 3: N$^1$,N$^{1'}$-([1,1'-biphenyl]-3,5-diylbis(methylene))bis(N$^3$-(3-ammoniopropyl)propane-1,3-diaminium) chloride To the crude N$^1$,N$^{1'}$-([1,1'-biphenyl]-3,5-diylbis(methylene))bis(N$^3$-(3-ammoniopropyl)propane-1,3-diaminium) chloride from Step 2 was added methanolic HCl (150 mL, 1.0 M). The reaction mixture was stirred for 2 h and concentrated under reduced pressure. The solid was collected by vacuum filtration and washed with Et$_2$O (30 mL) and hot MeOH (30 mL) to afford the desired product (6.8 g, 60%) as a white solid. $^1$H NMR (D$_2$O, 500 MHz) δ ppm 7.85 (s, 2H), 7.74 (d, J=7.5 Hz, 2H), 7.59-7.56 (m, 3H), 7.50-7.49 (m, 1H), 4.38 (s, 4H), 3.29 (t, J=8.0 Hz, 4H), 3.23 (q, J=5.0 Hz, 8H), 3.14 (t, J=8.0 Hz, 4H), 2.25-2.19 (m, 4H), 2.17-2.11 (m, 4H). $^{13}$C NMR (125 MHz, D$_2$O) 142.3, 138.8, 132.1, 130.0, 129.5, 129.2, 128.4, 127.0, 50.8, 44.7, 44.6, 44.2, 36.5, 23.7, 22.7. LRMS [M+H]$^+$ 441.4.

Example 46

Preparation of N$^1$,N$^{1'}$-((5-(benzo[d][1,3]dioxol-5-yl)-1,3-phenylene)bis(methylene))bis(N$^3$-(3-ammoniopropyl)propane-1,3-diaminium) chloride (CZ-61)

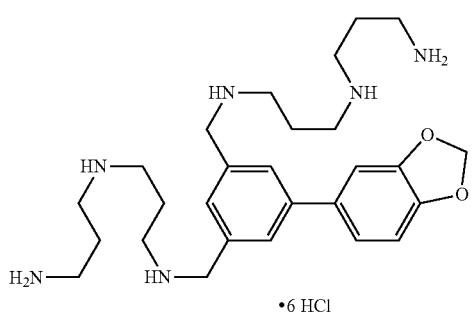 [SMILES: NCCCNCCCNCc1cc(CNCCCNCCCN)cc(-c2ccc3c(c2)OCO3)c1]

Example 46 was prepared in a similar fashion to Example 45 (CZ-58) from 5-bromoisophthaldehyde, benzo[d][1,3]dioxol-5-ylboronic acid, and tert-butyl (3-((3-aminopropyl)amino)propyl)carbamate. N$^1$,N$^{1'}$-((5-(benzo[d][1,3]dioxol-5-yl)-1,3-phenylene)bis(methylene))bis(N$^3$-(3-aminopropyl)propane-1,3-diamine), hydrochloride salt: $^1$H NMR (500 MHz, D$_2$O) δ 7.72 (s, 2H), 7.49 (s, 1H), 7.15 (s, 2H), 6.93 (d, J=8.5 Hz, 1H), 5.95 (s, 2H), 4.30 (s, 4H), 3.21-3.12 (m, 8H), 3.05 (t, J=8.0 Hz, 4H), 2.17-2.02 (m, 8H). $^{13}$C NMR (125 MHz, D$_2$O) δ 148.1, 147.6, 142.3, 133.3, 132.2, 130.8, 129.7, 129.6, 129.4, 121.1, 109.0, 107.5, 101.6, 51.0, 44.8, 44.8, 44.4, 36.6, 23.9, 22.8.

Example 47

Preparation of N$^1$,N$^{1'}$,N$^{1''}$-([1,1'-biphenyl]-3,3',5-triyltris(methylene))tris(N$^3$-(3-aminopropyl)propane-1,3-diamine), hydrochloride salt (CZ-62)

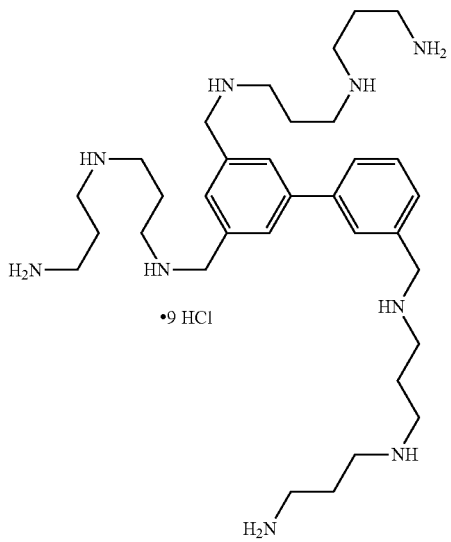 [SMILES: NCCCNCCCNCc1cccc(-c2cc(CNCCCNCCCN)cc(CNCCCNCCCN)c2)c1]

Example 47 was prepared in a similar fashion to Example 45 (CZ-58) from 5-bromoisophthaldehyde, (3-formylphenyl)boronic acid and tert-butyl (3-((3-aminopropyl)amino)propyl)carbamate. $^1$H NMR (400 MHz, D$_2$O) δ 7.96 (s, 2H), 7.93-7.85 (m, 2H), 7.71-7.61 (m, J=8.5 Hz, 3H), 4.47 (s, 4H), 4.44 (s, 2H), 3.36-3.23 (m, 18H), 3.17 (t, J=8.0 Hz, 6H), 2.30-2.22 (m, 6H), 2.20-2.13 (m, 6H). LRMS [M+H]$^+$ 584.5.

Example 48

Preparation of N$^1$,N$^{1'}$-((2'-methyl-[1,1'-biphenyl]-3,5-diyl)bis(methylene))bis(N$^3$-(3-aminopropyl)propane-1,3-diamine), hydrochloride salt (CZ-63)

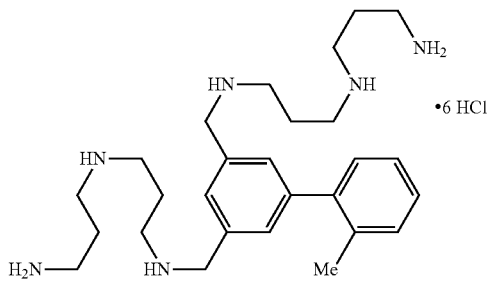 [SMILES: Cc1ccccc1-c1cc(CNCCCNCCCN)cc(CNCCCNCCCN)c1]

Example 48 was prepared in a similar fashion to Example 45 (CZ-58) from 5-bromoisophthaldehyde, o-tolylboronic acid and tert-butyl (3-((3-aminopropyl)amino)propyl)carbamate. $^1$H NMR (500 MHz, D$_2$O) δ 7.59 (s, 1H), 7.56 (d, J=1.0 Hz, 2H), 7.41-7.40 (m, 2H), 7.38-7.35 (m, 1H), 7.32-7.31 (m, 1H), 4.38 (s, 4H), 3.25 (t, J=7.5 Hz, 4H), 3.20-3.18 (m, 8H), 3.11 (t, J=8.0 Hz, 4H), 2.25 (m, 3H), 2.20-2.15 (m, 4H), 2.14-2.07 (m, 4H)). $^{13}$C NMR (125 MHz, D$_2$O) δ 143.3, 139.9, 135.6, 131.8, 131.7, 131.5, 131.0, 130.5, 129.9, 129.7, 128.2, 126.1, 50.8, 44.7, 44.6, 44.2, 36.6, 23.7, 22.7. LRMS [M+H]$^+$ 455.4.

Example 49

Preparation of N$^1$,N$^{1'}$-((4'-morpholino-[1,1'-biphenyl]-3,5-diyl)bis(methylene))bis(N$^3$-(3-aminopropyl)propane-1,3-diamine), hydrochloride salt (CZ-64)

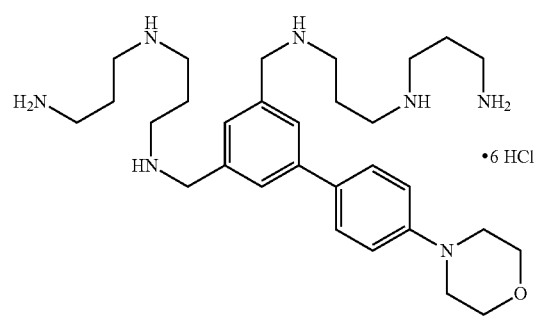 [SMILES: NCCCNCCCNCc1cc(CNCCCNCCCN)cc(-c2ccc(N3CCOCC3)cc2)c1]

Example 49 was prepared in a similar fashion to Example 45 (CZ-58) from 5-bromoisophthaldehyde, (4-morpholinophenyl)boronic acid and tert-butyl (3-((3-aminopropyl)amino)propyl)carbamate.

Example 50

Preparation of N$^1$,N$^{1'}$,N$^{1''}$-([1,1'-biphenyl]-3,4',5-triyltris(methylene))tris(N$^3$-(3-aminopropyl)propane-1,3-diamine), hydrochloride salt (CZ-65)

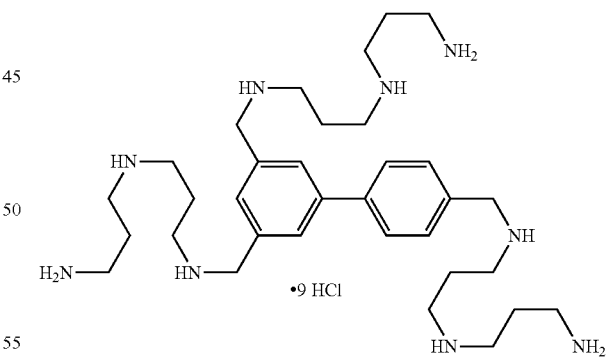

Example 50 was prepared in a similar fashion to Example 45 (CZ-58) from 5-bromoisophthaldehyde, (4-formylphenyl)boronic acid and tert-butyl (3-((3-aminopropyl)amino)propyl)carbamate. $^1$H NMR (500 MHz, D$_2$O) δ 7.92 (s, 2H), 7.84 (d, J=8.5 Hz, 2H), 7.65 (d, J=8.5 Hz, 3H), 4.43 (s, 4H), 4.37 (s, 2H), 3.31-3.28 (m, 6H), 3.26-3.20 (m, 12H), 3.14 (t, J=8.0 Hz, 6H), 2.25-2.17 (m, 6H), 2.16-2.10 (m, 6H). $^{13}$C NMR (125 MHz, D$_2$O) δ 141.6, 140.1, 132.2, 130.6, 130.4, 129.7, 127.8, 50.8, 44.7, 44.6, 44.2, 36.5, 23.7, 22.7, 22.6. LRMS [M+H]$^+$ 584.5.

Example 51

Preparation of N¹,N¹',N¹''-((4'-isopropoxy-[1,1'-biphenyl]-3,3',5-triyl)tris(methylene))-tris(N³-(3-aminopropyl)propane-1,3-diamine), hydrochloride salt (CZ-66)

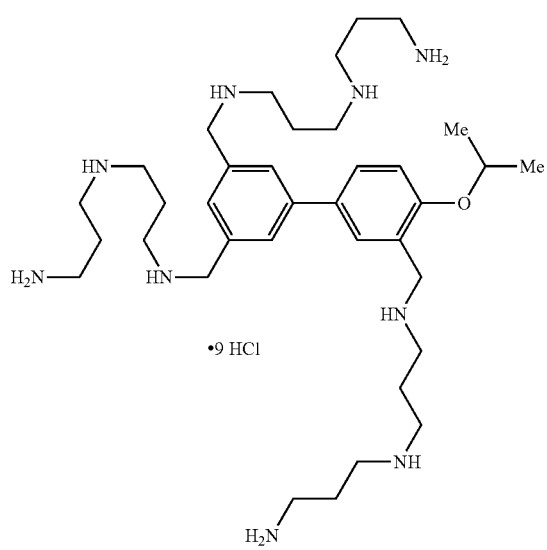 [SMILES: CC(C)Oc1ccc(-c2cc(CNCCCNCCCN)cc(CNCCCNCCCN)c2)cc1CNCCCNCCCN]

Example 51 was prepared in a similar fashion to Example 45 (CZ-58) from 5-bromoisophthaldehyde, (3-formyl-4-isopropoxyphenyl)boronic acid and tert-butyl (3-((3-aminopropyl)amino)propyl)carbamate. $^1$H NMR (500 MHz, D$_2$O) δ 7.93 (s, 2H), 7.88-7.82 (m, 2H), 7.65 (s, 1H), 7.35 (d, J=9.0 Hz, 1H), 4.94-4.87 (m, 1H), 4.47 (s, 4H), 4.43 (s, 2H), 3.39-3.28 (m, 18H), 3.22 (t, J=8.0 Hz, 6H), 2.33-2.18 (m, 12H), 1.48 (d, J=6.5 Hz, 6H). $^{13}$C NMR (125 MHz, D$_2$O) δ 158.9, 143.9, 134.8, 133.8, 132.9, 132.6, 132.3, 131.8, 122.7, 117.0, 84.4, 74.5, 53.5, 49.6, 47.3, 47.3, 47.0, 46.9, 46.7, 39.2, 26.3, 25.3, 25.2, 23.9. LRMS [M+H]$^+$ 642.5.

Example 52

Preparation of N¹,N¹'-((4'-isopropoxy-[1,1'-biphenyl]-3,5-diyl)bis(methylene))bis(N³-(3-aminopropyl)propane-1,3-diamine), hydrochloride salt (CZ-67)

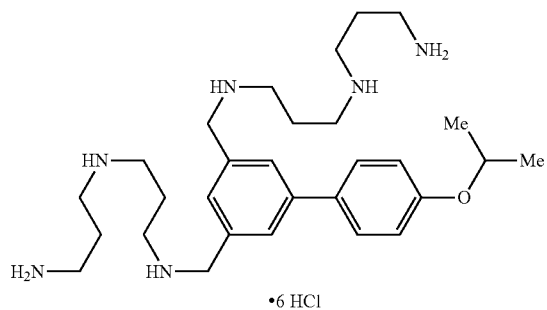 [SMILES: CC(C)Oc1ccc(-c2cc(CNCCCNCCCN)cc(CNCCCNCCCN)c2)cc1]

Example 52 was prepared in a similar fashion to Example 45 (CZ-58) from 5-bromoisophthaldehyde, (4-isopropoxyphenyl)boronic acid, and tert-butyl (3-((3-aminopropyl)amino)propyl)carbamate. $^1$H NMR (500 MHz, D$_2$O) δ 7.81 (s, 2H), 7.68 (d, J=8.5 Hz, 2H), 7.54 (s, 1H), 7.12 (d, J=8.5 Hz, 2H), 4.78-4.72 (m, 1H), 4.37 (s, 4H), 3.28 (t, J=8.0 Hz, 4H), 3.24-3.19 (m, 8H), 3.13 (t, J=8.0 Hz, 4H), 2.24-2.19 (m, 4H), 2.17-2.09 (m, 4H), 1.35 (d, J=6.0 Hz, 6H). $^{13}$C NMR (125 MHz, D$_2$O) δ 157.0, 141.8, 132.0, 131.8, 129.4, 129.0, 128.3, 116.8, 71.6, 50.8, 44.6, 44.6, 44.1, 36.4, 23.6, 22.6, 21.0.

Example 53

Preparation of N¹,N¹'-((5-(thiophen-2-yl)-1,3-phenylene)bis(methylene))bis(N³-(3-aminopropyl)propane-1,3-diamine), hydrochloride salt (CZ-68)

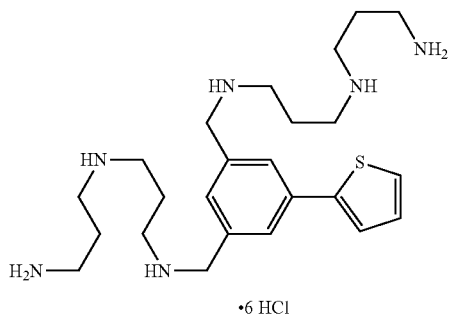 [SMILES: NCCCNCCCNCc1cc(CNCCCNCCCN)cc(-c2cccs2)c1]

Example 53 was prepared in a similar fashion to Example 45 (CZ-58) from 5-bromoisophthaldehyde, (4-(thiophen-2-yl)phenyl)boronic acid and tert-butyl (3-((3-aminopropyl)amino)propyl)carbamate. $^1$H NMR (500 MHz, D$_2$O) δ 7.90 (s, 2H), 7.83 (t, J=1.0 Hz, 1H), 7.63-7.61 (m, 1H), 7.60-7.57 (m, 1H), 7.53 (s, 1H), 4.38 (s, 4H), 3.27 (t, J=8.0 Hz, 4H), 3.23-3.19 (m, 8H), 3.13 (t, J=8.0 Hz, 4H), 2.23-2.17 (m, 4H), 2.15-2.09 (m, 4H). $^{13}$C NMR (125 MHz, D$_2$O) δ 139.9, 137.1, 132.2, 129.6, 128.7, 127.7, 125.9, 122.3, 50.8, 44.7, 44.6, 44.1, 36.5, 23.7, 22.6. LRMS [M+H]$^+$ 447.3.

Example 54

Preparation of N¹,N¹',N¹''-((4'-(trifluoromethyl)-[1,1'-biphenyl]-3,3',5-triyl)tris(methylene))tris(N3-(3-aminopropyl)propane-1,3-diamine), hydrochloride salt (CZ-69)

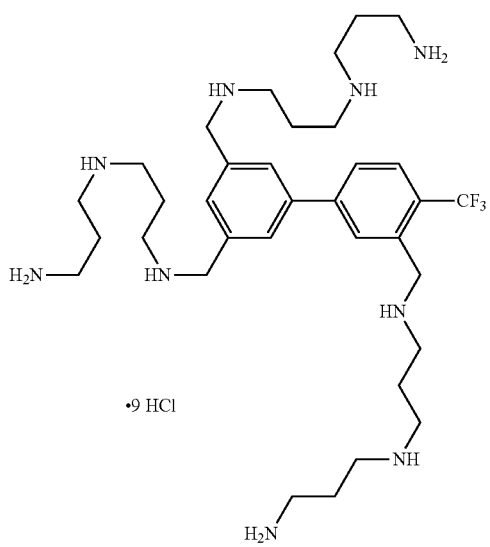 [SMILES: NCCCNCCCNCc1cc(CNCCCNCCCN)cc(-c2ccc(C(F)(F)F)c(CNCCCNCCCN)c2)c1]

Example 54 was prepared in a similar fashion to Example 45 (CZ-58) from 5-bromoisophthaldehyde, (3-formyl-4-(trifluoromethyl)phenyl)boronic acid and tert-butyl (3-((3-aminopropyl)amino)propyl)carbamate. $^1$H NMR (500 MHz, D$_2$O) δ 7.93 (s, 2H), 7.87 (s, 2H), 7.61 (s, 2H), 4.45 (s, 2H), 4.38 (s, 4H), 3.27-3.14 (m, 16H), 3.10-06 (m, 8H), 2.25-2.05 (m, 12H).

Example 55

Preparation of N$^1$,N$^{1'}$-((3',5'-bis(trifluoromethyl)-[1,1'-biphenyl]-3,5-diyl)bis(methylene))bis(N$^3$-(3-aminopropyl)propane-1,3-diamine), hydrochloride salt (CZ-70)

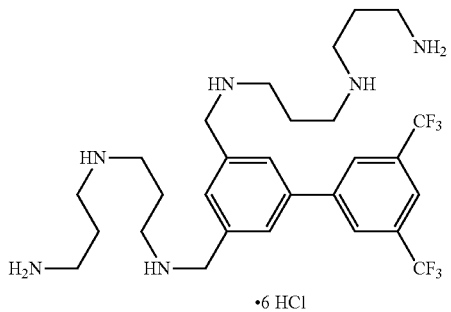 [SMILES: NCCCNCCCNCc1cc(CNCCCNCCCN)cc(-c2cc(C(F)(F)F)cc(C(F)(F)F)c2)c1]

Example 55 was prepared in a similar fashion to Example 45 (CZ-58) from 5-bromoisophthaldehyde, (3,5-bis(trifluoromethyl)phenyl)boronic acid and tert-butyl (3-((3-aminopropyl)amino)propyl)carbamate. $^1$H NMR (500 MHz, D$_2$O) δ 8.20 (s, 2H), 8.07 (s, 1H), 7.91 (s, 2H), 7.69 (s, 1H), 4.41 (s, 4H), 3.30 (t, J=7.5 Hz, 4H), 3.26-3.21 (m, 8H), 3.14 (t, J=8.0 Hz, 4H), 2.23-2.19 (m, 4H), 2.17-2.10 (m, 4H). $^{13}$C NMR (125 MHz, D$_2$O) δ 140.6, 139.7, 132.4, 131.5, 131.2, 129.9, 127.5, 124.4, 122.2, 50.7, 44.7, 44.6, 44.3, 36.5, 23.7, 22.6. LRMS [M+H]$^+$ 577.3.

Example 56

Preparation of N$^1$,N$^{1'}$-((5-(pyridin-4-yl)-1,3-phenylene)bis(methylene))bis(N$^3$-(3-aminopropyl)propane-1,3-diamine), hydrochloride salt (CZ-71)

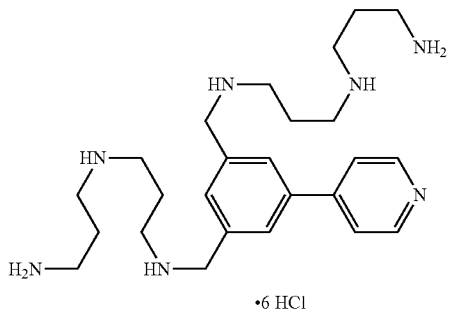 [SMILES: NCCCNCCCNCc1cc(CNCCCNCCCN)cc(-c2ccncc2)c1]

Example 56 was prepared in a similar fashion to Example 45 (CZ-58) from 5-bromoisophthaldehyde, pyridin-4-ylboronic acid and tert-butyl (3-((3-aminopropyl)amino)propyl)carbamate. $^1$H NMR (500 MHz, D$_2$O) δ 8.87 (d, J=6.0 Hz, 2H), 8.39 (d, J=6.5 Hz, 2H), 8.15 (s, 2H), 7.88 (s, 1H), 4.47 (s, 4H), 3.30 (t, J=8.0 Hz, 4H), 3.24-3.19 (m, 8H), 3.12 (t, J=8.0 Hz, 4H), 2.24-2.19 (m, 4H), 2.15-2.08 (m, 4H). $^{13}$C NMR (125 MHz, D$_2$O) δ 156.6, 141.6, 136.8, 134.4, 133.2, 131.0, 125.2, 50.8, 44.9, 44.8, 44.6, 36.7, 23.9, 22.9. LRMS [M+H]$^+$ 442.4.

Example 57

Preparation of N$^1$,N$^{1'}$-((5-(6-methoxypyridin-3-yl)-1,3-phenylene)bis(methylene))bis(N$^3$-(3-aminopropyl)propane-1,3-diamine), hydrochloride salt (CZ-72)

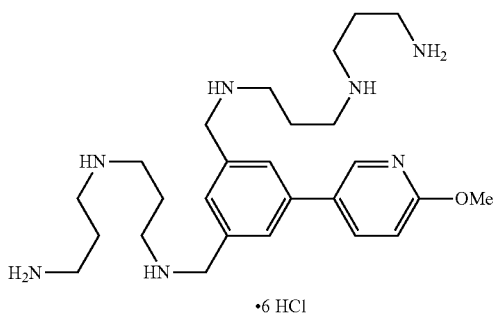 [SMILES: COc1ccc(-c2cc(CNCCCNCCCN)cc(CNCCCNCCCN)c2)cn1]

Example 57 was prepared in a similar fashion to Example 45 (CZ-58) from 5-bromoisophthaldehyde, (6-methoxypyridin-3-yl)boronic acid and tert-butyl (3-((3-aminopropyl)amino)propyl)carbamate. LRMS [M+H]$^+$ 472.4.

Example 58

Preparation of N$^1$,N$^{1'}$-([1,1'-biphenyl]-3,5-diylbis(methylene))bis(N$^3$-(3-((3-aminopropyl)amino)propyl)propane-1,3-diamine), hydrochloride salt (CZ-73)

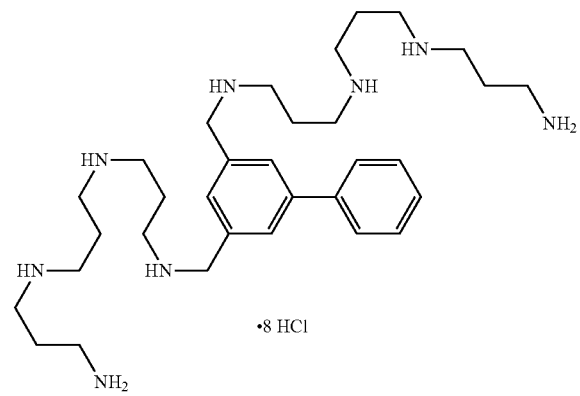 [SMILES: NCCCNCCCNCCCNCc1cc(CNCCCNCCCNCCCN)cc(-c2ccccc2)c1]

Example 58 was prepared in a similar fashion to Example 45 (CZ-58) from 5-bromoisophthaldehyde, phenylboronic acid and tert-butyl (3-((3-((3-aminopropyl)amino)propyl)amino)propyl)carbamate.

Example 59

Preparation of N¹,N¹'-((5-phenoxy-1,3-phenylene)bis(methylene))bis(N³-(3-aminopropyl)propane-1,3-diamine), hydrochloride salt (CZ-74)

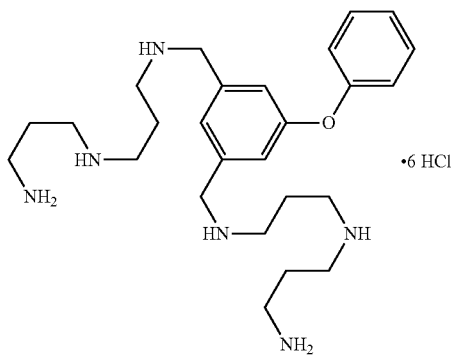 [SMILES: NCCCNCCCNCc1cc(CNCCCNCCCN)cc(Oc2ccccc2)c1]

•6 HCl

Step 1: Dimethyl 5-phenoxyisophthalate

5-Hydroxyisophthalate (210 mg, 1.00 mmol), phenylboronic acid (0.244 g, 2.0 mmol), copper(II) acetate (0.182 mg, 1.0 mmol) and triethylamine (0.303 mg, 3.0 mmol) in $CH_2Cl_2$ (20 mL) was stirred at rt in the open air for 38 h. Additional phenylboronic acid (0.061 mg, 0.50 mmol) was added, and the reaction mixture was stirred at rt in the open air. After 24 h, additional phenylboronic acid (0.061 g, 0.50 mmol) and copper acetate (0.020 g, 0.11 mmol) were added to the reaction mixture, and the mixture was stirred for 6 h. The mixture was diluted with $CHCl_2$ (20 mL) and aqueous HCl (10 mL). The organic layer was separated, washed with aq HCl, aq $NaHCO_3$, dried over $MgSO_4$, and concentrated under reduced pressure. Purification by column chromatography (10% EtOAc/hexanes) afforded the desired product (0.200 g 70%) as a white solid. $^1$H NMR (300 MHz, $CDCl_3$) δ ppm 8.42-8.41 (m, 1H), 7.85 (d, J=1.5 Hz, 2H), 7.42-7.36 (m, 2H), 7.21-7.16 (m, 1H), 7.05-7.01 (m, 2H), 3.93 (s, 6H).

Step 2: 5-Phenoxyisophthalaldehyde

To a solution of dimethyl 5-phenoxyisophthalate (0.143 g, 0.50 mmol) in toluene (12 mL) was added drop-wise a solution of Red-Al (60% in toluene, 0.673 mL, 2.0 mmol) and 1-methylpiperazine (0.243 mL, 2.2 mmol) in THF at 5° C., and the resulting mixture was stirred for 2 h. The reaction was quenched with $H_2O$ (4 mL), and then extracted with EtOAc (20 mL). The organic layer was washed with $H_2O$ (10 mL), dried over anhydrous $Na_2SO_4$, and then concentrated under reduced pressure. Purification by flash column chromatography (10% EtOAc/hexanes) afforded the desired product (0.094 g, 83%) as a white solid. $^1$H NMR (300 MHz, $CDCl_3$) δ ppm 10.04 (s, 2H), 8.08 (s, 1H), 7.72 (t, J=1.5 Hz, 2H), 7.46-7.40 (m, 2H), 7.28-7.24 (m, 1H), 7.09-7.06 (m, 2H).

Step 3: Di-tert-butyl ((((((5-phenoxy-, 3-phenylene)bis(methylene))-bis(azanediyl))bis(propane-3,1-diyl))bis(azanediyl))bis(propane-3, 1-diyl))dicarbamate To a solution of 5-phenoxyisophthalaldehyde (0.060 g, 0.27 mmol) and 3 Å mol. sieves in MeOH, was added N1-(3-aminopropyl)-N3-isobutylpropane-1,3-diamine (0.122 g, 0.53 mmol). The resultant mixture was stirred for 18 h. Sodium borohydride (0.020 g, 0.53 mmol) was added portionwise, and the reaction mixture was stirred for 1 h. The MeOH was evaporated, and the white solid was taken up in EtOAc (10 mL) and washed with aq. NaOH (10%, 4 mL). The aqueous layer was back-extracted with EtOAc (10 mL). The organic layers were combined, dried over $Na_2SO_4$, filtered and evaporated to afford clear oil. Methanolic HCl (30 mL, 1.0 M) was added to the resultant oil, and the reaction mixture was stirred for 1 h. Evaporation and collection by vacuum filtration afforded a white solid, which was washed hot MeOH (25 mL) to give the desired product (0.064 g, 52%) as a white solid. $^1$H NMR (500 MHz, $D_2O$) δ 7.50 (t, J=7.5 Hz, 2H), 7.36 (S, 1H), 7.30 (d, J=7.5 Hz, 1H), 7.24 (s, 2H), 7.17 (d, J=8.0 Hz, 2H), 4.29 (s, 4H), 3.25-3.18 (m, 12H), 3.14 (t, J=8.0 Hz, 4H), 2.21-2.10 (m, 8H). $^{13}$C NMR (125 MHz, $D_2O$) δ 158.2, 155.6, 133.3, 130.3, 124.8, 120.5, 119.7, 119.3, 50.5, 44.7, 44.6, 44.2, 36.5, 23.7, 22.6. LRMS [M+H]$^+$ 457.4.

Example 60

Preparation of N¹,N¹'-((4'-fluoro-[1,1'-biphenyl]-3,5-diyl)bis(methylene))bis(N3-(3-aminopropyl)propane-1,3-diamine), hydrochloride salt (CZ-75)

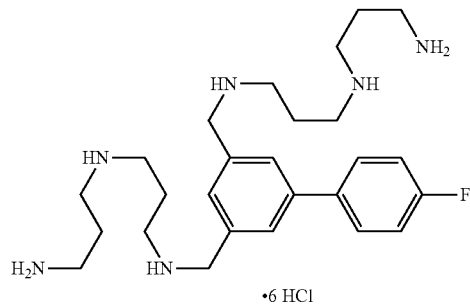 [SMILES: NCCCNCCCNCc1cc(CNCCCNCCCN)cc(-c2ccc(F)cc2)c1]

•6 HCl

Example 60 was prepared in a similar fashion to Example 45 (CZ-58) from 5-bromoisophthaldehyde, (4-fluorophenyl)boronic acid and tert-butyl (3-((3-aminopropyl)amino)propyl)carbamate. $^1$H NMR (500 MHz, $D_2O$) δ 7.80 (s, 2H), 7.71-7.68 (m, 2H), 7.56 (s, 1H), 7.25 (t, J=9 Hz, 2H), 4.37 (s, 4H), 3.26 (t, J=8 Hz, 4H), 3.19 (q, J=8 Hz, 8H), 3.11 (t, J=7.5 Hz, 4H), 2.22-2.07 (m, 8H). $^{13}$C NMR (125 MHz, $D_2O$) δ 162.9 (d, 244 Hz), 135.3 (d, 3 Hz), 132.3, 130.1, 129.7, 129.1 (d, 8 Hz), 116.1 (d, 21 Hz), 51.1, 44.9, 44.8, 44.4, 36.7, 23.9, 22.9. LRMS [M+H]$^+$ 459.4.

Example 61

Preparation of N¹,N¹'-([1,1'-biphenyl]-3,5-diylbis(methylene))bis(propane-1,3-diamine), hydrochloride salt (CZ-77)

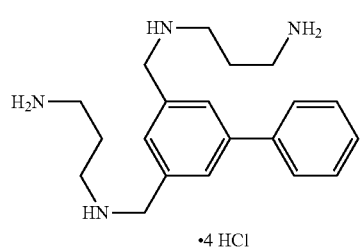 [SMILES: NCCCNCc1cc(CNCCCN)cc(-c2ccccc2)c1]

•4 HCl

Example 61 was prepared in a similar fashion to Example 45 (CZ-58) from 5-bromoisophthaldehyde, phenylboronic acid and tert-butyl (3-aminopropyl)carbamate. $N^1,N^{1'}$-([1,1'-biphenyl]-3,5-diylbis(methylene))bis(propane-1,3-diamine). $^1$H NMR (300 MHz, D$_2$O) δ 7.82 (s, 2H), 7.71-7.64 (m, 2H), 7.54-7.41 (m, 4H), 4.34 (s, 4H), 3.22 (t, J=7.8 Hz, 4H), 3.08 (t, J=7.5 Hz, 4H), 2.11 (quint, J=7.5 Hz, 4H).

Example 62

Preparation of $N^1,N^{1'}$-((5-butoxy-1,3-phenylene)bis(methylene))bis(N3-(3-aminopropyl)propane-1,3-diamine), hydrochloride salt (CZ-76)

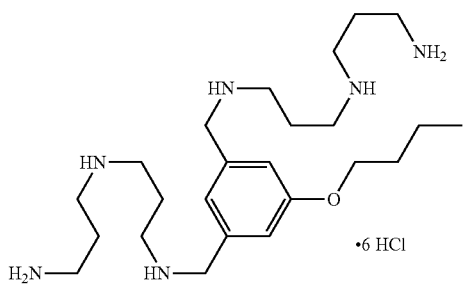 [SMILES: CCCCOc1cc(CNCCCNCCCN)cc(CNCCCNCCCN)c1]

Step 1: Dimethyl 5-butoxyisophthalate

Dimethyl 5-hydroxyisophthalate (0.40 g, 1.90 mmol), cesium carbonate (1.30 g, 3.80 mmol) and CH$_3$CN (12 mL) were added to a round-bottom flask and stirred for 15-30 min. Iodobutane (0.42 g, 2.28 mmol) was added, and the reaction was stirred for 16 h. The solvent was concentrated under reduced pressure, and the reaction mixture was partitioned between EtOAc (50 mL) and H$_2$O (50 mL). The organic layer was separated and the aqueous layer extracted with EtOAc (50 mL). The combined organics were dried over Na$_2$SO$_4$, filtered, and concentrated under reduced pressure to afford the desired product which was used without further purification.

Step 2: (5-Butoxy-1,3-phenylene)dimethanol

To a solution of dimethyl 5-butoxyisophthalate (0.51 g, 1.90 mmol) in THF (16 mL) was slowly added LiAlH$_4$ (0.40 g, 10.5 mmol). The reaction mixture was stirred for 8 h. The reaction was quenched by the addition of 2N aq. HCl (5 mL). The mixture was extracted with Et$_2$O (2×25 mL) and EtOAc (2×25 mL), the organics layers combined, dried over Na$_2$SO$_4$, filtered, and concentrated under reduced pressure to afford the desired product (0.24 g) as an oil, which was used without further purification.

Step 3: 5-Butoxyisophthalaldehyde (5-Butoxy-1,3-phenylene)dimethanol (0.24 g, 1.15 mmol) and CH$_2$Cl$_2$ (10 mL) were added to a round-bottom flask. To the solution was added PCC (0.74 g, 3.45 mmol), and the reaction was stirred at rt for 16 h. The reaction mixture was concentrated under reduced pressure. Purification by column chromatography (90% hexanes/EtOAc) afforded the desired product (0.18 g, 44%, 3 steps) as a white semi-solid. $^1$H NMR (300 MHz, CDCl$_3$) δ ppm 9.99 (s, 2H), 7.89 (s, 1H), 7.58 (s, 2H), 4.03 (t, J=6.6 Hz, 2H), 1.77 (quint, J=6.6 Hz, 2H), 1.47 (sext, J=7.2 Hz, 2H), 0.94 (t, J=7.5 Hz, 3H). $^{13}$C NMR (75 MHz, CDCl$_3$) δ ppm 191.3, 160.6, 138.6, 124.2, 120.1, 68.9, 31.3, 19.4, 14.1.

Step 4: Di-tert-butyl ((((((5-butoxy-1,3-phenylene)bis(methylene))bis(azanediyl))-bis(propane-3,1-diyl))bis(azanediyl))bis(propane-3,1-diyl))dicarbamate 5-Butoxyisophthalaldehyde (0.80 g, 0.85 mmol) and MeOH (15 mL) were added to a round-bottom flask. To the solution was added tert-butyl (3-((3-aminopropyl)amino)propyl)-carbamate (0.39 g, 1.70 mmol), and the reaction mixture was stirred at rt for 24 h. Sodium borohydride (0.13 g, 3.40 mmol) was added and the reaction mixture stirred for 1 h. The reaction mixture was concentrated under reduced pressure and aq. NaOH (10%, 50 mL) and EtOAc (50 mL) were added. The layers were separated and the aqueous layer was extracted with EtOAc (50 mL). The organic layers combined, dried over Na$_2$SO$_4$, filtered, and concentrated under reduced pressure to afford the desired product as a clear oil which was used without further purification.

Step 5: $N^1,N^{1'}$-((5-Butoxy-1,3-phenylene)bis(methylene))bis(N3-(3-aminopropyl)propane-1,3-diamine), hydrochloride salt To the crude di-tert-butyl ((((((5-butoxy-1,3-phenylene)bis(methylene))bis(azanediyl))bis(propane-3,1-diyl))bis(azanediyl))-bis(propane-3,1-diyl))dicarbamate from Step 4 was added methanolic HCl (50 mL, 1.0 M). The reaction mixture was stirred for 2 h and concentrated under reduced pressure. The solid was collected by vacuum filtration and washed with Et$_2$O (10 mL) and hot MeOH (10 mL) to afford the desired product (0.27 g, 48%) as a white solid. $^1$H NMR (500 MHz, D$_2$O) δ ppm 7.20 (s, 3H), 4.30 (s, 4H), 4.15 (t, J=6.5 Hz, 2H), 3.26-3.20 (m, 12H), 3.14 (t, J=7.5 Hz, 4H), 2.22-2.10 (m, 8H), 1.79 (quint, J=6.5 Hz, 2H), 1.48 (sext, J=7.5 Hz, 2H), 0.96 (t, J=7 Hz, 3H). $^{13}$C NMR (125 MHz, D$_2$O) 159.2, 132.9, 123.5, 117.3, 68.8, 50.8, 44.7, 44.6, 44.1, 36.5, 30.3, 23.7, 22.6, 18.5, 13.0. LRMS [M+H]$^+$ 437.4.

Example 63

Preparation of $N^1,N^{1'}$-((5-((2-ethylhexyl)oxy)-1,3-phenylene)bis(methylene))bis($N^3$-(3-aminopropyl)propane-1,3-diamine), hydrochloride salt (CZ-81)

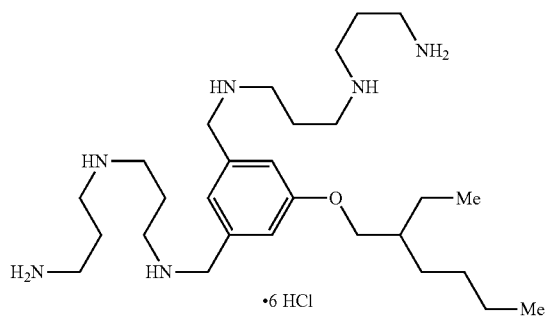 [SMILES: CCCCC(CC)COc1cc(CNCCCNCCCN)cc(CNCCCNCCCN)c1]

Example 63 was prepared in a similar fashion to Example 62 (CZ-76) from dimethyl 5-butoxyisophthalate, 3-(bromomethyl)heptane and tert-butyl (3-((3-aminopropyl)amino)propyl)carbamate. LRMS [M+H]$^+$ 493.5.

Example 64

Preparation of N$^1$,N$^{1'}$-((5-(2-ethylbutoxy)-1,3-phenylene)bis(methylene))bis(N$^3$-(3-aminopropyl)propane-1,3-diamine), hydrochloride salt (CZ-90)

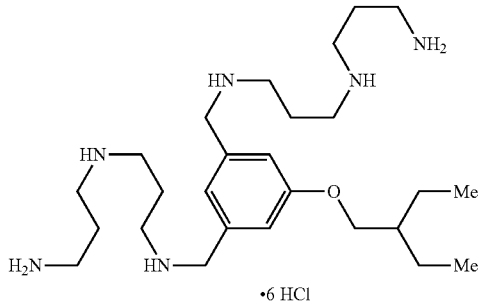 [SMILES: CCC(CC)COc1cc(CNCCCNCCCN)cc(CNCCCNCCCN)c1]

Example 64 was prepared in a similar fashion to Example 62 (CZ-76) from dimethyl 5-butoxyisophthalate, 3-(bromomethyl)pentane and tert-butyl (3-((3-aminopropyl)amino)propyl)carbamate. $^1$H NMR (500 MHz, D$_2$O) δ 7.23 (s, 2H), 7.22 (s, 1H), 4.32 (s, 4H), 4.06 (t, J=7.0 Hz, 2H), 3.27-3.18 (m, 12H), 3.15 (t, J=8.0 Hz, 4H), 2.24-2.12 (m, 8H), 1.72 (m, J=6.0 Hz, 1H), 1.52-1.44 (m, 4H), 0.94-0.91 (m, 6H). $^{13}$C NMR (125 MHz, D$_2$O) δ 159.6, 132.9, 123.5, 117.5, 71.43, 50.8, 44.7, 44.6, 44.1, 40.1, 36.5, 23.7, 22.6, 10.3. LRMS [M+H]$^+$ 465.4.

Example 65

Preparation of N$^1$,N$^{1'}$-((5-(Benzyloxy)-1,3-phenylene)bis(methylene))bis(N$^3$-(3-aminopropyl)propane-1,3-diamine), hydrochloride salt (CZ-95)

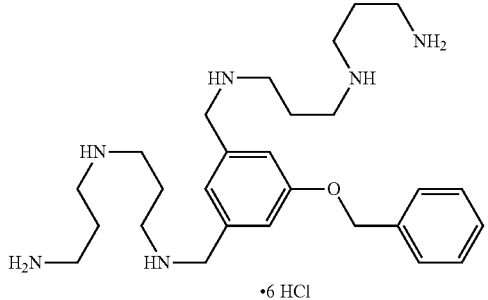 [SMILES: NCCCNCCCNCc1cc(CNCCCNCCCN)cc(OCc2ccccc2)c1]

Example 65 was prepared in a similar fashion to Example 62 (CZ-76) from dimethyl 5-butoxyisophthalate, benzyl bromide and tert-butyl (3-((3-aminopropyl)amino)propyl) carbamate. $^1$H NMR (500 MHz, D$_2$O) δ 7.52 (d, J=7.0 Hz, 2H), 7.49-7.41 (m, 3H), 7.23 (s, 2H), 7.20 (s, 1H), 5.23 (s, 2H), 4.29 (s, 4H), 3.22-3.15 (m, 12H), 3.13 (t, J=8.0 Hz, 4H), 2.20-2.09 (m, 8H). $^{13}$C NMR (125 MHz, D$_2$O) δ 158.7, 136.0, 133.0, 132.5, 128.8, 128.5, 128.0, 123.9, 117.7, 70.4, 50.7, 44.7, 44.6, 44.3, 44.0, 36.5, 23.7, 22.6. LRMS [M+H]$^+$ 471.4.

Example 66

Preparation of N$^1$,N$^{1'}$-((5-(cyclohexylmethoxy)-1,3-phenylene)bis(methylene))bis(N$^3$-(3-aminopropyl)propane-1,3-diamine), hydrochloride salt (CZ-101)

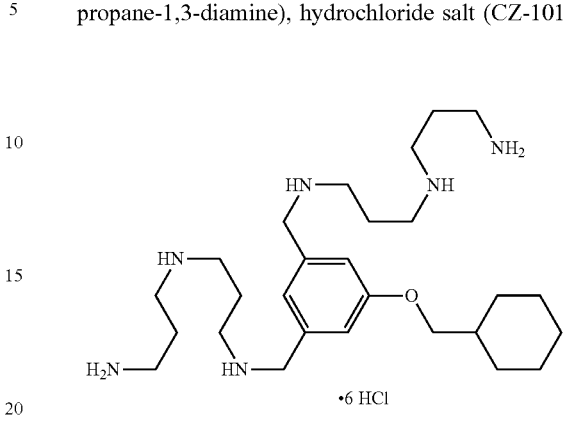

Example 66 was prepared in a similar fashion to Example 62 (CZ-76) from dimethyl 5-butoxyisophthalate, (bromomethyl)cyclohexane and tert-butyl (3-((3-aminopropyl)amino)propyl)carbamate. $^1$H NMR (500 MHz, D$_2$O) δ 7.16 (d, J=7.5 Hz, 3H), 4.27 (s, 4H), 3.93 (t, J=6.0 Hz, 2H), 3.23-3.09 (m, 16H), 2.19-2.07 (m, 8H), 1.83-1.66 (m, 6H), 1.31-1.17 (m, 3H), 1.10-1.05 (m, 2H). $^{13}$C NMR (125 MHz, D$_2$O) δ 131.4, 131.2, 131.1, 130.2, 50.8, 47.9, 44.6, 44.6, 44.2, 44.1, 30.9, 28.1, 28.1, 25.6, 25.4, 22.6, 21.9, 13.3.

Example 67

Preparation of N$^1$,N$^{1'}$-([1,1'-biphenyl]-3,5-diylbis(methylene))bis(N$^3$-(3-(butylamino)propyl)propane-1,3-diamine), hydrochloride salt (CZ-83)

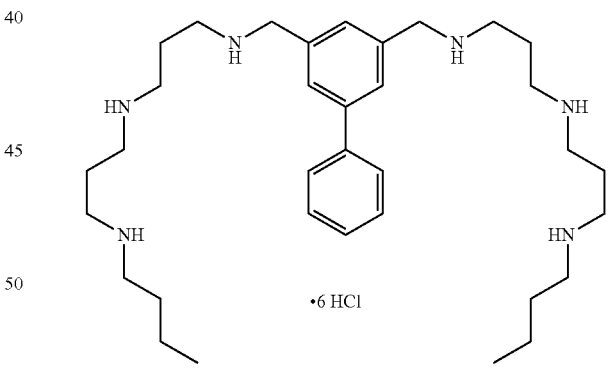

Step 1: [1,1'-Biphenyl]-3,5-dicarbaldehyde

A solution of 5-bromoisophthaldehyde (40.0 g, 187.8 mmol), phenylboronic acid (22.9 g, 187.8 mmol) and potassium carbonate (64.8 g, 469.5 mmol) in DME/H$_2$O (5:1 600 mL) was purged with N$_2$ for 5 min. Tetrakispalladium triphenylphosphine (1.1 g mg, 0.9 mmol) was added and the reaction mixture was heated to 90° C. and stirred for 16 h. The reaction mixture was cooled, filtered through a pad of celite and the solvent evaporated under reduced pressure. Purification by column chromatography (10% EtOAc/hexanes) afforded the desired product (74%, 29.1 g) as a tan solid. $^1$H NMR (300 MHz, CDCl$_3$) δ ppm 10.18 (s, 2H), 8.37 (d, J=1.2 Hz, 2H), 8.35 (t, J=1.5 Hz, 1H), 7.70-7.66 (m, 2H), 7.55-7.43 (m, 3H).

Step 2: N$^1$,N$^{1'}$-([1,1'-biphenyl]-3,5-diylbis(methylene))bis(N$^3$-(3-(butylamino)propyl)propane-1,3-diamine)

[1,1'-Biphenyl]-3,5-dicarbaldehyde (0.66 g, 3.15 mmol) and MeOH (50 mL) were added to a round-bottom flask. To the solution was added N$^1$-(3-aminopropyl)-N$^3$-butylpropane-1,3-diamine (1.18 g, 6.31 mmol) and the reaction mixture was stirred at rt for 24 h. Sodium borohydride (0.48 g, 12.62 mmol) was added and the reaction mixture stirred for 1 h. The reaction mixture was concentrated under reduced pressure to afford a white solid. Aq. NaOH (10%, 100 mL) and EtOAc (100 mL) were added and the reaction mixture stirred for 1 h. The layers were separated and the aqueous layer was extracted with EtOAc (100 mL). The organic layers were combined, dried over Na$_2$SO$_4$, filtered, and concentrated under reduced pressure to afford a clear oil which was used without further purification.

Step 3: N$^1$,N$^{1'}$-([1,1'-biphenyl]-3,5-diylbis(methylene))bis(N$^3$-(3-(butylamino)propyl)propane-1,3-diamine) hydrochloride salt To the crude N$^1$,N$^{1'}$-([1,1'-biphenyl]-3,5-diylbis(methylene))bis(N$^3$-(3-(butylamino)propyl)propane-1,3-diamine) from step 2 was subjected to acidification with methanolic HCl (100 mL, 1.0M). The reaction mixture stirred at rt for 2 h. The reaction mixture was concentrated under reduced pressure and the solid was collected by vacuum filtration and washed with Et$_2$O (50 mL) and hot MeOH (50 mL) to afford the desired product (1.24 g, 51%) as a white solid. $^1$H NMR (500 MHz, D$_2$O) δ 7.83 (s, 2H), 7.71 (d, J=7.5 Hz, 2H), 7.55-7.52 (m, 3H), 7.49-7.45 (m, 1H), 4.35 (s, 4H), 3.26 (t, J=7.5 Hz, 4H), 3.21-3.16 (m, 8H), 3.14 (t, J=8.0 Hz, 4H), 3.05 (t, J=8.0 Hz, 4H), 2.21-2.10 (m, 8H), 1.65 (quint, J=7.0 Hz, 4H), 1.37 (sext, J=8.0 Hz, 4H), 0.91 (t, J=7.0 Hz, 6H). $^{13}$C NMR (125 MHz, D$_2$O) δ 142.5, 138.9, 132.3, 130.3, 129.8, 129.5, 128.7, 127.3, 51.0, 47.8, 44.9, 44.5, 44.4, 27.7, 22.9, 22.9, 19.3, 13.0. LRMS [M+H]$^+$ 553.5.

Example 68

Preparation of N$^1$,N$^{1'}$-([1,1'-biphenyl]-3,5-diylbis(methylene))bis(N$^3$-(3-(isobutylamino)propyl)propane-1,3-diamine), hydrochloride salt (CZ-86)

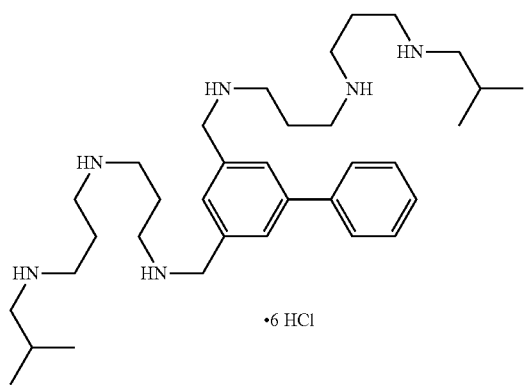 [SMILES: CC(C)CNCCCNCCCNCc1cc(CNCCCNCCCNCC(C)C)cc(-c2ccccc2)c1]

Step 1: [1,1'-Biphenyl]-3,5-dicarbaldehyde

A solution of 5-bromoisophthaldehyde (40.0 g, 187.8 mmol), phenylboronic acid (22.9 g, 187.8 mmol) and potassium carbonate (64.8 g, 469.5 mmol) in DME/H$_2$O (5:1 600 mL) was purged with N$_2$ for 5 min. Tetrakispalladium triphenylphosphine (1.1 g mg, 0.9 mmol) was added and the reaction mixture was heated to 90° C. and stirred for 16 h. The reaction mixture was cooled, filtered through a pad of celite and the solvent evaporated under reduced pressure. Purification by column chromatography (10% EtOAc/hexanes) afforded the desired product (74%, 29.1 g) as a tan solid. $^1$H NMR (300 MHz, CDCl$_3$) δ ppm 10.18 (s, 2H), 8.37 (d, J=1.2 Hz, 2H), 8.35 (t, J=1.5 Hz, 1H), 7.70-7.66 (m, 2H), 7.55-7.43 (m, 3H).

Step 2: Di-tert-butyl ((((([1,1'-biphenyl]-3,5-diylbis(methylene))bis(azanediyl))-bis(propane-3,1-diyl))bis(azanediyl))bis(propane-3,1-diyl))dicarbamate

[1,1'-Biphenyl]-3,5-dicarbaldehyde (3.62 g, 17.2 mmol, 1) and MeOH (100 mL) were added to a round-bottom flask. To the solution was added tert-butyl (3-((3-aminopropyl)amino)propyl)-carbamate (7.96 g, 34.4 mmol), and the reaction mixture was stirred at rt for 24 h. Sodium borohydride (2.62 g, 69.0 mmol) was added and the reaction mixture stirred for 1 h. The reaction mixture was concentrated under reduced pressure to afford a white solid. Aqueous NaOH (10%, 200 mL) and EtOAc (200 mL) were added, and the reaction mixture was stirred for 1 h. The layers were separated, and the aqueous layer was extracted with EtOAc (200 mL). The organic layers were combined, dried over Na$_2$SO$_4$, filtered, and concentrated under reduced pressure to afford a clear oil that was used without further purification.

Step 3: N$^1$,N$^{1'}$-([1,1'-biphenyl]-3,5-diylbis(methylene))bis(N$^3$-(3-aminopropyl)propane-1,3-diamine), hydrochloride salt To the crude di-tert-butyl ((((([1,1'-biphenyl]-3,5-diylbis(methylene))bis(azanediyl))bis(propane-3,1-diyl))bis(azanediyl))-bis(propane-3,1-diyl))dicarbamate from Step 2 was subjected to acidification with methanolic HCl (200 mL, 1.0 M). The reaction mixture stirred at rt for 2 h. The reaction mixture was concentrated under reduced pressure, and the solid was collected by vacuum filtration and washed with Et$_2$O (50 mL) and hot MeOH (50 mL) to afford the desired product (6.8 g, 60%) as a white solid. $^1$H NMR (500 MHz, D$_2$O) δ 7.85 (s, 2H), 7.74 (d, J=7.5 Hz, 2H), 7.59-7.56 (m, 3H), 7.50-7.49 (m, 1H), 4.38 (s, 4H), 3.29 (t, J=8.0 Hz, 4H), 3.23 (q, J=5.0 Hz, 8H), 3.14 (t, J=8.0 Hz, 4H), 2.25-2.19 (m, 4H), 2.17-2.11 (m, 4H). LRMS [M+H]$^+$ 441.4.

Step 4: N$^1$,N$^{1'}$-([1,1'-Biphenyl]-3,5-diylbis(methylene))bis(N$^3$-(3-(isobutylamino)propyl)propane-1,3-diamine)

To N$^1$,N$^{1'}$-([1,1'-biphenyl]-3,5-diylbis(methylene))bis(N$^3$-(3-aminopropyl)propane-1,3-diamine), hydrochloride salt was added aq. NaOH (10%, 100 mL) and 75% CHCl$_3$/i-propanol (100 mL). The layers were separate and the aqueous layer was extracted with 75% CHCl$_3$/i-propanol (4×100 mL). The organic layers were combined dried over Na$_2$SO$_4$, filtered, and concentrated under reduced pressure to afford a clear oil which was used without further purification.

To a round-bottom flask was added the crude $N^1,N^{1'}$-([1,1'-biphenyl]-3,5-diylbis(methylene))bis($N^3$-(3-aminopropyl)propane-1,3-diamine) (3.5 g, 8.0 mmol) and MeOH (50 mL). To the solution was added isobutyraldehyde (1.15 g, 15.9 mmol) and the reaction mixture was stirred at rt for 24 h. Sodium borohydride (1.2 g, 31.9 mmol) was added and the reaction mixture was stirred for 1 h. The reaction mixture was concentrated under reduced pressure to afford a white solid. Aq. NaOH (10%, 200 mL) and EtOAc (200 mL) were added, and the mixture was stirred for 1 h. The layers were separated and the aqueous layer was extracted with EtOAc (200 mL). The combined organics were dried over $Na_2SO_4$, filtered, and concentrated under reduced pressure to afford the desired product as a clear oil which was used without further purification.

Step 5: $N^1,N^{1'}$-([1,1'-Biphenyl]-3,5-diylbis(methylene))bis($N^3$-(3-(isobutylamino)propyl)propane-1,3-diamine), hydrochloride salt To the crude $N^1,N^{1'}$-([1,1'-biphenyl]-3,5-diylbis(methylene))bis($N^3$-(3-(isobutylamino)propyl)propane-1,3-diamine) was added methanolic HCl (200 mL, 1.0 M). The reaction mixture was stirred at rt for 1 h. The reaction mixture was concentrated under reduced pressure, and the solid was collected by vacuum filtration and washed with $Et_2O$ (50 mL) and hot MeOH (50 mL) to afford the desired product as a white solid (3.07 g, 50%). $^1H$ NMR (500 MHz, $D_2O$) δ 7.87 (s, 2H), 7.75 (d, J=7.5, 2H), 7.59-7.48 (m, 4H), 4.39 (s, 4H), 3.26 (t, J=8.0 Hz, 4H), 3.21-3.12 (m, 12H), 2.92 (d, J=7.0 Hz, 4H), 2.21-2.10 (m, 8H), 2.01 (sept, J=7.0 Hz, 2H), 0.99 (d, J=7.0 Hz, 12H). $^{13}C$ NMR (125 MHz, $D_2O$) δ 142.8, 139.1, 132.4, 130.1, 129.8, 129.5, 128.7, 127.3, 55.1, 51.1, 44.9, 44.8, 44.4, 25.8, 22.8, 22.7, 19.2. LRMS $[M+H]^+$ 553.5.

Method 1I

Step 1: [1,1'-Biphenyl]-3,5-dicarbaldehyde

A solution of 5-bromoisophthaldehyde (40.0 g, 187.8 mmol), phenylboronic acid (22.9 g, 187.8) and potassium carbonate (64.8 g, 469.5 mmol) in $DME/H_2O$ (5:1, 600 mL) was purged with $N_2$ for 5 min. Tetrakispalladium triphenylphosphine (1.1 g mg, 0.9 mmol) was added and the reaction mixture was heated to 90° C. and stirred for 16 h. The reaction mixture was cooled, filtered through a pad of Celite diatomaceous earth, and the solvent was evaporated under reduced pressure. Purification by column chromatography (10% EtOAc/hexanes) afforded the desired product (74%, 29.1 g) as a tan solid. $^1H$ NMR (300 MHz, $CDCl_3$) δ ppm 10.18 (s, 2H), 8.37 (d, J=1.2 Hz, 2H), 8.35 (t, J=1.5 Hz, 1H), 7.70-7.66 (m, 2H), 7.55-7.43 (m, 3H).

Step 2: $N^1,N^{1'}$-([1,1'-Biphenyl]-3,5-diylbis(methylene))bis($N^3$-(3-(isobutylamino)propyl)propane-1,3-diamine)

[1,1'-Biphenyl]-3,5-dicarbaldehyde (3.03 g, 14.4 mmol) and MeOH (60 mL) were added to a round-bottom flask. To the solution was added N-(3-aminopropyl)-$N^3$-isobutylpropane-1,3-diamine (5.40 g, 28.8 mmol), and the reaction mixture was stirred at rt for 24 h. Sodium borohydride (0.55 g, 14.4 mmol) was added, and the reaction mixture was stirred for 2 h. The reaction mixture was concentrated under reduced pressure to afford a white solid. Aqueous NaOH (10%, 50 mL) was added, and the reaction mixture stirred for 30 min. The solution was extracted with $CHCl_3$ (3×75 mL). The organic layers were combined, dried over $Na_2SO_4$, filtered, and concentrated under reduced pressure to afford a clear oil which was used without further purification.

Step 3: $N,N^{1'}$-([1,1'-Biphenyl]-3,5-diylbis(methylene))bis($N^3$-(3-(isobutylamino)propyl)propane-1,3-diamine) hydrochloride salt To the crude $N^1,N^{1'}$-([1,1'-biphenyl]-3,5-diylbis(methylene))bis($N^3$-(3-(isobutylamino)propyl)propane-1,3-diamine) from step 2 was added methanolic HCl (75 mL, 2.0M). The resulting white solid was collected by vacuum filtration and washed with minimal MeOH and $Et_2O$ and stored under high vacuum to afford the desired product (9.3 g, 89%) as a white solid.

Example 69

Preparation of 3,5-bis(((3-((3-aminopropyl)amino)propyl)amino)methyl)phenol, hydrochloride salt (CZ-87)

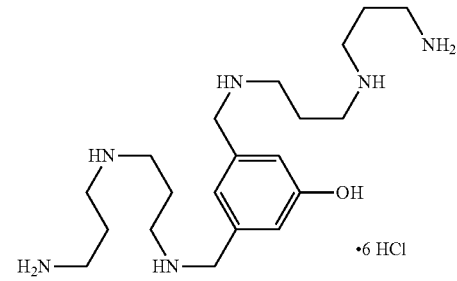 [SMILES: NCCCNCCCNCc1cc(O)cc(CNCCCNCCCN)c1]

Example 69 was prepared in a similar fashion to Example 62 (CZ-76) from dimethyl 5-butoxyisophthalate and tert-butyl (3-((3-aminopropyl)amino)propyl)carbamate.

Example 70

Preparation of (3',5'-Bis(((3-((3-aminopropyl)amino)propyl)amino)methyl)-[1,1'-biphenyl]-4-yl) (piperidin-1-yl)methanone, hydrochloride salt (CZ-88)

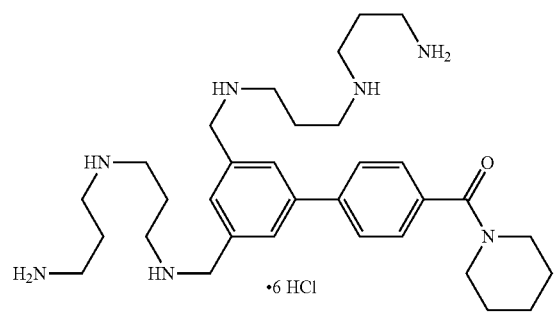 [SMILES: NCCCNCCCNCc1cc(CNCCCNCCCN)cc(-c2ccc(C(=O)N3CCCCC3)cc2)c1]

Example 70 was prepared in a similar fashion to Example 68 (CZ-86) from 5-bromoisophthaldehyde, piperidin-1-yl(4-(4,4,5,5-tetramethyl-1,3,2-dioxaborolan-2-yl)-phenyl)methanone and tert-butyl (3-((3-aminopropyl)amino)propyl)carbamate. $^1H$ NMR (300 MHz, $D_2O$) δ 7.87 (s, 2H), 7.78 (d, J=8.4 Hz, 2H), 7.58 (s, 1H), 7.54-7.49 (m, 2H), 4.37 (s, 4H), 3.68 (bs, 2H), 3.42-3.38 (m, 2H), 3.26-3.13 (m, 12H), 3.07 (t, J=7.8 Hz, 4H), 2.20-2.01 (m, 8H), 1.71-1.64 (m, 4H), 1.58-1.49 (m, 4H). LRMS [M+H]⁺ 552.4.

Example 71

Preparation of 1,1'-((([1,1'-biphenyl]-3,5diylbis(methylene))bis(azanediyl))bis(propane-3,1-diyl))bis(tetrahydropyrimidin-2(1H)-one), hydrochloride salt (CZ-89)

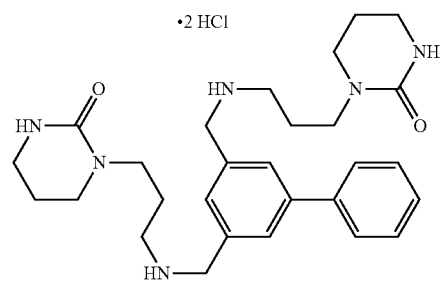 [SMILES: O=C1NCCCN1CCCNCc1cc(CNCCCN2CCCNC2=O)cc(-c2ccccc2)c1]

Example 71 was prepared in a similar fashion to Example 68 (CZ-86) from 5-bromoisophthaldehyde, phenyl boronic acid, 1-(3-aminopropyl)tetrahydropyrimidin-2(1H)-one and tert-butyl (3-((3-aminopropyl)amino)propyl)carbamate. ¹H NMR (300 MHz, D₂O) δ 7.80 (d, J=6.5 Hz, 2H), 7.71-7.68 (m, 2H), 7.56-7.45 (m, 4H), 4.30 (s, 4H), 3.34 (t, J=6.6 Hz, 4H), 3.21 (t, J=6.0 Hz, 4H), 3.11 (t, J=6.0 Hz, 4H), 3.04 (t, J=7.2 Hz, 4H), 1.97-1.88 (m, 4H), 1.78 (p, J=6.0 Hz, 4H). LRMS [M+H]⁺ 493.4.

Example 72

Preparation of N¹,N¹'-([1,1'-biphenyl]-3,5-diylbis(methylene))bis(N³-(3-(octylamino)propyl)-propane-1,3-diamine), hydrochloride salt (CZ-92)

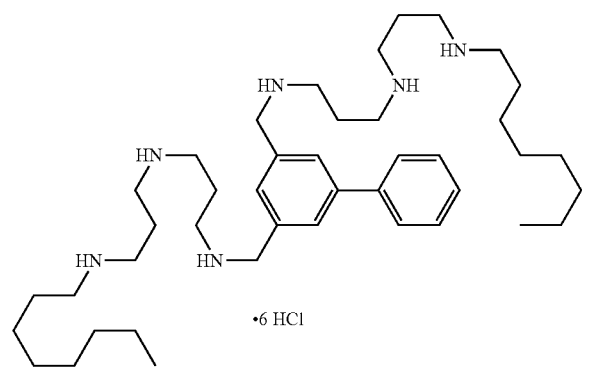 [SMILES: CCCCCCCCNCCCNCCCNCc1cc(CNCCCNCCCNCCCCCCCC)cc(-c2ccccc2)c1]

Example 72 was prepared in a similar fashion to Example 68 (CZ-86) from 5-bromoisophthaldehyde, phenylboronic acid, tert-butyl (3-((3-aminopropyl)amino)propyl)-carbamate, and octanal. ¹H NMR (500 MHz, D₂O) δ 7.88 (s, 2H), 7.75 (d, J=8.0 Hz, 2H), 7.60-7.56 (m, 3H), 7.53-7.50 (m, 1H), 4.40 (s, 4H), 3.26 (t, J=8.0 Hz, 4H), 3.21-3.16 (m, 8H), 3.14 (t, J=8.0 Hz, 4H), 3.06 (t, J=8.0 Hz, 4H), 2.21-2.09 (m, 4H), 1.69-1.65 (m, 4H), 1.38-1.28 (m, 20H), 0.86 (t, J=6.0 Hz, 4H). ¹³C NMR (125 MHz, D₂O) δ 142.5, 138.8, 132.2, 129.9, 129.5, 129.3, 128.5, 127.0, 50.8, 47.8, 44.6, 44.1, 30.9, 28.1, 28.0, 25.6, 25.4, 22.7, 22.6, 21.9, 13.3. LRMS [M+H]/2⁺ 333.3.

Example 73

Preparation of N¹,N¹'-([1,1'-biphenyl]-3,5-diylbis(methylene))bis(N³-(3-(benzylamino)propyl)propane-1,3-diamine), hydrochloride salt (CZ-94)

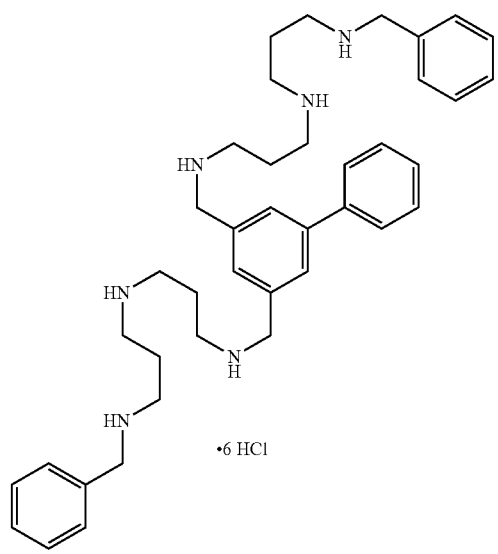 [SMILES: c1ccc(CNCCCNCCCNCc2cc(CNCCCNCCCNCc3ccccc3)cc(-c3ccccc3)c2)cc1]

Example 73 was prepared in a similar fashion to Example 68 (CZ-86) from 5-bromoisophthaldehyde, phenylboronic acid, tert-butyl (3-((3-aminopropyl)amino)propyl)-carbamate, and benzaldehyde. ¹H NMR (300 MHz, D₂O) δ 7.84 (s, 2H), 7.74-7.70 (m, 2H), 7.58-7.50 (m, 4H), 7.47 (s, 10H), 4.37 (s, 4H), 4.24 (s, 4H), 3.26-3.11 (m, 16H), 2.20-2.05 (m, 8H).

Example 74

Preparation of N¹,N¹'-([1,1'-biphenyl]-3,5-diylbis(methylene))bis(N³-(3-((cyclohexylmethyl)amino)propyl)propane-1,3-diamine), hydrochloride salt (CZ-96)

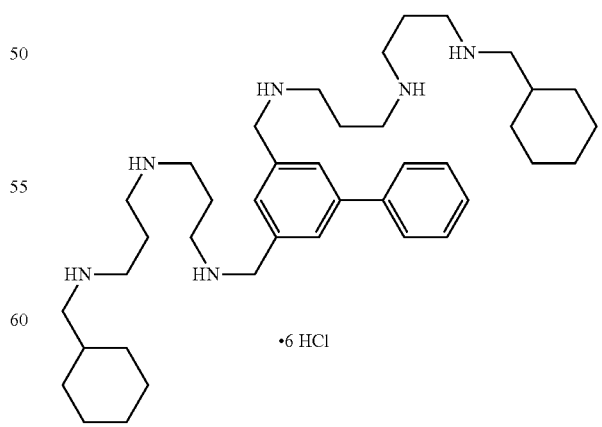

Example 74 was prepared in a similar fashion to Example 68 (CZ-86) from 5-bromoisophthaldehyde, phenylboronic acid and N¹-(3-aminopropyl)-N³-(cyclohexylmethyl)propane-1,3-diamine. ¹H NMR (500 MHz, D₂O) δ 7.87 (s, 2H), 7.75 (d, J=7.5 Hz, 2H), 7.59-7.56 (m, 3H), 7.51-7.49 (m, 1H), 4.40 (s, 4H), 3.28 (t, J=8.0 Hz, 4H), 3.24-3.18 (m, 8H), 3.15 (t, J=8.0 Hz, 4H), 2.93 (d, J=7.0 Hz, 4H), 2.24-2.12 (m, 8H), 1.74-1.60 (m, 12H), 1.30-1.14 (m, 6H), 1.05-0.98 (m, 4H). ¹³C NMR (125 MHz, D₂O) δ 142.4, 138.8, 132.1, 130.0, 129.6, 129.3, 128.5, 127.0, 53.7, 50.8, 44.7, 44.6, 44.2, 34.5, 29.7, 25.4, 24.9, 22.6, 22.5. LRMS [M+H]⁺ 633.5.

Example 75

Preparation of N¹,N¹'-((5-(1-methyl-1H-pyrazol-4-yl)-1,3-phenylene)bis(methylene))bis(N3-(3-(isobutylamino)propyl)propane-1,3-diamine), hydrochloride salt (CZ-102)

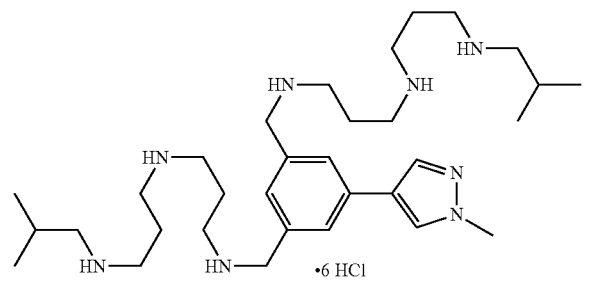 [SMILES: CC(C)CNCCCNCCCNCc1cc(CNCCCNCCCNCC(C)C)cc(-c2cnn(C)c2)c1]

Example 75 was prepared in a similar fashion to Example 68 (CZ-86) from 5-bromoisophthaldehyde, (1-methyl-1H-pyrazol-4-yl)boronic acid and tert-butyl (3-((3-aminopropyl)amino)propyl)carbamate. ¹H NMR (300 MHz, D₂O) δ 7.75-7.69 (m, 4H), 6.60 (d, J=2.1 Hz, 2H), 4.38 (s, 4H), 3.92 (s, 3H), 3.27-3.09 (m, 16H), 2.89 (d, J=7.2 Hz, 4H), 2.21-2.06 (m, 8H), 2.03-1.94 (m, 2H), 0.97 (d, J=6.9 Hz, 12H). ¹H NMR (300 MHz, D₂O) δ 7.75-7.69 (m, 4H), 6.60 (d, J=2.1 Hz, 2H), 4.38 (s, 4H), 3.92 (s, 3H), 3.27-3.09 (m, 16H), 2.89 (d, J=7.2 Hz, 4H), 2.21-2.06 (m, 8H), 2.03-1.94 (m, 2H), 0.97 (d, J=6.9 Hz, 12H).

Example 76

Preparation of N¹,N¹'-([1,1'-biphenyl]-3,5-diylbis(methylene))bis(N⁴-(3-(isobutylamino)propyl)butane-1,4-diamine), hydrochloride salt (CZ-111)

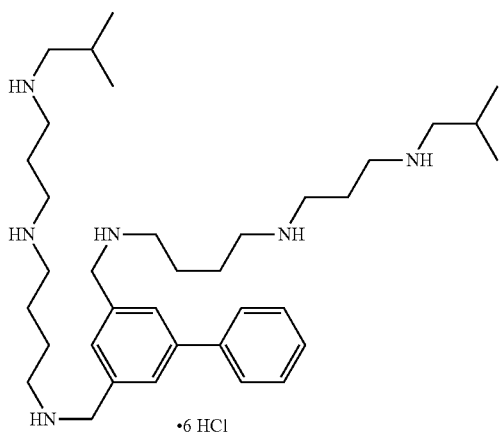 [SMILES: CC(C)CNCCCNCCCCNCc1cc(CNCCCCNCCCNCC(C)C)cc(-c2ccccc2)c1]

Example 76 was prepared in a similar fashion to Example 76 (CZ-86) from 5-bromoisophthaldehyde, phenylboronic acid and N¹-(3-aminopropyl)-N³-isobutylpropane-1,3-diamine. ¹H NMR (500 MHz, D₂O) δ 7.86 (s, 2H), 7.75 (d, J=7.5 Hz, 2H), 7.58 (t, J=8.0 Hz, 3H), 7.50 (t, J=7.5 Hz, 1H), 4.37 (s, 4H), 3.20-3.11 (m, 16H), 2.92 (d, J=7.5 Hz, 4H), 2.16-2.10 (m, 4H), 2.06-1.97 (m, 2H), 1.88-1.80 (m, 8H), 0.99 (d, J=6.5 Hz, 12H). ¹³C NMR (125 MHz, D₂O) δ 142.7, 139.1, 132.6, 130.1, 129.7, 129.5, 128.7, 127.7, 55.1, 50.9, 47.2, 46.7, 44.5, 44.7, 25.8, 23.0, 22.9, 22.7, 19.2. LRMS [M+H]⁺ 581.5.

Example 77

Preparation of N¹,N¹'-([1,1'-biphenyl]-3,5-diylbis(methylene))bis(N³-(3-(isobutylamino)propyl)-2,2-dimethylpropane-1,3-diamine), hydrochloride salt (CZ-112)

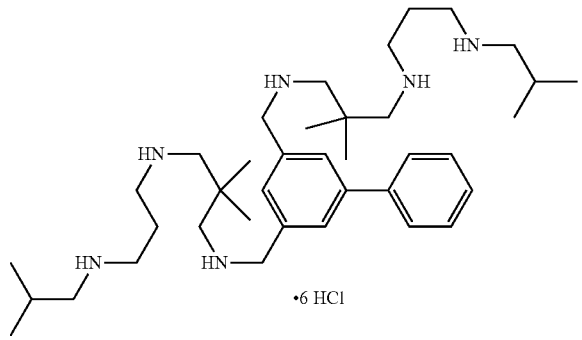 [SMILES: CC(C)CNCCCNCC(C)(C)CNCc1cc(CNCC(C)(C)CNCCCNCC(C)C)cc(-c2ccccc2)c1]

Example 77 was prepared in a similar fashion to Example 68 (CZ-86) from 5-bromoisophthaldehyde, phenylboronic acid and N¹-(3-(isobutylamino)propyl)-2,2-dimethylpropane-1,3-diamine. NMR (500 MHz, D₂O) δ 7.89 (s, 2H), 7.71 (d, J=7.5 Hz, 2H), 7.62 (s, 1H), 7.52 (t, J=7.5 Hz, 2H), 7.44 (t, J=7.5 Hz, 1H), 4.39 (s, 4H), 3.19-3.01 (m, 16H), 2.89 (d, J=7.5 Hz, 4H), 2.21-2.15 (m, 4H), 2.03-1.96 (m, 2H), 1.18 (s, 12H), 0.97 (d, J=6.5 Hz, 12H). ¹³C NMR (125 MHz, D₂O) δ 142.2, 138.8, 131.7, 131.4, 130.2, 129.5, 128.7, 127.2, 55.6, 55.1, 4.9, 52.1, 46.3, 45.0, 33.2, 25.8, 22.5, 22.4, 21.9, 19.3. LRMS [M+H]⁺ 609.5.

Example 78

Preparation of N¹,N¹'-([1,1'-biphenyl]-3,5-diylbis(methylene))bis(N³-(3-(hexylamino)propyl)propane-1,3-diamine), hydrochloride salt (CZ-114)

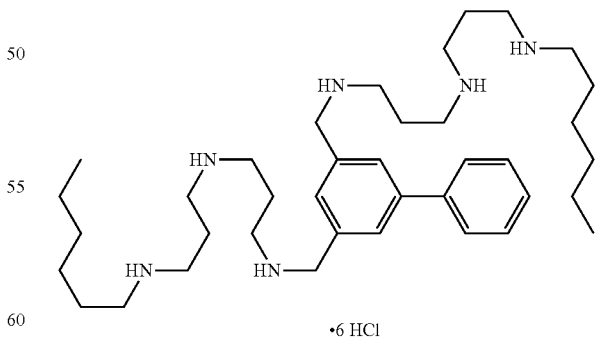

Example 78 was prepared in a similar fashion to Example 68 (CZ-86) from 5-bromoisophthaldehyde, phenylboronic acid and N¹-(3-aminopropyl)-N³-hexylpropane-1,3-diamine. ¹H NMR (500 MHz, D₂O) δ 7.83 (s, 2H), 7.71 (d, J=7.5 Hz, 2H), 7.55-7.53 (m, 3H), 7.47 (t, J=6.5 Hz, 1H), 4.34 (s, 4H), 3.25 (t, J=8 Hz, 4H), 3.19 (q, J=8 Hz, 8H), 3.13 (t, J=8 Hz, 4H), 3.04 (t, J=8.5 Hz, 4H), 2.22-2.09 (m, 8H), 1.66 (p, J=7.5 Hz, 4H), 1.36-1.31 (m, 4H), 1.28-1.27 (m, 8H), 0.85 (t, J=7 Hz, 6H). $^{13}$C NMR (125 MHz, D$_2$O) δ 142.5, 139.0, 132.3, 130.3, 129.8, 129.5, 128.7, 127.3, 51.0, 48.1, 44.9, 44.4, 44.4, 30.6, 25.6, 25.5, 22.9, 22.8, 21.9, 13.5. LRMS [M+H]$^+$ 609.5.

Example 79

Preparation of N$^1$,N$^{1'}$-([1,1'-biphenyl]-3,5-diylbis(methylene))bis(dodecane-1,12-diamine), hydrochloride salt (CZ-115)

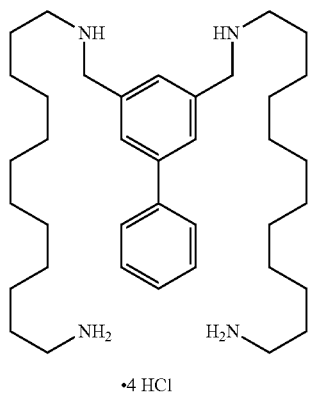 [SMILES: NCCCCCCCCCCCCNCc1cc(CNCCCCCCCCCCCCN)cc(-c2ccccc2)c1]

Example 79 was prepared in a similar fashion to Example 68 (CZ-86) from 5-bromoisophthaldehyde, phenylboronic acid and tert-butyl (12-aminododecyl)carbamate. $^1$H NMR (500 MHz, D$_2$O) δ 7.92 (s, 2H), 7.80 (d, J=8.5 Hz, 2H), 7.61-7.64 (m, 3H), 7.57-7.54 (m, 1H), 4.41 (s, 4H), 3.10 (t, J=7.5 Hz, 4H), 3.03 (t, J=7.5 Hz, 4H), 1.77-1.66 (m, 8H), 1.39-1.36 (m, 12H), 1.35-1.28 (m, 22H). $^{13}$C NMR (125 MHz, D$_2$O) δ 142.5, 139.0, 132.3, 130.3, 129.8, 129.5, 128.7, 127.3, 51.0, 48.1, 44.9, 44.4, 44.4, 30.6, 25.6, 25.5, 22.9, 22.8, 21.9, 13.5. LRMS [M+H]$^+$ 579.5.

Example 80

Preparation of N$^1$,N$^{1'}$-([1,1'-biphenyl]-3,5-diylbis(methylene))bis(N$^{12}$-isobutyldodecane-1,12-diamine), hydrochloride salt (CZ-116)

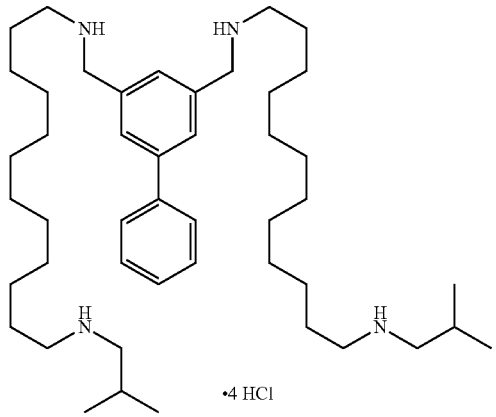 [SMILES: CC(C)CNCCCCCCCCCCCCNCc1cc(CNCCCCCCCCCCCCNCC(C)C)cc(-c2ccccc2)c1]

Example 80 was prepared in a similar fashion to Example 68 (CZ-86) from 5-bromoisophthaldehyde, phenylboronic acid and N$^1$-isobutyldodecane-1,12-diamine. $^1$H NMR (500 MHz, D$_2$O+CD$_3$OD) δ 7.90 (s, 2H), 7.76 (d, J=7.5 Hz, 2H), 7.60-7.56 (m, 3H), 7.52 (t, J=7.5 Hz, 1H), 4.38 (s, 4H), 3.04 (t, J=8.0 Hz, 4H), 3.01 (t, J=8.5 Hz, 4H), 2.88 (d, J=7.5, 4H), 2.06-1.98 (m, 2H), 1.74-1.65 (m, 8H), 1.33-1.30 (m, 12H), 1.28-1.23 (m, 20H), 1.01 (d, J=7.5, 12H). $^{13}$C NMR (125 MHz, D$_2$O+CD$_3$OD) δ 142.5, 138.8, 132.4, 130.1, 129.5, 129.3, 128.5, 127.0, 51.1, 46.6, 39.5, 28.6, 28.5, 28.4, 28.2, 28.0, 26.7, 25.6, 25.6, 25.2. LRMS [M+H]$^+$ 691.6.

Example 81

Preparation of N$^1$,N$^{1'}$,N$^{1''}$-([1,1'-biphenyl]-3,3',5-triyltris(methylene))tris(N$^{12}$-isobutyldodecane-1,12-diamine) (CZ-117)

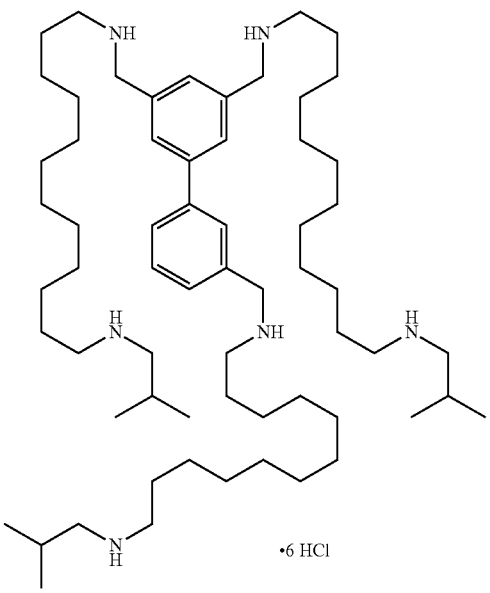 [SMILES: CC(C)CNCCCCCCCCCCCCNCc1cccc(-c2cc(CNCCCCCCCCCCCCNCC(C)C)cc(CNCCCCCCCCCCCCNCC(C)C)c2)c1]

Example 81 was prepared in a similar fashion to Example 68 (CZ-86) from 5-bromoisophthaldehyde, 3-formyl-phenylboronic acid and N$^1$-isobutyldodecane-1,12-diamine. $^1$H NMR (500 MHz, D$_2$O) δ 7.97 (s, 2H), 7.89 (d, J=8.0 Hz, 2H), 7.69-7.66 (m, 3H), 4.43 (s, 4H), 4.37 (s, 2H), 3.14-3.05 (m, 12H), 2.94 (d, J=7.0, 6H), 2.10-2.01 (m, 3H), 1.78-1.71 (m, 12H), 1.39-1.26 (m, 48H), 1.50 (d, J=6.5, 18H). 13C NMR (125 MHz, D$_2$O) δ 144.1, 142.5, 135.1, 133.4, 133.2, 133.1, 132.5, 132.1, 130.3, 130.3, 57.0, 52.9, 52.7, 50.6, 49.4, 49.3, 31.2, 31.1, 31.1, 31.0, 30.6, 28.3, 28.3, 28.2, 28.0, 27.8, 21.7. LRMS [M+H]$^+$ 960.0.

Example 82

Preparation of N¹,N¹'-([1,1'-biphenyl]-3,5-diylbis(methylene))bis(N⁴-(3-(hexylamino)propyl)butane-1,4-diamine), hydrochloride salt (CZ-118)

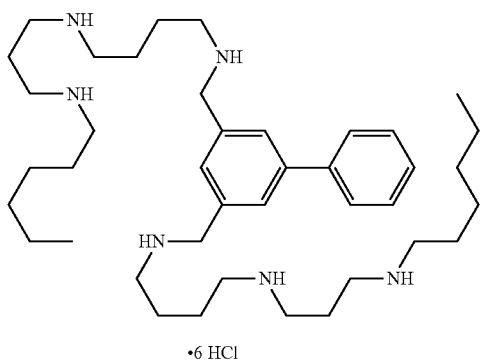 [SMILES: CCCCCCNCCCNCCCCNCc1cc(CNCCCCNCCCNCCCCCC)cc(-c2ccccc2)c1]

• 6 HCl

Example 82 was prepared in a similar fashion to Example 68 (CZ-86) from 5-bromoisophthaldehyde, phenylboronic acid and N¹-(3-aminopropyl)-N³-hexylpropane-1,3-diamine. ¹H NMR (500 MHz, D₂O) δ 7.87 (s, 2H), 7.76 (d, J=7.5 Hz, 2H), 7.58 (t, J=8.0 Hz, 3H), 7.51 (t, J=7.5 Hz, 1H), 4.37 (s, 4H), 3.21-3.14 (m, 12H), 3.07 (t, J=7.0 Hz, 4H), 2.16-2.09 (m, 4H), 1.90-1.77 (m, 10H), 1.69 (quint, J=7 Hz, 4H), 1.39-1.37 (m, 4H), 1.32-1.31 (m, 10H), 0.86 (t, J=7 Hz, 6H). ¹³C NMR (125 MHz, D₂O) δ 142.6, 139.1, 132.6, 130.2, 129.7, 129.5, 128.7, 127.3, 50.9, 48.1, 47.2, 46.7, 44.7, 44.5, 30.6, 25.6, 25.5, 23.0, 23.0, 22.8, 21.9, 13.4. LRMS [M+H]⁺ 637.6.

Example 83

Preparation of N¹,N¹'-((5-(2-ethylbutoxy)-1,3-phenylene)bis(methylene))bis(N³-(3-(isobutylammonio) propyl)propane-1,3-diaminium) chloride (CZ-91)

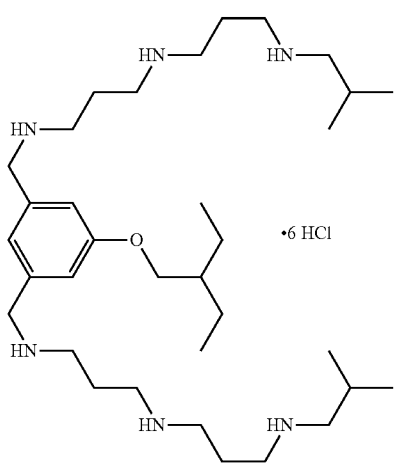 [SMILES: CCC(CC)COc1cc(CNCCCNCCCNCC(C)C)cc(CNCCCNCCCNCC(C)C)c1]

• 6 HCl

Step 1: Dimethyl 5-(2-ethylbutoxy)isophthalate

Dimethyl 5-hydroxyisophthalate (0.44 g, 2.10 mmol) cesium carbonate (1.37 g, 4.20 mmol) and CH₃CN (20 mL) were added to a round-bottom flask and stirred for 15-30 min. 3-(Bromomethyl)pentane (0.42 g, 2.52 mmol) was added and the reaction was stirred for 16 h. The solvent was removed under reduced pressure and the reaction mixture was partitioned between EtOAc (50 mL) and H₂O (50 mL). The layers were separated and the aqueous layer was extracted with EtOAc (50 mL). The combined organics were dried over Na₂SO₄, filtered, and concentrated under reduced pressure to afford the desired product which was used without further purification.

Step 2: (5-(2-Ethylbutoxy)-1,3-phenylene)dimethanol

To a solution of dimethyl 5-(2-ethylbutoxy)isophthalate (0.62 g, 2.10 mmol) in THF (20 mL) was added LiAlH₄ (0.24 g, 6.32 mmol). The reaction mixture was stirred for 8 h and subsequently quenched with 2N HCl (10 mL) and extracted with Et₂O (2×25 mL) and EtOAc (2×25 mL). The combined organics were dried over Na₂SO₄, filtered, and concentrated under reduced pressure to afford the desired product which was used without further purification.

Step 3: 5-(2-Ethylbutoxy)isophthalaldehyde (5-(2-Ethylbutoxy)-1,3-phenylene)dimethanol (0.50 g, 2.10 mmol) and CH₂Cl₂ (10 mL) were added to a round-bottom flask. To this solution was added PCC (1.35 g, 6.30 mmol), and the reaction was stirred for 16 h. The reaction mixture was concentrated under reduced pressure. Purification by column chromatography (90% hexanes/EtOAc) afforded the desired product (0.13 g, 25%, 3 steps) as a white semi-solid. ¹H NMR (500 MHz, CDCl₃) δ ppm 10.01 (s, 2H), 7.90 (s, 1H), 7.62 (s, 2H), 3.94 (d, J=5.5 Hz, 2H), 1.68 (hept, J=6.5 Hz, 1H), 1.46 (dec, J=6.5 Hz, 4H), 0.91 (t, J=7.5 Hz, 6H). ¹³C NMR (125 MHz, CDCl₃) δ ppm 191.1, 160.7, 138.5, 124.1, 120.0, 71.1, 40.9, 23.5, 11.3.

Step 4: N¹,N¹'-((5-(2-Ethylbutoxy)-1,3-phenylene) bis(methylene))bis(N³-(3-(isobutylamino)propyl) propane-1,3-diamine)

5-(2-Ethylbutoxy)isophthalaldehyde (0.20 g, 0.88 mmol) and MeOH (15 mL) were added to a round-bottom flask. To the solution was added N¹-(3-aminopropyl)-N³-isobutylpropane-1,3-diamine (0.33 g, 1.76 mmol) and the reaction mixture was stirred for 24 h. Sodium borohydride (0.13 g, 3.52 mmol) was added and the reaction mixture stirred for 1 h. The reaction mixture was concentrated under reduced pressure to afford a white solid. Aqueous NaOH (10%, 50 mL) and EtOAc (50 mL) were added and the reaction mixture stirred for 1 h. The layers were separated and the aqueous layer was extracted with EtOAc (50 mL). The organic layers were combined, dried over Na₂SO₄, filtered, and concentrated under reduced pressure to afford the desired product a clear oil.

Step 5: N¹,N¹'-((5-(2-Ethylbutoxy)-1,3-phenylene) bis(methylene))bis(N³-(3-(isobutylammonio) propyl)propane-1,3-diaminium) chloride To N¹,N¹'-((5-(2-ethylbutoxy)-1,3-phenylene)bis(methylene))bis(N³-(3-(isobutylamino)propyl) propane-1,3-diamine) from step 4 was added methanolic HCl (50 mL, 1.0 M). The reaction mixture was stirred for 1 h, the reaction mixture was concentrated under reduced pressure and the solid collected by vacuum filtration. The solid was washed with Et$_2$O (10 mL) and hot MeOH (10 mL) to afford the desired product (0.42 g, 59%) as a white solid. $^1$H NMR (500 MHz, D$_2$O) δ 7.20 (s, 2H), 7.18 (s, 1H), 4.29 (s, 4H), 4.05 (d, J=6.0 Hz, 2H), 3.25-3.15 (m, 16H), 2.94 (d, J=7.0 Hz, 2H), 2.21-2.12 (m, 8H), 2.07-1.99 (m, 2H), 1.72 (p, J=6.5 Hz, 1H), 1.50-1.43 (m, 4H), 1.00 (d, J=7.0 Hz, 12H), 0.92 (t, J=6.0 Hz, 6H). $^{13}$C NMR (125 MHz, D$_2$O) δ 159.6, 132.9, 123.4, 117.4, 71.4, 54.8, 50.8, 44.7, 44.6, 44.6, 44.1, 40.1, 25.5, 22.6, 22.5, 19.0, 10.2. LRMS [M+H]$^+$ 577.6.

Example 84

Preparation of N$^1$,N$^{1'}$-((5-isopropoxy-1,3-phenylene)bis(methylene))bis(N$^3$-(3-aminopropyl)propane-1,3-diamine), hydrochloride salt (CZ-93)

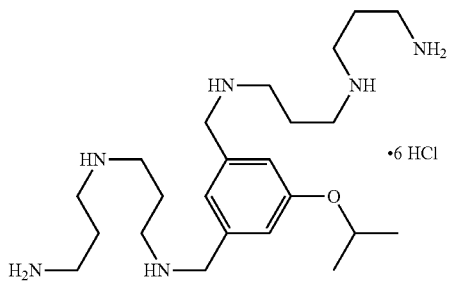 [SMILES: CC(C)Oc1cc(CNCCCNCCCN)cc(CNCCCNCCCN)c1]

Example 84 was prepared in a similar fashion to Example 83 (CZ-91) from 5-isopropoxyisophthalaldehyde and tert-butyl (3-((3-aminopropyl)amino)propyl)carbamate. $^1$H NMR (300 MHz, D$_2$O) δ 7.13 (s, 3H), 4.78-4.72 (m, 1H), 4.23 (s, 4H), 3.27-3.18 (m, 12H), 3.13 (t, J=7.8 Hz, 4H), 2.23-2.18 (m, 4H), 2.18-2.10 (m, 4H), 1.36 (d, J=10.2 Hz, 6H).

Example 85

Preparation of N$^1$,N$^{1'}$-((5-(cyclohexylmethoxy)-1,3-phenylene)bis(methylene))bis(N$^3$-(3-(octylamino)propyl)propane-1,3-diamine), hydrochloride salt (CZ-103)

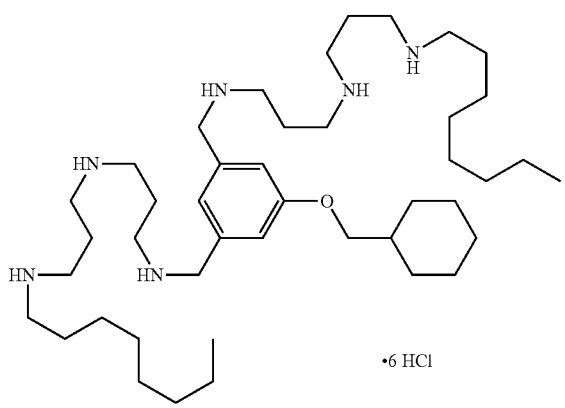 [SMILES: CCCCCCCCNCCCNCCCNCc1cc(CNCCCNCCCNCCCCCCCC)cc(OCC2CCCCC2)c1]

Example 85 was prepared in a similar fashion to Example 83 (CZ-91) from dimethyl 5-butoxyisophthalate, (bromomethyl)cyclohexane, tert-butyl (3-((3-aminopropyl)amino)propyl)carbamate and octanal. $^1$H NMR (500 MHz, D$_2$O) δ 7.18 (s, 3H), 4.28 (s, 4H), 3.95 (s, 2H) 3.20-3.14 (m, 16H), 3.06 (t, J=7.5 Hz, 4H), 2.22-2.10 (m, 8H), 1.88-1.80 (m, 3H), 1.76-1.64 (m, 8H), 1.41-1.20 (m, 22H), 1.12-1.03 (m, 2H), 0.89-0.83 (m, 6H). $^{13}$C NMR (125 MHz, D$_2$O) δ 159.5, 133.0, 123.4, 117.3, 74.4, 50.8, 47.8, 44.6, 44.6, 44.2, 44.1, 36.8, 30.9, 29.1, 28.1, 28.0, 25.9, 25.6, 25.4, 25.2, 22.6, 22.6, 21.9, 13.3. LRMS [M+H]$^+$ 701.7.

Example 86

Preparation of N$^1$,N$^{1'}$-((5-(cyclohexyloxy)-1,3-phenylene)bis(methylene))bis(N$^3$-(3-(isobutylamino)propyl)propane-1,3-diamine), hydrochloride salt (CZ-104)

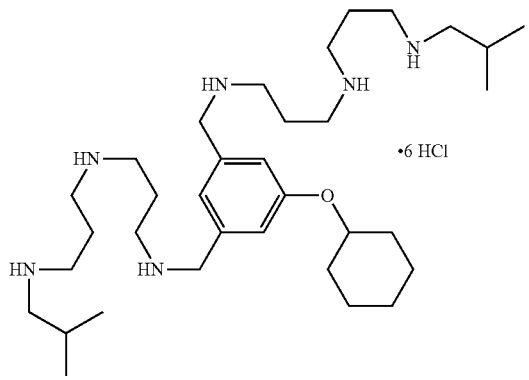 [SMILES: CC(C)CNCCCNCCCNCc1cc(CNCCCNCCCNCC(C)C)cc(OC2CCCCC2)c1]

Example 86 was prepared in a similar fashion to Example 83 (CZ-91) from 5-(cyclohexyloxy)isophthalaldehyde and N$^1$-(3-aminopropyl)-N$^3$-isobutylpropane-1,3-diamine. $^1$H NMR (300 MHz, D$_2$O) δ 7.60 (s, 2H), 7.53 (s, 1H), 4.73 (t, J=1.2 Hz, 1H), 4.42 (s, 4H), 3.26-3.13 (m, 16H), 2.84 (d, J=6.9 Hz, 2H), 2.23-2.08 (m, 8H), 2.06-1.96 (m, 2H), 1.87-1.78 (m, 4H), 1.65-1.36 (m, 6H), 0.99 (d, J=6.6 Hz, 12H). LRMS [M+H]$^+$ 575.5.

Example 87

Preparation of N$^1$,N$^{1'}$-((5-(cyclohexyloxy)-1,3-phenylene)bis(methylene))bis(N$^3$-(3-aminopropyl)propane-1,3-diamine, hydrochloride salt (CZ-105)

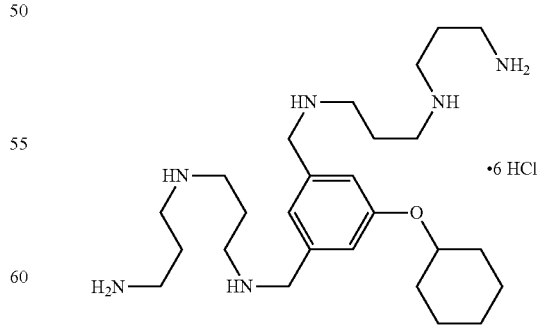

Example 87 was prepared in a similar fashion to Example 83 (CZ-91) from 5-(cyclohexyloxy)isophthalaldehyde and tert-butyl (3-((3-aminopropyl)amino)propyl)-carbamate. $^1$H NMR (300 MHz, D$_2$O) δ 7.22 (s, 2H), 7.18 (s, 1H), 4.68 (t, J=1.2 Hz, 1H), 4.30 (s, 4H), 3.28-3.18 (m, 12H), 3.14 (t, J=7.8 Hz, 4H), 2.21-2.06 (m, 8H), 1.84-1.75 (m, 4H), 1.63-1.34 (m, 6H). LRMS [M+H]$^+$ 463.5.

Example 88

Preparation of N$^1$,N$^{1'}$-((5-(benzyloxy)-1,3-phenylene)bis(methylene))bis(N$^3$-(3-(isobutylamino)propyl)propane-1,3-diamine), hydrochloride salt (CZ-106)

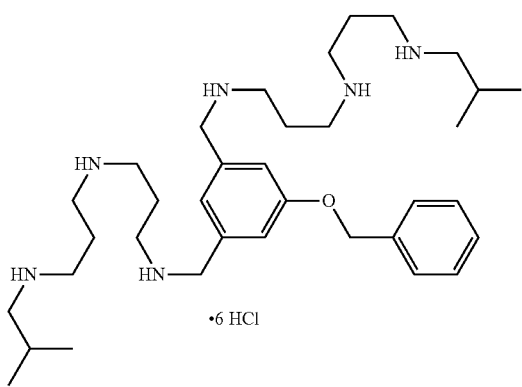 [SMILES: CC(C)CNCCCNCCCNCc1cc(CNCCCNCCCNCC(C)C)cc(OCc2ccccc2)c1]

Example 88 was prepared in a similar fashion to Example 83 (CZ-91) from dimethyl 5-butoxyisophthalate, benzyl bromide, tert-butyl (3-((3-aminopropyl)amino)-propyl)carbamate and isobutyraldehyde.

Example 89

Preparation of N$^1$,N$^{1'}$-(1,3-phenylenebis(methylene))bis(N$^3$-(3-((cyclohexylmethyl)-amino)propyl)propane-1,3-diamine), hydrochloride salt (CZ-97)

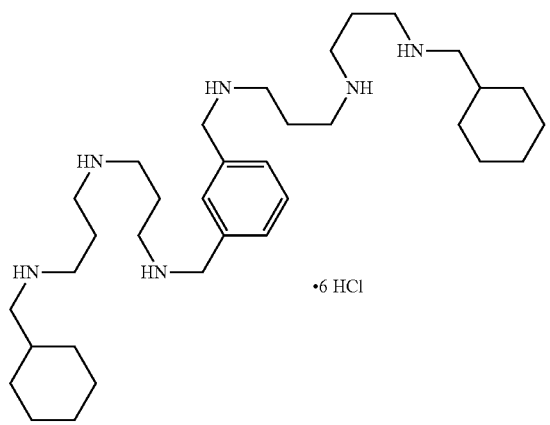 [SMILES: c1cc(CNCCCNCCCNCC2CCCCC2)cc(CNCCCNCCCNCC2CCCCC2)c1]

Step 1: N$^1$,N$^{1'}$-(1,3-Phenylenebis(methylene))bis(N$^3$-(3-((cyclohexylmethyl)-amino)propyl)propane-1,3-diamine)

Isophthalaldehyde (0.34 g, 2.57 mmol, 1) and MeOH (20 mL) were added to a round-bottom flask. To the solution was added N$^1$-(3-aminopropyl)-N$^3$-(cyclohexylmethyl)propane-1,3-diaminediamine (1.17 g, 5.14 mmol, 2) and the reaction mixture was stirred at rt for 24 h. Sodium borohydride (0.39 g, 10.28 mmol, 4) was added and the reaction mixture stirred for 1 h. The reaction mixture was concentrated under reduced pressure to afford a white solid. Aqueous NaOH (10%, 100 mL) and EtOAc (100 mL) were added and the reaction mixture stirred for 1 h. The layers were separated and the aqueous layer was extracted with EtOAc (100 mL). The organic layers were combined, dried over Na$_2$SO$_4$, filtered, and concentrated under reduced pressure to afford a clear oil which was used without further purification.

Step 2: N$^1$,N$^{1'}$-(1,3-phenylenebis(methylene))bis(N$^3$-(3-((cyclohexylmethyl)amino)-propyl)propane-1,3-diamine) hydrochloride salt To the crude N$^1$,N$^{1'}$-(1,3-phenylenebis-(methylene))bis(N$^3$-(3-((cyclohexylmethyl)amino)propyl)propane-1,3-diamine) from Step 1 was added methanolic HCl (100 mL, 1.0 M). The reaction mixture stirred at rt for 2 h. The reaction mixture was concentrated under reduced pressure and the solid was collected by vacuum filtration and washed with Et$_2$O (50 mL) and hot MeOH (50 mL) to afford the desire product (1.3 g, 67%) as a white solid. $^1$H NMR (500 MHz, D$_2$O) δ 7.57 (s, 4H), 4.30 (s, 4H), 3.22 (t, J=7.5 Hz, 4H), 3.18-3.15 (m, 8H), 3.12 (t, J=8.0 Hz, 4H), 2.91 (d, J=7.0 Hz, 4H), 2.18-2.08 (m, 8H), 1.72-1.62 (m, 12H), 1.28-1.11 (m, 6H), 1.03-0.96 (m, 4H). $^{13}$C NMR (125 MHz, D$_2$O) δ 131.4, 131.2, 131.0, 130.2, 53.7, 50.8, 48.8, 44.7, 44.6, 44.0, 34.5, 29.7, 25.3, 24.8, 22.6, 22.5. LRMS [M+H]$^+$ 557.5.

Example 90

Preparation of N$^1$,N$^{1'}$-(1,3-phenylenebis(methylene))bis(N$^3$-(3-(octylamino)propyl)propane-1,3-diamine), hydrochloride salt (CZ-100)

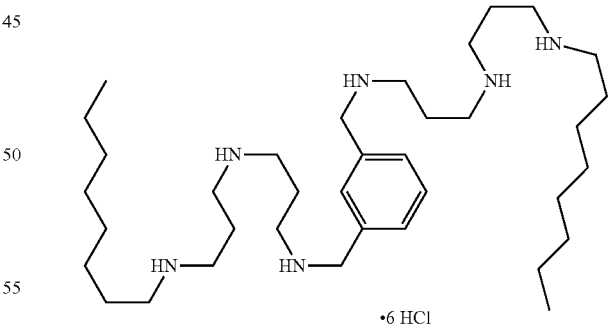

Example 90 was prepared in a similar fashion to Example 62 (CZ-76) from isophthaldehyde, tert-butyl (3-((3-aminopropyl)amino)propyl)carbamate and octanal. $^1$H NMR (500 MHz, D$_2$O) δ 7.58 (s, 4H), 4.32 (s, 4H), 3.10-2.98 (m, 16H), 2.91 (t, J=8.0 Hz, 4H), 2.05-1.95 (m, 8H), 1.53 (p, J=7 Hz, 4H), 1.24-1.13 (m, 20H), 0.71 (t, J=7.0 Hz, 6H). $^{13}$C NMR (125 MHz, D$_2$O) δ 131.4, 131.2, 131.1, 130.2, 50.8, 47.9, 44.6, 44.6, 44.2, 44.1, 30.9, 28.1, 28.1, 25.6, 25.4, 22.6, 21.9, 13.3. LRMS [M+H]$^+$ 589.5.

Example 91

Preparation of N¹,N¹'-(1,3-phenylenebis(methylene))bis(N³-(3-(isobutylamino)propyl)propane-1,3-diamine), hydrochloride salt (CZ-108)

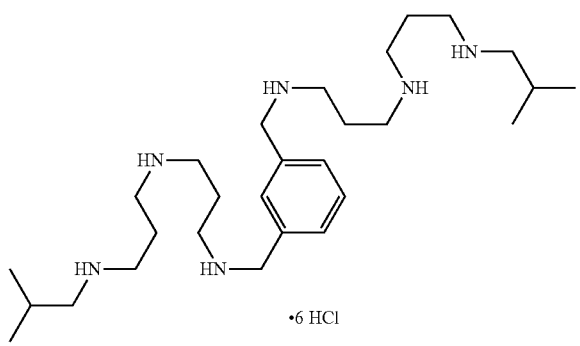 [SMILES: CC(C)CNCCCNCCCNCc1cccc(CNCCCNCCCNCC(C)C)c1]

Example 91 was prepared in a similar fashion to Example 89 (CZ-97) from isophthaldehyde and N¹-(3-aminopropyl)-N³-isobutylpropane-1,3-diamine. $^1$H NMR (300 MHz, D$_2$O) δ 7.54 (s, 4H), 4.28 (s, 4H), 3.19-3.08 (m, 16H), 2.88 (d, J=7.5 Hz, 4H), 2.15-2.05 (m, 8H), 2.02-1.90 (m, 2H), 0.95 (d, J=6.9 Hz, 12H). LRMS [M+H]$^+$ 477.4.

Example 92

Preparation of N¹,N¹'-((5-bromo-1,3-phenylene)bis(methylene))bis(N³-(3-(isobutylamino)propyl)propane-1,3-diamine), hydrochloride salt (CZ-109)

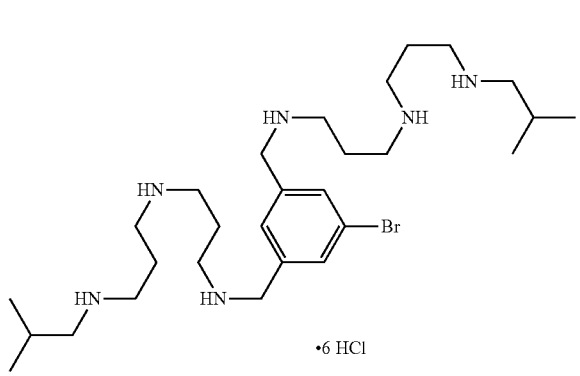

Example 92 was prepared in a similar fashion to Example 89 (CZ-97) from 4-bromo-isophthaldehyde and N¹-(3-aminopropyl)-N³-isobutylpropane-1,3-diamine. $^1$H NMR (300 MHz, D$_2$O) δ 7.76 (s, 2H), 7.51 (s, 1H), 4.27 (s, 4H), 3.21-3.08 (m, 16H), 2.88 (d, J=7.5 Hz, 4H), 2.16-2.06 (m, 8H), 2.02-1.93 (m, 2H), 0.96 (d, J=6.6 Hz, 12H). LRMS [M+H]$^+$ 555.4, 557.4.

Example 93

Preparation of N¹,N¹'-(1,3-phenylenebis(methylene))bis(N³-(3-(hexylamino)propyl)propane-1,3-diamine), hydrochloride salt (CZ-113)

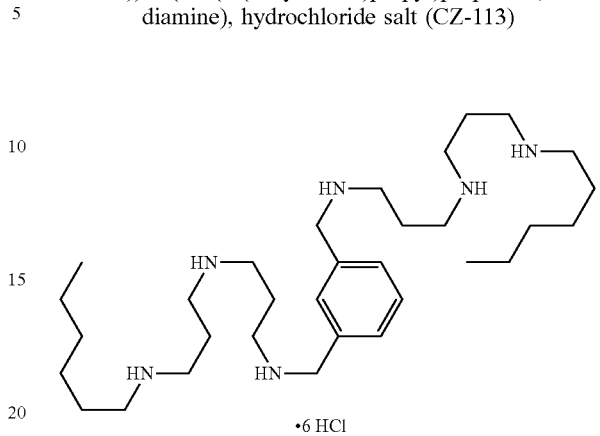

Example 93 was prepared in a similar fashion to Example 89 (CZ-97) from isophthaldehyde and N¹-(3-aminopropyl)-N³-hexylpropane-1,3-diamine. $^1$H NMR (500 MHz, D$_2$O) δ 7.58 (s, 3H), 4.32 (s, 4H), 3.24-3.13 (m, 16H), 3.05 (t, J=8.0 Hz, 4H), 2.20-2.09 (m, 8H), 1.68-1.63 (m, 4H), 1.38-1.33 (m, 4H), 1.32-1.26 (m, 8H), 0.85 (t, J=7.5 Hz, 6H). $^{13}$C NMR (125 MHz, D$_2$O) δ 131.6, 131.5, 131.4, 130.4, 51.1, 48.1, 44.9, 44.8, 44.5, 44.3, 30.6, 25.6, 25.5, 22.8, 21.9, 13.5. LRMS [M+H]$^+$ 533.6.

Example 94

Preparation of N¹,N¹'-(1,3-phenylenebis(methylene))bis(N⁴-(3-(hexylamino)propyl)butane-1,4-diamine), hydrochloride salt (CZ-119)

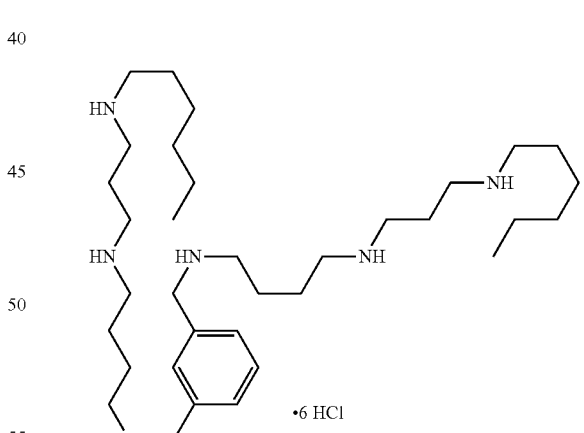

Example 94 was prepared in a similar fashion to Example 89 (CZ-97) from isophthaldehyde and N¹-(3-aminopropyl)-N⁴-hexylbutane-1,4-diamine. $^1$H NMR (500 MHz, D$_2$O) δ 7.65 (s, 4H), 4.37 (s, 4H), 3.26-3.19 (m, 16H), 3.14 (t, J=7.5 Hz, 4H), 2.20 (quint, J=8.0 Hz, 4H), 1.88 (br s, 8H), 1.75 (quint, J=8.0 Hz, 4H), 1.46-1.42 (m, 4H), 1.39-1.36 (m, 8H), 0.94 (t, J=6.5 Hz, 6H). $^{13}$C NMR (125 MHz, D$_2$O) δ 134.2, 133.7, 133.5, 132.7, 53.3, 50.4, 49.6, 49.1, 47.1, 46.8, 32.9, 27.9, 27.8, 25.4, 25.3, 25.2, 24.2, 15.8. LRMS [M+H]$^+$ 561.5.

Example 95

Preparation of N¹,N¹',N¹''-([1,1'-biphenyl]-3,3',5-triyltris(methylene))tris(N³-(3-(isobutylamino)propyl)propane-1,3-diamine), hydrochloride salt (CZ-99)

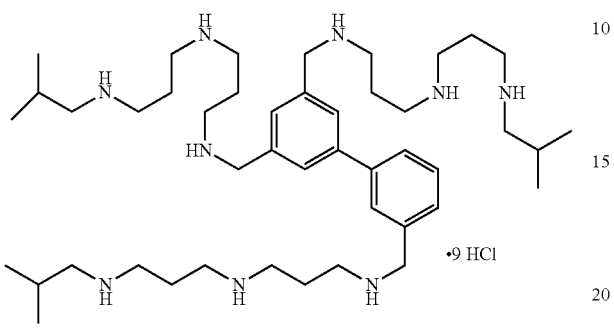

Step 1: [1,1'-Biphenyl]-3,3',5-tricarbaldehyde

A solution of 5-bromoisophthaldehyde (2.13 g, 10.0 mmol), 3-formylphenylboronic acid (1.49 g, 10.0 mmol) and potassium carbonate (2.76 g, 20.0 mmol) in DME/H$_2$O (5:1 50 mL) was purged with N$_2$ for 5 min. Tetrakispalladium triphenylphosphine (0.12 g, 0.1 mmol) was added and the reaction mixture was heated to 90° C. and stirred for 16 h. The reaction mixture was cooled, filtered through a pad of Celite diatomaceous earth and the solvent evaporated under reduced pressure. Purification by column chromatography (10% EtOAc/hexanes) afforded the desired product (1.47 g, 62%) as a tan solid. $^1$H NMR (300 MHz, CDCl$_3$) δ ppm 10.20 (s, 2H), 10.10 (s, 1H), 8.42 (s, 3H), 8.21 (s, 1H), 7.98 (t, J=5.4 Hz, 2H), 7.72 (t, J=5.4 Hz, 2H).

Step 2: N¹,N¹',N¹''-([1,1'-Biphenyl]-3,3',5-triyltris(methylene))tris(N³-(3-(isobutylamino)propyl)propane-1,3-diamine)

[1,1'-biphenyl]-3,3',5-tricarbaldehyde (0.24 g, 1.0 mmol) and MeOH (20 mL) were added to a round-bottom flask. To the solution was added N¹-(3-aminopropyl)-N³-isobutylpropane-1,3-diamine (570 mg, 3.0 mmol, 3 equiv.) and the reaction mixture was stirred at rt for 24 h. Sodium borohydride (0.34 g, 9.0 mmol) was added and the reaction mixture stirred for 1 h. The reaction mixture was concentrated under reduced pressure to afford a white solid. Aqueous NaOH (10%, 100 mL) and EtOAc (100 mL) were added and the reaction mixture stirred for 1 h. The layers were separated and the aqueous layer was extracted with EtOAc (100 mL). The organic layers were combined, dried over Na$_2$SO$_4$, filtered, and concentrated under reduced pressure to afford a clear oil which was used without further purification.

Step 3: N¹,N¹',N¹''-([1,1'-Biphenyl]-3,3',5-triyltris(methylene))tris(N³-(3-(isobutylamino)propyl)propane-1,3-diamine), hydrochloride salt N¹,N¹',N¹''-([1,1'-biphenyl]-3,3',5-triyltris(methylene))tris(N³-(3-(isobutylamino)propyl)propane-1,3-diamine) from step 2 was subjected to acidification with methanolic HCl (100 mL, 1.0M). The reaction mixture stirred at rt for 2 h. The reaction mixture was concentrated under reduced pressure and the solid was collected by vacuum filtration and washed with Et$_2$O (50 mL) and hot MeOH (50 mL) to afford the desired product (0.58 g, 52%) as a white solid. $^1$H NMR (500 MHz, D$_2$O) δ ppm 7.91 (s, 1H), 7.85-7.82 (m, 3H), 7.65-7.56 (m, 3H), 4.42 (s, 4H), 4.39 (s, 2H), 3.29-3.16 (m, 24H), 2.93 (d, J=6.0 Hz, 6H), 2.20-2.13 (m, 12H), 2.07-2.00 (m, 3H), 0.99 (d, J=6.0 Hz, 18H). $^{13}$CNMR (125 MHz, D$_2$O) δ ppm 141.6, 139.8, 132.2, 131.3, 130.4, 130.3, 129.7, 129.5, 128.6, 128.4, 54.8, 54.8, 51.1, 50.8, 44.7, 44.6, 44.2, 44.0, 25.5, 22.7, 22.5, 19.0. LRMS [M+2H+]$^{2+}$ 376.8.

Example 96

Preparation of N¹,N¹'-((5-(3-(isoButylammonio)propoxy)-1,3-phenylene)bis(methylene))-bis(N³-(3-ammoniopropyl)propane-1,3-diaminium) chloride (CZ-107)

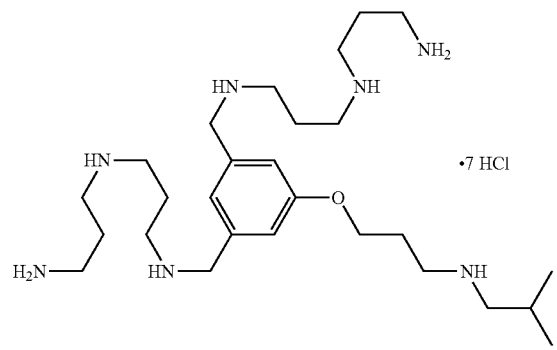 [SMILES: CC(C)CNCCCOc1cc(CNCCCNCCCN)cc(CNCCCNCCCN)c1]

Step 1: tert-Butyl (3-hydroxypropyl)(isobutyl)carbamate 3-(iso-Butylamino)propan-1-ol (7.92 g, 60.5 mmol) and THF (100 mL) were added to a round-bottom flask. To the solution was added aqueous NaOH (10%, 100 mL) followed by the slow addition of di-tert-butyl dicarbonate (11.86 g, 54.4 mmol). The reaction mixture was stirred for 12 h. The reaction mixture was extracted with CH$_2$Cl$_2$ (3×100 mL). The combined organics were dried over Na$_2$SO$_4$, filtered, and concentrated under reduced pressure to afford the desired product (12.0 g, 86%) which was used without further purification.

Step 2: 3-((tert-Butoxycarbonyl)(isobutyl)amino)propyl methanesulfonate tert-Butyl (3-hydroxypropyl)(isobutyl)carbamate (0.73 g, 3.15), triethylamine (0.64 g, 6.30 mmol) and CH$_2$Cl$_2$ (30 mL) were added to a round-bottom flask. To the solution was added methanesulfonyl chloride (0.54 g, 4.72 mmol) and the reaction mixture was stirred for 5 h. The reaction mixture was concentrated under reduced pressure and purified by column chromatography (hexanes/EtOAC) to afford the desired product (0.63 g, 64%) as a yellow oil.

Step 3: Dimethyl 5-(3-((tert-butoxycarbonyl)(isobutyl)amino)propoxy)isophthalate Dimethyl 5-hydroxyisophthalate (0.30 g, 1.44 mmol) cesium carbonate (0.95 g, 2.88 mmol) and CH$_3$CN (25 mL)

were stirred for 30 min. 3-((tert-Butoxycarbonyl)(isobutyl) amino)-propyl methanesulfonate (0.63 g, 2.02 mmol) was added and the reaction mixture was stirred for 16 h. The reaction mixture was concentrated under reduced pressure and partitioned between EtOAc (50 mL) and H$_2$O (50 mL). The layers were separated and the aqueous layer was extracted with EtOAc (50 mL). The combined organics were dried over Na$_2$SO$_4$, filtered, and concentrated under reduced pressure to afford the desired product, which was used without further purification.

Step 4: tert-Butyl (3-(3,5-bis(hydroxymethyl)phenoxy)propyl)(isobutyl)carbamate

To a solution of dimethyl 5-(3-((tert-butoxycarbonyl) (isobutyl)amino)propoxy)isophthalate (0.60 g, 1.44 mmol) in THF (10 mL) was added LiAlH$_4$ (0.30 g, 7.89 mmol). The reaction mixture was stirred for 8 h and subsequently quenched with 2N HCl (10 mL) and extracted with Et$_2$O (2×25 mL) and EtOAc (2×25 mL). The combined organic layers were dried over Na$_2$SO$_4$, filtered, and concentrated under reduced pressure to afford the desired product (0.28 g, 54%) as an oil, which was used without further purification.

Step 5: tert-Butyl (3-(3,5-diformylphenoxy)propyl)(isobutyl)carbamate tert-Butyl (3-(3,5-bis(hydroxymethyl)phenoxy)propyl) (isobutyl)carbamate (0.29 g, 0.78 mmol) and CH$_2$Cl$_2$ (20 mL) were added to a round-bottom flask. To the solution was added PCC (0.42 g, 1.94 mmol) and the reaction was stirred for 16 h. The reaction mixture was concentrated under reduced pressure. Purification by column chromatography (90% Hexanes/EtOAc) afforded the desired product (0.15 g, 20% 3 steps) as a white semi-solid, which was used without further purification.

Step 6: N$^1$,N$^{1'}$-((5-(3-(iso-Butylamino)propoxy)-1,3-phenylene)bis(methylene))-bis(N$^3$-(3-aminopropyl) propane-1,3-diamine)

tert-Butyl (3-(3,5-diformylphenoxy)propyl)-(isobutyl) carbamate (0.15 g, 0.42 mmol) and MeOH (10 mL) were added to a round-bottom flask. To the solution was added tert-butyl (3-((3-aminopropyl)amino)propyl)carbamate (0.20 g, 0.84 mmol) and the reaction mixture was stirred for 24 h. Sodium borohydride (0.06 g, 1.69 mmol) was added and the reaction mixture stirred for 1 h. The reaction mixture was concentrated under reduced pressure to afford a white solid. Aqueous NaOH (10%, 50 mL) and EtOAc (50 mL) were added, the layers separated and the aqueous layer was extracted with EtOAc (50 mL). The organic layers were combined, dried over Na$_2$SO$_4$, filtered, and concentrated under reduced pressure to afford the desired product as clear oil which was used without further purification.

Step 7: N$^1$,N$^{1'}$-((5-(3-(iso-Butylammonio)propoxy)-1,3-phenylene)bis(methylene))-bis(N$^3$-(3-ammoniopropyl)propane-1,3-diaminium) chloride To N$^1$,N$^{1'}$-((5-(3-(iso-butylamino)propoxy)-1,3-phenylene)bis(methylene))bis(N$^3$-(3-aminopropyl)propane-1,3-diamine) from step 6 was added methanolic HCl (50 mL, 1.0 M). The reaction mixture was stirred for 1 h, the reaction mixture was concentrated under reduced pressure and the solid collected by vacuum filtration. The solid was washed with Et$_2$O (10 mL) and hot MeOH (10 mL) to afford the desired product (0.14 g, 43%) as a white solid. $^1$H NMR (500 MHz, D$_2$O) δ ppm 7.21 (s, 1H), 7.19 (s, 2H), 4.30 (s, 4H), 4.23 (t, J=5.5 Hz, 2H), 3.29 (t, J=7 Hz, 2H), 3.25-3.19 (m, 12H), 3.12 (t, J=7.5 Hz, 4H), 2.95 (d, J=7 Hz, 2H), 2.25-2.03 (m, 11H), 1.01 (d, J=7.5 Hz, 6H). $^{13}$C NMR (125 MHz, D$_2$O) 158.9, 133.0, 123.7, 117.1, 65.8, 54.8, 50.7, 45.7, 44.7, 44.6, 44.2, 36.7, 25.5, 25.2, 23.7, 22.6, 19.1. LRMS [M+H]$^+$ 494.4.

Example 97

Preparation of N$^1$,N$^{1'}$-((5-(3-(isobutylamino) propoxy)-1,3-phenylene)bis(methylene))bis(N$^3$-(3-(octylamino)propyl)propane-1,3-diamine), hydrochloride salt (CZ-110)

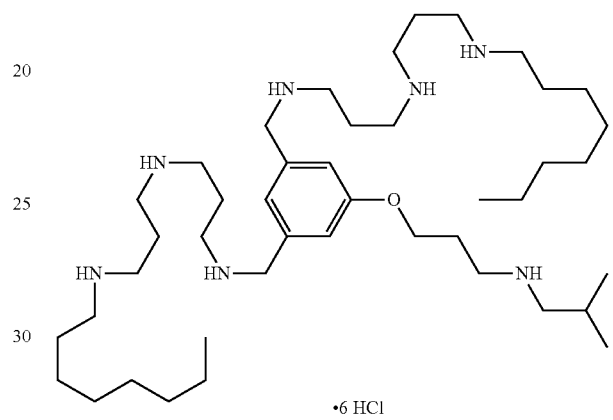

·6 HCl

Step 1: tert-Butyl (3-hydroxypropyl)(isobutyl)carbamate 3-(iso-Butylamino)propan-1-ol (7.92 g, 60.5 mmol) and THF (100 mL) were added to a round-bottom flask. To the solution was added aqueous NaOH (10%, 100 mL) followed by the slow addition of di-tert-butyl dicarbonate (11.86 g, 54.4 mmol). The reaction mixture was stirred for 12 h. The reaction mixture was extracted with CH$_2$Cl$_2$ (3×100 mL). The combined organics were dried over Na$_2$SO$_4$, filtered, and concentrated under reduced pressure to afford the desired product (12.0 g, 86%), which was used without further purification.

Step 2: 3-((tert-Butoxycarbonyl)(isobutyl)amino)propyl methanesulfonate tert-Butyl (3-hydroxypropyl)(isobutyl)carbamate (0.73 g, 3.15), triethylamine (0.64 g, 6.30 mmol) and CH$_2$Cl$_2$ (30 mL) were added to a round-bottom flask. To the solution was added methanesulfonyl chloride (0.54 g, 4.72 mmol) and the reaction mixture was stirred for 5 h. The reaction mixture was concentrated under reduced pressure and purified by column chromatography (hexanes/EtOAC) to afford the desired product (0.63 g, 64%) as a yellow oil.

Step 3: Dimethyl 5-(3-((tert-butoxycarbonyl) (isobutyl)amino)propoxy)isophthalate Dimethyl 5-hydroxyisophthalate (0.30 g, 1.44 mmol) cesium carbonate (0.95 g, 2.88 mmol) and CH$_3$CN (25 mL)

were stirred for 30 min. 3-((tert-Butoxycarbonyl)(isobutyl) amino)-propyl methanesulfonate (0.63 g, 2.02 mmol) was added, and the reaction mixture was stirred for 16 h. The reaction mixture was concentrated under reduced pressure and partitioned between EtOAc (50 mL) and H$_2$O (50 mL). The layers were separated, and the aqueous layer was extracted with EtOAc (50 mL). The combined organics were dried over Na$_2$SO$_4$, filtered, and concentrated under reduced pressure to afford the desired product, which was used without further purification.

Step 4: tert-Butyl (3-(3,5-bis(hydroxymethyl)phenoxy)propyl)(isobutyl)carbamate To a solution of dimethyl 5-(3-((tert-butoxycarbonyl) (isobutyl)amino)propoxy)isophthalate (0.60 g, 1.44 mmol) in THF (10 mL) was added LiAlH$_4$ (0.30 g, 7.89 mmol). The reaction mixture was stirred for 8 h and subsequently quenched with 2N HCl (10 mL) and extracted with Et$_2$O (2×25 mL) and EtOAc (2×25 mL). The combined organic layers were dried over Na$_2$SO$_4$, filtered, and concentrated under reduced pressure to afford the desired product (0.28 g, 54%) as an oil, which was used without further purification.

Step 5: tert-Butyl (3-(3,5-diformylphenoxy)propyl)(isobutyl)carbamate tert-Butyl (3-(3,5-bis(hydroxymethyl)phenoxy)propyl) (isobutyl)carbamate (0.29 g, 0.78 mmol) and CH$_2$Cl$_2$ (20 mL) were added to a round-bottom flask. To the solution was added PCC (0.42 g, 1.94 mmol) and the reaction was stirred for 16 h. The reaction mixture was concentrated under reduced pressure. Purification by column chromatography (90% hexanes/EtOAc) afforded the desired product (0.15 g, 20% 3 steps) as a white semi-solid which was used without further purification.

Step 6: N$^1$,N$^{1'}$-((5-(3-(iso-Butylamino)propoxy)-1,3-phenylene)bis(methylene))-bis(N$^3$-(3-aminopropyl) propane-1,3-diamine)

tert-Butyl (3-(3,5-diformylphenoxy)propyl)-(isobutyl) carbamate (0.15 g, 0.42 mmol) and MeOH (10 mL) were added to a round-bottom flask. To the solution was added tert-butyl (3-((3-aminopropyl)amino)propyl)carbamate (0.20 g, 0.84 mmol), and the reaction mixture was stirred for 24 h. Sodium borohydride (0.06 g, 1.69 mmol) was added and the reaction mixture stirred for 1 h. The reaction mixture was concentrated under reduced pressure to afford a white solid. Aqueous NaOH (10%, 50 mL) and EtOAc (50 mL) were added, the layers separated, and the aqueous layer was extracted with EtOAc (50 mL). The organic layers were combined, dried over Na$_2$SO$_4$, filtered, and concentrated under reduced pressure to afford the desired product as a clear oil, which was used without further purification.

Step 7: N$^1$,N$^{1'}$-((5-(3-(iso-Butylammonio)propoxy)-1,3-phenylene)bis(methylene))bis(N$^3$-(3-ammoniopropyl)propane-1,3-diaminium) chloride To N$^1$,N$^{1'}$-((5-(3-(iso-Butylamino)propoxy)-1,3-phenylene)bis(methylene))bis(N$^3$-(3-aminopropyl)propane-1, 3-diamine) from step 6 was added methanolic HCl (50 mL, 1.0M). The reaction mixture was stirred for 1 h, the reaction mixture was concentrated under reduced pressure and the solid collected by vacuum filtration. The solid was washed with Et$_2$O (10 mL) and hot MeOH (10 mL) to afford the desired product (0.14 g, 43%) as a white solid. $^1$H NMR (500 MHz, D$_2$O) δ ppm 7.21 (s, 1H), 7.19 (s, 2H), 4.30 (s, 4H), 4.23 (t, J=5.5 Hz, 2H), 3.29 (t, J=7 Hz, 2H), 3.25-3.19 (m, 12H), 3.12 (t, J=7.5 Hz, 4H), 2.95 (d, J=7 Hz, 2H), 2.25-2.03 (m, 11H), 1.01 (d, J=7.5 Hz, 6H). $^{13}$C NMR (125 MHz, D$_2$O) 158.9, 133.0, 123.7, 117.1, 65.8, 54.8, 50.7, 45.7, 44.7, 44.6, 44.2, 36.7, 25.5, 25.2, 23.7, 22.6, 19.1. LRMS [M+H]$^+$ 494.4.

Step 8

To N$^1$,N$^{1'}$-((5-(3-(isoButylammonio)propoxy)-1,3-phenylene)bis-(methylene))bis(N$^3$-(3-ammoniopropyl)propane-1,3-diaminium) hydrochloride salt was added aqueous NaOH (10%, 100 mL) and 75% CHCl$_3$/isopropanol (100 mL). The layers were separated, and the aqueous layer was extracted with 75% CHCl$_3$/isopropanol (4×100 mL). The organic layers were combined, dried over Na$_2$SO$_4$, filtered, and concentrated under reduced pressure to afford a clear oil, which was used without further purification.

Step 9

To a round-bottom flask was added the crude N$^1$,N$^{1'}$-((5-(3-(isobutylammonio)propoxy)-1,3-phenylene)bis(methylene))bis(N$^3$-(3-ammoniopropyl)propane-1,3-diaminium) (0.91 g, 1.84 mmol) and MeOH (20 mL). To the solution was added octanal (0.47 g, 3.68 mmol) and the reaction mixture was stirred at rt for 24 h. Sodium borohydride (0.28 g, 7.36 mmol) was added and the reaction mixture was stirred for 1 h. The reaction mixture was concentrated under reduced pressure to afford a white solid. Aq. NaOH (10%, 100 mL) and EtOAc (100 mL) were added and the mixture stirred for 1 h. The layers were separated and the aqueous layer was extracted with EtOAc (100 mL). The combined organics were dried over Na$_2$SO$_4$, filtered, and concentrated under reduced pressure to afford the desired product as a clear oil which was used without further purification.

Step 10: N$^1$,N$^{1'}$-((5-(3-(isobutylamino)propoxy)-1, 3-phenylene)bis(methylene))-bis(N$^3$-(3-(octylamino) propyl)propane-1,3-diamine), hydrochloride salt To the crude N$^1$,N$^{1'}$-((5-(3-(isobutylamino)propoxy)-1,3-phenylene)bis(methylene))bis(N$^3$-(3-(octylamino)propyl) propane-1,3-diamine) was added methanolic HCl (100 mL, 1.0M). The reaction mixture was stirred at rt for 1 h. The reaction mixture was concentrated under reduced pressure, and the solid was collected by vacuum filtration and washed with Et$_2$O (50 mL) and hot MeOH (50 mL) to afford the desired product as a white solid (0.75 g, 42%). 1H NMR (500 MHz, D$_2$O) δ 7.21 (s, 1H), 7.20 (s 2H), 4.30 (s, 4H), 4.24 (t, J=5 Hz, 2H), 3.30 (t, J=7 Hz, 2H), 3.26-3.14 (m, 16H), 3.07 (t, J=7 Hz, 4H), 2.96 (d, J=7.5 Hz, 2H), 2.26-2.03 (m, 11H), 1.69 (p, J=6.5 Hz, 4H), 1.38-1.28 (m, 20H), 1.02 (d, J=6.5 Hz, 6H), 0.87 (t, J=5.5 Hz, 6H). 13C NMR (125 MHz, D$_2$O) δ 158.9, 133.0, 123.7, 117.1, 65.8, 54.8, 50.8, 47.9, 45.7, 44.6, 44.6, 44.2, 44.1, 30.9, 28.1, 28.1, 25.6, 25.5, 25.4, 25.2, 22.6, 22.6, 19.1, 13.4.

Example 98

Antimicrobial Activity of Polyamines in Agar Media

Figure 30A:
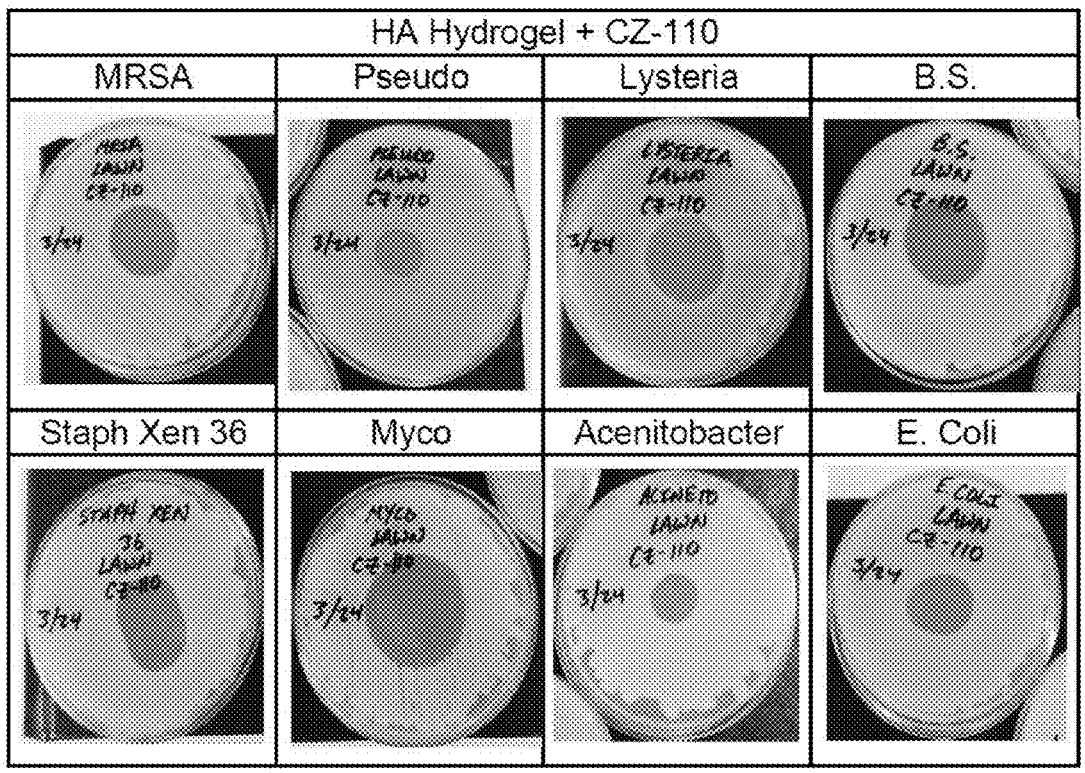
FIGS. 30A to 30I show the effects of the polyamine compounds CZ-86 and CZ-110 on various bacterial cell cultures.
Figure 30B:
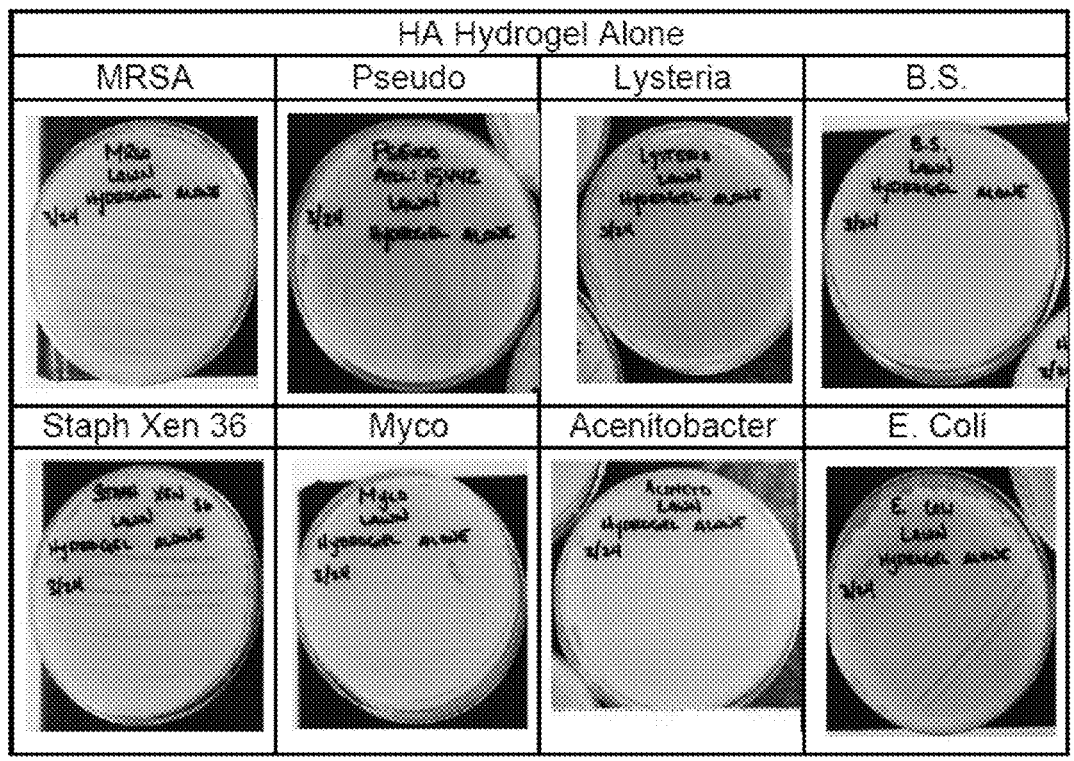
Figure 30C:
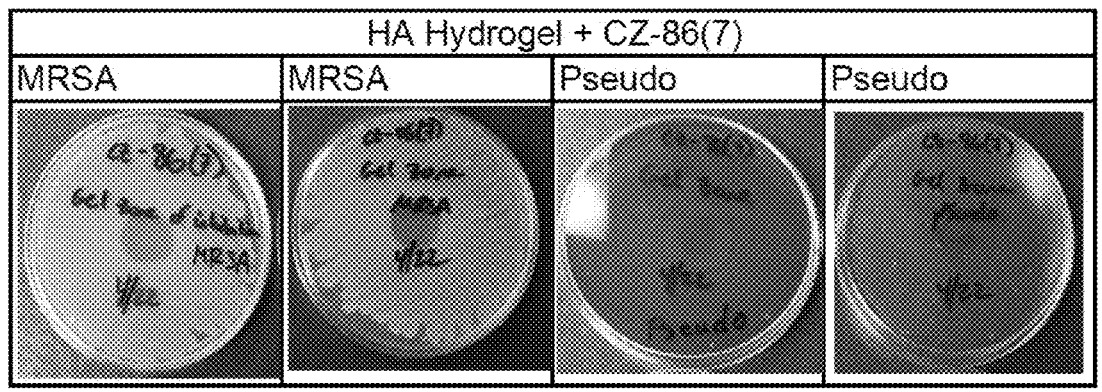
Figure 30D:
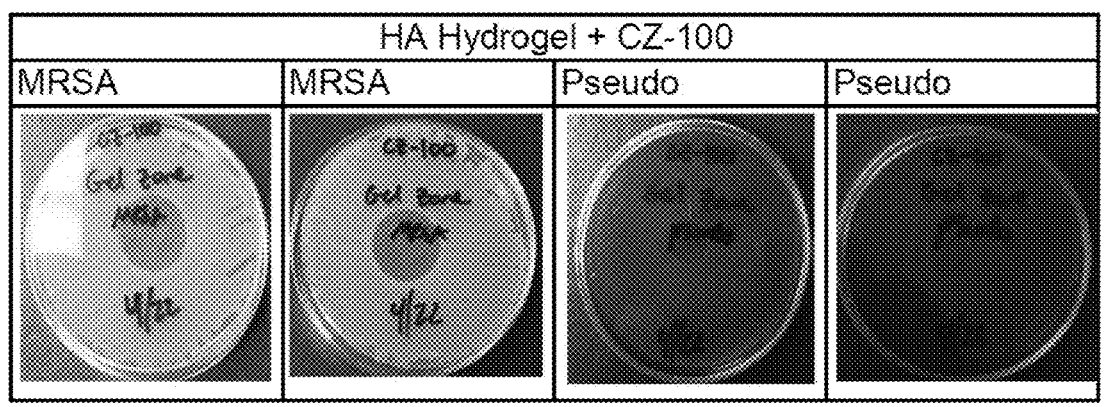
Figure 30E:
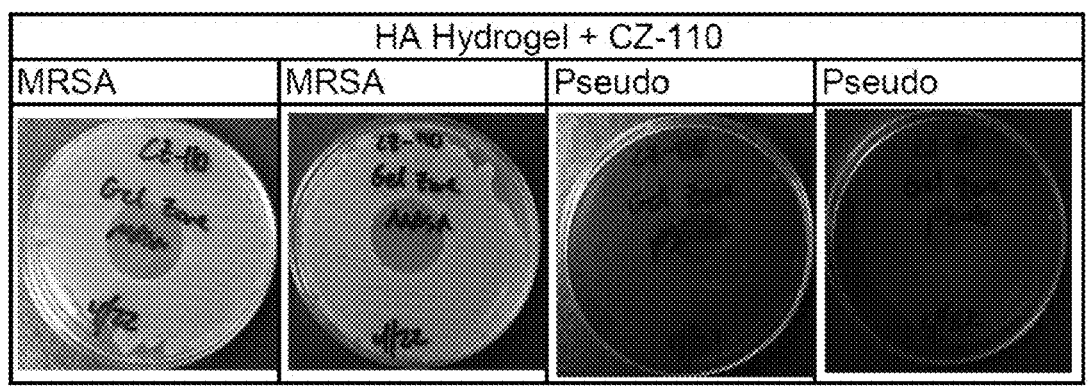
Figure 30F:
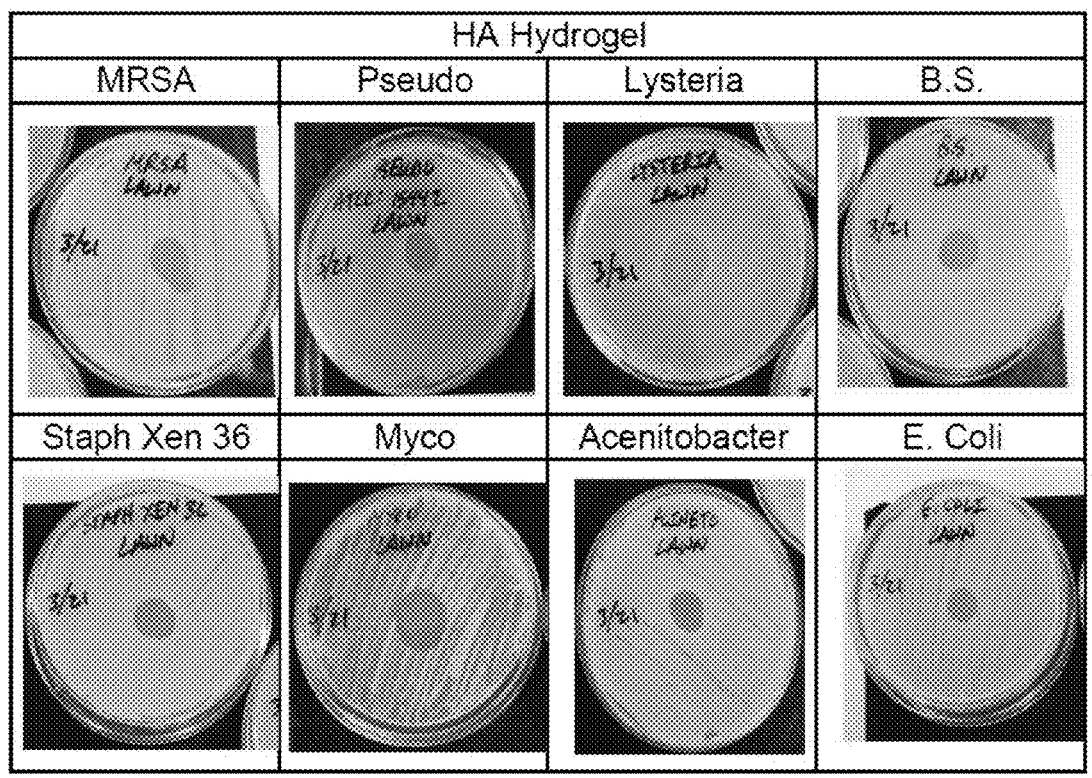
Figure 30G:
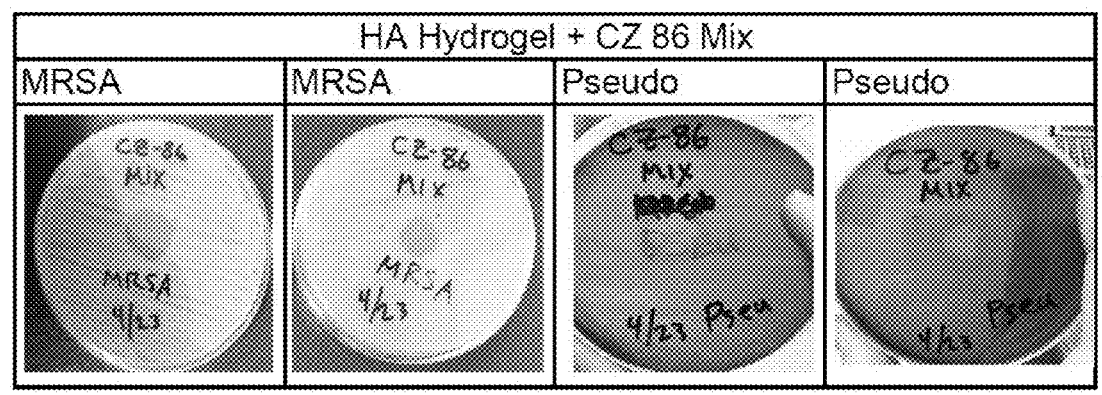
Figure 30H:
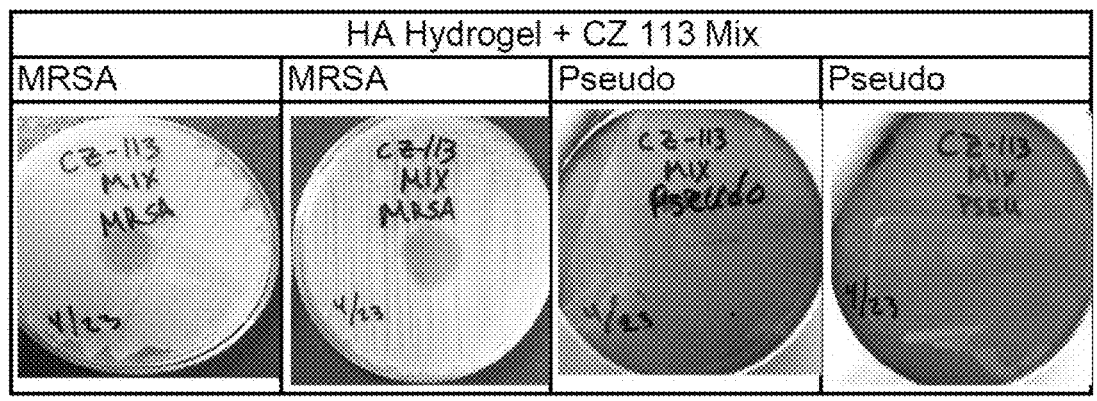
Figure 30I:
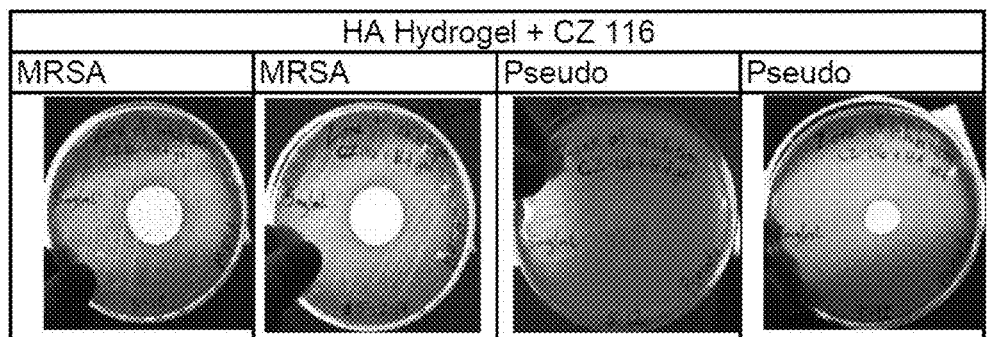
Figure 30I:
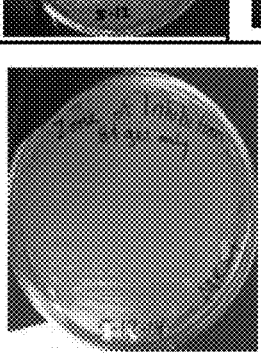
Figure 30I:
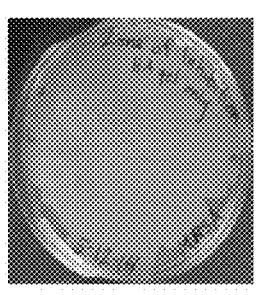
Figure 30I:
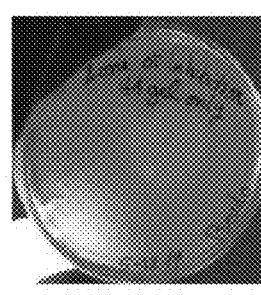
Figure 30I:
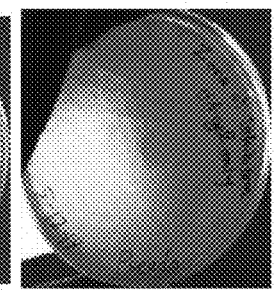

A 0.5 McFarland standard of each bacteria was made, then individual lawns of bacteria spread onto the surface of tryptic soy agar (TSA). 500 uL of the suspended gel were placed on the center of each lawn. Plates were incubated at 37 C for 24 hours, then imaged. Images of the resulting gels are shown in FIGS. 30A to 30I show the effects of the polyamines CZ-86, CZ-100, and CZ-110 on various bacterial cell cultures. The data shown indicated that when the polyamine compounds were mixed with the gel, the compounds diffused out of the gel and created zones of inhibition in the bacterial lawns. The gel alone showed no signs of antimicrobial activity (FIG. 30B).

The hydrogel that was used for those images is a LifeCore gel with 1% sodium hyaluronate (1% Sodium Hyaluronate Solution Part #82). The CZ compound was suspended in water at 1% (w/w) concentration and combined with the LifeCore gel 1:1 for a final product that contained 0.5% sodium hyaluronate and 0.5% CZ compound.

Example 99

CZ-86 and CZ-90 Polyamine Hemolysis Activity

The polyamines CZ-86 and CZ-90 were tested for hemolytic activity. The difference between the hemolytic indexes of both polyamines and the negative control was 0.00 percent. This places both test articles in the non-hemolytic range according to the grade outlined below in Table 6A.

TABLE 6A

Hemolytic Index and Grade:

| Hemolytic Index | Hemolytic Grade |
|---|---|
| 0-2 | Non-Hemolytic |
| 2-5 | Slightly Hemolytic |
| >5 | Hemolytic |

All test method acceptance criteria were met. The test procedures listed below were followed without deviation.

TABLE 6B

Results

| Test Article/ Control | Optical Density | Average Optical Density | Hemolytic Index | Average Hemolytic Index (% Hemolysis) | Corrected Hemolytic Index (% Hemolysis) |
|---|---|---|---|---|---|
| CZ-86 | 0.003 | 0.003 | 0.764 | 0.76 | 0.00 |
|  | 0.003 |  | 0.764 |  |  |
|  | 0.003 |  | 0.764 |  |  |
| CZ-90 | 0.003 | 0.003 | 0.764 | 0.76 | 0.00 |
|  | 0.003 |  | 0.764 |  |  |
|  | 0.003 |  | 0.764 |  |  |
| Negative Control | 0.003 | 0.003 | 0.764 | 0.76 | 0.00 |
|  | 0.003 |  | 0.764 |  |  |
|  | 0.003 |  | 0.764 |  |  |
| Positive Control | 0.430 | 0.450 | 97.068 | 101.7 | 100.8 |
|  | 0.468 |  | 105.638 |  |  |
|  | 0.453 |  | 102.255 |  |  |
| Phosphate Buffered Saline (PBS) Blank | 0.005 | 0.003 | 1.215 | 0.84 | N/A |
|  | 0.003 |  | 0.764 |  |  |
|  | 0.002 |  | 0.539 |  |  |

TABLE 6C

Hemoglobin Standard: Regression Output

| Constant | 0.00056 |
|---|---|
| Standard Error of Y Estimate | 0.00604 |
| $R^2$ | 0.99961 |
| Degrees of Freedom | 6 |

TABLE 6C-continued

Hemoglobin Standard: Regression Output

| X Coefficient(s) | 1.44547 |
|---|---|
| Standard Error of Coefficient | 0.01164 |

Acceptance Criteria: The negative control must produce a corrected hemolytic index of less than 2%. The positive control must produce a corrected hemolytic index of greater than 5%.

Procedure: The PBS used in testing was calcium and magnesium free. The method has been validated using human blood from one donor. This is in compliance with ISO 10993-4 which states due to differences in blood activity, human blood should be used where possible. Furthermore, pooling unmatched human blood from multiple donors may cause red blood cell agglutination which in turn could cause hemolysis; this supports the use of a single donor.

The blood was drawn using vacutainers containing 0.1 M sodium citrate at a ratio of 9:1 (3.2% anticoagulant to blood). The blood in this test was used within four hours of blood draw. The collected blood was refrigerated until testing was performed.

A hemoglobin standard was diluted with Drabkin's reagent to give solutions at concentrations of 0.80, 0.60, 0.40, 0.30, 0.20, 0.10, 0.02, and 0.01 mg/ml. These solutions were allowed to stand at room temperature for a minimum of five minutes. The absorbance was read on a spectrophotometer at 540 nanometers (nm). A standard curve was determined with the absorbance values and the standard concentrations of hemoglobin.

Human blood was centrifuged at 700-800×g for 15 minutes. A 1 mL aliquot of the plasma was added into 1 mL of Drabkin's reagent, and placed at room temperature for a minimum of 15 minutes. The absorbance was read on a spectrophotometer at 540 nm. The hemoglobin concentration was determined from the standard curve and then multiplied by a factor of 2 to obtain the total plasma free hemoglobin. The plasma free hemoglobin was less than 2 mg/mL (actual value 0.221 mg/mL). A 20 µL aliquot of blood was added to 5 mL of Drabkin's reagent in duplicate and allowed to stand at room temperature for a minimum of 15 minutes. The absorbance was read on a spectrophotometer at 540 nm then multiplied by 251 to account for the dilution.

Based on the plasma hemoglobin and the blood absorbance against Drabkin's reagent, the blood was diluted out to 10±1 mg/mL with PBS. To verify the blood dilution, a 300 µL aliquot of this blood was added to 4.5 mL of Drabkin's reagent in triplicate and allowed to stand at room temperature for a minimum of 15 minutes. The absorbance was read on a spectrophotometer at 540 nm then multiplied by 16 to account for the dilution.

Glass test tubes were labeled appropriately. Both samples were prepared the same way. The samples were allowed to thaw prior to testing. To each test tube, 7 mL of the test article and 1 mL of the diluted blood were added. The controls consisted of the appropriate amount of control material, 7 mL of PBS and 1 mL of blood. Three tubes were prepared for each test article and control. The tubes were incubated at 37±2° C. for 3 hours±5 minutes. Tubes were gently inverted twice at 30 minute intervals throughout the incubation period. A non-hemolytic negative control, a hemolytic positive control and a PBS blank were included.

After incubation, test articles were centrifuged at 700-800×g for 15 minutes and 1 mL of the supernatant fluid was combined with 1 mL of Drabkin's reagent and allowed to stand at room temperature for a minimum of 15 minutes. Following the centrifugation phase, the supernatant of both test articles visually appeared clear and were particulate free. The PBS blank and the negative control supernatant visually appeared clear and were particulate free. The supernatant of the positive control visually appeared red and were particulate free. The test articles and controls were read at 540 nm in a spectrophotometer.

The hemolytic index (percent hemolysis) was interpreted using the following equation:

$$\text{Hemolytic Index} = \frac{\text{Hemoglobin Released (mg/mL)}}{\text{Hemoglobin Present (mg/mL)}} \times 100$$

Where:

Hemoglobin Released (mg/mL)=(Optical Density×X Coefficient+Constant)×16

Hemoglobin Present (mg/ml)=Diluted Blood 10±1 mg/mL

The corrected hemolytic index was calculated by subtracting the hemolytic index of the PBS blank solution from the hemolytic index of the test article and controls.

The test article is compared to the negative control by subtracting the hemolytic index of the negative control from the hemolytic index of the test article.

TABLE 6D

| Test Parameters: | |
| --- | --- |
| Blood Type Used: | Human, Citrated |
| Positive Control: | Nitrile Glove Material, tested at 3 cm²/mL |
| Negative Control: | Polypropylene Pellets tested at 0.2 grams/mL |
| Total Hemoglobin Kit: | Stanbio, 80 mg/dL |
| Incubation Time: | 3 hours ± 5 minutes |
| Incubation Temperature: | 37 ± 2° C. |

Example 100

Minimum Elution Media (MEM) Elution Test of CZ-25

Summary: The Minimal Essential Media (MEM) Elution test was designed to determine the cytotoxicity of extractable substances. The test article was added to cell monolayers and incubated. The cell monolayers were examined and scored based on the degree of cellular destruction. All test method acceptance criteria were met. The test procedure(s) listed above were followed without deviation.

TABLE 7A

Results of Test

| Dilution of CZ-25 | Results Pass/Fail | Scores #1 | #2 | #3 | Average |
| --- | --- | --- | --- | --- | --- |
| Initial Concentration 2.5 mg/mL | Fail | 4 | 4 | 4 | 4 |
| 1:2 | Fail | 4 | 4 | 4 | 4 |
| 1:4 | Fail | 4 | 4 | 4 | 4 |
| 1:8 | Fail | 4 | 4 | 4 | 4 |
| 1:16 | Fail | 4 | 4 | 4 | 4 |

TABLE 7B

Controls:

| Identification | Scores #1 | #2 | #3 | Average | Extraction Ratio | Amount Tested/ Extraction Solvent Amount |
| --- | --- | --- | --- | --- | --- | --- |
| Negative Control - Polypropylene Pellets | 0 | 0 | 0 | 0 | 0.2 g/mL | 4 g/20 mL |
| Media Control | 0 | 0 | 0 | 0 | N/A | 20 ml |
| Positive Control - Latex Natural Rubber | 4 | 4 | 4 | 4 | 0.2 g/mL | 4 g/20 mL |

Acceptance Criteria: The United States Pharmacopeia & National Formulary (USP <87>) states that the test article meets the requirements, or receives a passing score (Pass) if the reactivity grade is not greater than grade 2 or a mild reactivity. The ANSI/AAMI/ISO 10993-5 standard states that the achievement of a numerical grade greater than 2 is considered a cytotoxic effect, or a failing score (Fail).

Acceptance criteria were based upon the negative and media controls receiving "0" reactivity grades and positive controls receiving a 3-4 reactivity grades (moderate to severe). The test was considered valid as the control results were within acceptable parameters.

The cell monolayers were examined microscopically. The wells were scored as to the degree of discernable morphological cytotoxicity on a relative scale of 0 to 4:

TABLE 7C

Standards for Grades

| Conditions of All Cultures | Reactivity | Grade |
| --- | --- | --- |
| No cell lysis, intracytoplasmic granules. | None | 0 |
| Not more than 20% rounding, occasional lysed cells. | Slight | 1 |
| Not more than 50% rounding, no extensive cell lysis. | Mild | 2 |
| Not more than 70% rounding and lysed cells. | Moderate | 3 |
| Nearly complete cell destruction. | Severe | 4 |

The results from the three wells were averaged to give a final cytotoxicity score.

Procedure: The test article was added to 1X Minimal Essential Media+5% bovine serum at an initial concentration of 2.5 mg/ml. This initial concentration was then diluted 1:2, 1:4, 1:8, and 1:16. Multiple well cell culture plates were seeded with a verified quantity of industry standard L-929 cells (ATCC CCL-1) and incubated until approximately 80% confluent. The test articles and control extracts were added to the cell monolayers in triplicate. The cells were incubated at 37±1° C. with 5±1% $CO_2$ for 48±3 hours.

Example 101

Minimum Elution Media (MEM) Elution Test of CZ-86

Summary: The polyamine compound CZ-86 was added to cell monolayers and incubated according to the procedure described in Example 100.

TABLE 8A

Results

| Dilution of CZ-86 | Results Pass/Fail | Scores #1 | #2 | #3 | Average |
|---|---|---|---|---|---|
| 400 µg/mL | Fail | 4 | 4 | 4 | 4 |
| 1:2 | Fail | 4 | 4 | 4 | 4 |
| 1:4 | Fail | 3 | 3 | 3 | 3 |
| 1:8 | Pass | 0 | 0 | 0 | 0 |
| 1:16 | Pass | 0 | 0 | 0 | 0 |

TABLE 8B

Controls:

| Identification | Scores #1 | #2 | #3 | Average | Extraction Ratio | Amount Tested/ Extraction Solvent Amount |
|---|---|---|---|---|---|---|
| Negative Control - Polypropylene Pellets | 0 | 0 | 0 | 0 | 0.2 g/mL | 4 g/20 mL |
| Media Control | 0 | 0 | 0 | 0 | N/A | 20 ml |
| Positive Control - Latex Natural Rubber | 4 | 4 | 4 | 4 | 0.2 g/mL | 4 g/20 mL |

The cell monolayers were examined microscopically. The wells were scored as to the degree of discernable morphological cytotoxicity on a relative scale of 0 to 4:

TABLE 8C

Standards for Grades

| Conditions of All Cultures | Reactivity | Grade |
|---|---|---|
| No cell lysis, intracytoplasmic granules. | None | 0 |
| Less than or equal to 20% rounding, occasional lysed cells. | Slight | 1 |
| Greater than 20% to less than or equal to 50% rounding, no extensive cell lysis. | Mild | 2 |
| Greater than 50% to less than 70% rounding and lysed cells. | Moderate | 3 |
| Nearly complete destruction of the cell layers. | Severe | 4 |

Example 102

Minimum Elution Media (MEM) Elution Test of CZ-52 and CZ-100

Summary: The test articles shown below was added to cell monolayers and incubated according to the procedure of Example 100.

TABLE 9A

Results

| | Identification | Results Pass/Fail | Scores #1 | #2 | #3 | Average |
|---|---|---|---|---|---|---|
| 1 | 25 µg/mL | Fail | 4 | 4 | 4 | 4 |
| | 12.5 µg/mL | Pass | 2 | 2 | 2 | 2 |
| | 6.25 µg/mL | Pass | 0 | 0 | 0 | 0 |
| | 3.125 µg/mL | Pass | 0 | 0 | 0 | 0 |
| | 1.563 | Pass | 0 | 0 | 0 | 0 |
| 2 | 25 µg/mL | Fail | 4 | 4 | 4 | 4 |
| | 12.5 µg/mL | Fail | 4 | 4 | 4 | 4 |
| | 6.25 µg/mL | Fail | 3 | 3 | 3 | 3 |
| | 3.125 µg/mL | Pass | 1 | 1 | 1 | 1 |
| | 1.563 | Pass | 0 | 0 | 0 | 0 |
| 3 | 25 µg/mL | Fail | 4 | 4 | 4 | 4 |
| | 12.5 µg/mL | Fail | 4 | 4 | 4 | 4 |
| | 6.25 µg/mL | Fail | 4 | 4 | 4 | 4 |
| | 3.125 µg/mL | Pass | 2 | 2 | 2 | 2 |
| | 1.563 | Pass | 0 | 0 | 0 | 0 |
| 4 | 25 µg/mL | Fail | 4 | 4 | 4 | 4 |
| | 12.5 µg/mL | Pass | 2 | 2 | 2 | 2 |
| | 6.25 µg/mL | Pass | 0 | 0 | 0 | 0 |
| | 3.125 µg/mL | Pass | 0 | 0 | 0 | 0 |
| | 1.563 | Pass | 0 | 0 | 0 | 0 |
| 5 | 25 µg/mL | Pass | 0 | 0 | 0 | 0 |
| | 12.5 µg/mL | Pass | 0 | 0 | 0 | 0 |
| | 6.25 µg/mL | Pass | 0 | 0 | 0 | 0 |
| | 3.125 µg/mL | Pass | 0 | 0 | 0 | 0 |
| | 1.563 | Pass | 0 | 0 | 0 | 0 |
| 6 | 25 µg/mL | Fail | 4 | 4 | 4 | 4 |
| | 12.5 µg/mL | Fail | 4 | 4 | 4 | 4 |
| | 6.25 µg/mL | Fail | 4 | 4 | 4 | 4 |
| | 3.125 µg/mL | Fail | 4 | 4 | 4 | 4 |
| | 1.563 | Fail | 3 | 3 | 3 | 3 |

Code for Test Article:
1) Chlorhexidine gluconate
2) Glutaraldehyde
3) CZ-52
4) CZ-100
5) Vancomycin
6) Benzethonium chloride

TABLE 9B

Controls:

| Identification | Scores #1 | #2 | #3 | Average | Extraction Ratio | Amount Tested/ Extraction Solvent Amount |
|---|---|---|---|---|---|---|
| Negative Control - Polypropylene Pellets | 0 | 0 | 0 | 0 | 0.2 g/mL | 4 g/20 mL |
| Media Control | 0 | 0 | 0 | 0 | N/A | 20 ml |
| Positive Control - Latex Natural Rubber | 4 | 4 | 4 | 4 | 0.2 g/mL | 4 g/20 mL |

The cell monolayers were examined microscopically. The wells were scored as to the degree of discernable morphological cytotoxicity on a relative scale of 0 to 4:

TABLE 9C

Standards for Grades

| Conditions of All Cultures | Reactivity | Grade |
|---|---|---|
| No cell lysis, intracytoplasmic granules. | None | 0 |
| Not more than 20% rounding, occasional lysed cells. | Slight | 1 |

TABLE 9C-continued

Standards for Grades

| Conditions of All Cultures | Reactivity | Grade |
|---|---|---|
| Not more than 50% rounding, no extensive cell lysis. | Mild | 2 |
| Not more than 70% rounding and lysed cells. | Moderate | 3 |
| Nearly complete cell destruction. | Severe | 4 |

Example 103

Minimum Elution Media (MEM) Elution Test of CZ-58, CZ-62, CZ-65 and CZ-66

Summary: The test articles shown below was added to cell monolayers and incubated according to the procedure of Example 100.

TABLE 10A

Results

| Identification | Dilution | Pass/Fail | #1 | #2 | #3 | Average |
|---|---|---|---|---|---|---|
| CZ-58 | 25 µg/mL | Fail | 4 | 4 | 4 | 4 |
|  | 1:2 | Fail | 4 | 4 | 4 | 4 |
|  | 1:4 | Pass | 2 | 2 | 2 | 2 |
|  | 1:8 | Pass | 1 | 1 | 1 | 1 |
|  | 1:16 | Pass | 1 | 1 | 1 | 1 |
| CZ-62 | 25 µg/mL | Fail | 4 | 4 | 4 | 4 |
|  | 1:2 | Fail | 4 | 4 | 4 | 4 |
|  | 1:4 | Fail | 3 | 3 | 3 | 3 |
|  | 1:8 | Pass | 1 | 1 | 1 | 1 |
|  | 1:16 | Pass | 1 | 1 | 1 | 1 |
| CZ-65 | 25 µg/mL | Fail | 4 | 4 | 4 | 4 |
|  | 1:2 | Fail | 4 | 4 | 4 | 4 |
|  | 1:4 | Pass | 2 | 2 | 2 | 2 |
|  | 1:8 | Pass | 1 | 1 | 1 | 1 |
|  | 1:16 | Pass | 1 | 1 | 1 | 1 |
| CZ-66 | 25 µg/mL | Fail | 4 | 4 | 4 | 4 |
|  | 1:2 | Fail | 4 | 4 | 4 | 4 |
|  | 1:4 | Pass | 2 | 2 | 2 | 2 |
|  | 1:8 | Pass | 1 | 1 | 1 | 1 |
|  | 1:16 | Pass | 1 | 1 | 1 | 1 |

TABLE 10B

Controls:

| Identification | #1 | #2 | #3 | Average | Extraction Ratio | Amount Tested/Extraction Solvent Amount |
|---|---|---|---|---|---|---|
| Negative Control - Polypropylene Pellets | 0 | 0 | 0 | 0 | 0.2 g/mL | 4 g/20 mL |
| Media Control | 0 | 0 | 0 | 0 | N/A | 20 ml |
| Positive Control - Latex Natural Rubber | 4 | 4 | 4 | 4 | 0.2 g/mL | 4 g/20 mL |

The cell monolayers were examined microscopically. The wells were scored as to the degree of discernable morphological cytotoxicity on a relative scale of 0 to 4:

TABLE 10C

Standards for Grades

| Conditions of All Cultures | Reactivity | Grade |
|---|---|---|
| No cell lysis, intracytoplasmic granules. | None | 0 |
| Not more than 20% rounding, occasional lysed cells. | Slight | 1 |
| Not more than 50% rounding, no extensive cell lysis. | Mild | 2 |
| Not more than 70% rounding and lysed cells. | Moderate | 3 |
| Nearly complete cell destruction. | Severe | 4 |

Example 104

Minimum Elution Media (MEM) Elution Test of CZ-92, CZ-96 and CZ-99

Summary: The test articles shown below was added to cell monolayers and incubated according to the procedure of Example 100.

TABLE 11A

Results

| Identification | Dilution | Pass/Fail | #1 | #2 | #3 | Average |
|---|---|---|---|---|---|---|
| CZ-92 | 25 µg/mL | Fail | 4 | 4 | 4 | 4 |
|  | 1:2 | Fail | 4 | 4 | 4 | 4 |
|  | 1:4 | Fail | 4 | 4 | 4 | 4 |
|  | 1:8 | Fail | 3 | 3 | 2 | 3 |
|  | 1:16 | Pass | 1 | 1 | 1 | 1 |
| CZ-96 | 25 µg/mL | Pass | 2 | 2 | 2 | 2 |
|  | 1:2 | Pass | 0 | 0 | 0 | 0 |
|  | 1:4 | Pass | 0 | 0 | 0 | 0 |
|  | 1:8 | Pass | 0 | 0 | 0 | 0 |
|  | 1:16 | Pass | 0 | 0 | 0 | 0 |
| CZ-99 | 25 µg/mL | Pass | 0 | 0 | 0 | 0 |
|  | 1:2 | Pass | 0 | 0 | 0 | 0 |
|  | 1:4 | Pass | 0 | 0 | 0 | 0 |
|  | 1:8 | Pass | 0 | 0 | 0 | 0 |
|  | 1:16 | Pass | 0 | 0 | 0 | 0 |

TABLE 11B

Controls:

| Identification | #1 | #2 | #3 | Average | Extraction Ratio | Amount Tested/Extraction Solvent Amount |
|---|---|---|---|---|---|---|
| Negative Control - Polypropylene Pellets | 0 | 0 | 0 | 0 | 0.2 g/mL | 4 g/20 mL |
| Media Control | 0 | 0 | 0 | 0 | N/A | 20 ml |
| Positive Control - Latex Natural Rubber | 4 | 4 | 4 | 4 | 0.2 g/mL | 4 g/20 mL |

The cell monolayers were examined microscopically. The wells were scored as to the degree of discernable morphological cytotoxicity on a relative scale of 0 to 4:

TABLE 11C

Standards for Grades

| Conditions of All Cultures | Reactivity | Grade |
|---|---|---|
| No cell lysis, intracytoplasmic granules. | None | 0 |
| Less than or equal to 20% rounding, occasional lysed cells. | Slight | 1 |
| Greater than 20% to less than or equal to 50% rounding, no extensive cell lysis. | Mild | 2 |
| Greater than 50% to less than 70% rounding and lysed cells. | Moderate | 3 |
| Nearly complete destruction of the cell layers. | Severe | 4 |

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for dispersing or killing a biofilm on a subject, the method comprising a step of topically, orally, transmucosally, vaginally, or rectally administering an anti-biofilm composition to a surface of the subject, thereby effectively dispersing or killing the biofilm;
wherein the anti-biofilm composition comprises
(i) a pharmaceutically acceptable carrier; and
(ii) a therapeutically effective amount of a biocidal polyamine compound;
wherein the biocidal polyamine compound is selected from the group consisting of:

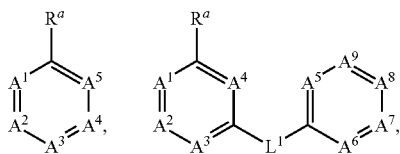

and a salt thereof;
wherein:
each $R^a$ is independently a group of Formula II:

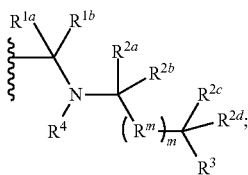

each of the $A''$ members is independently selected from the group consisting of $CR^a$ and $CR^5$; or, alternatively, a pair of adjacent $A''$ members join to form a cycloalkyl, aryl, heterocyclyl, or heterocycloaryl ring; wherein at least one $A''$ member and at most three $A''$ members are independently selected $CR^a$, each $R^{1a}$ and $R^{1b}$ is a member independently selected from the group consisting of hydrogen, fluoro, alkyl, and fluoroalkyl;

each $R^{2a}$, $R^{2b}$, $R^{2c}$, and $R^{2d}$ is a member independently selected from the group consisting of hydrogen, alkyl, fluoroalkyl, alkenyl, alkynyl, aryl, heteroaryl, arylalkyl, or heteroarylalkyl; alternatively, a pair of $R^{2n}$ members from the $R^a$ group independently selected from the group $R^{2a}$ and $R^{2b}$, and $R^{2c}$ and $R^{2d}$ join to form a ring independently selected from the group consisting of spirocycloalkyl and spiroheterocycyl; or, alternatively, the $R^{2a}$ and the $R^{2c}$ from the $R^a$ group join to form a ring independently selected from the group consisting of cycloalkyl and heterocycyl;

each $R^m$ is a member independently selected from the group consisting of $-CR^{2a}R^{2b}-$, $-CR^{2c}R^{2d}-$, $-C(R^{2a})=(R^{2b})-$, $-CC-$ and $-C(R^{2a})(R^{2b})-L^2-C(R^{2c})(R^{2d})-$;

m is 1;

each $L^1$ and $L^2$ is a member independently selected from the group consisting of a bond, $-O-$, $-C(O)O-$, $-NR^4-$, $-NR^4C(O)-$, and $C(O)NR^4-$;

each $R^3$ is a member independently selected from the group consisting of $-Z^1-Y^1-R^4$ and $-Z^1-Y^1-Y^2-R^4$;

each $R^4$ is a member independently selected from the group consisting of hydrogen, alkyl, fluoroalkyl, alkenyl, alkynyl, aryl, heteroaryl, arylalkyl, and heteroarylalkyl; or, alternatively, for a $-N(R^4)_2$ group, one of the two $R^4$ in the group is a member selected from the group consisting of $-(CO)OR^{6a}-$, $(CO)N(R^{6a})(R^{6b})$, and $-C(NR^{6a})N(R^{6b})(R^{6c})$;

each $R^5$ is a member independently selected from the group consisting of hydrogen, alkyl, hydroxyl, alkoxy, alkylamino, alkenyl, alkynyl, aryl, aryloxy, arylamino, cycloalkyl, cycloalkoxy, cycloalkylamino, heterocyclyl, heterocycyloxy, heterocycylamino, halo, haloalkyl, fluoroalkyloxy, heteroaryl, heteroaryloxy, heteroarylamino, arylalkyl, arylalkyloxy, arylalkylamino, heteroarylalkyl, heteroarylalkyloxy, heteroarylalkylamino; hydroxyalkyl, aminoalkyl, and alkylaminoalkyl;

each $Y^1$ and $Y^2$ is an independently selected group of Formula IA:

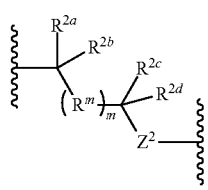

each $Z^1$ and $Z^2$ is an independently selected $NR^4$; and each $R^{6a}$, $R^{6b}$, and $R^{6c}$ is a member independently selected from the group consisting of hydrogen, alkyl, fluoroalkyl, alkenyl, alkynyl, aryl, heteroaryl, arylalkyl, cycloalkyl, and heteroarylalkyl; or, alternatively, two $R^{6n}$ members $R^{6a}$ and $R^{6b}$ or $R^{6a}$ and $R^{6c}$ form a heterocycyl ring;

wherein the biocidal polyamine compound comprises at least two primary or secondary amino groups.

2. The method of claim 1, wherein:
each $R^{2a}$, $R^{2b}$, $R^{2c}$, and $R^{2d}$ is a member independently selected from the group consisting of hydrogen, alkyl, fluoroalkyl, alkenyl, alkynyl, aryl, heteroaryl, arylalkyl, or heteroarylalkyl.

3. The method of claim 2, wherein:
each $R^{1a}$ and $R^{1b}$ is a member independently selected from the group consisting of hydrogen and alkyl.

4. The method of claim 1, wherein the biocidal polyamine compound comprises at least four primary or secondary amino groups.

5. The method of claim 1, wherein the biocidal polyamine compound is selected from the group consisting of

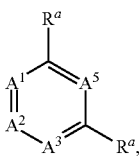 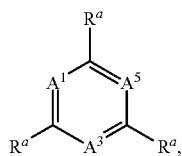

and a salt thereof;
wherein each $A^n$ member is an independently selected $CR^5$.

6. The method of claim 5, wherein the biocidal polyamine compound is selected from the group consisting of

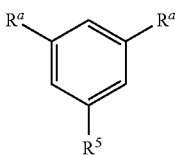

and a salt thereof; and
wherein $R^a$ is an independently selected group of Formula VII:

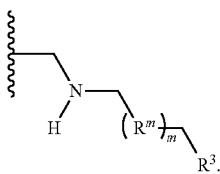

VII

7. The method of claim 5, wherein $R^a$ is —CH$_2$[NH CH$_2$)$_n$]$_p$NH$_2$;
wherein each n is an integer independently selected from 3 to 12; and
wherein each p is an integer independently selected from 1 to 3.

8. The method of claim 5, wherein the biocidal polyamine compound is selected from the group consisting of

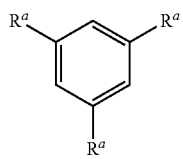

and a salt thereof.

9. The method of claim 1, wherein the anti-biofilm composition is a liquid, a gel, a paste, or a powder.

10. The method of claim 1, wherein the biofilm comprises an antibiotic-resistant bacterial species.

11. The method of claim 1, wherein the anti-biofilm composition is an aerosol spray, a solution, a suspension, a gel, a paste, a cream, or a foam.

12. The method of claim 11, wherein the anti-biofilm composition is the cream.

13. The method of claim 1, wherein the anti-biofilm composition is a tablet, a pill, a troche, or a capsule.

14. The method of claim 1, the surface is a dermal surface, a mucosal surface, an oral surface, a urinary tract surface, a vaginal tract surface, or a lung surface.

15. The method of claim 1, wherein the surface is skin or soft tissue that has been compromised by dermatitis, ulcers, a burn injury, or trauma.

16. The method of claim 1, wherein the method comprises a step of treating a patient with a biofilm-related disorder.

17. The method of claim 16, wherein the biofilm-related disorder is an infection, pneumonia, cystic fibrosis, otitis media, a urinary tract disorder, a periodontal disease, bronchiectasis, dental caries, or acne.

* * * * *